(12) United States Patent
Cashman

(10) Patent No.: US 8,168,635 B2
(45) Date of Patent: May 1, 2012

(54) MODULATORS OF CENTRAL NERVOUS SYSTEM NEUROTRANSMITTERS

(75) Inventor: John Cashman, San Diego, CA (US)

(73) Assignee: Human BioMolecular Research Institute, San Diego, CA (US)

( * ) Notice: Subject to any disclaimer, the term of this patent is extended or adjusted under 35 U.S.C. 154(b) by 986 days.

(21) Appl. No.: 11/629,797

(22) PCT Filed: Jun. 20, 2005

(86) PCT No.: PCT/US2005/021818
§ 371 (c)(1),
(2), (4) Date: Dec. 20, 2007

(87) PCT Pub. No.: WO2006/025920
PCT Pub. Date: Mar. 9, 2006

(65) Prior Publication Data
US 2008/0261967 A1    Oct. 23, 2008

Related U.S. Application Data

(60) Provisional application No. 60/581,210, filed on Jun. 19, 2004.

(51) Int. Cl.
*A61K 31/502* (2006.01)
*C07D 237/30* (2006.01)
(52) U.S. Cl. ........................ 514/248; 544/237
(58) Field of Classification Search .................. 514/248; 544/237
See application file for complete search history.

(56) References Cited

U.S. PATENT DOCUMENTS

| | | | |
|---|---|---|---|
| 2,857,397 | A | 10/1958 | Cope |
| 3,536,809 | A | 10/1970 | Applezweig |
| 3,598,123 | A | 8/1971 | Zaffaroni |
| 3,845,770 | A | 11/1974 | Theeumes et al. |
| 3,916,899 | A | 11/1975 | Theeumes et al. |
| 4,008,719 | A | 2/1977 | Theeumes et al. |
| 5,010,060 | A | 4/1991 | Lambert et al. |
| 5,013,556 | A | 5/1991 | Woodle et al. |
| 5,583,147 | A | 12/1996 | Ko et al. |
| 6,121,307 | A | 9/2000 | Mewshaw |
| 6,472,384 | B1 | 10/2002 | Inukai et al. |

FOREIGN PATENT DOCUMENTS

| | | | |
|---|---|---|---|
| EP | 0158922 | A | 10/1985 |
| EP | 0289913 | A | 11/1988 |
| GB | 268742 | A | 1/1994 |
| WO | WO 01/77089 | * | 4/2001 |
| WO | WO 2005/066162 | A | 7/2005 |

OTHER PUBLICATIONS

Dini et al., Bioorg. Medicinal. Chem. Lettrs. (2002), vol. 12(8), pp. 1209-1213.*
Szarvasi et al., Chim. Ther. (1967), vol. 2(6), pp. 407-409.*
Szarvasi et al., Bull. De la Societe. Chimique de France, (1966), vol. 6, pp. 1838-1846.*
King, Med. Chem. Principle and Practice (1994), pp. 206-208).*
Baraldi et al., *J. Med. Chem.* 39:802-806 (1996).
Beavo et al., *Mol Pharmacol* 46:399-405 (1994).
Blough et al., *J Med Chem* 40:3861-3864 (1997).
Boja et al., *J Med Chem* 37:1220-1223 (1994).
Broekamp et al., *J Med Chem* 38:4615-4633 (1995).
Buchwald et al., *Surgery* 88:507 (1980).
Carroll et al., J Med Chem 35:969-981 (1992).
Clarke et al., *J Med Chem* 16:1260-1267 (1973).
Conti & Jin *Prog Nucleic Acid Res* 63:1-38 (1999).
Cope, A. et al. *Journal of the American Chemical Society* 81:4577-4583 (1959).
Denton et al., *J Med Chem* 48:224-239 (2004).
During et al., *Ann Neurol* 25:351 (1989).
Eckmann et al., *Curr Ther Res* 43:291-295 (1988).
Eshleman et al., *J Pharmacol Exp Ther* 274:276-283 (1995).
Eshleman et al., *J Pharmacol Exp Ther* 289:877-885 (1999).
Fandrick et al., *Bioorganic Med Chem Lett* 13:2151-2154 (2003).
Feng et al., *Bioorg Med Chem* 11:775-780 (2003).
Fleischhacker et al., *Neuropsychobiology* 26:59-64 (1992).
Holmquist et al., *J Med Chem* 39:4139-4141 (1996).
Horowski et al., *Curr Ther Res* 38:23-29 (1985).
Houslay, *Prog Nucleic Acid Res Mol Biol* 69:249-315 (2001).
Howard et al., *J Neurosurg* 71:105 (1989).
International Search Report and Written Opinion for PCT/US05/21818 dated Jun. 1, 2006.
Javanmard et al., *J Med Chem* 42:4836-4843.
Langer and Peppas, *J Macromol Sci Rev Macromol Chem* 23:61(1983).
Langer, *Science* 249:1527-1533 (1990).
Levy et al., *Science* 228:190 (1985).
Lucki, *Behav Pharmacol* 8:523-532 (1997).
Lucki et al., *Psychopharmacol* 155:315-322 (2001).
Meltzer et al., *J Med Chem* 40:2661-2673.
O'Donnell, *J Pharmacol Exp Ther* 254:147-157 (1990).
O'Donnell & Frith, *Pharmacol Biocehm Behav* 63:185-192 (1999).
Overstreet, *Neurosci Biobehav Rev* 17:51-68 (1993).
Oya et al., *J Med Chem* 42:333-335 (1999).
Porsolt, *Rev Neurosci* 11:53-38 (2000).
Richter, et al., *Inorganica Chimica Acta* 238:155-158 (1998).
Robins, M.J., et al., *Journal of Heterocyclic Chemistry, Hero Corp.*, 38:1297-1306 (2001).
Robinson, R. et al. *Journal of the Chemical Society, Database CA Chemical Abstracts Service* Assession No. 1940:6253.
Saccomano et al., *J Med Chem* 34:291-298 (1991).
Saudek et al, *N Engl J Med* 321:574 (1989).
Schudt et al. Loughney & Ferguson, in *Phosphodiesterase Inhibitors*, Eds., Academic Press: San Diego, pp. 1-19 ((1996).

(Continued)

*Primary Examiner* — Taofiq A Solola
(74) *Attorney, Agent, or Firm* — Sam K. Tahmassebi; TechLaw LLP

(57) ABSTRACT

Disclosed are agents having pharmacological activity against cellular receptors and intracellular signaling, particularly receptors and signaling pathways of central nervous system (CNS) neurotransmitters. Also disclosed are related methods and compositions for the treatment or prevention of diseases or disorders using the agents.

13 Claims, 27 Drawing Sheets

OTHER PUBLICATIONS

Scott et al., *Eur J Clin Pharmacol* 40:127-129 (1991).
Sefton, *CRC Crit Ref Biomed Eng* 14:201 (1987).
Sh. Harusawa et al. *Journal of Organic Chemistry* 64:8608-8615 (1999).
Supplementary Partial European Search Report for EP 05812931 (PCT/US2005)021818 dated Jan. 11, 2008.
Tamiz et al., *J Med Chem* 43:1215-1222 (2000).
Treat, In *Liposomes in the Therapy of Infectious Disease and Cancer*, Lopez-Berestein and Fidler eds., Liss, New York, pp. 353-365 (1989).
Wachtel, *J Pharm Pharmacol* 35:440-444 (1983).
Wachtel, *Neuropharmacol* 25:1119-1126 (1986).
Wolf et al., *Neurochem Int* 18:33-38 (1991).
Ye & O'Donnell, *J neurochem* 66:1894-1902 (1996).
Zhang et al., *Neuropsychopharmacol* 27:587-595 (2002).
Zeller, *Pharmacopsychiatry* 17:188-190 (1984).

\* cited by examiner

Scheme 1 a, CH$_3$OCH$_2$PPh$_3$Cl, NaH, THF; b, acetone, H$_2$SO$_4$, reflux;
c, Ph$_3$PCHCOOEt, CH$_2$Cl$_2$; d, Pd/C, H$_2$, EtOH; e, DIBAL, toluene, MeOH, Scheme 2 a, 1-butenylmagnesium bromide, THF, 0°C-room T; b, NBS, CH$_2$Cl$_2$, 0°C-room T; c, potassium phthilimide, NaI (cat.), DMSO, 70°C, 12 h; d, N$_2$H$_4$, MeOH; e, KCN, NaI (cat.), DMSO, 70°C, 12 h; f, Raney Ni, H$_2$; g, Raney Ni, NaBH$_4$, MeOH

Scheme 3 a) 3,4-dimethoxyphenylmagnesium bromide, THF;
b) H₂NNH₂, EtOH, reflux; c) NaH, Br(CH₂)Br, DMF;
d) CsOH·H₂O, 13 or 15, DMF.

Scheme 4 a) LiAlH4, THF / reflux; b) di-t-butyldicarbonate, CH2Cl2, 0 °C; c) (COCl)2, DMSO, TEA, CH2Cl2, -78 °C; d) benzyltriphenylphosphonium chloride, nBuLi, -78 °C; e) TFA, 0 oC to 25 oC; f) H2CO, NaBH4, HOAc.

Scheme 5 a) ethyl chloroformate, $K_2CO_3$, THF; b) LAH, THF.

Scheme 6 a) MeOCH=PPh$_3$, THF; b) acetone, H$_2$SO$_4$; c) EtOC(O)CH-PPh$_3$, DCM;
d) H$_2$, Pd/C; e) DiBAL, toluene; f) [2-(1,3-dioxolan-2-yl)ehtyl]triphenylphosphonium bromide.

Scheme 7 a) 1-Butenylmagnesium bromide; b) NBS, DCM; c) Potassium phthalimide, NaI, DMSO; d) $NH_2NH_2$, MeOH; e) KCN, NaI, DMSO; f) Raney Ni, $H_2$, 1 M $NH_3$ in MeOH.

Scheme 8 a) Ethylchloroformate, K₂CO₃, THF; b) LAH, THF.
*mix of *cis/trans* diastereomers

Scheme 9 a) EtOC(O)CH-PPH$_3$, DCM; b) H$_2$, Pd/C; c) DiBAL, toluene;
d) [2-(1,3-dioxolan-2-yl)ehtyl]triphenylphosphonium bromide; e) acetone, H$_2$SO$_4$.

Scheme 10 a) 1-Butenylmagnesium bromide; b) NBS, DCM; c) KCN, NaI, DMSO;
d) Raney Ni, $H_2$, 1 M $NH_3$ in MeOH.

Scheme 11 a) Mg turlings, THF, reflux; b) cis-1,2,3,6-tetrahydrophthalic anhydride, THF;
c) $H_2NNH_2$, EtOH, reflux; d) 1,5-dibromopentane, NaH, DMF.

Scheme 12

21 n = 2
22 n = 3 a) CsOH·H₂O, 4 Å sieves, 14 or 15, DMF.

Scheme 13 a) Ethylchloroformate, K₂CO₃, THF; b) LAH, THF.

a) Triphenylphosphine, DIAD, (R) or (S)-α,α,α-triflouro-p-cresol; b) Potassium phthalimide, NaI, DMSO, Δ;
c) H₂NNH₂·H₂O, DCM/MeOH (1:1).

22(S) or 22(R) →ᵃ a) NaH, DMF.

a) SnCl$_4$, benzene; b) NaBH$_4$, EtOH; c) Novozyme 435 (CALB); d) NH$_2$CH$_3$, THF;
e) 1-flouronaphthalene, dimethylacetamide.

MODULATORS OF CENTRAL NERVOUS SYSTEM NEUROTRANSMITTERS

CROSS-REFERENCES TO RELATED APPLICATIONS

This application is filed under 35 U.S.C. §371 as the U.S. national phase of International Application PCT/US2005/021818, filed Jun. 20, 2005, which designated the U.S. and in turn claims benefit of U.S. Provisional Application No. 60/581,210, filed Jun. 19, 2004, which is incorporated herein by reference in its entirety.

FIELD OF THE INVENTION

The present invention pertains generally to the field of pharmacological modulation of cellular receptors and signaling.

BACKGROUND OF THE INVENTION

Human central nervous system (CNS) disorders are heterogeneous diseases that affect a growing number of the population. Over 9.5% of the population in the United States suffers from depressive disorders. Pharmacological studies have shown that alteration of the storage and/or metabolism of neurotransmitters such as serotonin and norepinephrine in the vesicles of presynaptic nerve endings could improve CNS disorders and diseases such as depression, memory or cognitive impairment, anxiety, and other diseases. For example, upon stimulation, nerve cells release serotonin and other neurotransmitters into the synaptic cleft to propagate nerve impulses. Thus, a potential treatment for depression may involve the inhibition of the natural reuptake of serotonin or other neurotransmitters back into the cells. For example, serotonin reuptake inhibition by selective serotonin reuptake inhibitors (SSRIs) result in a progressive increase in extracellular serotonin neurotransmitter concentrations and stimulation of postsynaptic receptors. However, SSRIs have a number of shortcomings including the slow onset of therapeutic action and tolerance and/or recalcitrance of efficacy.

Another target of antidepressant administration is the cAMP signal transduction system, because chronic SSRI antidepressant treatment up-regulates this intracellular cascade at several levels. It has been noted that in animals treated repeatedly with SSRIs, cyclic AMP phosphodiesterase (form 4) (PDE4) is upregulated. Inhibitors of PDE4, such as rolipram, produce both antidepressant-like and memory-enhancing effects in preclinical models. Consistent with this, it has been shown that drugs from this class possess clinical antidepressant efficacy, including reversal of cognitive deficits that occur in depression, as well as memory improvement and cognition enhancement for Alzheimer's Disease.

Current drug development theory suggests that compounds with molecular weight exceeding 500 daltons do not enter the CNS. In addition, the synergistic effects of combining SSRI functional activity and PDE4 inhibitory activity in one molecule has previously not been recognized. For many antidepressants in clinical use today, metabolism of a prodrug moiety is responsible for converting the molecule into a pharmacologically active compound. Thus, it is suggested that imipramine is converted to desimipramine that also possesses significant pharmacological activity. In this way, the drug may attain a more desirable pharmacokinetic or pharmacodynamic profile. It is likely that this is taking place for numerous CNS agents in this class of therapeutics.

Additional agents with pharmacological activity against CNS neurotransmitter receptors and/or intracellular signaling events downstream of neurotransmitter receptor binding are needed. This present invention as described herein meets this and other needs.

BRIEF SUMMARY OF THE INVENTION

In one embodiment, the present invention provides compounds of Formula X:

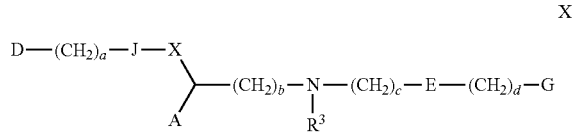

In Formula X, D is a member selected from the group consisting of optionally substituted aryl, optionally substituted heteroaryl, optionally substituted cycloalkyl and optionally substituted heterocycloalkyl; J is a direct bond or optionally combined with A and X to form a 5-6 membered heterocylic ring, substituted with an $R^1$ and an $R^2$ group each independently selected from the group consisting of hydrogen and optionally substituted aryl, or optionally combined with D to form an optionally substituted aryl; X is a member selected from the group consisting of O, N and S; A is a member selected from the group consisting of optionally substituted aryl, optionally substituted heteroaryl, optionally substituted cycloalkyl and optionally substituted heterocycloalkyl; E is a member selected from the group consisting of a direct bond and optionally substituted heterocycloalkyl; G is a member selected from the group consisting of hydrogen, optionally substituted aryl, optionally substituted heteroaryl, optionally substituted cycloalkyl and optionally substituted heterocycloalkyl; $R^3$ is a member selected from the group consisting of hydrogen and $C_1$-$C_6$ alkyl, or optionally combined with G to form an optionally substituted heterocycloalkyl; each of subscript a, c and d is independently an integer from 0-6; and subscript b is an integer from 1-6; or a pharmaceutically acceptable salt, hydrate, solvate, stereoisomer, prodrug or polymorph thereof.

In other embodiments, the present invention provides a compound having Formula XI:

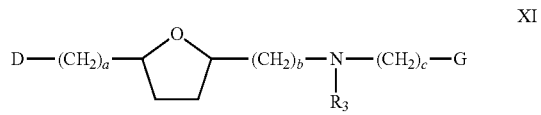

In still other embodiments, the compounds of Formula XI are those where G is hydrogen or combined with $R^3$ to form a 5-6 membered heterocycloalkyl containing 1-2 heteroatoms each independently selected from the group consisting of N and O; and subscript b is 1-3. In another embodiment, the compounds of Formula XI are those where D is a member selected from the group consisting of optionally substituted phenyl, optionally substituted naphthyl and optionally substituted biphenyl; and subscript a is 0-3.

In other embodiments, the present invention provides compounds of Formula XII:

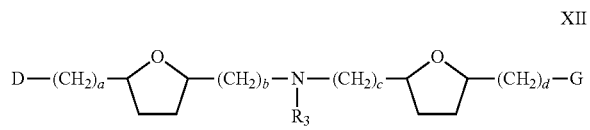

In Formula XII, D and G are both the same; subscripts a and d are both 0-3 and are the same; and subscripts b and c are both 2.

In further embodiments, the present invention provides a compound of Formula XIII:

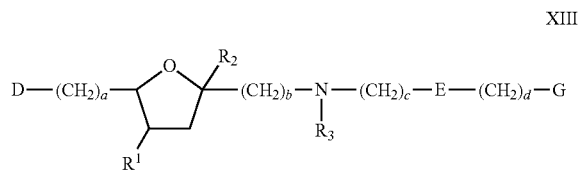

Compounds of Formula XIII include those where E is an optionally substituted heterocycloalkyl having at least from 1-3 nitrogen atoms; $R^1$ is hydrogen or optionally combined with D to form an optionally substituted aryl; and $R^2$ is a member selected from the group consisting of hydrogen and optionally substituted phenyl.

In yet other variations, the present invention provides a compound of Formula XIV:

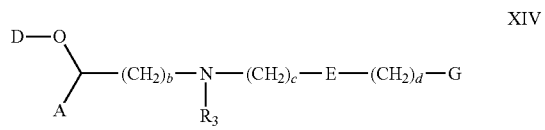

Compounds of Formula XIV include those where D is an optionally substituted phenyl; A is an optionally substituted phenyl; E is an optionally substituted heterocycloalkyl having from 1-3 nitrogen atoms; G is an optionally substituted phenyl; subscripts b and c are each independently 1-6; and subscript d is 0.

Particularly preferred compounds of the present invention include compounds having dual inhibitory activity against serotonin reuptake and phosphodiesterase 4 (PDE4) enzyme.

In another aspect, the present invention provides pharmaceutical compositions comprising a compound as described herein and a pharmaceutically acceptable carrier. The pharmaceutical compositions are useful in the treatment or prevention of a disease or disorder amenable to therapeutic or prophylactic intervention via inhibition of neurotransmitter reuptake and/or PDE4 activity. Diseases or disorders amenable to treatment or prevention using the pharmaceutical compositions of the present invention include, for example, depression, drug addiction, anxiety, attention-deficit disorder, schizophrenia, bipolar disorder, and neurodegenerative disease such as, e.g., Parkinson's Disease and Alzheimer's Disease.

In still another aspect, the present invention provides methods for the treatment preventions of a disease or disorder in a subject. In certain embodiments, the method includes the step of administering to a subject an effective amount of a compound as described herein, wherein said subject is suffering from a central nervous system (CNS) disease or disorder amenable to treatment or prevention by inhibition of at least one of serotonin reuptake and phosphodiesterase 4 (PDE4) activity. In some preferred variations, the compound is a dual inhibitor of serotonin reuptake and phosphodiesterase 4 (PDE4) enzyme activity.

Diseases and disorders particularly amenable to treatment or prevention using the methods described herein include, for example, depression, drug addiction, anxiety, attention-deficit disorder, schizophrenia, bipolar disorder, memory loss, and cognitive impairment. In some embodiments, the compound has anti-neurodegenerative activity and is used for the treatment or prevention of a neurodegenerative disease or disorder (e.g., Parkinson's Disease or Alzheimer's Disease). Particularly suitable compounds for use in the present methods are compounds that induce non-addicting CNS stimulation in the subject.

In specific embodiments of the therapeutic and prophylactic methods, the subject has been diagnosed with the disease or disorder, is not suffering from a second disease or disorder, and/or is monitored for one or more symptoms of the disease or disorder.

DEFINITIONS

Unless defined otherwise, all technical and scientific terms used herein have the same meaning as commonly understood by one of ordinary skill in the art to which this invention belongs. Although any methods and material similar to those described herein can be used in the practice or testing of the present invention, only exemplary methods and materials are described. For purposes of the present invention, the following terms are defined below.

The terms "a," "an," and "the" include plural referents unless the context clearly dictates otherwise.

The term "agent" refers generally to the compounds described herein; accordingly, the terms "agent" and "compound" are used synonymously.

The term "hydrido" refers to a single hydrogen.

The term "alkyl" refers to saturated aliphatic groups including straight chain, branched chain, and cyclic groups, all of which may be optionally substituted. Suitable alkyl groups include methyl, ethyl, propyl, sec-butyl, tert-butyl, cycloalkyl, cyclopentyl, and the like, and may be optionally substituted.

The term "alkenyl" refers to unsaturated groups which contain at least one carbon-carbon double bond and includes straight chain, branched chain, and cyclic groups, all of which may be optionally substituted. Exemplary alkenyl groups include, but are not limited to, ethenyl, propenyl, and isopropenyl and the like which may be optionally substituted.

The term "alkynyl" refers to unsaturated groups which contain at least one carbon-carbon triple bond and includes straight chain, branched chain, and cyclic groups, all of which may be optionally substituted. Suitable alkynyl groups include ethynyl, propynyl, butynyl and the like which may be optionally substituted.

The term "alkoxy" refers to the ether —OR where R is alkyl, alkenyl, alkynyl, aryl, aralkyl, and cycloalkyl.

The term "aryloxy" refers to the ether —OR where R is aryl or heteroaryl.

The term "alkenyloxy" refers to ether —OR where R is alkenyl.

The term "alkylthio" refers to —SR where R is alkyl, alkenyl, alkynyl, aryl, aralkyl.

The term "alkylthioalkyl" refers to an alkylthio group attached to an alkyl radical of about one to twenty carbon atoms through a divalent sulfur atom.

The term "alkylsulfinyl" refers to —S(O)R where R is alkyl, alkenyl, alkynyl, aryl, aralkyl.

The term "sulfonyl" refers to a —SO$_2$—R group where R is alkyl, alkenyl, alkynyl, aryl, aralkyl.

The term "aminosulfonyl", "sulfamyl", "sulfonamidyl" refer to —SO$_2$NRR' where R and R' are independently selected from alkyl, alkenyl, alkynyl, aryl, aralkyl.

The term "hydroxyalkyl" refers to linear or branched alkyl radicals having one to about twenty carbon atoms any one of which may be substituted with a hydroxyl group.

The term "cyanoalkyl" refers to linear or branched alkyl radicals having one to about twenty carbon atoms any one of which could be substituted with one or more cyano groups.

The term "alkoxyalkyl" refers to alkyl groups having one or more alkoxy radicals attached to the alkyl group. The alkoxy radical may be further substituted with one or more halo atoms. Preferred haloalkoxy groups may contain one to twenty carbons.

The term "oximinoalkoxy" refers to alkoxy radicals having one to about twenty carbon atoms, any one of which may be substituted with an oximino radical.

The term "aryl" refers to a 6-15 membered ring system wherein there can be a single ring or multiple rings that are fused or linked together. Exemplary aryl groups of the present invention include, but are not limited to, phenyl, naphthyl, anthracene, pyrene, and biphenyl, all of which may be optionally substituted.

The term "carbocyclic aryl" refers to groups wherein the ring atoms on the aromatic ring are carbon atoms. Carbocyclic groups include phenyl and naphthyl groups which may be optionally substituted with 1 to 5 substituents such as alkyl, alkoxy, amino, amido, cyano, carboxylate ester, hydroxyl, halogen, acyl, nitro.

The term "aralkyl" refers to an alkyl group substituted with an aryl group. Suitable aralkyl groups include benzyl, and the like, and may be optionally substituted.

The term "aroyl" refers to —C(O)R where R is aryl group.

The term "alkoxycarbonyl" refers to —C(O)OR wherein R is alkyl, alkenyl, alkynyl, aryl, aralkyl.

The term "acyl" refers to the alkanoyl group —C(O)R where R is alkyl, alkenyl, alkynyl, aryl, aralkyl.

The term "acyloxy" refers to the alkanoyl group —OC(O)R where R is alkyl, alkenyl, alkynyl, aryl, aralkyl.

The term "aminoalkyl" refers to alkyl which is substituted with amino groups.

The term "arylamino" refers to amino groups substituted with one or more aryl radicals.

The term "aminocarbonyl" or "amido" refers to —C(O)NRR$_1$ wherein R and R$_1$ are independently selected from hydrogen, alkyl, alkenyl, alkynyl, aryl, aralkyl.

The azidoalkyl refers to alkyl R which is substituted with azido —N$_3$

The term "amino" refers to —NRR$_1$ where R and R$_1$ are independently hydrogen, lower alkyl or are joined together to give a 5 or 6-membered ring such as pyrrolidine or piperidine rings which are optionally substituted.

The term "alkylamino" includes amino groups substituted with one or more alkyl groups.

The term "dialkylamino" refers to —NRR$_1$ and R$_1$ are independently lower alkyl groups or together form the rest of ring such as morpholino. Suitable dialkylamino groups include dimethylamino, diethylamino and morpholino.

The term "morpholinoalkyl" refers to alkyl R substituted with morpholine group.

The term "isocyanoalkyl" refers to alkyl R that is substituted with isocyano group —NCO.

The term "isothiocyanoalkyl" refers to alkyl R that is substituted with isothiocyano group —NCS.

The term "isocyanoalkenyl" refers to alkenyl R that is substituted with isocyano group —NCO.

The term "isothiocyanoalkenyl" refers to alkenyl R that is substituted with isothiocyano group —NCS.

The term "isocyanoalkynyl" refers to alkynylyl R that is substituted with isocyano group —NCO.

The term "isothiocyanoalkynyl" refers to alkynyl R that is substituted with isothiocyano group —NCS.

The term "alkanoylamino" or "carbamoyl" refers to —NRC(O)OR$_1$ where R and R$_1$ are independently hydrogen, lower alkyl, alkenyl, alkynyl, aryl, aralkyl.

The term "formylalkyl" refers to alkyl R substituted with —CHO.

The term "optionally substituted" or "substituted" refers to groups substituted by one to five substituents, independently selected from lower alkyl (acyclic or cyclic), aryl (carboaryl or heteroaryl) alkenyl, alkynyl, alkoxy, halo, haloalkyl (including trihaloalkyl, such as trifluoromethyl), amino, mercapto, alkylthio, alkylsulfinyl, alkylsulfonyl, nitro, alkanoyl, alkanoyloxy, alkanoyloxyalkanoyl, alkoxycarboxy, (—COOR, where R is lower alkyl), aminocarbonyl (—CONRR$_1$, where R and R$_1$ are independently lower alkyl), formyl, carboxyl, hydroxyl, cyano, azido, oxo, carbonyl, keto, and cyclic ketals thereof, alkanoylamido, heteroaryloxy, and heterocarbocyclicoxy.

The term "lower" refers herein in connection with organic radicals or compounds defines such as one up to and including ten, preferably up to and including six, and more preferably one to four carbon atoms. Such groups may be straight chain, branched chain, or cyclic.

The term "heterocyclic" refers to a 3-10 membered ring having 1-4 heteroatoms such as O, N, S or P. The ring structure can be a single ring, or multiple rings fused together. Exemplary heterocycles include, but are not limited to, thiazolidine, tetrahydrofuran, 1,4-dioxane, 1,3,5-trioxane, pyrrolidine, piperidine, quinuclidine, dithiane, tetrahydropyran, phthalazin-1-one and morpholine.

The term "heteroaryl" refers to carbon containing 5-14 membered cyclic unsaturated radicals containing one, two, three, or four O, N, P, or S atoms and having 6, 10 or 14π electrons delocalized in one or more than one rings, e.g., pyridine, oxazole, indole, purine, pyrimidine, imidazole, benzimidazole, indazole, 2H-1,2,4-triazole, 1,2,3-triazole, 2H-1,2,3,4-tetrazole, 1H-1,2,3,4-triazolebenztriazole, 1,2,3-triazolo[4,5-b]pyridine, thiazole, isoxazole, pyrazole, quinoline, cytosine, thymine, uracil, adenine, guanine, pyrazine, picoline, picolinic acid, furoic acid, furfural, furyl alcohol, carbazole, isoquinoline, pyrrole, thiophene, furan, phenoxazine, phthalazine and phenothiazine, each of which may be optionally substituted.

The term "salt" refers to a compound of the present invention formed by replacing all or part of the hydrogen ions of an acid with metal ions or electropositive radicals.

The term "hydrate" refers to the formation of a complex of a compound of the present invention and a water molecule. The complex can exist in a 1:1 ratio of compound to water, or 2:1, or 1:2. One of skill in the art will appreciate that other ratios of hydrates are also useful in the present invention.

The term "solvate" refers to the formation of a complex of a compound of the present invention and a solvent molecule. The complex can exist in a 1:1 ratio of compound to solvent, or 2:1, or 1:2, or others. Furthermore, the complex can use a combination of solvents. Solvents useful for formation of solvates of the present invention include, but are not limited to alcoholic solvents such as ethanol, methanol and propylene glycol; ethers such as tetrahydrofuran, dioxane, and diethyl ether; halogenated solvents such as methylene chloride, chloroform and carbon-tetrachloride; alkanes such as pentane, hexane and octane; as well as solvents such as acetone, ethyl acetate, pyridine, dimethyl formamide, hexamethyl phosphoric acid, dimethylsulfoxide, as well as others. One of skill in the art will appreciate that other solvents are also useful in the present invention.

The term "stereoisomer" refers to compounds of the present invention having at least one stereocenter where the compounds are linked in the same order but have different spatial orientation. Specific stereoisomers include enantiomers and diastereomers.

The term "prodrug" refers to compounds that are combined with a biological substance such that when placed in the body, the prodrug reacts to produce a compound of the present invention.

The term "polymorph" refers to a compound of the present invention in one of several crystalline structures that the compound can adopt.

The term "modulate," in reference to compounds of the present invention, refers to an ability of a compound to regulate a physiological activity in vitro and/or in vivo. In certain embodiments of the present invention, compounds are modulators of cellular signaling events such as by inhibition or stimulation of cellular receptors and/or intracellular signaling molecules.

The term "modulator of CNS neurotransmitter" and "CNS modulator" are used synonymously herein to refer to a compound that is capable of modulating signaling via one or more neurotransmitters, such as by modulation of neurotransmitter reuptake or by modulation of intracellular signaling downstream of a neurotransmitter receptor. In accordance with certain embodiments of the compositions and methods of the present invention, CNS modulators are capable of inhibiting serotonin reuptake and/or enzymatic activity of phosphodiesterase 4 (PDE4). In some variations, CNS modulators are capable of stimulating one or more G protein-coupled receptor kinases (GRKs).

The term "inhibit" means to reduce by a measurable amount, or to prevent entirely.

"Treating," "treatment," or "therapy" of a disease or disorder means slowing, stopping, or reversing progression of the disease or disorder, as evidenced by a reduction or elimination of either clinical or diagnostic symptoms, using the compositions and methods of the present invention as described herein.

"Preventing," "prophylaxis," or "prevention" of a disease or disorder means prevention of the occurrence or onset of a disease or disorder or some or all of its symptoms.

"Addiction" as used herein refers to a disease or disorder characterized by a habitual psychological and physiologic dependence on a substance or practice that is substantially beyond voluntary control. Addictions amenable to treatment using the compounds and methods described herein include drug addictions.

The term "subject" as used herein means any mammalian patient to which the compositions of the present invention may be administered according to the methods described herein. Subjects specifically intended for treatment or prophylaxis using the methods of the present invention include humans.

The term "therapeutically effective regime" means that a pharmaceutical composition or combination thereof is administered in sufficient amount and frequency and by an appropriate route to reduce pain, or to at least detectably prevent, delay, inhibit, or reverse development of at least one symptom or biochemical marker of a disease or disorder amenable to treatment or prevention by inhibition of serotonin reuptake and/or inhibition of PDE4 activity.

The term "therapeutically effective amount" refers to an amount of an agent of the present invention, or a combination of an agent of the present invention with other agent(s), that is present to achieve a desired result, e.g., preventing, delaying, inhibiting, or reversing a symptom or biochemical marker of a disease or disorder amenable to treatment by inhibition of serotonin reuptake and/or inhibition of PDE4 activity, when administered in an appropriate regime.

μmol/kg and 3 mg/kg, 5 μmol/kg). Vehicle (Veh) or test agent was injected i.p. 30 min prior to the test. n=9-11; *P<0.05 vs. Veh.

Figure 16:
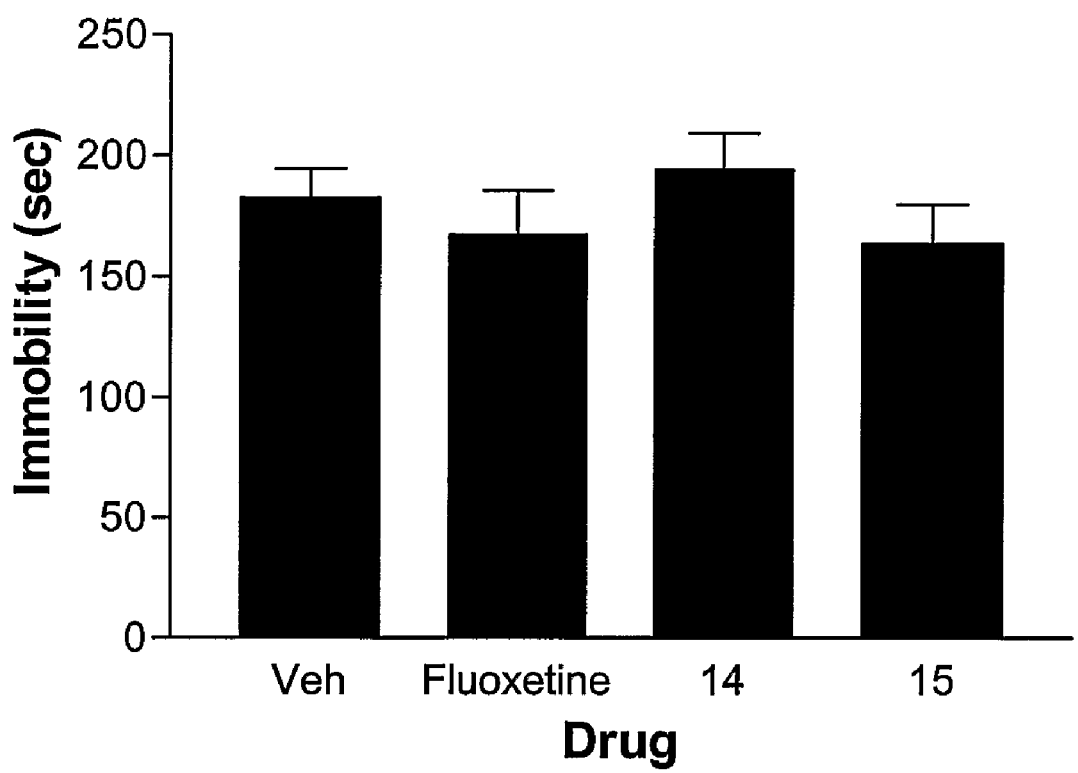

FIG. 16 depicts an effect of acute treatment with fluoxetine (20 mg/kg, 65 μmol/kg), compound 14 (10 mg/kg, 37.4 μmol/kg), and compound 15 (10 mg/kg, 35.5 μmol/kg) on immobility in the forced-swim test in Balb/c mice. Vehicle or test agent was injected i.p. 30 min prior to the test. n=10-11.

Figure 17:
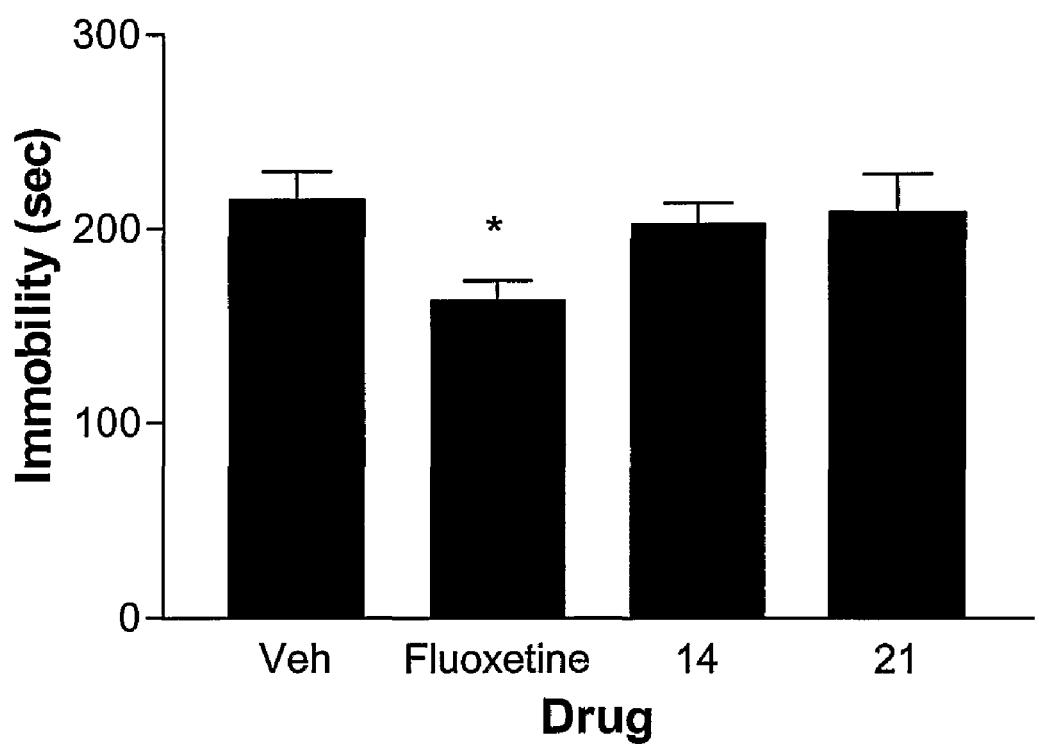

FIG. 17 depicts an effect of subchronic administration of fluoxetine (10 mg/kg, 32.3 μmol/kg), compound 14 (10 mg/kg, 37.4 μmol/kg) and compound 21 (1.0 mg/kg, 1.6 μmol/kg) on immobility in the forced-swim test in Balb/c mice. Vehicle or the test agent was injected i.p. 23, 5, and 1 hr prior to the test. n=10-11; *P<0.05 vs. vehicle.

Figure 18:
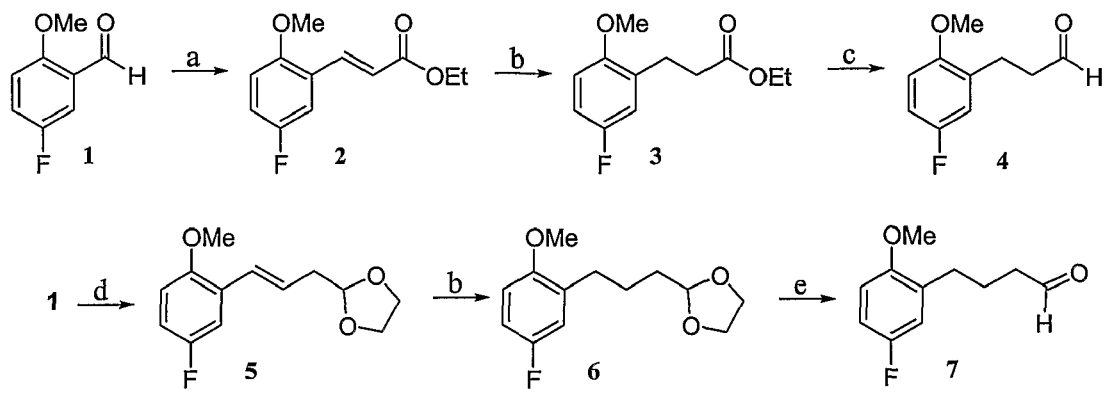

FIG. 18 depicts scheme 9 (of schemes 9 to 13) of a method for synthesis of certain embodiments of the present invention. (See Example 29.)

Figure 19:
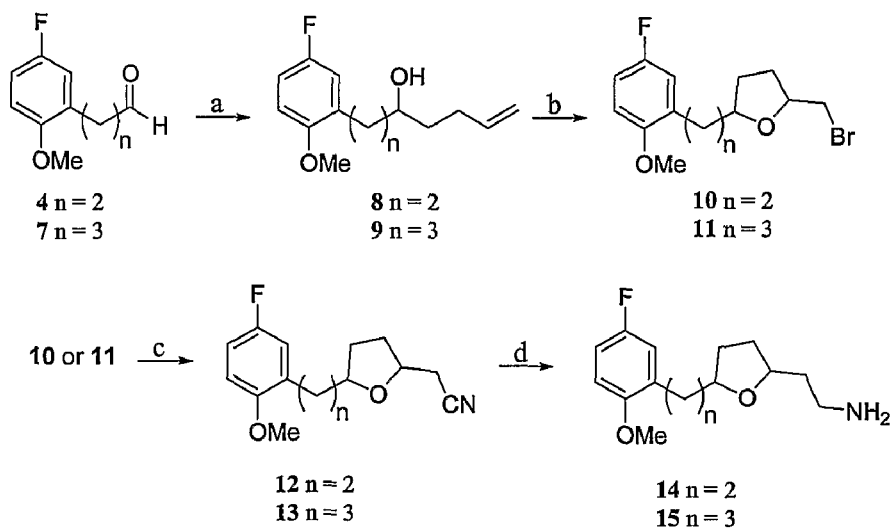

FIG. 19 depicts scheme 10 (of schemes 9 to 13) of a method for synthesis of certain embodiments of the present invention. (See Example 29.)

Figure 20:
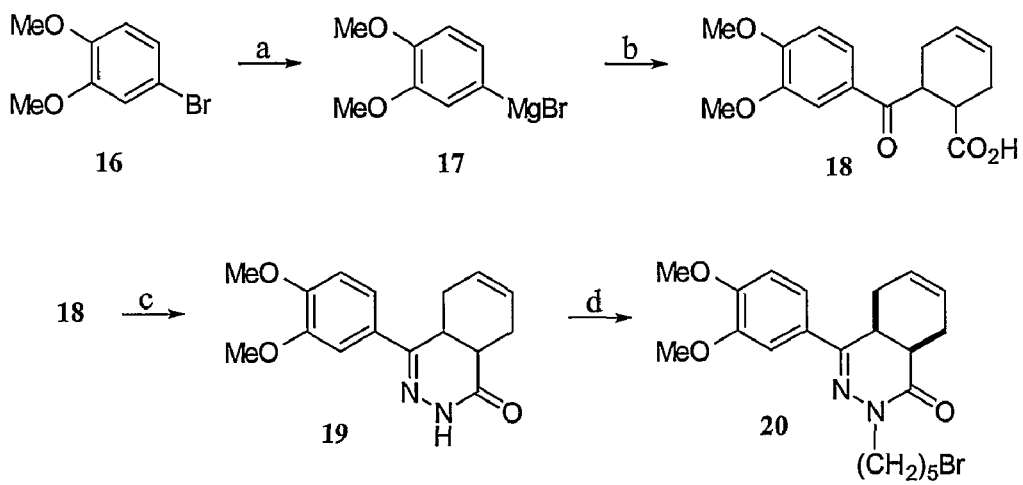

FIG. 20 depicts scheme 11 (of schemes 9 to 13) of a method for synthesis of certain embodiments of the present invention. (See Example 29.)

Figure 21:
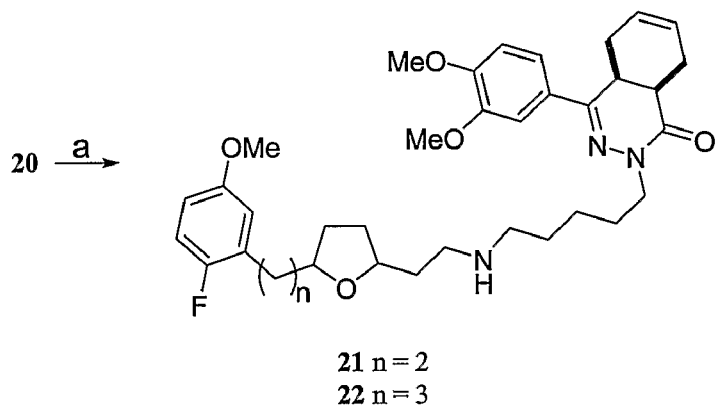

FIG. 21 depicts scheme 12 (of schemes 9 to 13) of a method for synthesis of certain embodiments of the present invention. (See Example 29.)

Figure 22:
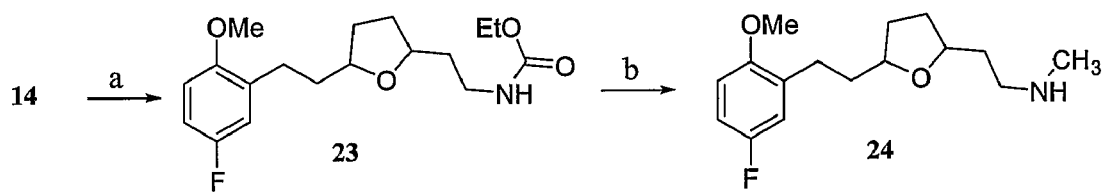

FIG. 22 depicts scheme 13 (of schemes 9 to 13) of a method for synthesis of certain embodiments of the present invention. (See Example 29.)

Figure 23:
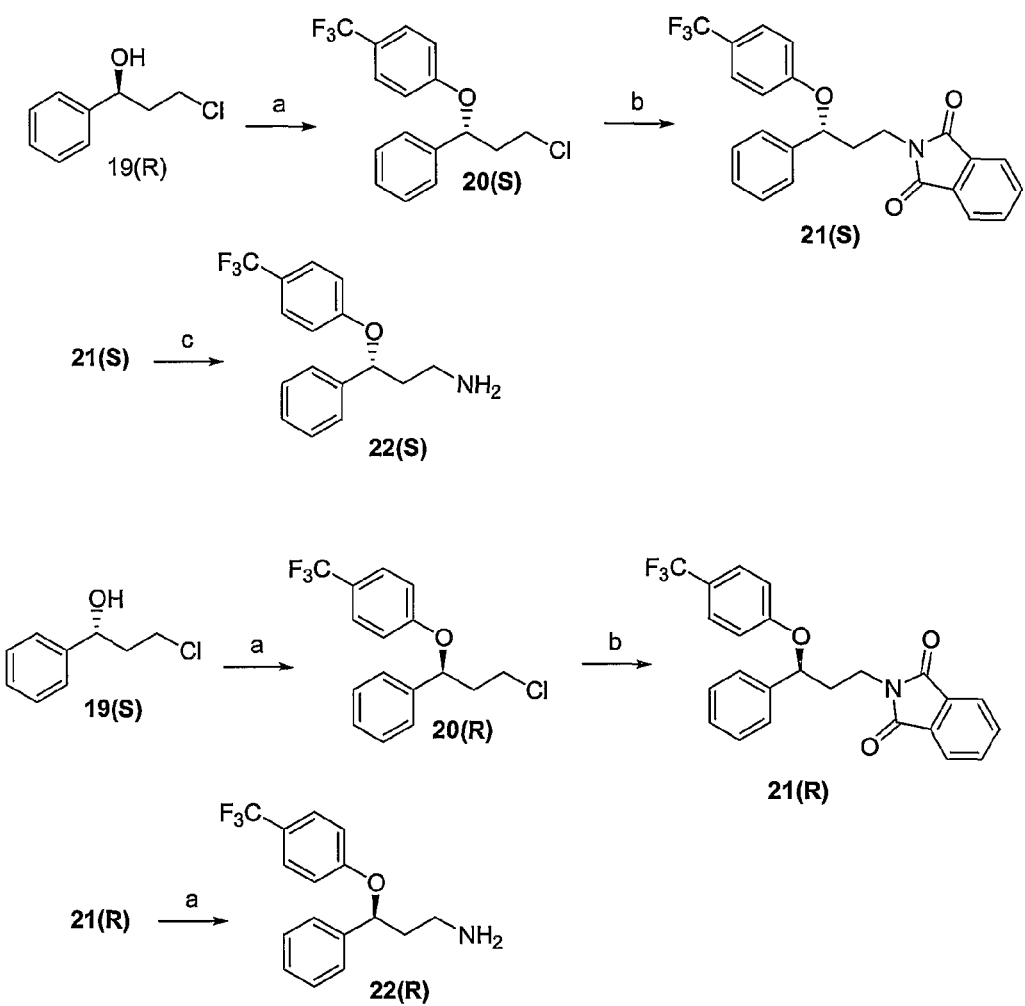

FIG. 23 depicts an asymmetric synthesis of norfluoxetine.

Figure 24:
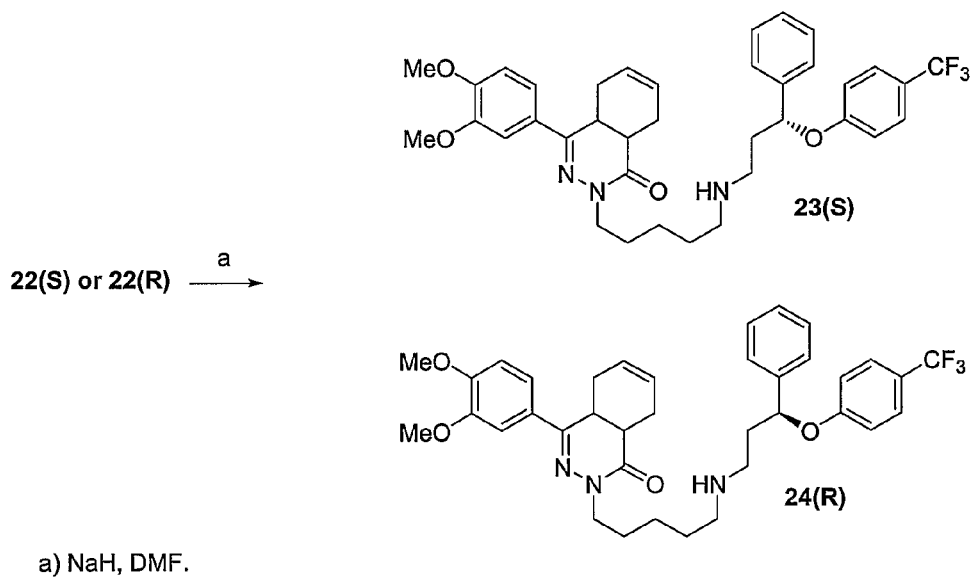

FIG. 24 depicts a synthesis of dual SSRI/PDE4 inhibitors (23(S) and 24(R)).

Figure 25:
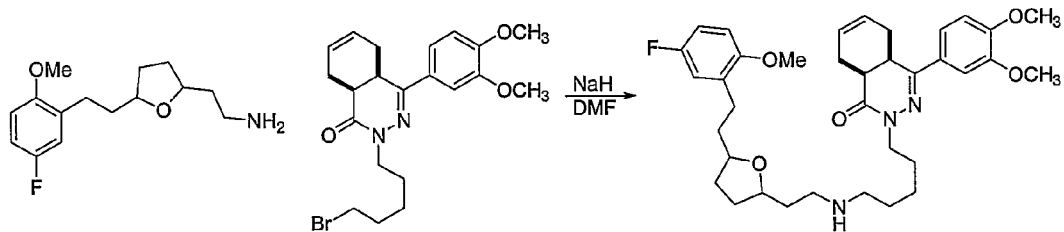

FIG. 25 depicts a synthesis of a dual SSRI/PDE4 dual inhibitor.

Figure 26:
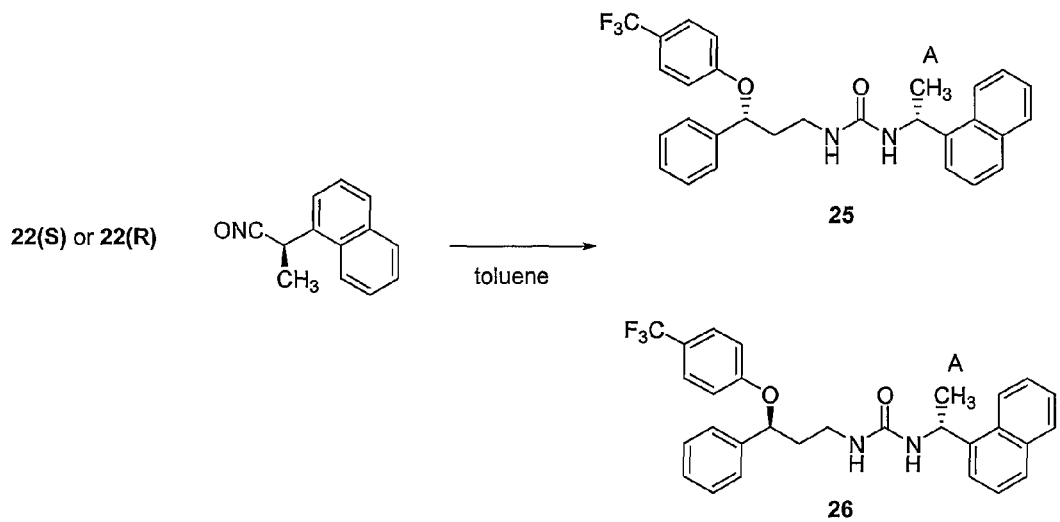

FIG. 26 depicts a synthesis of urea diastereomers.

Figure 27:
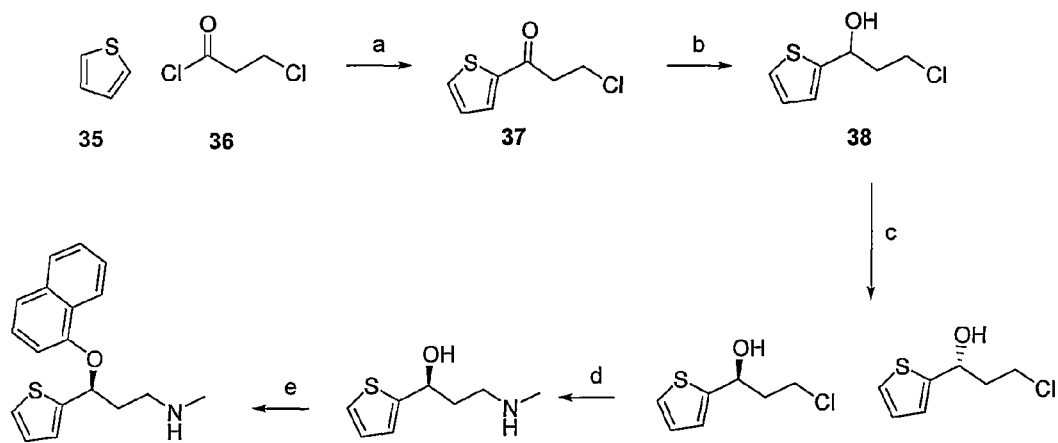

FIG. 27 depicts a synthesis of Duloxetine.

Figure 28:
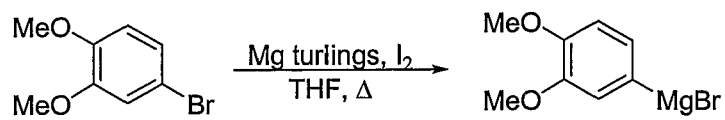

FIG. 28 depicts a synthesis of the Grignard reagent.

Figure 29:
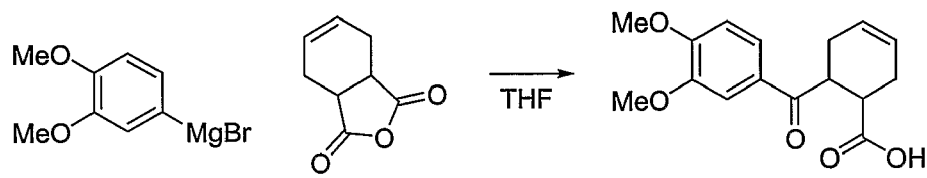

FIG. 29 depicts a Grignard reaction with cis-1,2,3,6-tetrahydrophthalic anhydride.

Figure 30:
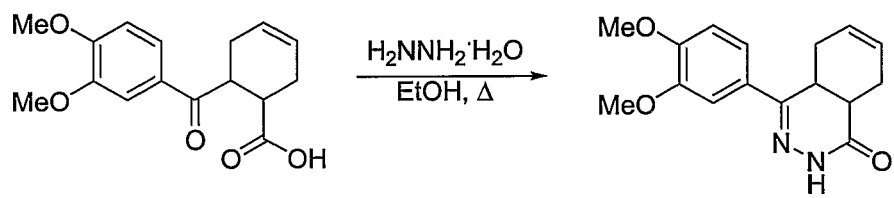

FIG. 30 depicts a synthesis of the phthalazinone.

Figure 31:
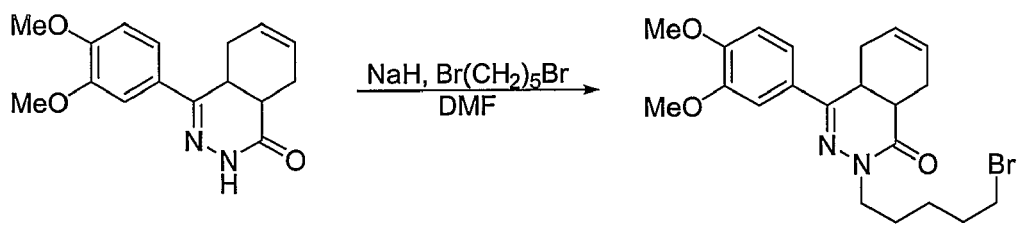

FIG. 31 depicts a synthesis of the 5 carbon linker.

Figure 32:
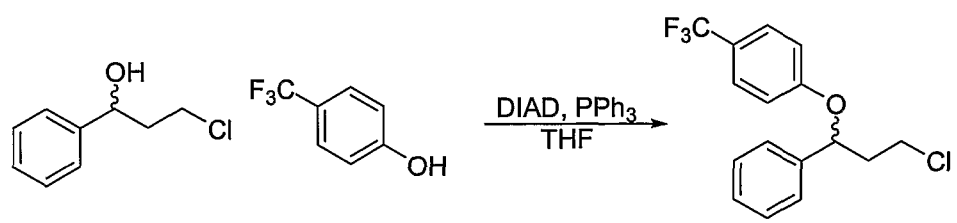

FIG. 32 depicts a Mitsunobu reaction with chiral alcohol.

Figure 33:
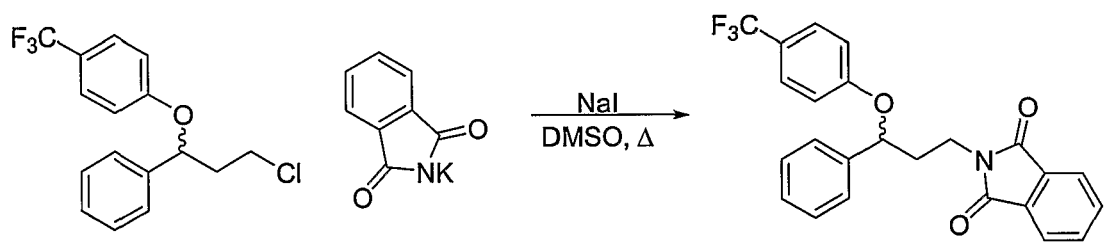

FIG. 33 depicts a synthesis of the phthalimide from the Mitsunobu product.

Figure 34:
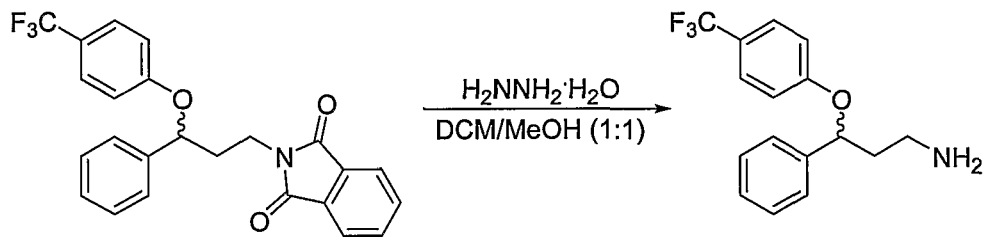

FIG. 34 depicts a synthesis of (R) or (S)-norfluoxetine.

Figure 35:
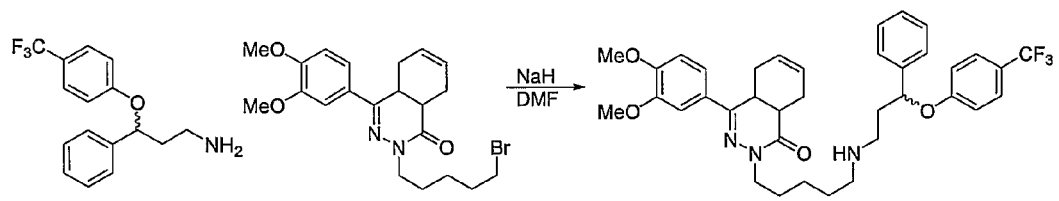

FIG. 35 depicts a synthesis of PDE4/SSRI dual inhibitor with the phthalazinone and norfluoxetine.

Figure 36:
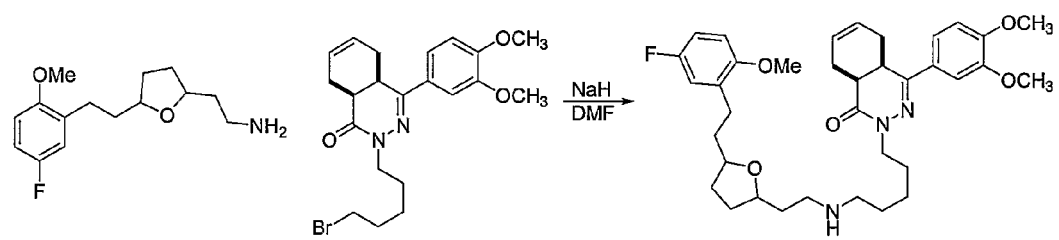

FIG. 36 depicts a synthesis of 4-(3,4-Dimethoxy-phenyl)-2-[5-(2-{5-[2-(5-fluoro-2-methoxy-phenyl)-ethyl]-tetrahydro-furan-2-yl}-ethylamino)-pentyl]-4,5,8,8a-tetrahydro-2H-phthalazin-1-one (21).

Figure 37:
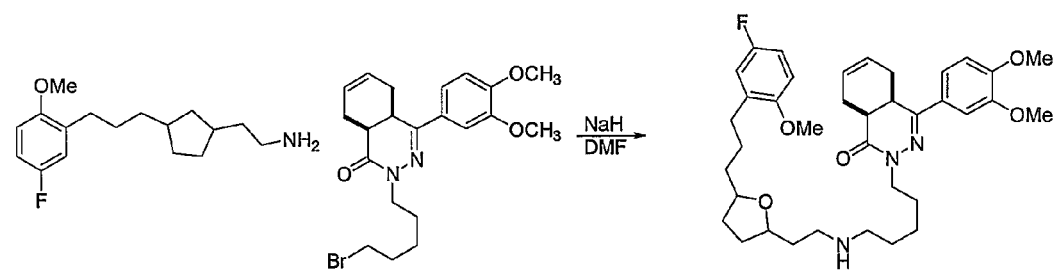

FIG. 37 depicts a synthesis of 4-(3,4-Dimethoxy-phenyl)-2-[5-(2-{5-[3-(5-fluoro-2-methoxy-phenyl)-propyl]-tetrahydro-furan-2-yl}-ethylamino)-pentyl-4a,5,8,8a-tetrahydro-2H-phthalazin-1-one (22).

Figure 38:
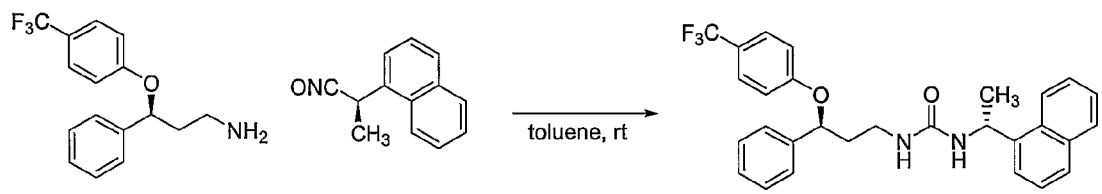

FIG. 38 depicts a synthesis of N'-(R)-[1-(1-naphthyl)ethyl]-N-(S)-3-[4-(trifluoromethyl)phenoxy]-3-phenylpropylurea.

Figure 39:
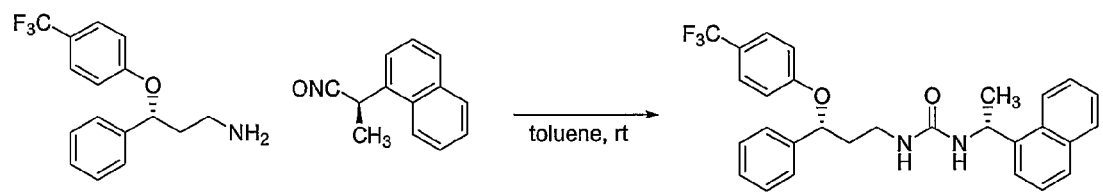

FIG. 39 depicts a synthesis of N'-(S)-[1-(1-naphthyl)ethyl]-N-(S)-3-[4-(trifluoromethyl)phenoxy]-3-phenylpropylurea.

DETAILED DESCRIPTION OF THE SPECIFIC EMBODIMENTS

The present invention pertains generally to agents having pharmacological activity on cells, particularly cells of the central nervous system (CNS). In a specific aspect, the invention relates to compounds that selectively modulate neurotransmitter binding, uptake and release for use in human disorders of the CNS and other diseases. For example, in certain embodiments, the present invention relates to the selective inhibition of serotonin reuptake. In certain preferred embodiments, the present invention relates to combining the cAMP-modulating activity of a PDE4 inhibitor with a neurotransmitter reuptake inhibitor (e.g., a selective serotonin reuptake inhibitor (SSRI)) to produce a synergistic effect. In some variations, the present invention also relates to the modulation of G protein-coupled receptors (GRKs).

The compositions and methods are useful, for example, in the treatment of mood disorders, enhancement of memory and/or cognition, and providing neuroprotective effects. Diseases and disorders amenable to treatment using the compositions and methods described herein include, for example, depression, drug addiction, anxiety, attention-deficit disorder, schizophrenia, bipolar disorder, memory loss, cognitive impairment, and neurodegenerative disease.

Compositions and methods are therefore provided herein for treating or preventing CNS diseases or disorders by the inhibition of neurotransmitter reuptake, as well as the dual inhibition of the reuptake of serotonin and/or other neurotransmitters combined with the inhibition of PDE4. In some embodiments, compounds as described herein and having SSRI activity are used for the treatment or prevention of a CNS disease or disorder such as, e.g., bipolar disorder, through stimulation of one or more GRKs (e.g., GRK2 and/or GRK3).

With particular regard to dual inhibition of serotonin reuptake and PDE4 activity, dual PDE4 inhibitor/SSRIs offer an advantage beyond simple additive effects. Dual PDE4 inhibitor/SSRIs offer the advantage of blocking the effect of the up-regulation of PDE4. Thus, the overall increase in serotonin receptor-mediated cAMP signaling will be preserved with repeated treatment. In addition, the onset of pharmacological action will be much faster than traditional anti-depressants or SSRIs as well as have a longer sustained mechanism of action. When animals are treated repeatedly with SSRIs, PDE4 is up-regulated. This may be a result of an increase in 5-HT receptor-mediated cAMP signaling. It has been shown that increased cAMP increases the expression of a number of PDE4 variants in neurons. Thus, in this case, the adaptation of PDE4 that occurs in response to repeated treatment with SSRIs is homeostatic and in opposition to the acute effect of the drugs. That is, with acute treatment, SSRIs will increase 5-HT receptor-mediated cAMP signaling. With repeated treatment, this effect will be blunted (i.e., some tolerance development), since PDE4 is up-regulated and cAMP hydrolysis is increased.

With respect to modulation of GRKs, G-protein coupled receptors (GPCRs) are responsible for many cell-signalling processes. In humans, genetic evidence suggests that individuals that have defective GRK3 have a higher prevalence of bipolar disorder than individuals with normal GRK3. Pharmacological stimulation of GRK3 can provide a means to upregulate GRK3 and serve as a therapy for, e.g., mood disorders such as bipolar disorder. GRK2 and GRK3 are very similar proteins and very similar pharmacology is expected from stimulation of either protein. Small molecules that stimulate GRK2 are expected to also stimulate GRK3 and are useful for the treatment of, e.g., bipolar disorder.

Compounds

In one embodiment, the present invention provides compounds of Formula X:

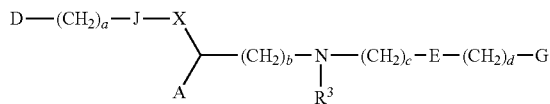

In Formula X, D is a member selected from the group consisting of optionally substituted aryl, optionally substituted heteroaryl, optionally substituted cycloalkyl and optionally substituted heterocycloalkyl; J is a direct bond or optionally combined with A and X to form a 5-6 membered heterocylic ring, substituted with an $R^1$ and an $R^2$ group each independently selected from the group consisting of hydrogen and optionally substituted aryl, or optionally combined with D to form an optionally substituted aryl; X is a member selected from the group consisting of O, N and S; A is a member selected from the group consisting of optionally substituted aryl, optionally substituted heteroaryl, optionally substituted cycloalkyl and optionally substituted heterocycloalkyl; E is a member selected from the group consisting of a direct bond and optionally substituted heterocycloalkyl; G is a member selected from the group consisting of hydrogen, optionally substituted aryl, optionally substituted heteroaryl, optionally substituted cycloalkyl and optionally substituted heterocycloalkyl; $R^3$ is a member selected from the group consisting of hydrogen and $C_1$-$C_6$ alkyl, or optionally combined with G to form an optionally substituted heterocycloalkyl; each of subscript a, c and d is independently an integer from 0-6; and subscript b is an integer from 1-6; or a pharmaceutically acceptable salt, hydrate, solvate, stereoisomer, prodrug or polymorph thereof.

In other embodiments, the present invention provides a compound having Formula XI:

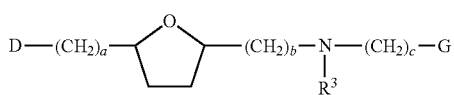

In still other embodiments, the compounds of Formula XI are those where G is hydrogen or combined with $R^3$ to form a 5-6 membered heterocycloalkyl containing 1-2 heteroatoms each independently selected from the group consisting of N and O; and subscript b is 1-3. In another embodiment, the compounds of Formula XI are those where D is a member selected from the group consisting of optionally substituted phenyl, optionally substituted naphthyl and optionally substituted bi-phenyl; and subscript a is 0-3.

In a further embodiment, the present invention provides compounds of Formula XI such as:
2-(aminomethyl)-5-phenyltetrahydrofuran,
2-(aminomethyl)-5-(4'-chlorophenyl)tetrahydrofuran,
2-(aminomethyl)-5-(4'-bromophenyl)tetrahydrofuran,
2-(aminomethyl)-5-(4'-methoxyphenyl)tetrahydrofuran,
2-(aminomethyl)-5-(4'-t-butylphenyl)tetrahydrofuran,
trans-2-(aminomethyl)-5-(2'-methoxy-5'-fluorophenyl)tetrahydrofuran,
cis-2-(aminomethyl)-5-(2'-methoxy-5'-fluorophenyl)tetrahydrofuran,
2-(aminomethyl)-5-(3'-fluoro-4'-methylphenyl)tetrahydrofuran,
2-(aminomethyl)-5-cyclohexyltetrahydrofuran,
2-(aminomethyl)-5-(1'-naphthyl)tetrahydrofuran,
2-(aminomethyl)-5-(2'-methoxy-1'-naphthyl)tetrahydrofuran,
2-(aminomethyl)-5-(2'-naphthyl)tetrahydrofuran,
2-(aminoethyl)-5-phenyltetrahydrofuran,
2-(aminoethyl)-5-(4'-fluorophenyl)tetrahydrofuran,
2-(aminoethyl)-5-(4'-bromophenyl)tetrahydrofuran,
2-(aminoethyl)-5-(4'-t-butylphenyl)tetrahydrofuran,
trans-2-(aminoethyl)-5-(2'-methoxy-5'-fluorophenyl)tetrahydrofuran,
cis-2-(aminoethyl)-5-(2'-methoxy-5'-fluorophenyl)tetrahydrofuran,
2-(aminoethyl)-5-cyclohexyltetrahydrofuran, and
2-(aminoethyl)-5-(2'-furyl)tetrahydrofuran.

In still another embodiment, the present invention provides compounds of Formula XI such as:
2-(aminomethyl)-5-benzyltetrahydrofuran,
2-(aminoethyl)-5-benzyltetrahydrofuran,
trans-2-(aminomethyl)-5-(2'-methoxy-5'-fluorobenzyl)tetrahydrofuran,
cis-2-(aminomethyl)-5-(2'-methoxy-5'-fluorobenzyl)tetrahydrofuran,
trans-2-(aminoethyl)-5-(2'-methoxy-5'-fluorobenzyl)tetrahydrofuran, and
cis-2-(aminoethyl)-5-(2'-methoxy-5'-fluorobenzyl)tetrahydrofuran.

In further embodiments, the present invention provides compounds of Formula XI such as:
2-(aminomethyl)-5-(phenethyl)tetrahydrofuran,
2-(aminomethyl)-5-(4'-fluorophenethyl)tetrahydrofuran,
2-(aminomethyl)-5-(3'-pyridylethyl)tetrahydrofuran,
2-(aminomethyl)-5-(2'-chloro-5'-trifluoromethylphenethyl)tetrahydrofuran,
2-(aminomethyl)-5-(pentafluorophenethyl)tetrahydrofuran,
2-(aminomethyl)-5-(2'-methoxy-5'-fluorophenyl)tetrahydrofuran,
2-(aminoethyl)-5-(3',4'-dimethoxyphenethyl)tetrahydrofuran,
2-(aminomethyl)-5-(1'-naphthylethyl)tetrahydrofuran,
2-(aminomethyl)-5-(2'-methoxy-1'-naphthylethyl)tetrahydrofuran,
2-(aminomethyl)-5-(4'-methoxy-1'-naphthylethyl)tetrahydrofuran,
2-(aminomethyl)-5-(2'-tetrahydrofuryl-2'-ethyl)tetrahydrofuran,
2-(aminoethyl)-5-(phenethyl)tetrahydrofuran,
2-(aminoethyl)-5-(4'-fluorophenethyl)tetrahydrofuran,
2-(aminoethyl)-5-(4'-hydroxyphenethyl)tetrahydrofuran,
2-(aminoethyl)-5-(4'-methoxyphenethyl)tetrahydrofuran,
2-(aminoethyl)-5-(4'-trifluoromethoxyphenethyl)tetrahydrofuran,
2-(aminoethyl)-5-(4'-methylphenethyl)tetrahydrofuran,
2-(aminoethyl)-5-(4'-phenylphenethyl)tetrahydrofuran,
2-(aminoethyl)-5-(4'-t-butylphenethyl)tetrahydrofuran,
2-(aminoethyl)-5-(5'-fluoro-2'-methoxyphenethyl)tetrahydrofuran,
2-(aminoethyl)-5-(4'-fluoro-3'-methylphenethyl)tetrahydrofuran,
2-(aminoethyl)-5-(3'-fluoro-4'-methylphenethyl)tetrahydrofuran,
2-(aminoethyl)-5-(cyclohexylethyl)tetrahydrofuran,
2-(aminoethyl)-5-(3'-pyridylethyl)tetrahydrofuran,
2-(aminoethyl)-5-(1'-naphthylethyl)tetrahydrofuran, 2-(aminoethyl)-5-(2'-methoxy-1'-naphthylethyl)tetrahydrofuran, 2-(aminoethyl)-5-(4'-methoxy-1'-naphthylethyl)tetrahydrofuran, 2-(aminoethyl)-5-(2'-naphthylethyl)tetrahydrofuran, trans-2-piperidylmethyl-5-(2'-methoxy-5'-fluorophenethyl)tetrahydrofuran, trans-2-(N,N-diethylaminomethyl)-5-(2'-methoxy-5'-fluorophenethyl)tetrahydrofuran, and trans-2-(morpholinomethyl)-5-(2'-methoxy-5'-fluorophenethyl)tetrahydrofuran.

In other embodiments, the present invention provides compounds of Formula XII:

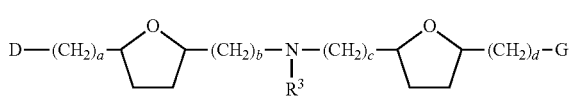

XII

In Formula XII, D and G are both the same; subscripts a and d are both 0-3 and are the same; and subscripts b and c are both 2. In some embodiments, the present invention provides compounds of Formula XII such as:

N,N-bis(5'-phenyl-2'-tetrahydrofurylethyl)amine,

N,N-bis(5'-(p-fluorophenyl)-2'-tetrahydrofurylethyl)amine,

N,N-bis(5'-(p-bromophenyl)-2'-tetrahydrofurylethyl)amine,

N,N-bis(5'-(p-t-butylphenyl)-2'-tetrahydrofurylethyl)amine,

N,N-bis(5'-cyclohexyl-2'-tetrahydrofurylethyl)amine,

N,N-bis(trans-5'-(2"-methoxy-5"-fluorophenyl-2'-tetrahydrofuryl)ethyl)amine,

N,N-bis(cis-5'-(2"-methoxy-5"-fluorophenyl-2'-tetrahydrofuryl)ethyl)amine,

N,N-bis(5'-benzyl-2'-tetrahydrofurylethyl)amine,

N,N-bis(5'-phenethyl-2'-tetrahydrofurylethyl)amine,

N,N-bis(5'-phenethyl-2'-tetrahydrofurylethyl)methylamine,

N,N-bis(5'-(p-hydroxyphenethyl)-2'-tetrahydrofurylethyl)amine,

N,N-bis(5'-(m-fluoro-p-methylphenethyl)-2'-tetrahydrofurylethyl)amine,

N,N-bis(5'-(p-fluoro-m-methylphenethyl)-2'-tetrahydrofurylethyl)amine,

N,N-bis(5'-(5"-fluoro-2"-methoxyphenethyl)-2'-tetrahydrofurylethyl)amine,

N,N-bis(5'-(3"-pyridylethyl)-2'-tetrahydrofurylethyl)amine,

N,N-bis(5'-(1"-naphthethyl)-2'-tetrahydrofurylethyl)amine,

N,N-bis(5'-(2"-methoxy-1"-naphthethyl)-2'-tetrahydrofurylethyl)amine,

N,N-bis(5'-(4"-methoxy-1"-naphthethyl)-2'-tetrahydrofurylethyl)amine,

N,N-bis(trans-5'-(2"-methoxy-5"-fluorobenzyl-2'-tetrahydrofuranyl)ethyl)amine,

N,N-bis(cis-5'-(2"-methoxy-5"-fluorobenzyl-2'-tetrahydrofuranyl)ethyl)amine, and N,N-bis(trans-5-(2"-methoxy-5"-fluorophenyl-3'-propyl-2'-tetrahydrofuryl)ethyl)amine.

In a further embodiment, the present invention provides a compound of Formula XIII:

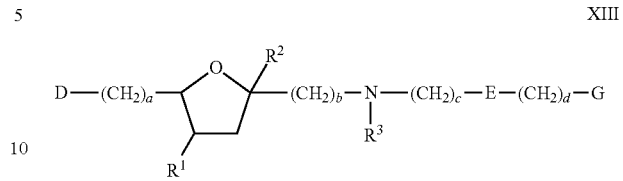

XIII

Compounds of Formula XIII include those where E is an optionally substituted heterocycloalkyl having at least from 1-3 nitrogen atoms; $R^1$ is hydrogen or optionally combined with D to form an optionally substituted aryl; and $R^2$ is a member selected from the group consisting of hydrogen and optionally substituted phenyl. In some embodiments, the present invention provides compounds of Formula XIII such as:

4-(3,4-Dimethoxyphenyl)-2-[5-(2-{5-[2-(5-fluoro-2-methoxyphenyl)-ethyl]-tetrahydrofuran-2-yl}-ethylamino)-pentyl]-4a,5,8,8a-tetrahydro-2H-phthalazin-1-one, 4-(3,4-Dimethoxyphenyl)-2-[5-(2-{5-[2-(5-fluoro-2-methoxyphenyl)-propyl]-tetrahydrofuran-2-yl}-ethylamino)-pentyl]-4a,5,8,8a-tetrahydro-2H-phthalazin-1-one, 4-(3-Cyclopentyloxy-4-methoxy-phenyl)-1-[5-(2-{5-[2-(5-fluoro-2-methoxy-phenyl)-ethyl]-tetrahydro-furan-2-yl}-ethylamino)-pentyl]-pyrrolidin-2-one, 4-(3-Cyclopentyloxy-4-methoxy-phenyl)-1-[5-(2-{5-[3-(5-fluoro-2-methoxy-phenyl)-propyl]-tetrahydro-furan-2-yl}-ethylamino)-pentyl]-pyrrolidin-2-one, 2-(3-{5-[4-(3,4-Dimethoxy-phenyl)-1-oxo-4a,5,8,8a-tetrahydro-1H-phthalazin-2-yl]-pentylamino}-propyl)-2-(4-fluoro-phenyl)-2,3-dihydro-benzofuran-6-carbonitrile, 2-(3-{5-[4-(3-Cyclopentyloxy-4-methoxy-phenyl)-2-oxo-pyrrolidin-1-yl]-pentylamino}-propyl)-2-(4-fluoro-phenyl)-2,3-dihydro-benzofuran-6-carbonitrile, 4-(3,4-Dimethoxy-phenyl)-2-(5-{[5-(4-methoxy-phenyl)-tetrahydro-furan-2-ylmethyl]-amino}-pentyl)-4a,5,8,8a-tetrahydro-2H-phthalazin-1-one, 4-(3-Cyclopentyloxy-4-methoxy-phenyl)-1-(5-{[5-(4-methoxy-phenyl)-tetrahydro-furan-2-ylmethyl]-amino}-pentyl)-pyrrolidin-2-one, 2-{5-[(5-Cyclohexyl-tetrahydro-furan-2-ylmethyl)-amino]-pentyl}-4-(3,4-dimethoxy-phenyl)-4a,5,8,8a-tetrahydro-2H-phthalazin-1-one, 1-{5-[(5-Cyclohexyl-tetrahydro-furan-2-ylmethyl)-amino]-pentyl}-4-(3-cyclopentyloxy-4-methoxy-phenyl)-pyrrolidin-2-one, 4-(3,4-Dimethoxy-phenyl)-2-(5-{[5-(3-fluoro-4-methyl-phenyl)-tetrahydro-furan-2-ylmethyl]-amino}-pentyl)-4a,5,8,8a-tetrahydro-2H-phthalazin-1-one, and 4-(3-Cyclopentyloxy-4-methoxy-phenyl)-1-(5-{[5-(3-fluoro-4-methyl-phenyl)-tetrahydro-furan-2-ylmethyl]-amino}-pentyl)-pyrrolidin-2-one.

In another embodiment, the present invention provides a compound of Formula XIV:

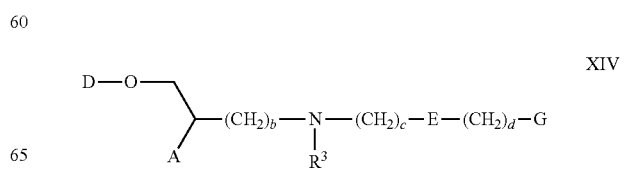

XIV

Compounds of Formula XIV include those where D is an optionally substituted phenyl; A is an optionally substituted phenyl; E is an optionally substituted heterocycloalkyl having from 1-3 nitrogen atoms; G is an optionally substituted phenyl; subscripts b and c are each independently 1-6; and subscript d is 0. In other embodiments, the present invention provides compounds of Formula XIV such as:
4-(3,4-Dimethoxy-phenyl)-2-{5-[3-phenyl-3-(4-trifluoromethyl-phenoxy)-propylamino]-pentyl}-4a,5,8,8a-tetrahydro-2H-phthalazin-1-one, and
4-(3-Cyclopentyloxy-4-methoxy-phenyl)-1-{5-[3-phenyl-3-(4-trifluoromethyl-phenoxy)-propylamino]-pentyl}-pyrrolidin-2-one.

Other Embodiments of Compounds of the Present Invention

In certain other embodiments, the present invention provides compounds of Formula I:

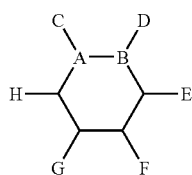

I

Compounds of Formula I useful in the present invention include those where A and B constitute part of a 5- or 6-member ring system from unsaturated, partially unsaturated or saturated heterocyclic and carbocyclic rings wherein A is optionally substituted with hydrido, acyl, halo, lower acyl, lower haloalkyl, oxo, cyano, nitro, carboxyl, amino, lower alkoxy, aminocarbonyl, lower alkoxycarbonyl, alkylamino, arylamino, lower carboxyalkyl, lower cyanoalkyl, lower hydroxyalkyl, alkylthio, alkylsulfinyl and aryl, lower aralkylthio, lower alkylsulfinyl, lower alkylsulfonyl, aminosulfonyl, lower N-arylaminosulfonyl, lower arylsulfonyl, lower N-alkyl-N-arylaminosulfonyl; wherein aryl is selected from phenyl, biphenyl, and naphthyl, and 5- and 6-membered heteroaryl, wherein aryl is optionally substituted with one or two substituents selected from halo, hydroxyl, amino, nitro, cyano, carbamoyl, lower alkyl, lower alkenyloxy, lower alkoxy, lower alkylthio, lower alkylsulfinyl, lower alkylsulfonyl, lower alkylamino, lower dialkylamino, lower haloalkyl, lower alkoxycarbonyl, lower N-alkylcarbamoyl, lower N,N-dialkylcarbamoyl, lower alkanoylamino, lower cyanoalkoxy, lower carbamoylalkoxy, lower carbonylalkoxy; wherein the acyl group is optionally substituted with a substituent selected from hydrido, alkyl, halo, and alkoxy.

In other embodiments, compounds of Formula I useful in the present invention include those where the A, B ring system is a radical selected from pyranyl, furyl, tetrahydrofuryl, tetrahydrothienyl, thienyl, oxazolyl, pyrolyl, thiazolyl, imidazolyl, isothiazolyl, isoxazoyl, pyrazolyl, cyclopentyl, phenyl, and pyridyl.

In further embodiments, C, D, E, F, G, and H of Structure I are selected from aminoalkyl, aralkyl, aryl, heteroaryl, heteroaralkyl, heteroaralkyloxy, aroyl, arylalkyl, aryloxy, aryloxyalkyl, hydrido, alkyl, alkenyl, alkynyl, alkoxy, alkoxyalkyl, acyl, acylalkyl, acyloxy, acyloxyalkyl, halo, haloalkyl, cyano, cyanoalkyl, nitro, nitroalkyl, carboxyl, carboxylalkyl, amino, aminoalkyl, aminocarbonyl, aminocarbonylalkyl, carbamoylalkyl, carbamoylalkoxy, iminoalkyl, imidoalkyl, alkoxycarbonyl, alkoxycarbonylalkyl, alkylamino, alkylaminoalkyl, dialkylamino, dialkylaminoalkyl, arylamino, arylaminoalkyl, hydroxy, hydroxyalkyl, isocyano, isocyanoalkyl, isothiocyano, isothiocyanoalkyl, oximinoalkoxy, morpholino, morpholinoalkyl, azido, azidoalkyl, formyl, formylalkyl, alkylthio, alkylthioalkyl, alkylsulfinyl, alkylsulfinylalkyl, alkylsulfonyl, alkylsulfonylalkyl, aminosulfonyl, arylsulfonyl, N-alkyl-N-arylaminosulfonyl; wherein aryl is selected from phenyl, biphenyl, and naphthyl, and 5- and 6-membered heteroaryl, wherein aryl is optionally substituted. In addition, two adjacent groups can be together to form a part of a fused carbocyclic or heterocyclic ring system. For example, E and F may be part of a ring that is fused to the ring.

In some embodiments, the compounds of Formula I have a central ring system where the A and B substituents include, but are not limited to, pyrrolidine, piperidine, piperazine, heptamethyleneimine, hexamethyleneimine, homopiperazine, perhydroindole, azetidine, 4-piperidinopiperidine, 1-azacycloheptane, perhydroisoquioline, decahydroquinoline, 1-phenylpiperazine. 4-phenylpiperidine, 1-(fluorophenyl)piperazine, 1,3,5-hexa-hydrotriazine, morpholine, phenylmorpholine, thiomorpholine, tetrahydrothiophene, thiazolidine, ω-thiocaprolactam, 1,4-thioxane, 1,3-dithiane, 1,4,7-trithiacyclononane, 1,3,5-trithiane, tetrahydrofuran, tetramethyleneoxide, tetrahydropyran, 1,3,5-trioxane, oxepane and the like, optionally having one or two ring hydrogens substituted with substituents selected from Cl, Br, I, —OR$_4$, —R$_5$, —OC(O)R$_6$, OC(O)NR$_7$R$_8$, —C(O)R$_9$, —CN, —NR$_{10}$R$_{11}$, —SR$_{12}$, —S(O)R$_{11}$, —S(O)$_2$R$_{14}$, —C(O)OR$_{15}$, —S(O)$_2$NR$_{16}$R$_{17}$; —R$_{18}$NR$_{19}$R$_{20}$ wherein R$_4$, R$_5$, R$_6$, R$_7$, R$_8$, R$_9$, R$_{10}$, R$_{11}$, R$_{12}$, R$_{13}$, R$_{14}$, R$_{15}$, R$_{16}$, R$_{17}$, R$_{18}$, R$_{19}$, and R$_{20}$ are the same or different and are branched or unbranched alkyl groups from one to eight carbon atoms or hydrogen radicals. When the above radicals are incorporated into the parent molecule, the present invention includes all possible stereochemical arrangements of the substituents. In addition, the optional agent includes racemic or stereochemically pure compounds.

In another embodiment, the compounds of the present invention include those of Formula II where A is carbon, oxygen, sulfur, nitrogen or phosphorus:

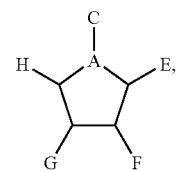

II

The compounds of the present invention of Formula II are those where A is oxygen, and E and H are selected from aminoalkyl, alkylaminoalkyl, arylaminoalkyl, dialkylaminoalkyl, aryl, aralkyl, heteroaryl, heteroaralkyl, hydrido, alkyl, alkenyl, alkynyl, haloalkyl, cyano, cyanoalkyl, nitroalkyl, iminoalkyl, imidoalkyl, hydroxyalkyl, thioalkyl, alkylthioalkyl, isocyanoalkyl, isothiocyanoalkyl, oximinoalkyl, morpholinoalkyl, azidoalkyl, formylalkyl, alkylthioalkyl, alkylsulfinylaminoalkyl, alkylsulfonylaminoalkyl; and F and G are hydrogen. In a further embodiment, E and H are selected from aminoalkyl, alkylaminoalkyl, arylaminoalkyl, dialkylaminoalkyl, aryl, aralkyl, heteroaryl, heteroaralkyl, alkyl, haloalkyl, cyanoalkyl, iminoalkyl, imidoalkyl, isothiocyanoalkyl, morpholinoalkyl, azidoalkyl, formylalkyl. In still another embodiment, E or H is an aryl or heteroaryl.

In still other embodiments, the compounds of the present invention are those of Structure II where E and H are selected from N-methyl aminomethyl, N-methyl aminoethyl, aminomethyl, aminoethyl, aminopropyl, alkylaminomethyl, alkylaminoethyl, alkylaminopropyl, arylaminoethyl, dialkylaminomethyl, dialkylaminoethyl, dialkylaminopropyl, aryl, arylmethyl, arylethyl, arylpropyl, heteroaryl, heteroarylmethyl, heteroarylethyl, heteroarylpropyl, alkyl, halomethyl, thiomethyl, alkylthiomethyl, cyanomethyl, cyanoethyl, nitromethyl, nitroethyl, iminomethyl, iminoethyl, iminopropyl, imidomethyl, hydroxymethyl, isocyanomethyl, isothiocyanomethyl, oximinomethyl, oximinoethyl, oximinopropyl, morpholinomethyl, azidomethyl, alkylsulfinylaminomethyl, alkylsulfinylaminoethyl, alkylsulfinylaminopropyl, alkylsulfonylaminomethyl, alkylsulfonylaminoethyl, alkylsulfonylaminopropyl; and F and G are hydrogen.

In some embodiments, the present invention provides the following compounds when E or H is an aryl or heteroaryl:
2-(aminomethyl)-5-phenyltetrahydrofuran,
2-(aminomethyl)-5-(4'-chlorophenyl)tetrahydrofuran,
2-(aminomethyl)-5-(4'-bromophenyl)tetrahydrofuran,
2-(aminomethyl)-5-(4'-methoxyphenyl)tetrahydrofuran,
2-(aminomethyl)-5-(4'-t-butylphenyl)tetrahydrofuran,
trans-2-(aminomethyl)-5-(2'-methoxy-5'-fluorophenyl)tetrahydrofuran,
cis-2-(aminomethyl)-5-(2'-methoxy-5'-fluorophenyl)tetrahydrofuran,
2-(aminomethyl)-5-(3'-fluoro-4'-methylphenyl)tetrahydrofuran,
2-(aminomethyl)-5-cyclohexyltetrahydrofuran,
2-(aminomethyl)-5-(1'-naphthyl)tetrahydrofuran,
2-(aminomethyl)-5-(2'-methoxy-1'-naphthyl)tetrahydrofuran,
2-(aminomethyl)-5-(2'-naphthyl)tetrahydrofuran,
2-(aminoethyl)-5-phenyltetrahydrofuran,
2-(aminoethyl)-5-(4'-fluorophenyl)tetrahydrofuran,
2-(aminoethyl)-5-(4'-bromophenyl)tetrahydrofuran,
2-(aminoethyl)-5-(4'-t-butylphenyl)tetrahydrofuran,
trans-2-(aminoethyl)-5-(2'-methoxy-5'-fluorophenyl)tetrahydrofuran,
cis-2-(aminoethyl)-5-(2'-methoxy-5'-fluorophenyl)tetrahydrofuran,
2-(aminoethyl)-5-cyclohexyltetrahydrofuran, and
2-(aminoethyl)-5-(2'-furyl)tetrahydrofuran.

In other embodiments, E or H of Formula II is an arylethyl or heteroaryl ethyl. In those embodiments, the present invention provides compounds such as:
2-(aminomethyl)-5-benzyltetrahydrofuran,
2-(aminoethyl)-5-benzyltetrahydrofuran,
trans-2-(aminomethyl)-5-(2'-methoxy-5'-fluorobenzyl)tetrahydrofuran,
cis-2-(aminomethyl)-5-(2'-methoxy-5'-fluorobenzyl)tetrahydrofuran,
trans-2-(aminoethyl)-5-(2'-methoxy-5'-fluorobenzyl)tetrahydrofuran, and
cis-2-(aminoethyl)-5-(2'-methoxy-5'-fluorobenzyl)tetrahydrofuran.

In still other embodiments, the present invention provides compounds where E or H of Formula II is an arylethyl or heteroarylethyl. In those embodiments, the present invention includes compounds such as:
2-(aminomethyl)-5-(phenethyl)tetrahydrofuran,
2-(aminomethyl)-5-(4'-fluorophenethyl)tetrahydrofuran,
2-(aminomethyl)-5-(3'-pyridylethyl)tetrahydrofuran,
2-(aminomethyl)-5-(2'-chloro-5'-trifluoromethylphenethyl)tetrahydrofuran,
2-(aminomethyl)-5-(pentafluorophenethyl)tetrahydrofuran,
2-(aminomethyl)-5-(2'-methoxy-5'-fluorophenyl)tetrahydrofuran,
2-(aminoethyl)-5-(3',4'-dimethoxyphenethyl)tetrahydrofuran,
2-(aminomethyl)-5-(1'-naphthylethyl)tetrahydrofuran,
2-(aminomethyl)-5-(2'-methoxy-1'-naphthylethyl)tetrahydrofuran,
2-(aminomethyl)-5-(4'-methoxy-1'-naphthylethyl)tetrahydrofuran,
2-(aminomethyl)-5-(2"-tetrahydrofuryl-2'-ethyl)tetrahydrofuran,
2-(aminoethyl)-5-(phenethyl)tetrahydrofuran,
2-(aminoethyl)-5-(4'-fluorophenethyl)tetrahydrofuran,
2-(aminoethyl)-5-(4'-hydroxyphenethyl)tetrahydrofuran,
2-(aminoethyl)-5-(4'-methoxyphenethyl)tetrahydrofuran,
2-(aminoethyl)-5-(4'-trifluoromethoxyphenethyl)tetrahydrofuran,
2-(aminoethyl)-5-(4'-methylphenethyl)tetrahydrofuran,
2-(aminoethyl)-5-(4'-phenylphenethyl)tetrahydrofuran,
2-(aminoethyl)-5-(4'-t-butylphenethyl)tetrahydrofuran,
2-(aminoethyl)-5-(5'-fluoro-2'-methoxyphenethyl)tetrahydrofuran,
2-(aminoethyl)-5-(4'-fluoro-3'-methylphenethyl)tetrahydrofuran,
2-(aminoethyl)-5-(3'-fluoro-4'-methylphenethyl)tetrahydrofuran,
2-(aminoethyl)-5-(cyclohexylethyl)tetrahydrofuran,
2-(aminoethyl)-5-(3'-pyridylethyl)tetrahydrofuran,
2-(aminoethyl)-5-(1'-naphthylethyl)tetrahydrofuran,
2-(aminoethyl)-5-(2'-methoxy-1'-naphthylethyl)tetrahydrofuran,
2-(aminoethyl)-5-(4'-methoxy-1'-naphthylethyl)tetrahydrofuran,
2-(aminoethyl)-5-(2'-naphthylethyl)tetrahydrofuran,
trans-2-piperidylmethyl-5-(2'-methoxy-5'-fluorophenethyl)tetrahydrofuran,
trans-2-(N,N-diethylaminomethyl)-5-(2'-methoxy-5'-fluorophenethyl)tetrahydrofuran, and
trans-2-(morpholinomethyl)-5-(2'-methoxy-5'-fluorophenethyl)tetrahydrofuran.

In certain embodiments, the present invention provides compounds where E or H of Formula II is an arylpropyl or heteroarylpropyl. In those embodiments, the present invention provides compounds such as:
2-(aminomethyl)-5-(3'-phenylpropyl)tetrahydrofuran,
2-(aminoethyl)-5-(3'-phenylpropyl)tetrahydrofuran,
trans-2-(aminomethyl)-5-(3'-(2"-methoxy-5"-fluorophenyl)propyl)tetrahydrofuran,
trans-2-(aminoethyl)-5-(2"-methoxy-5"-fluorophenyl-3'-propyl)tetrahydrofuran,
cis-2-(aminoethyl)-5-(2"-methoxy-5"-fluorophenyl-3'-propyl)tetrahydrofuran, and
trans-2-(piperidinomethyl)-5-(2"-methoxy-5"-fluorophenyl-3'-propyl)tetrahydrofuran.

In other embodiments, the present invention provides the following compounds:
cis-2-(phenethylaminoethyl)-5-(2'-methoxy-5'-fluorophenyl)tetrahydrofuran, and
trans-2-(phenethylaminoethyl)-5-(2'-methoxy-5'-fluorophenyl)tetrahydrofuran.

In another embodiment, the present invention provides a compound of Structure II where A is a nitrogen, and E, and G are hydrogen and H is selected from aminoalkyl, alkylaminoalkyl, arylaminoalkyl, dialkylaminoalkyl, aryl, aralkyl, heteroaryl, heteroaralkyl, alkyl, haloalkyl, cyanoalkyl, iminoalkyl, imidoalkyl, isothiocyanoalkyl, morpholinoalkyl, azidoalkyl, formylalkyl. In a further embodiment, Structure II provides compounds such as 1-Methyl-2-Styrenyl Pyrrolidine and 2-Styrenyl Pyrrolidine.

In a further embodiment, the present invention provides a compound of Formula III:

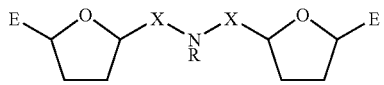

The compounds of the present invention of Formula III are those where E is as defined above, X is saturated carbon chains from C2-C8 and R is alkyl, alkenyl, alkynyl, optionally substituted aryl and aralkyl. In another embodiment, X is ethylene and E is an aryl, aralkyl, heteroaryl, or heteroaralkyl.

In other embodiments, the present invention provides compounds of Structure III such as:
N,N-bis(5'-phenyl-2'-tetrahydrofurylethyl)amine,
N,N-bis(5'-(p-fluorophenyl)-2'-tetrahydrofurylethyl)amine,
N,N-bis(5'-(p-bromophenyl)-2'-tetrahydrofurylethyl)amine,
N,N-bis(5'-(p-t-butylphenyl)-2'-tetrahydrofurylethyl)amine,
N,N-bis(5'-cyclohexyl-2'-tetrahydrofurylethyl)amine,
N,N-bis(trans-5'-(2"-methoxy-5"-fluorophenyl-2'-tetrahydrofuryl)ethyl)amine,
N,N-bis(cis-5'-(2"-methoxy-5"-fluorophenyl-2'-tetrahydrofuryl)ethyl)amine,
N,N-bis(5'-benzyl-2'-tetrahydrofurylethyl)amine,
N,N-bis(5'-phenethyl-2'-tetrahydrofurylethyl)amine,
N,N-bis(5'-phenethyl-2'-tetrahydrofurylethyl)methylamine,
N,N-bis(5'-(p-hydroxyphenethyl)-2'-tetrahydrofurylethyl)amine,
N,N-bis(5'-(m-fluoro-p-methylphenethyl)-2'-tetrahydrofurylethyl)amine,
N,N-bis(5'-(p-fluoro-m-methylphenethyl)-2'-tetrahydrofurylethyl)amine,
N,N-bis(5'-(5'-fluoro-2'-methoxyphenethyl)-2'-tetrahydrofurylethyl)amine,
N,N-bis(5'-(3"-pyridylethyl)-2'-tetrahydrofurylethyl)amine,
N,N-bis(5'-(1"-naphthethyl)-2'-tetrahydrofurylethyl)amine,
N,N-bis(5'-(2"-methoxy-1"-naphthethyl)-2'-tetrahydrofurylethyl)amine,
N,N-bis(5'-(4"-methoxy-1"-naphthethyl)-2'-tetrahydrofurylethyl)amine,
N,N-bis(trans-5'-(2"-methoxy-5"-fluorobenzyl-2'-tetrahydrofuranyl)ethyl)amine,
N,N-bis(cis-5'-(2"-methoxy-5"-fluorobenzyl-2'-tetrahydrofuranyl)ethyl)amine, and
N,N-bis(trans-5-(2"-methoxy-5"-fluorophenyl-3'-propyl-2'-tetrahydrofuryl)ethyl)amine.

In other embodiments, the present invention provides a compound of Formula IV:

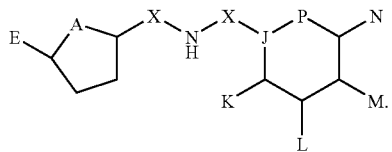

Compounds of Formula IV are those where E is as defined above, X is a saturated carbon chain from $C_2$-$C_8$, and J and P constitute part of a 6-member ring system from unsaturated, partially unsaturated or saturated heterocyclic and carbocyclic rings wherein A is optionally substituted with hydrido, acyl, halo, lower acyl, lower haloalkyl, oxo, cyano, nitro, carboxyl, amino, lower alkoxy, aminocarbonyl, lower alkoxycarbonyl, alkylamino, arylamino, lower carboxyalkyl, lower cyanoalkyl, lower hydroxyalkyl, alkylthio, alkylsulfinyl and aryl, lower aralkylthio, lower alkylsulfinyl, lower alkylsulfonyl, aminosulfonyl, lower N-arylaminosulfonyl, lower arylsulfonyl, lower N-alkyl-N-arylaminosulfonyl; wherein aryl is selected from phenyl, biphenyl, and naphthyl, and 5- and 6-membered heteroaryl, wherein aryl is optionally substituted with one or two substituents selected from halo, hydroxyl, amino, nitro, cyano, carbamoyl, lower alkyl, lower alkenyloxy, lower alkoxy, lower alkylthio, lower alkylsulfinyl, lower alkylsulfonyl, lower alkylamino, lower dialkylamino, lower haloalkyl, lower alkoxycarbonyl, lower N-alkylcarbamoyl, lower N,N-dialkylcarbamoyl, lower alkanoylamino, lower cyanoalkoxy, lower carbamoylalkoxy, lower carbonylalkoxy; wherein the acyl group is optionally substituted with a substituent selected from hydrido, alkyl, halo, and alkoxy.

In still other embodiments, compounds of Formula IV are those where the J and H ring system is selected from the group consisting of phthalazinone, pyranyl, furyl, tetrahydrofuryl, tetrahydrothienyl, thienyl, oxazolyl, pyrolyl, thiazolyl, imidazolyl, isothiazolyl, isoxazoyl, pyrazolyl, cyclopentyl, phenyl, and pyridyl.

In another embodiment, compounds of Formula IV are those where K, L, M, and N are selected from aminoalkyl, aralkyl, aryl, heteroaryl, heteroaralkyl, heteroaralkyloxy, aroyl, arylalkyl, aryloxy, aryloxyalkyl, hydrido, alkyl, alkenyl, alkynyl, alkoxy, alkoxyalkyl, acyl, acylalkyl, acyloxy, acyloxyalkyl, halo, haloalkyl, cyano, cyanoalkyl, nitro, nitroalkyl, carboxyl, carboxylalkyl, amino, aminoalkyl, aminocarbonyl, aminocarbonylalkyl, carbamoylalkyl, carbamoylalkoxy, iminoalkyl, imidoalkyl, alkoxycarbonyl, alkoxycarbonylalkyl, alkylamino, alkylaminoalkyl, catechol, dialkylamino, dialkylaminoalkyl, arylamino, arylaminoalkyl, hydroxy, hydroxyalkyl, isocyano, isocyanoalkyl, isothiocyano, isothiocyanoalkyl, oximinoalkoxy, morpholino, morpholinoalkyl, azido, azidoalkyl, formyl, formylalkyl, alkylthio, alkylthioalkyl, alkylsulfinyl, alkylsulfinylalkyl, alkylsulfonyl, alkylsulfonylalkyl, aminosulfonyl, arylsulfonyl, N-alkyl-N-arylaminosulfonyl; wherein aryl is selected from phenyl, biphenyl, and naphthyl, and 5- and 6-membered heteroaryl, wherein aryl is optionally substituted. In addition, two adjacent groups are joint together to form a part of a fused carbocyclic or heterocyclic ring system. In some embodiments, L and M may be part of a ring that is fused to the ring.

In still further embodiments, the present invention provides compounds such as:
4-(3,4-Dimethoxyphenyl)-2-[5-(2-{5-[2-(5-fluoro-2-methoxyphenyl)-ethyl]-tetrahydrofuran-2-yl}-ethylamino)-pentyl]-4a,5,8,8a-tetrahydro-2H-phthalazin-1-one,
4-(3,4-Dimethoxyphenyl)-2-[5-(2-{5-[2-(5-fluoro-2-methoxyphenyl)-propyl]-tetrahydrofuran-2-yl}-ethylamino)-pentyl]-4a,5,8,8a-tetrahydro-2H-phthalazin-1-one,
4-(3-Cyclopentyloxy-4-methoxy-phenyl)-1-[5-(2-{5-[2-(5-fluoro-2-methoxy-phenyl)-ethyl]-tetrahydro-furan-2-yl}-ethylamino)-pentyl]-pyrrolidin-2-one,
4-(3-Cyclopentyloxy-4-methoxy-phenyl)-1-[5-(2-{5-[3-(5-fluoro-2-methoxy-phenyl)-propyl]-tetrahydro-furan-2-yl}-ethylamino)-pentyl]-pyrrolidin-2-one,
2-(3-{5-[4-(3,4-Dimethoxy-phenyl)-1-oxo-4a,5,8,8a-tetrahydro-1H-phthalazin-2-yl]-pentylamino}-propyl)-2-(4-fluoro-phenyl)-2,3-dihydro-benzofuran-6-carbonitrile,
2-(3-{5-[4-(3-Cyclopentyloxy-4-methoxy-phenyl)-2-oxo-pyrrolidin-1-yl]-pentylamino}-propyl)-2-(4-fluoro-phenyl)-2,3-dihydro-benzofuran-6-carbonitrile, 4-(3,4-Dimethoxy-phenyl)-2-(5-{[5-(4-methoxy-phenyl)-tetrahydro-furan-2-ylmethyl]-amino}-pentyl)-4a,5,8,8a-tetrahydro-2H-phthalazin-1-one, 4-(3-Cyclopentyloxy-4-methoxy-phenyl)-1-(5-{[5-(4-methoxy-phenyl)-tetrahydro-furan-2-ylmethyl]-amino}-pentyl)-pyrrolidin-2-one, 2-{5-[(5-Cyclohexyl-tetrahydro-furan-2-ylmethyl)-amino]-pentyl}-4-(3,4-dimethoxy-phenyl)-4a,5,8,8a-tetrahydro-2H-phthalazin-1-one, 1-{5-[(5-Cyclohexyl-tetrahydro-furan-2-ylmethyl)-amino]-pentyl}-4-(3-cyclopentyloxy-4-methoxy-phenyl)-pyrrolidin-2-one, 4-(3,4-Dimethoxy-phenyl)-2-(5-{[5-(3-fluoro-4-methyl-phenyl)-tetrahydro-furan-2-ylmethyl]-amino}-pentyl)-4a,5,8,8a-tetrahydro-2H-phthalazin-1-one, and 4-(3-Cyclopentyloxy-4-methoxy-phenyl)-1-(5-{[5-(3-fluoro-4-methyl-phenyl)-tetrahydro-furan-2-ylmethyl]-amino}-pentyl)-pyrrolidin-2-one.

In certain other embodiments, the present invention provides a compound of Formula V:

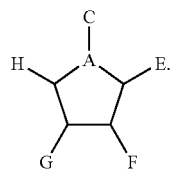

V

Compounds of Formula V include those where A is nitrogen, E, F and G are hydrogen, and H is selected from aminoalkyl, alkylaminoalkyl, arylaminoalkyl, dialkylaminoalkyl, aryl, aralkyl, heteroaryl, heteroaralkyl, hydrido, alkyl, alkenyl, alkynyl, haloalkyl, cyano, cyanoalkyl, nitroalkyl, iminoalkyl, imidoalkyl, hydroxyalkyl, thioalkyl, alkylthioalkyl, isocyanoalkyl, isothiocyanoalkyl, oximinoalkyl, morpholinoalkyl, azidoalkyl, formylalkyl, alkylthioalkyl, alkylsulfinylaminoalkyl, and alkylsulfonylaminoalkyl.

In other embodiments, the present invention provides compounds of Formula V where E and H are selected from aminomethyl, amino ethyl, aminopropyl, alkylaminomethyl, alkylaminoethyl, alkylaminopropyl, arylaminoethyl, dialkylaminomethyl, dialkylaminoethyl, dialkylaminopropyl, aryl, arylmethyl, arylethyl, arylpropyl, heteroaryl, heteroarylmethyl, heteroarylethyl, heteroarylpropyl, alkyl, halomethyl, thiomethyl, alkylthiomethyl, cyanomethyl, cyanoethyl, nitromethyl, nitroethyl, iminomethyl, iminoethyl, iminopropyl, imidomethyl, hydroxymethyl, isocyanomethyl, isothiocyanomethyl, oximinomethyl, oximinoethyl, oximinopropyl, morpholinomethyl, azidomethyl, alkylsulfinylaminomethyl, alkylsulfinylaminoethyl, alkylsulfinylaminopropyl, alkylsulfonylaminomethyl, alkylsulfonylaminoethyl, and alkylsulfonylaminopropyl; and F and G are hydrogen.

One of skill in the art will recognize that the compounds of the present invention can also be present as the salt, hydrate, solvate, stereoisomer, prodrug, stereoisomer or polymorph thereof.

Preparation of Compounds of the Present Invention

The compounds described in the invention may be prepared using conventional techniques and standard synthetic methods as described in books such as "Organic Synthesis" or methods in journals such as "Journal of Organic Chemistry", "Journal of Medicinal Chemistry", or "Journal of American Chemical Society".

General Methods

Figure 1:
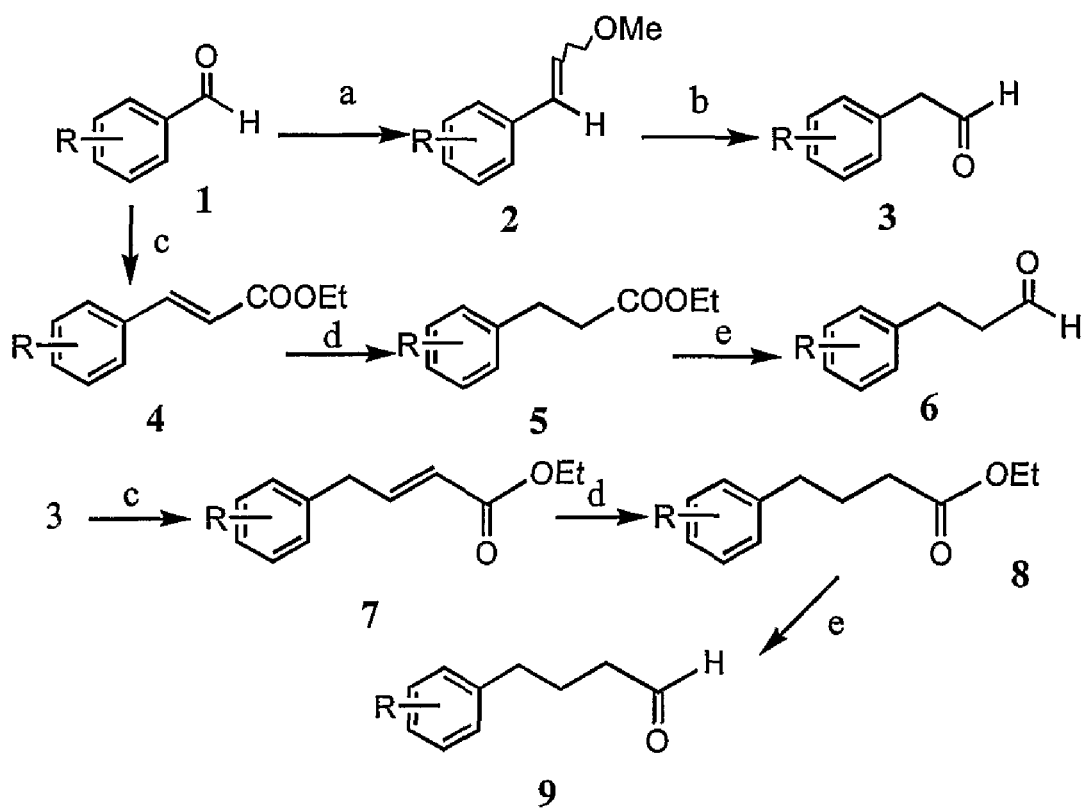
FIG. 1 depicts scheme 1 (of schemes 1 to 3) of a general method for synthesis of certain embodiments of the present invention.
Figure 2:
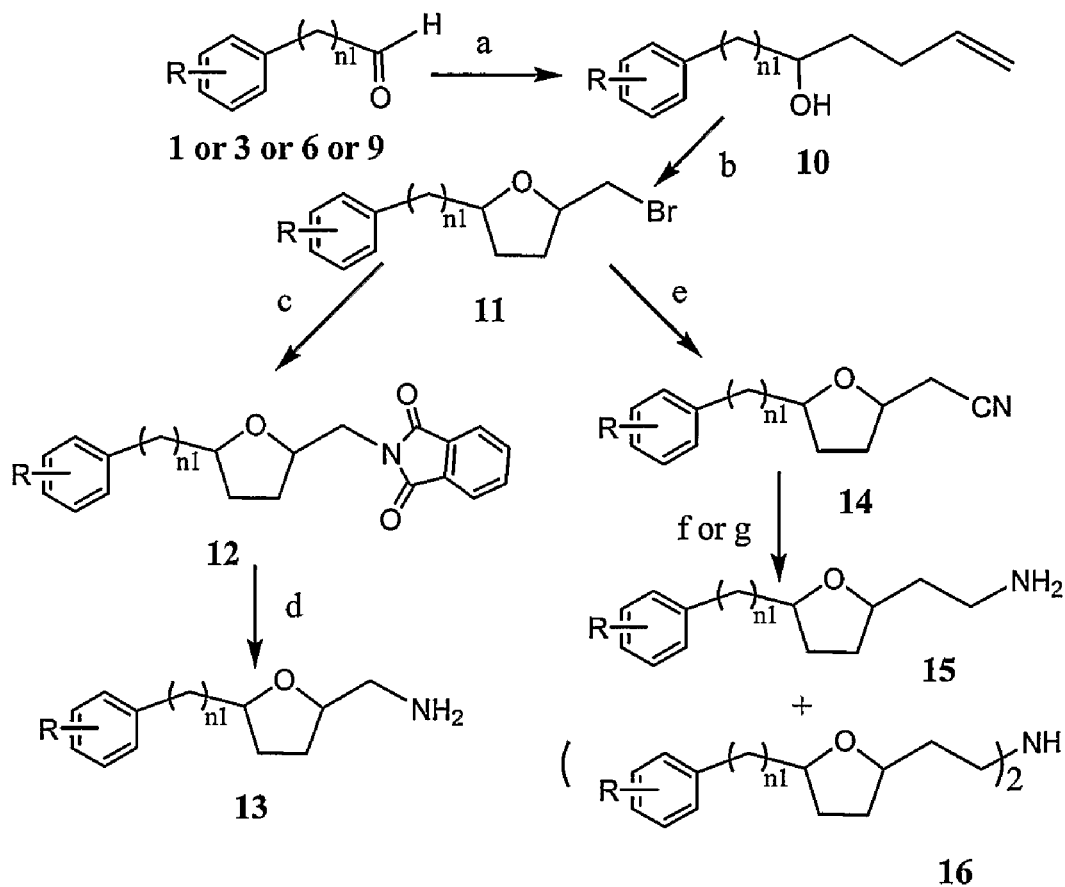
FIG. 2 depicts scheme 2 (of schemes 1 to 3) of a general method for synthesis of certain embodiments of the present invention.
Figure 3:
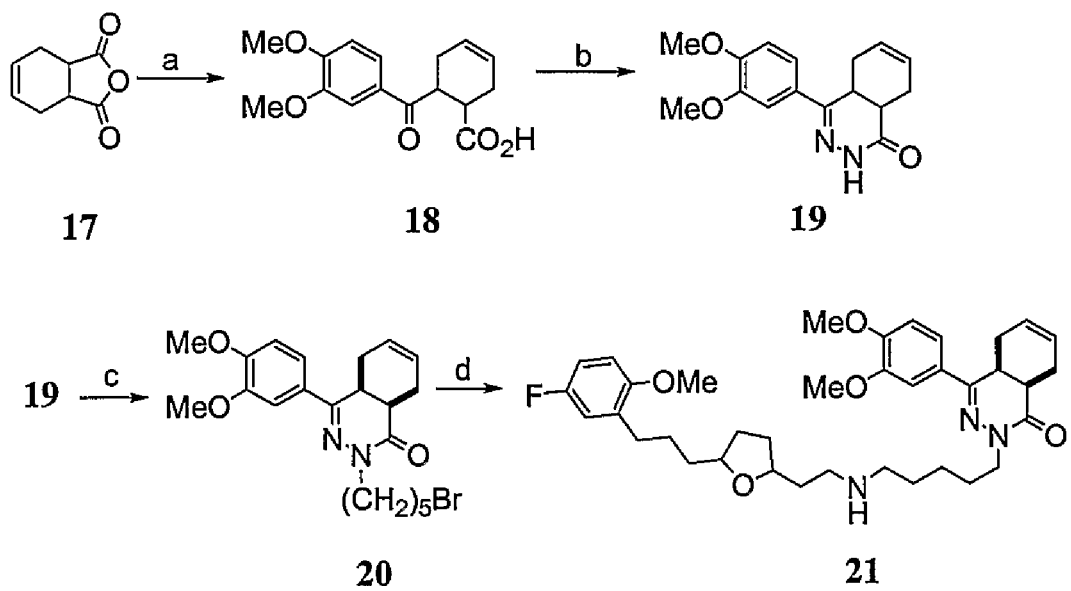
FIG. 3 depicts scheme 3 (of schemes 1 to 3) of a general method for synthesis of certain embodiments of the present invention.

The general method for the preparation of the compounds in the invention is outlined in Scheme 1, Scheme 2, and Scheme 3 (see FIGS. 1-3, respectively). The synthesis starts from the aryl substituted aldehyde. Some of these aldehydes are commercially available; others can be synthesized as illustrated in Scheme 1 (see FIG. 1). The aldehydes 1 were treated with a Wittig reagent that was obtained from methoxymethyltriphenylphosphonium chloride and sodium hydride to give enol ethers 2 as mixtures of E- and Z-isomers. Hydrolysis of 2 produced the aldehydes 3. Treatment of 1 with the commercially available Wittig reagent carbethoxytriphenylphosphorane gave the unsaturated esters 4 which was hydrogenated in the presence of palladium on activated carbon to produce the saturated esters 5. Reduction of 5 with DiBAL in toluene resulted in the formation of aldehydes 6. Combining the strategy for synthesis of 3 and 6 produced the aldehydes 9. The synthetic sequence presented here provides a general method for making the aryl-substituted aldehydes of any chain length.

The aldehydes (1 or 3 or 6 or 9) that were obtained according to Scheme 1 were then treated with the commercially available 1-butenylmagnesium bromide to form the ring-closure precursor enols 10 (see FIG. 2). 5-bromomethyl substituted tetrahydrofurans 11 were formed by treating 10 with N-bromosuccinimide (NBS) in $CH_2C_{12}$ (See id.). Bromides 11 were treated with potassium phthalimide in DMSO catalyzed by NaI at 70° C. to produce phthalimido derivatives 12. Hydrolysis of 12 with hydrazine hydrate gave the desired amines 13. The cyano compounds 14 were formed in a similar manner. The cyano compounds 14 were catalytically hydrogenated in the presence of Raney nickel and one atmosphere of $H_2$ to give the desired primary amines 15 as the major products and secondary amines 16 as the minor products. Alternatively, amines 15 were synthesized by reducing 14 with sodium borohydride in the presence of Raney nickel.

The synthetic procedures used for the preparation of cis-(±)-4a,5,8,8a-tetrahydro-2H-phthalazin-1-ones that were linked to the 2,5-disubstituted tetrahydrofurans and derivatives thereof is depicted in Scheme 3 (see FIG. 3). Nucleophilic addition of Grignard reagent, 3,4-dimethoxyphenylmagnesium bromide to cis-1,2,3,6-tetrahydrophthalic anhydride afforded γ-keto acid in moderate yield (40%). The γ-keto acid readily underwent cyclization upon treatment with hydrazine hydrate in EtOH to give the corresponding phthalazinone. A five carbon linker is attached to the phthalazinone with NaH and 1,5-dibromopentane. This adduct is then linked to the 2,5-disubstituted tetrahydrofurans with CsOH in DMF.

Synthesis of (S)-2-alkyl Pyrrolidines, Compounds 25b-25c

S-Proline was a useful starting material for the synthesis of 2-alkylpyrrolidines because it provided a 2-substituted pyrrolidine with the desired (S)-stereochemistry. Further elaboration of the 2-monosubstituted pyrrolidine was made via the Wittig reaction to form compound 25. Compound 23 was converted into 1-tBoc-2-formylpyrrolidine, compound 24, by an oxidative reaction sequence and as described below, the t-Boc was a useful protecting group.

Figure 4:
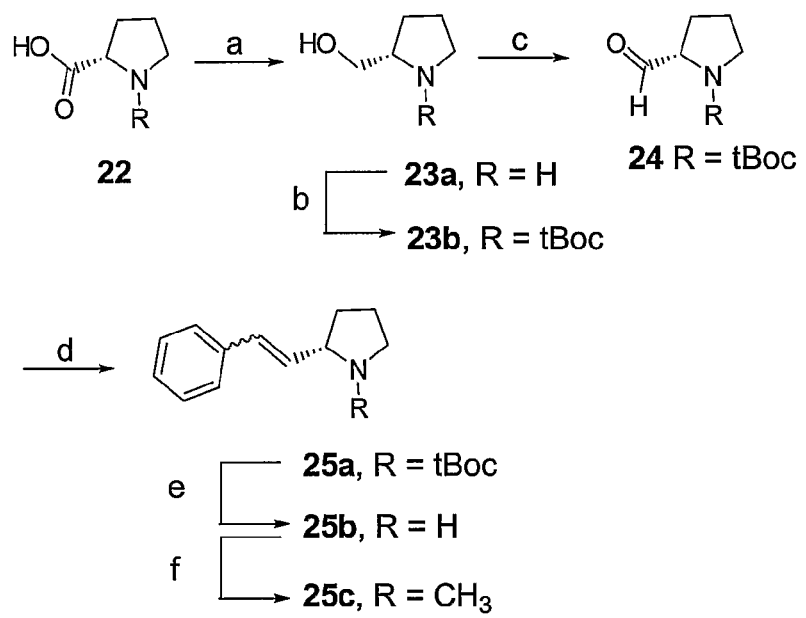
FIG. 4 depicts a scheme for a synthesis of (S)-2-alkyl pyrrolidines (compounds 25b and 25c).

Reduction of compound 23a with lithium aluminum hydride and then N-protection with a tBoc group afforded 2-pyrrolidine methanol, compound 23b. Oxidation of compound 23b by Swern oxidation gave 1-tBoc-2-formylpyrrolindine, compound 24. Compound 24 was treated with benzyltriphenylphosphonium chloride under standard Wittig conditions to provide a double bond at the C-2 position, compound 25a. Compound 25a was then deprotected and methylated to produce compounds 25b and 25c as depicted in Scheme 4. (See FIG. 4.)

Figure 5:
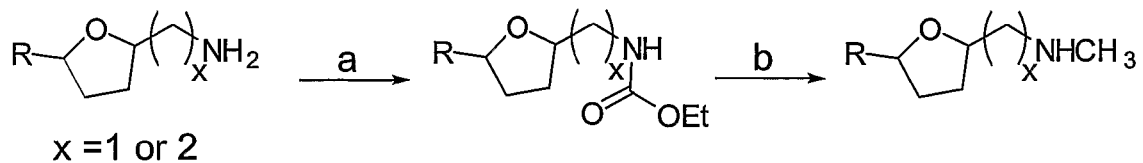
FIG. 5 depicts a scheme for a synthesis of monomethyl amine adducts for prodrugs of the primary amines.

Monomethyl amine adducts were prepared for prodrugs of the primary amines. The general synthesis is diagrammed in Scheme 5 (see FIG. 5) where the ethyl carbamate is made from the primary amine with ethyl chloroformate in THF. The carbamate is then reduced to the methyl group with LAH in THF to yield the monomethyl secondary amine.

Pharmaceutical Compositions and Methods of Administration

The agents of the present invention are useful in a variety of applications relating to modulation of cellular signaling. For example, in a preferred aspect of the invention, the agents are useful for modulation of CNS neurotransmitter signaling. Modulation of CNS neurotransmitter signaling can be achieved, e.g., by the ability of an agent to modulate neurotransmitter reuptake (e.g., selective inhibition of serotonin reuptake) and/or to modulate cellular signaling downstream of a neurotransmitter receptor (e.g., inhibition of phosphodiesterase 4 (PDE4) activity or G protein-coupled receptor kinase activity). Thus, in certain embodiments, the agents of the present invention are useful for the treatment or prevention of disorders or diseases amenable to therapeutic or prophylactic intervention via modulation (e.g., inhibition) of neurotransmitter reuptake and/or neurotransmitter receptor intracellular signaling pathways. For example, the agents are particularly useful for the treatment or prevention of CNS disorders or diseases amenable to therapeutic or prophylactic intervention by inhibition of serotonin reuptake and/or inhibition of phosphodiesterase 4 (PDE4) enzyme activity. Disorders and diseases amenable to treatment or prevention in accordance with the present invention include, e.g., depression, drug addiction, anxiety, attention-deficit disorder, schizophrenia, and bipolar disorder. In other variations, the disease or disorder is a neurodegenerative disease or disorder. In typical embodiments, the compound induces non-addicting CNS stimulation in a subject.

Accordingly, the present invention further provides pharmaceutical compositions and methods for the treatment or prevention of CNS diseases or disorders. The CNS modulators of the present invention can be delivered or administered to a mammal, e.g., human subject, alone, in the form of a pharmaceutically acceptable salt or hydrolysable precursor thereof, or in the form of a pharmaceutical composition wherein the compound is mixed with suitable carriers or excipient(s) in a therapeutically effective amount. When administered in an appropriate therapeutically effective regime, a sufficient amount of the agent is present to inhibit serotonin reuptake and/or to inhibit PDE4 activity in vivo so as to modulate neurotransmitter receptor signaling.

The CNS modulators that are used in the methods of the present invention can be administered as pharmaceutical compositions comprising the agent together with one or more other pharmaceutically acceptable components. Pharmaceutical compositions can be in the form of solids (such as, e.g., powders, granules, dragees, tablets, or pills), semi-solids (such as, e.g., gels, slurries, or ointments), liquids, or gases (such as, e.g., aerosols or inhalants).

Suitable formulations for use in the present invention are found in, for example, *Remington's Pharmaceutical Sciences* (Mack Publishing Company, Philadelphia, Pa., 17th ed. 1985) and Langer, *Science* 249:1527-1533, 1990. The pharmaceutical compositions described herein can be manufactured in a conventional manner, e.g., mixing, dissolving, granulating, dragee-making, levigating, emulsifying, encapsulating, entrapping, or lyophilizing processes.

In preparing the formulations of the present invention, pharmaceutically recognized equivalents of each of the compounds can be alternatively used. These pharmaceutically recognized equivalents can be pharmaceutically acceptable esters, amides, or salts or pharmaceutically acceptable acid addition salts.

A pharmaceutically acceptable salt is a non-toxic metal, alkaline earth metal, or an ammonium salt commonly used in the pharmaceutical industry including, for example, a sodium, potassium, lithium, calcium, magnesium, barium, ammonium, and protamine zinc salt, which is prepared by methods well-known in the art. The term also includes a non-toxic acid addition salt, which is generally prepared by reacting the compounds of the present invention with a suitable organic or inorganic acid. Representative salts include, e.g., hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, and napsylate.

A pharmaceutically acceptable acid addition salt is a salt that retains the biological effectiveness and properties of the free bases and that is not biologically or otherwise undesirable, formed with inorganic acids such as, e.g., hydrochloric acid, hydrobromic acid, sulfuric acid, nitric acid, phosphoric acid, and the like, and organic acids such as, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid, and the like (see, e.g., Bundgaard ed., *Design of Prodrugs* (Elsevier Science Publishers, Amsterdam 1985)).

The CNS modulators can be formulated with common excipients, diluents, or carriers, and compressed into tablets, or formulated as elixirs or solutions for convenient oral administration. The CNS modulators can also be formulated as sustained release dosage forms and the like.

In order to exert the desired therapeutic or prophylactic effects associated with inhibition of serotonin reuptake and/or PDE4 activity, the agents of the present invention must reach brain cells and brain tissue, requiring their passage from the blood to the brain by crossing the blood brain barrier, comprising the microcapillary membranes of the cerebrovascular endothelium. The present invention provides methods for administering a therapeutically effective dosage regime of the CNS modulator to a peripheral tissue in a patient (i.e., tissues other than central nervous system tissues). This can be achieved in various ways, including oral, buccal, rectal, parenteral, intraperitoneal, intradermal, transdermal, intratracheal, and intramuscular administration. Moreover, the agents can be administered in a local rather than systemic manner, in a depot or sustained release formulation. In addition, the agents can be administered in a vesicle, in particular a liposome (see, e.g., Langer, supra; Treat et al., In *Liposomes in the Therapy of Infectious Disease and Cancer*, Lopez-Berestein and Fidler eds., Liss, New York, pp. 353-365, 1989).

For injection, the CNS modulators of the present invention can be formulated into preparations by dissolving, suspending, or emulsifying them in an aqueous or nonaqueous solvent such as, e.g., vegetable or other similar oils, synthetic aliphatic acid glycerides, esters of higher aliphatic acids, or propylene glycol; and, if desired, with conventional additives such as, e.g., solubilizers, isotonic agents, suspending agents, emulsifying agents, stabilizers, and preservatives. Preferably, for injection, the compounds of the present invention can be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art.

For oral administration, the CNS modulator can be formulated readily by combining with pharmaceutically acceptable carriers that are well-known in the art. Such carriers enable the compounds to be formulated as tablets, pills, dragees, capsules, emulsions, lipophilic and hydrophilic suspensions, liquids, gels, syrups, slurries, suspensions, and the like, for oral ingestion by a subject to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Particularly suitable excipients include fillers such as, for example, sugars (e.g., lactose, sucrose, mannitol, or sorbitol), cellulose preparations (e.g., maize starch, wheat starch, rice starch, potato starch, gelatin, gum tragacanth, methyl cellulose, hydroxypropylmethyl-cellulose, sodium carboxymethylcellulose, and/or polyvinyl pyrrolidone (PVP). If desired, disintegrating agents can be added, such as the cross-linked polyvinyl pyrrolidone, agar, or alginic acid or a salt thereof such as, e.g., sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, titanium dioxide, lacquer solutions, and/or suitable organic solvents or solvent mixtures. Dyestuffs or pigments can be added to the tablets or dragee coatings for identification or to characterize different combinations of active compound doses.

Pharmaceutical preparations that can be used orally include, for example, push-fit capsules made of gelatin, as well as soft, sealed capsules made of gelatin and a plasticizer, such as, e.g., glycerol or sorbitol. The push-fit capsules can contain the active ingredients in admixture with filler such as, for example, lactose, binders (e.g., starches), and/or lubricants (e.g., talc or magnesium stearate) and, optionally, stabilizers. In soft capsules, the active compounds can be dissolved or suspended in suitable liquids, such as, e.g., fatty oils, liquid paraffin, or liquid polyethylene glycol.

For buccal administration, the compositions can take the form of tablets or lozenges formulated in a conventional manner.

For administration by inhalation, the compounds for use in accordance with the present invention are conveniently delivered in the form of an aerosol spray preparation from pressurized packs or a nebulizer, with the use of a suitable propellant, e.g., dichlorodifluoromethane, trichlorofluoromethane, dichlorotetrafluoroethane, carbon dioxide or other suitable gas, or from propellant-free, dry-powder inhalers. In the case of a pressurized aerosol the dosage unit can be determined by, for example, providing a valve to deliver a metered amount. Capsules and cartridges of, e.g., gelatin for use in an inhaler or insufflator can be formulated containing a powder mix of the compound and a suitable powder base such as, for example, lactose or starch.

CNS modulators of the present invention can be formulated for parenteral administration by injection, e.g., by bolus injection or continuous infusion. Formulations for injection can be presented in unit dosage form, e.g., in ampules or in multidose containers, with an added preservative. The compositions can take such forms as, e.g., suspensions, solutions, or emulsions in oil-based or aqueous vehicles, and can contain formulator agents such as, for example, suspending, stabilizing, and/or dispersing agents.

Pharmaceutical formulations for parenteral administration include aqueous solutions of the active compounds in water-soluble form. Alternatively, suspensions of the active compounds can be prepared as appropriate oily injection suspensions. Suitable lipophilic solvents or vehicles include fatty oils (e.g., sesame oil), synthetic fatty acid esters (e.g., ethyl oleate or triglycerides), or liposomes. Aqueous injection suspensions can contain substances that increase the viscosity of the suspension, such as, for example, sodium carboxymethyl cellulose, sorbitol, or dextran. Optionally, the suspension can also contain suitable stabilizers or agents that increase the solubility of the compounds to allow for the preparation of highly concentrated solutions. Alternatively, the active ingredient can be in powder form for constitution with a suitable vehicle, e.g., sterile pyrogen-free water, before use.

CNS modulators as described herein can also be formulated in rectal compositions such as suppositories or retention enemas, e.g., containing conventional suppository bases such as, for example, cocoa butter, carbowaxes, polyethylene glycols, or other glycerides, all of which melt at body temperature, yet are solidified at room temperature.

In addition to the formulations described previously, the compounds can also be formulated as a depot preparation. Such long-acting formulations can be administered by implantation (for example, subcutaneously or intramuscularly) or by intramuscular injection. Accordingly, for example, the compounds can be formulated with suitable polymeric or hydrophobic materials (e.g., as an emulsion in an acceptable oil) or ion exchange resins, or as sparingly soluble derivatives (e.g., a sparingly soluble salt).

Alternatively, other delivery systems for hydrophobic pharmaceutical compounds can be employed. Liposomes and emulsions are well-known examples of delivery vehicles or carriers for hydrophobic drugs. In some methods, long-circulating, e.g., stealth, liposomes can be employed. Such liposomes are generally described in U.S. Pat. No. 5,013,556 to Woodle et al.

The compounds of the present invention can also be administered by controlled release means and/or delivery devices. In certain variations, a pump is used (see, e.g., Langer, supra; Sefton, *CRC Crit. Ref. Biomed. Eng.* 14:201, 1987; Buchwald et al., *Surgery* 88:507, 1980; Saudek et al., *N. Engl. J. Med.* 321:574, 1989). In other embodiments, polymeric materials are used (see, e.g., *Medical Applications of Controlled Release*, Langer and Wise eds., CRC Pres., Boca Raton, Fla., 1974; *Controlled Drug Bioavailability, Drug Product Design and Performance*, Smolen and Bull eds., Wiley, New York, 1984; Ranger and Peppas, *J. Macromol. Sci. Rev. Macromol. Chem.* 23:61, 1983; see also Levy et al., *Science* 228:190, 1985; During et al., *Ann. Neurol.* 25:351, 1989; Howard et al., *J. Neurosurg.* 71:105, 1989). Controlled release means and delivery devices are also described in, e.g., U.S. Pat. Nos. 3,845,770; 3,916,899; 3,536,809; 3,598,123; and 4,008,719.

Certain organic solvents such as, e.g., dimethylsulfoxide (DMSO) also can be employed, although usually at the cost of greater toxicity. Additionally, the compounds can be delivered using a sustained-release system such as, for example, semipermeable matrices of solid hydrophobic polymers containing the therapeutic agent. Various types of sustained-release materials have been established. Sustained-release capsules can, depending on their chemical nature, release the compounds for a few hours up to over 100 days.

The pharmaceutical compositions can also comprise suitable solid or gel phase carriers or excipients. Examples of such carriers or excipients include, but are not limited to, calcium carbonate, calcium phosphate, various sugars, starches, cellulose derivatives, gelatin, and polymers such as, e.g., polyethylene glycols.

For treatment or prevention of drug addiction, compounds of the present invention may also be administered by incorporating the agent into a drug-containing product (for example, in the case of nicotine ingestion, a tobacco product such as, e.g., a cigarette). For example, in certain embodiments, a compound of the present invention is sprayed or otherwise applied onto the drug-containing product prior to ingestion.

Pharmaceutical compositions suitable for use in accordance with the present invention include compositions wherein the active ingredients are contained in a therapeutically effective amount. The therapeutically effective amounts for the methods of the present invention can depend on a variety of factors, including, e.g., age, body weight, general health, sex, diet, time and manner of administration, rate of excretion, drug combination, the judgment of the treating physician, and the severity of the particular affliction being treated. The amount of active agent will also depend upon the specific activity of the CNS modulator and whether that agent is co-administered with any other therapeutic or prophylactic ingredients.

Typically, a subject treated in accordance with the methods provided herein has been diagnosed with a disease or disorder amenable to treatment using a compound of the present invention; has been identified as at risk of a disease or disorder amenable to prophylaxis using the compound; or has otherwise been identified as a subject that will obtain a physiological benefit using the compound. In certain variations, the subject has not been diagnosed with a second disease or disorder (for example, another disease or disorder amenable to treatment using the compounds of the present invention). Further, in some embodiments, the subject is monitored during treatment for a physiological and/or clinical effect. For example, a subject can be monitored for one or more symptoms associated with the disease or disorder (e.g., for the treatment of depression, anxiety, bipolar disorder, attention deficit disorder, or schizophrenia in a subject, the subject can be monitored for one or more symptoms of depression, anxiety, bipolar disorder, attention deficit disorder, or schizophrenia, respectively).

EXAMPLES

The following examples are offered to illustrate but not to limit the claimed invention.

(Note: relative to the compound numbering scheme used elsewhere herein, each of Examples 28, 29, and 30 (and corresponding Figures and Tables) uses different compound reference designations.)

Example 1

Trans-2-(Aminomethyl)-5-(2'-methoxy-5'-fluorophenyl)tetrahydrofuran 1-(2'-Methoxy-5'-fluorophenyl)pent-4-en-1-ol: To a solution of 2-methoxy-5-fluorobenzaldehyde (3.0 g, 19.5 mmol) in THF (20 mL) at 0° C. was added a solution 1-butenylmagnesium bromide (0.5 M in THF, 45 mL, 22.5 mmol) dropwise for 15 min. Then the reaction mixture was poured to a solution of saturated ammonium chloride (80 mL) in a separatory funnel. The organic fraction was extracted with ethyl acetate (3×60 mL) and the combined organic layers were washed with brine (50 mL) and dried over sodium sulfate. The solvent then was removed in vacuo and crude product thus obtained was purified by flash column chromatography (10% EtOAc in hexane, $R_f$=0.11) to give the product as an oil (3.27 g, 93%).

2-(Bromomethyl)-5-(2'-methoxy-5'-fluorophenyl)tetrahydrofuran: To a solution of 1-(2'-methoxy-5'-fluorophenyl)pent-4-en-1-ol (3.24 g, 18.0 mmol) in dry $CH_2Cl_2$ (50 mL) at 0° C. was added portionwise N-bromosuccinimide (NBS, 3.56 g, 20.0 mmol) portionwise and the reaction was warmed to room temperature for 12 h. Solvent was then removed in vacuo and the residue was purified by flash column chromatography (10% EtOAc in Hexane, $R_f$=0.28) to give the product (2.28 g, 44%) as an oil.

2-(N-Phthalimidomethyl)-5-(2'-methoxy-5'-fluorophenyl)tetrahydrofuran: To a vial under $Ar_{(g)}$ was added 2-(bromomethyl)-5-(2'-methoxy-5'-fluorophenyl)tetrahydrofuran (1.28 g, 4.44 mmol), NaI (100 mg), potassium phthalimide (2.05 g, 11.1 mmol), and dry DMSO (10 mL). The mixture thus obtained was heated to 70° C. under Ar for 12 h. After it was cooled to room temperature, the reaction mixture was poured in to a separatory funnel containing sodium bicarbonate aqueous solution (sat. $NaHCO_3$:$H_2O$=1:1, 70 mL). The organic fraction was extracted with ethyl acetate (3×60 mL) and the combined organic layers were washed with brine (50 mL) and dried over sodium sulfate. The solvent then was removed in vacuo and crude product thus obtained was purified by flash column chromatography (20% EtOAc in hexane, $R_f$=0.12) to give the product (about 2:1 of trans cis isomers, 1.14 g, 72%) as an oil.

Trans-2-Aminomethyl-5-(2'-methoxy-5'-fluorophenyl)tetrahydrofuran: To a vial under $Ar_{(g)}$ was added 2-(N-phthalimidomethyl)-5-(2'-methoxy-5'-fluorophenyl)tetrahydrofuran (225 mg, 0.63 mmol), hydrazine hydrate (150 mg, 4.9 mmol), and methanol (10 mL). The mixture thus obtained was stirred at room temperature for 12 h. The solvent was then removed in vacuo and the crude product thus obtained was purified by column flash chromatography (10% methanol in $CH_2Cl_2$, 0.25% triethylamine) to give the title compound (41 mg, 30%, $R_f$=0.08, trans:cis=0.95:0.05).

Similar methods were used to prepare: 2-(aminomethyl)-5-phenyltetrahydrofuran, 2-(aminomethyl)-5-(4'-chlorophenyl)tetrahydrofuran, 2-(aminomethyl)-5-(4'-bromophenyl)tetrahydrofuran, 2-(aminomethyl)-5-(4'-methoxyphenyl)tetrahydrofuran, 2-(aminomethyl)-5-(4'-t-butylphenyl)tetrahydrofuran, cis-2-(aminomethyl)-5-(2'-methoxy-5'-fluorophenyl)tetrahydrofuran, 2-(aminomethyl)-5-(3'-fluoro-4'-methylphenyl)tetrahydrofuran, 2-(aminomethyl)-5-cyclohexyltetrahydrofuran, 2-(aminomethyl)-5-(1'-naphethyl)tetrahydrofuran, 2-(aminomethyl)-5-(2'-methoxy-1'-naphethyl)tetrahydrofuran, 2-(aminomethyl)-5-(2'-naphethyl)tetrahydrofuran, 2-(aminomethyl)-5-(3'-quinoline)tetrahydrofuran, trans-2-(aminomethyl)-5-(2'-pyridyl)tetrahydrofuran.

Example 2

Cis-2-Aminoethyl-5-(2'-methoxy-5'-fluorophenyl)tetrahydrofuran and N,N-Bis(5'-(2''-methoxy-5''-fluorophenyl-2'-tetrahydrofuryl)ethyl)amine Trans-2-(Cyanomethyl)-5-(2'-methoxy-5'-fluorophenyl)tetrahydrofuran and cis-2-(cyanomethyl)-5-(2'-methoxy-5'-fluorophenyl)tetrahydrofuran: To a vial under Ar was added 2-(bromomethyl)-5-(2'-methoxy-5'-fluorophenyl)tetrahydrofuran (1.23 g, 4.3 mmol), NaI (100 mg), potassium cyanide (0.7 g, 10.6 mmol), and dry DMSO (15 mL). The mixture thus obtained was heated to 70° C. under Ar for 12 h. After it was cooled to room temperature, the reaction mixture was poured in to a separatory funnel containing sodium bicarbonate aqueous solution (sat. $NaHCO_3:H_2O=1:1$, 80 mL). The organics were extracted with ethyl acetate (3×60 mL) and the combined organic layers were washed with brine (50 mL) and dried over sodium sulfate. The solvent then was removed in vacuo and crude product thus obtained was purified by flash column chromatography (20% EtOAc in hexane, $R_f=0.20$). Careful analysis and collection of early fractions resulted in isolation of the trans isomer (HJX-I-30, 0.55 g, 55%); The rest of the fractions were collected and upon removal of the solvents, a white colored solid was formed. Further purification of this solid by triturating with hexane resulted in the cis isomer (HJX-I-30B, 250 mg, 25%);

N,N-Bis(cis-5'-(2"-methoxy-5"-fluorophenyl-2'-tetrahydrofuranyl)ethyl)amine and cis-2-(aminoethyl)-5-(2'-methoxy-5'-fluorophenyl)tetrahydrofuran: To a vial under $Ar_{(g)}$ was added Raney Ni that was washed with ethanol (100%, 3 times) and cis-2-(cyanomethyl)-5-(2'-methoxy-5'-fluorophenyl)tetrahydrofuran (100 mg, 0.43 mmol) that was treated with a small amount of Raney Ni in ethanol. The vial was then evacuated and purged with $H_2$ three times each. Then a balloon was attached to the flask and the reaction was charged in $H_2$ and allowed to go for 6 days at room temperature. The reaction mixture was then filtered through a plug of Celite and the crude product obtained after the removal of the solvent was purified by flash column chromatography (10% MeOH in $CH_2Cl_2$, 1% TEA $R_f=0.31$) to result in N,N-Bis(cis-5'-(2"-methoxy-5"-fluorophenyl-2'-tetrahydrofuryl)ethyl)amine (HJX-I-40A) (11 mg, 6%) as a 1:1 diastereomers; and cis-2-(aminoethyl)-5-(2'-methoxy-5'-fluorophenyl)tetrahydrofuran (43 mg, 42%, $R_f=0.09$).

Similar methods were used to prepare: 2-(aminoethyl)-5-phenyltetrahydrofuran, 2-(aminoethyl)-5-(4'-fluorophenyl)tetrahydrofuran, 2-(aminoethyl)-5-(4'-bromophenyl)tetrahydrofuran, 2-(aminoethyl)-5-(4'-t-butylphenyl)tetrahydrofuran, trans-2-(aminoethyl)-5-(2'-methoxy-5'-fluorophenyl)tetrahydrofuran, 2-(aminoethyl)-5-cyclohexyltetrahydrofuran, 2-(aminoethyl)-5-(2'-furyl)tetrahydrofuran, and N,N-bis(5'-phenyl-2'-tetrahydrofurylethyl)amine, N,N-bis(5'-(p-fluorophenyl)-2'-tetrahydrofurylethyl)amine, N,N-bis(5'-(p-bromophenyl)-2'-tetrahydrofurylethyl)amine, N,N-bis(5'-(p-t-butylphenyl)-2'-tetrahydrofurylethyl)amine, N,N-bis(5'-cyclohexyl-2'-tetrahydrofurylethyl)amine, N,N-bis(trans-5'-(2"-methoxy-5"-fluorophenyl-2'-tetrahydrofuryl)ethyl)amine, N,N-bis(5'-(2"-naphthyl-2'-tetrahydrofuryl)ethyl)amine.

Example 3

Trans-2-(aminomethyl)-5-(5'-fluoro-2'-methoxybenzyl)tetrahydrofuran

5-Fluoro-2-methoxyphenacetaldehyde: To a suspension of methoxymethyltriphenylphosphonium chloride (10.0 g, 30.0 mmol) in THF (30 mL) under $Ar_{(g)}$ was added NaH (60% in mineral oil, 1.2 g, 30 mmol) and the mixture thus obtained was heated to reflux for 1 h. The orange suspension thus obtained was cooled to 0° C. and 5-fluoro-2-methoxybenzaldehyde (4.2 g, 26.0 mmol) was added and the reaction was continued for 12 h while warmed to room temperature. The reaction mixture was poured in to a separatory funnel containing ammonium chloride aqueous solution (sat. $NH_4Cl:H_2O=1:1$, 100 mL). The organic fraction was extracted with ethyl acetate (3×80 mL) and the combined organic layers were washed with brine (60 mL) and dried over sodium sulfate. The solvent was then removed in vacuo and crude product thus obtained was dissolved in acetone (50 mL) and $H_2SO_4$ (1 M, 1.5 mL) was added and the mixture thus obtained was heated to reflux for 6 h. It was then cooled to room temperature and the crude product obtained after the removal of the solvent was purified by flash column chromatography (10% ethyl acetate in hexane, $R_f=0.15$) to give the product (2.63 g, 66%) as an oil.

1-(2'-Methoxy-5'-fluorophenyl)hex-5-en-2-ol: To a solution of 1-butenylmagnesium bromide (0.5 M in THF, 9 mL, 4.5 mmol) at 0° C. was added a solution of 5-fluoro-2-methoxyphenylacetaldehyde (635 mg, 3.8 mmol) in THF (10 mL) dropwise for 15 min. Then the reaction mixture was poured in to a solution of saturated ammonium chloride (40 mL) in a separatory funnel. The organics were extracted with ethyl acetate (3×50 mL) and the combined organic layers were washed with brine (50 mL) and dried over sodium sulfate. The solvent was removed in vacuo and crude product thus obtained was purified by flash column chromatography (12.5% EtOAc in hexane, $R_f=0.18$) to give the product as an oil (642 mg, 74%).

2-(Bromomethyl)-5-(2'-methoxy-5'-fluorophenylmethyl)tetrahydrofuran (trans, cis, mixture): To a solution of 1-(2'-methoxy-5'-fluorophenyl)hex-5-en-2-ol (1.35 g, 6.0 mmol) in dry $CH_2Cl_2$ (30 mL) at 0° C. was added N-bromosuccinimide (NBS, 1.30 g, 7.2 mmol) portionwise and the reaction was warmed to room temperature for 12 h. Solvent was then removed in vacuo and the residue was purified by flash column chromatography (5% EtOAc in Hexane, $R_f=0.12$) to give in the trans isomer (663 mg, 36%) as an oil.

Trans-2-(N-Phthalimidomethyl)-5-(2'-methoxy-5'-fluorobenzyl)tetra-hydrofuran: To a vial under $Ar_{(g)}$ was added trans-2-(bromomethyl)-5-(2'-methoxy-5'-fluorobenzyl)tetrahydrofuran (0.45 g, 1.48 mmol), NaI (80 mg), potassium phthalimide (0.7 g, 3.7 mmol), and dry DMSO (5 mL). The mixture thus obtained was heated to 70° C. under Ar for 12 h. After it was cooled to room temperature, the reaction mixture was poured into a separatory funnel containing sodium bicarbonate aqueous solution (sat. $NaHCO_3:H_2O=1:1$, 50 mL). The organic fraction was extracted with ethyl acetate (3×50 mL) and the combined organic layers were washed with brine (50 mL) and dried over sodium sulfate. The solvent then was removed in vacuo and crude product thus obtained was purified by a flash column chromatography (15% EtOAc in hexane, $R_f=0.10$) to give the product (385 mg, 70%) as an oil.

Trans-2-Aminomethyl-5-(2'-methoxy-5'-fluorobenzyl)tetrahydrofuran: To a vial under Ar was added trans-2-(N-phthalimidomethyl)-5-(2'-methoxy-5'-fluorobenzyl)tetrahydrofuran (100 mg, 0.27 mmol), hydrazine hydrate (100 mg, 3.5 mmol), and methanol (5 mL). The mixture thus obtained was stirred at room temperature for 6 h. The solvent was then removed in vacuo and the crude product thus obtained was purified by flash column chromatography (10% methanol in $CH_2Cl_2$, 0.25% triethylamine, $R_f=0.09$) to give the product (54 mg, 60%, $R_f=0.10$) as a viscous oil.

Example 4

Trans-2-(Aminoethyl)-5-(2'-methoxy-5'-fluorobenzyl)tetrahydrofuran and N,N-Bis(trans-5'-(2"-methoxy-5"-fluorobenzyl-2'-tetrahydrofuranyl)-2-ethyl)amine Trans-2-(Cyanomethyl)-5-(2'-methoxy-5'-fluorobenzyl)tetrahydrofuran: To a vial under Ar was added 2-(bromomethyl)-5-(2'-methoxy-5'-fluorobenzyl)tetrahydrofuran (0.76 g, 2.5 mmol), NaI (80 mg), potassium cyanide (0.4 g, 6.3 mmol), and dry DMSO (5 mL). The mixture thus obtained was heated to 70° C. under Ar for 12 h. After it was cooled to room temperature, the reaction mixture was poured to a separatory funnel containing sodium bicarbonate aqueous solution (sat. NaHCO$_3$:H$_2$O=1:1, 40 mL). The organic fraction was extracted with ethyl acetate (2×50 mL) and the combined organic layers were washed with brine (50 mL) and dried over sodium sulfate. The solvent then was removed in vacuo and crude product thus obtained was purified by flash column chromatography (10% EtOAc in hexane). Careful analysis and collection of early fractions resulted in the trans isomer (170 mg, 27%).

N,N-Bis(trans-5'-(2"-methoxy-5"-fluorobenzyl-2'-tetrahydrofuryl)-2-ethyl)amine and trans-2-aminoethyl-5-(2'-methoxy-5'-fluorobenzyl)tetrahydrofuran: To a vial under Ar$_{(g)}$ was added Raney Ni that was washed with ethanol (100%, 3 times) and trans-2-(cyanomethyl)-5-(2'-methoxy-5'-fluorobenzyl)tetrahydrofuran (88.8 mg, 0.36 mmol) that was treated with a small amount of Raney Ni in ethanol. The vial was then evacuated and purged with H$_2$ three times each. Then a H$_2$ balloon was attached to the flask and charged with H$_2$ and the reaction was allowed to go for 6 days at room temperature. The reaction mixture was then filtered through a plug of Celite and the crude product obtained after the removal of the solvent was purified by flash column chromatography (10% MeOH in CH$_2$Cl$_2$, 1% TEA R$_f$=0.30) to result in (11 mg, 6%) as a 1:1 diastereomers; and (41 mg, 45%, R$_f$=0.09).

Similar methods were used to prepare: Cis-2-(aminoethyl)-5-(2'-methoxy-5'-fluorobenzyl)tetrahydrofuran and N,N-bis(cis-5'-(2"-methoxy-5"-fluorobenzyl-2'-tetrahydrofuranyl)-2-ethyl)amine.

Example 5

Trans-2-(Aminomethyl-5-(5'-fluoro-2'-methoxyphenethyl)tetrahydrofuran

Ethyl-3-(5'-fluoro-2'-methoxyphenyl)acrylate: To a solution of 5-fluoro-2-methoxybenzaldehyde (4.3 g, 28 mmol) in dry CH$_2$Cl$_2$ (40 mL) at 0° C. was added carbethoxymethylenetriphenylphosphorane (10.7 g, 30 mmol) portionwise and the reaction was warmed to room temperature for 12 h. The solvent was then removed in vacuo and the residue was purified by flash column chromatography (8% EtOAc in Hexane, R$_f$=0.20) to yield the product (4 g, 95%) as an oil.

Ethyl-3-(5'-fluoro-2'-methoxyphenyl)propionate: To a solution of ethyl-3-(5'-fluoro-2'-methoxyphenyl)acrylate (6.0 g, 27 mmol) in ethanol (100%, 80 mL) under Ar was added Pd/C (10%, 250 mg) very carefully and the flask containing the mixture was evacuated and purged with H$_2$ three time each. Then a H$_2$ balloon was attached to the flask and charged with H$_2$ and the reaction was allowed to go for 20 h at room temperature. Then the reaction mixture was filtered through a pad of silica eluted with mixed solvent of EtOAc and Hexane (1:1). The crude product that obtained by removal of the solvent in vacuo was purified by flash column chromatography (10% EtOAc in hexane, R$_f$=0.20) to give the product (5.8 g, 95%).

3-(5'-Fluoro-2'-methoxyphenyl)propionaldehyde: To a solution of ethyl-3-(5'-fluoro-2'-methoxyphenyl)propionate (5.8 g, 25.7 mmol) in dry toluene (40 mL) under Ar was added DIBAL solution (1 M in toluene, 30 mL, 30 mmol) at −78° C. The reaction was stirred at this temperature for 2 h. Methanol (2 mL) was added to the reaction mixture and the reaction was allowed to warm to 0° C. The reaction mixture was then poured into a separatory funnel containing HCl solution (1 N, 150 mL). The organic function was extracted with ethyl acetate (3×100 mL) and the combined organic layers were washed with brine (80 mL) and dried over sodium sulfate. The crude product that was obtained after removal of the solvent in vacuo was purified by flash column chromatography (20% EtOAc in hexane, R$_f$=0.20) to give the product (3.1 g, 66%).

1-(2'-Methoxy-5'-fluorophenyl)hept-5-en-3-ol: To a solution of 1-butenylmagnesium bromide (0.5 M in THF, 18 mL, 9.0 mmol) at 0° C. was added a solution of 3-(5'-fluoro-2'-methoxyphenyl)propionaldehyde (3.0 g, 16.5 mmol) in THF (30 mL) dropwise for 15 min. The reaction mixture was poured into a solution of saturated ammonium chloride (80 mL) in a separatory funnel. The organic function was extracted with ethyl acetate (3×80 mL) and the combined organic layers were washed with brine (80 mL) and dried over sodium sulfate. The solvent then was removed in vacuo and crude product thus obtained was purified by a flash column chromatography (15% EtOAc in hexane, R$_f$=0.20) to give the product as an oil (3.7 g, 94%).

2-(Bromomethyl)-5-(2'-methoxy-5'-fluorophenethyl)tetrahydrofuran (trans, cis): To a solution of 1-(2'-methoxy-5'-fluorophenyl)hept-5-en-3-ol (3.5 g, 14.7 mmol) in dry CH2Cl2 (90 mL) at 0° C. was added N-bromosuccinimide (NBS, 3.15 g, 17.0 mmol) portionwise and the reaction was warmed to room temperature for 12 h. Solvent was then removed in vacuo and the residue was purified by flash column chromatography (5% EtOAc in Hexane, R$_f$=0.12) to result in the trans isomer (2.05 g, 44%) as an oil; and the cis isomer (743 mg, 16%) as an oil; and mixture of both isomers (1.35 g, 29%).

Trans-2-(N-phthalimidomethyl)-5-(2'-methoxy-5'-fluorophenethyl)tetrahydrofuran: To a vial under Ar$_{(g)}$ was added trans-2-(bromomethyl)-5-(2'-methoxy-5'-fluorophenethyl) tetrahydrofuran (1.0 g, 3.2 mmol), NaI (75 mg), potassium phthalimide (1.5 g, 8 mmol), and dry DMSO (10 mL). The mixture thus obtained was heated to 70° C. under Ar for 12 h. After it was cooled to room temperature, the reaction mixture was poured into a separatory funnel containing sodium bicarbonate aqueous solution (sat. NaHCO$_3$: H$_2$O=1:1, 70 mL). The organics were extracted with ethyl acetate (3×60 mL) and the combined organic layers were washed with brine (50 mL) and dried over sodium sulfate. The solvent was removed in vacuo and crude product thus obtained was purified by a flash column chromatography (20% EtOAc in hexane, R$_f$=0.12) to give the product (0.695 g, 57%).

Trans-2-(Aminomethyl-5-(5'-fluoro-2'-methoxyphenethyl)tetrahydrofuran: To a vial under Ar$_{(g)}$ was added trans-2-(N-phthalimidomethyl)-5-(2'-methoxy-5'-fluorophenethyl)tetrahydrofuran (380 mg, 1.0 mmol), hydrazine hydrate (287 mg, 9 mmol), and methanol (10 mL). The mixture thus obtained was stirred at room temperature for 12 h. The solvent was then removed in vacuo and the crude product thus obtained was purified by column flash chromatography (10% methanol in CH$_2$Cl$_2$, 0.25% triethylamine) to give the title compound (197 mg, 78%, R$_f$=0.08, trans:cis=0.95:0.05).

Similar methods were used to prepare: 2-(aminomethyl)-5-(phenethyl)tetrahydrofuran, 2-(aminomethyl)-5-(4'-fluorophenethyl)tetrahydrofuran, 2-(aminomethyl)-5-(3'-pyridylethyl)tetrahydrofuran, 2-(aminomethyl)-5-(2'-chloro-5'-trifluoromethylphenethyl)tetrahydrofuran, 2-(aminomethyl)-5-(pentafluorophenethyl)tetrahydrofuran, 2-(aminomethyl)-5-(2'-methoxy-5'-fluorophenyl)tetrahydrofuran, 2-(aminoethyl)-5-(3',4'-dimethoxyphenethyl)tetrahydrofuran, 2-(aminomethyl)-5-(1'-naphthylethyl)tetrahydrofuran, 2-(aminomethyl)-5-(2'-methoxy-1'-naphthylethyl) tetrahydrofuran, 2-(aminomethyl)-5-(4'-methoxy-1'-naphthylethyl)tetrahydrofuran, 2-(aminomethyl)-5-(-2"-tetrahydrofuryl-2'-ethyl)tetrahydrofuran.

Example 6

Trans-2-(Aminoethyl)-5-(5'-fluoro-2'-methoxyphenethyl)tetrahydrofuran and N,N-Bis(trans-5-(2'-methoxy-5'-fluorophenyl-2-tetrahydrofuryl)ethyl)amine Trans-2-(Cyanomethyl)-5-(2'-methoxy-5'-fluorophenethyl)tetrahydrofuran: To a vial under $Ar_{(g)}$ was added 2-(bromomethyl)-5-(2'-methoxy-5'-fluorophenethyl)tetrahydrofuran (0.67 g, 2.1 mmol), NaI (70 mg), potassium cyanide (0.35 g, 5.3 mmol), and dry DMSO (5 mL). The mixture thus obtained was heated to 70° C. under Ar for 12 h. After it was cooled to room temperature, the reaction mixture was poured into a separatory funnel containing sodium bicarbonate aqueous solution (sat. $NaHCO_3$:$H_2O$=1:1, 40 mL). The organic function was extracted with ethyl acetate (2×50 mL) and the combined organic layers were washed with brine (50 mL) and dried over sodium sulfate. The solvent then was removed in vacuo and crude product thus obtained was purified by flash column chromatography (15% EtOAc in hexane) to result in the title product (448 mg, 86%).

N,N-Bis(trans-5'-(2"-methoxy-5"-fluorophenethyl-2'-tetrahydrofuranyl)-2-ethyl)amine and trans-2-(aminoethyl)-5-(2'-methoxy-5'-fluorophenethyl)tetrahydrofuran: To a vial under Ar was added Raney Ni that was washed with ethanol (200 proof, 3 times) and trans-2-(Cyanomethyl)-5-(2'-methoxy-5'-fluorophenethyl)tetrahydrofuran (448 mg, 1.8 mmol) that was treated with a small amount of Raney Ni in ethanol. The vial was then evacuated and purged with $H_2$ three times each. Then a $H_2$ balloon was attached to the flask and charged with $H_2$ and the reaction was allowed to go for 4 days at room temperature. The reaction mixture was then filtered through a plug of Celite and the crude product obtained after the removal of the solvent was purified by flash column chromatography (10% MeOH in $CH_2Cl_2$, 1% TEA $R_f$=0.30) to result in (114 mg, 24%) as a 1:1 diastereomers; and (192 mg, 40%, $R_f$=0.09).

Similar methods were used to prepare: 2-(aminoethyl)-5-(phenethyl)tetrahydrofuran, 2-(aminoethyl)-5-(4'-fluorophenethyl)tetrahydrofuran, 2-aminoethyl-5-((2"-methoxy-5"-fluorophenyl)-3'-propyl)tetrahydrofuran, 2-(aminoethyl)-5-(4'-hydroxyphenethyl)tetrahydrofuran, 2-(aminoethyl)-5-(4'-methoxyphenethyl)tetrahydrofuran, 2-(aminoethyl)-5-(4'-trifluoromethoxyphenethyl)tetrahydrofuran, 2-(aminoethyl)-5-(4'-methylphenethyl)tetrahydrofuran, 2-(aminoethyl)-5-(4'-phenylphenethyl)tetrahydrofuran, 2-(aminoethyl)-5-(4'-t-butylphenethyl)tetrahydrofuran, 2-(aminoethyl)-5-(5'-fluoro-2'-methoxyphenethyl)tetrahydrofuran, 2-(aminoethyl)-5-(4'-fluoro-3'-methylphenethyl)tetrahydrofuran, 2-(aminoethyl)-5-(3'-fluoro-4'-methylphenethyl)tetrahydrofuran, 2-(aminoethyl)-5-(cyclohexylethyl)tetrahydrofuran, 2-(aminoethyl)-5-(3'-pyridylethyl)tetrahydrofuran, 2-(aminoethyl)-5-(4'-pyridylethyl)tetrahydrofuran, 2-(aminoethyl)-5-(1'-naphthylethyl)tetrahydrofuran, 2-(aminoethyl)-5-(2'-methoxy-1'-naphthylethyl)tetrahydrofuran, 2-(aminoethyl)-5-(4'-methoxy-1'-naphthylethyl)tetrahydrofuran, 2-(aminoethyl)-5-(2'-naphthylethyl)tetrahydrofuran, and N,N-bis(5'-phenethyl-2'-tetrahydrofurylethyl)amine, N,N-bis(5'-phenethyl-2'-tetrahydrofurylethyl)methylamine, N,N-bis(5'-(p-hydroxyphenethyl)-2'-tetrahydrofurylethyl)amine, N,N-bis(5'-(m-fluoro-p-methylphenethyl)-2'-tetrahydrofurylethyl)amine, N,N-bis(5'-(p-fluoro-m-methylphenethyl)-2'-tetrahydrofurylethyl)amine, N,N-bis(5'-(5"-fluoro-2"-methoxyphenethyl)-2'-tetrahydrofurylethyl)amine, N,N-bis(5'-(3"-pyridylethyl)-2'-tetrahydrofurylethyl)amine, N,N-bis(5'-(4"-pyridylethyl)-2'-tetrahydrofurylethyl)amine, N,N-bis(5'-(1"-naphthethyl)-2'-tetrahydrofurylethyl)amine, N,N-bis(5'-(2"-methoxy-1"-naphthethyl)-2'-tetrahydrofurylethyl)amine, N,N-bis(5'-(4"-methoxy-1"-naphthethyl)-2'-tetrahydrofurylethyl)amine and related compounds.

Example 7

Trans-2-(Aminomethyl)-5-((2"-methoxy-5"-fluorophenyl)-3' propyl)tetrahydrofuran

Ethyl-4-(5'-fluoro-2'-methoxyphenyl)butyrate: To a solution of ethyl-3-(5'-fluoro-2'-methoxybenzyl)acrylate (2.36 g, 10.0 mmol) in ethanol (100%, 40 mL) under $Ar_{(g)}$ was added Pd/C (10%, 200 mg) very carefully and the flask containing the mixture was evacuated and purged with $H_2$ three time each. Then a balloon was attached to the flask and the reaction was allowed to go for 15 h at room temperature. The reaction mixture was filtered through a pad of silica eluted with mixed solvent of EtOAc and Hexane (1:1). The crude product that obtained by removal of the solvent in vacuo was purified by a flash column chromatography (10% EtOAc in hexane, $R_f$=0.20) to give the product (2.25 g, 95%).

4-(5'-Fluoro-2'-methoxyphenyl)butyraldehyde: To a solution of ethyl-4-(5'-fluoro-2'-methoxyphenyl)butyrate (2.25 g, 9.4 mmol) in dry toluene (30 mL) under $Ar_{(g)}$ was added DIBAL solution (1 M in toluene, 11 mL, 11 mmol) at −78° C. Then the reaction was stirred at this temperature for 2 h. Methanol (2 mL) was then added to the reaction mixture and the reaction was allowed to warm to 0° C. The reaction mixture was poured into a separatory funnel containing HCl solution (1 N, 100 mL). The organic function was extracted with ethyl acetate (3×60 mL) and the combined organic layers were washed with brine (80 mL) and dried over sodium sulfate. The crude product that obtained by removal of the solvent in vacuo was purified by flash column chromatography (10% EtOAc in hexane, $R_f$=0.10) to give the product (1.30 g, 70%).

8-(5'-Fluoro-2'-methoxyphenyl)oct-1-en-5-ol: To a solution of 4-(5'-fluoro-2'-methoxyphenyl)butyraldehyde (1.30 g, 6.6 mmol) in THF (15 mL) at 0° C. was added a solution 1-butenylmagnesium bromide (0.5 M in THF, 15 mL, 7.5 mmol) dropwise for 5 min. Then the reaction mixture was poured to a solution of saturated ammonium chloride (60 mL) in a separatory funnel. The organics were extracted with ethyl acetate (3×50 mL) and the combined organic layers were washed with brine (40 mL) and dried over sodium sulfate. The solvent then was removed in vacuo and crude product thus obtained was purified by a flash column chromatography (12.5% EtOAc in hexane, $R_f$=0.15) to give the product as a colorless oil (1.06 g, 61%).

Trans-2-(Bromomethyl)-5-((2"-methoxy-5"-fluorophenyl)-3'-propyl)tetrahydrofuran: To a solution of 8-(5'-fluoro-2'-methoxyphenyl)oct-1-en-5-ol (1.01 g, 4.01 mmol) in dry $CH_2Cl_2$ (30 mL) at 0° C. under $Ar_{(g)}$ was added N-bromosuccinimide (NBS, 890 mg, 5.0 mmol) portionwise and the reaction was warmed to room temperature for 12 h. Solvent was then removed in vacuo and the residue was purified by flash column chromatography (5% EtOAc in hexane, $R_f$=0.10) to result in the cis isomer enriched product (530 mg, >85% of cis-isomer, 40%) as a colorless oil.

2-(N-Phthalimidomethyl)-5-((2"-methoxy-5"-fluorophenyl)-3'-propyl)tetrahydrofuran: To a vial under Ar was added trans-2-(bromomethyl)-5-((2"-methoxy-5"-fluorophenyl)-3'-propyl)tetrahydrofuran (221 mg, 0.61 mmol), NaI (50 mg), potassium phthalimide (300 mg, 1.50 mmol), and dry DMSO (4 mL). The mixture thus obtained was heated to 70° C. under Ar for 12 h. After it was cooled to room temperature, the reaction mixture was poured into a separatory funnel containing sodium bicarbonate aqueous solution (sat. NaHCO$_3$: H$_2$O=1:1, 30 mL). The organic function was extracted with ethyl acetate (3×30 mL) and the combined organic layers were washed with brine (30 mL) and dried over sodium sulfate. The solvent then was removed in vacuo and crude product thus obtained was purified by flash column chromatography (15% EtOAc in hexane, R$_f$=0.09) to give the product (151 mg, 62%) as an oil.

Trans-2-Aminomethyl-5-((2"-methoxy-5"-fluorophenyl)-3'-propyl)tetrahydrofuran: To a vial under Ar was added 2-(N-phtlilimidomethyl)-5-((2"-methoxy-5"-fluorophenyl)-3'-propyl)tetrahydrofuran (72 mg, 0.18 mmol), hydrazine hydrate (70 mg, 2.4 mmol), and methanol (4 mL). The mixture thus obtained was stirred at room temperature for 12 h. The solvent was then removed in vacuo and the crude product thus obtained was purified by flash column chromatography (12.5% methanol in CH2Cl2, 1% triethylamine R$_f$=0.09) to give the product (42 mg, 87%) as a viscous oil.

Similar methods were used to prepare: cis-2-(aminomethyl)-5-((2"-methoxy-5"-fluorophenyl)-3'-propyl)tetrahydrofuran.

Example 8

Trans-2-(Aminoethyl)-5-(2"-methoxy-5"-fluorophenyl-3'-propyl)tetrahydrofuran and N,N-Bis(trans-5-(2"-methoxy-5"-fluorophenyl-3'-propyl-2'-tetrahydrofuryl)ethyl)amine Trans-2-(Cyanomethyl)-5-(2"-methoxy-5"-fluorophenyl-3'-propyl)tetrahydrofuran: To a vial under Ar was added 2-(bromomethyl)-5-(2"-methoxy-5"-fluorophenyl-3'-propyl)tetrahydrofuran (0.10 g, 0.3 mmol), NaI (20 mg), potassium cyanide (0.15 g, 2.5 mmol), and dry DMSO (5 mL). The mixture thus obtained was heated to 70° C. under Ar for 12 h. After it was cooled to room temperature, the reaction mixture was poured to a separatory funnel containing sodium bicarbonate aqueous solution (sat. NaHCO$_3$: H$_2$O=1:1, 40 mL). The organic function was extracted with ethyl acetate (2×50 mL) and the combined organic layers were washed with brine (50 mL) and dried over sodium sulfate. The solvent then was removed in vacuo and crude product thus obtained was purified by flash column chromatography (15% EtOAc in hexane) to result in the title product (71 mg, 89%).

N,N-Bis(trans-5-(2"-methoxy-5"-fluorophenyl-3'-propyl-2'-tetrahydrofuryl)ethyl)amine and trans-2-(aminoethyl)-5-(2"-methoxy-5"-fluorophenyl-3'-propyl)tetrahydrofuran: To a vial under Ar was added Raney Ni that was washed with ethanol (100%, 3 times) and trans-2-(cyanomethyl)-5-(2"-methoxy-5"-fluorophenyl-3'-propyl)tetrahydrofuran (71 mg, 0.27 mmol) that was treated with a small amount of Raney Ni in ethanol. The vial was then evacuated and purged with H$_2$ three times each. Then a balloon was attached to the flask and the reaction was allowed to go for 4 days at room temperature. The reaction mixture was then filtered through a plug of Celite and the crude product obtained after the removal of the solvent was purified by flash column chromatography (10% MeOH in CH$_2$Cl$_2$, 1% TEA R$_f$=0.30) to result in (7 mg, 19%) as a 1:1 diastereomers; and (36 mg, 50%, R$_f$=0.09).

Similar methods were used to prepare: cis-2-aminoethyl-5-(2"-methoxy-5"-fluorophenyl-3'-propyl)tetrahydrofuran.

Example 9

Cis-2-(Phenethylaminoethyl)-5-(2'-methoxy-5'-fluorophenyl)tetrahydrofuran

Cis-2-(Phenethylaminoethyl)-5-(2'-methoxy-5'-fluorophenyl)tetrahydrofuran: To a vial under Ar was added phenylacetaldehyde (18 mg, 0.15 mmol), cis-2-aminoethyl-5-(2'-methoxy-5'-fluorophenyl)tetrahydrofuran (30 mg, 0.13 mmol) and MeOH (5 mL) and the mixture thus obtained was stirred at room temperature for 30 min. NaCNBH$_3$ (20 mg, 0.30 mg) was added and the reaction was continued for 12 h. Solvent was removed and the product was purified by flash column chromatography (5% MeOH in CH$_2$Cl$_2$, 0.1% TEA, R$_f$=0.3) resulted in the product (14 mg, 31%).

Similar methods were used to prepare: cis-2-(phenethylaminoethyl)-5-(2'-methoxy-5'-fluorophenyl)tetrahydrofuran, trans-2-(dimethylaminomethyl)-5-(2'-methoxy-5'-fluorophenyl)tetrahydrofuran, N,N-bis(5'-phenethyl-2'-tetrahydrofurylethyl)methylamine.

Example 10

Trans-2-(Morpholinomethyl-5-(2'-methoxy-5'-fluorophenylethyl)tetrahydrofuran

To a flask under Ar was added trans-2-(bromomethyl)-5-(2'-methoxy-5'-fluorophenethyl)tetrahydrofuran (43 mg, 0.136 mmol), NaI (30 mg), morpholine (65 mg, 0.75 mmol), NaHCO$_3$ (130 mg) and dry DMSO (2.5 mL) and dry THF (4 mL). The mixture thus obtained was heated to reflux under Ar$_{(g)}$ for 12 h. After it was cooled to room temperature, the reaction mixture was poured to a separatory funnel containing sodium bicarbonate aqueous solution (sat. NaHCO$_3$: H$_2$O=1:1, 30 mL). The organic function was extracted with ethyl acetate (3×30 mL) and the combined organic layers were washed with brine (30 mL) and dried over sodium sulfate. The solvent then was removed in vacuo and crude product thus obtained was purified by flash column chromatography (2% MeOH in CH$_2$Cl$_2$, 0.1% TEA, R$_f$=0.21) to give the product (29 mg, 66%) as an oil.

Similar methods were used to prepare: trans-2-(piperidinomethyl)-5-(2"-methoxy-5"-fluorophenyl-3'-propyl)tetrahydrofuran, trans-2-piperidylmethyl-5-(2'-methoxy-5'-fluorophenylethyl)tetrahydrofuran.

Example 11

Trans-2-(N,N-diethylaminomethyl)-5-(2'-methoxy-5'-fluorophenethyl)tetrahydrofuran To a vial under Ar was added trans-2-(bromomethyl)-5-(2'-methoxy-5'-fluorophenethyl)tetrahydrofuran (50 mg, 0.16 mmol), NaI (30 mg), diethylamine (55 mg, 0.75 mmol), NaHCO$_3$ (120 mg), and dry DMSO (4 mL). The mixture thus obtained was heated to 50° C. under Ar for 72 h. After it was cooled to room temperature, the reaction mixture was poured into a separatory funnel containing sodium bicarbonate aqueous solution (sat. NaHCO$_3$:H$_2$O=1:1, 30 mL). The organic function was extracted with ethyl acetate (3×30 mL) and the combined organic layers were washed with brine (30 mL) and dried over sodium sulfate. The solvent then was removed in vacuo and crude product thus obtained was purified by flash column chromatography (15% EtOAc in hexane, R$_f$=0.09) to give the product (14 mg, 28%) as an oil.

Example 12

Trans-2-(Isothiocyanomethyl)-5-(2'-methoxy-5'-fluorophenethyl)tetrahydrofuran

To a solution of trans-2-(bromomethyl)-5-(2'-methoxy-5'-fluorophenethyl)tetrahydrofuran (33 mg, 0.13 mmol) in CHCl$_3$ (6 mL) was added a solution of NaHCO$_3$ (50 mg, in 3 mL of water) and the mixture was cooled to 0° C. A solution of thiophosgene (30 mg, 0.26 mmol) in CHCl$_3$ (1 mL) was added and the reaction was stirred for 2 h. then the reaction mixture was partitioned between water (20 mL) and CH$_2$C$_{12}$ (30 mL) and the organic layer was collected and dried over Na$_2$SO$_4$. The solvent was removed in vacuo and the crude product thus obtained was purified by flash chromatography (22 mg, 57%).

Example 13

3,4-Dimethoxyphenylmagnesium bromide

In a flame dried round bottom flask with magnetic stir bar was put anhydrous THF (150 mL) and Mg(s) turnings (1.43 g, 58.8 mmol, 1.0 eq). The flask was then fitted with a pressure equalizing addition funnel containing 4-bromo-1,2-dimethoxybenzene (12.7 g, 59 mmol, 1.03 eq) in THF (50 mL). The 4-bromo-1,2-dimethoxybenzene solution was then added dropwise over a period of 45 min while stirring at room temperature. Once the addition was complete I$_2$ (500 mg) was added and then the reaction was brought to reflux for 12 hr. The Grignard reagent was then used immediately to make the 6-(3,4-dimethoxy-benzoyl)-cyclohex-3-enecarboxylic acid.

Example 14

6-(3,4-dimethoxy-benzoyl)-cyclohex-3-enecarboxylic acid

A solution of 3,4-dimethoxyphenylmagnesium bromide (59 mmol, 0.29 M) in THF was added dropwise to an ice-cooled solution of cis-1,2,3,6-tetrahydrophthalic anhydride in THF (120 mL) over a 1 h period. After the addition was complete, the resulting mixture was stirred for another 30 min at 0° C. The reaction mixture was allowed to warm to room temperature overnight. The reaction was quenched with sat. NH$_4$Cl$_{(aq)}$ and then the pH was adjusted to 2 with concentrated HCl$_{(aq)}$ and extracted with diethyl ether. The combined organic extracts were washed with water and subsequently extracted with 1 M NaOH$_{(aq)}$. The combined aqueous extracts were neutralized with conc. HCl$_{(aq)}$ and extracted with EtOAc. The combined organic extracts were dried over MgSO$_4$, filtered through paper, and concentrated under reduced pressure to give an oil. The oil was dissolved in CH$_2$Cl$_2$ and filtered through silica to remove any dicarboxylic acid formed during the reaction work up. The product was recrystallized in diethyl ether to afford a white solid (1.62 g, 5.58 mmol, 10%).

Example 15

4-(3,4-Dimethoxy-phenyl)-4a,5,8,8a-tetrahydro-2H-phthalazin-1-one

A mixture of 6-(3,4-dimethoxy-benzoyl)-cyclohex-3-enecarboxylic acid (112 mg, 0.39 mmol, 1.0 eq) and hydrazine hydrate (31 mg, 0.96 mmol, 2.5 eq) in EtOH (3 mL) was refluxed for 4 hr. The reaction was then cooled to room temperature and then concentrated under reduced pressure to oil. The oil was dissolved in EtOAc and washed with water followed by brine. The organic layer was then dried over Na$_2$SO$_4$, filtered through paper, and concentrated under reduced pressure to oil. The product was recrystallized in EtOH to yield a white solid.

Example 16

2-(5-Bromo-pentyl)-4-(3,4-dimethoxyphenyl)-4a,5,8,8a-tetrahydro-2H-phthalaxin-1-one Sodium hydride (60% dispersion in oil, 44 mg, 1.1 mmol, 1.1 eq) was added to a solution of 4-(3,4-dimethoxy-phenyl)-4a,5,8,8a-tetrahydro-2H-phthalazin-1-one (287 mg, 1.0 mmol, 1.0 eq). The mixture was stirred for 30 min whereupon it took on a slight yellow color and then 1,5-dibromopentane (600 mg, 2.6 mmol, 2.6 eq) was added via syringe. After 30 min the yellow color had diminished and the reaction was poured into water. The solution was extracted with Et$_2$O and washed with brine. The organic layer was dried over MgSO$_4$, filtered through paper, and concentrated under reduced pressure to provide a clear oil. The product was chromatographed through silica with CH$_2$Cl$_2$ to afford a clear oil.

Example 17

4-(3,4-Dimethoxyphenyl)-2-[5-(2-{5-[2-(5-fluoro-2-methoxyphenyl)-ethyl]-tetrahydrofuran-2-yl}-ethylamino)-pentyl]-4a,5,8,8a-tetrahydro-2H-phthalazin-1-one Cesium hydroxide monohydrate (23 mg, 0.14 mmol, 1.0 eq) and DMF (0.5 mL) was stirred in a flame dried round bottom flask under Ar$_{(g)}$ for 30 min at room temperature. Then 2-aminoethyl-5-(2'-methoxy-5'-fluoro phenethyltetrahydrofuran (37 mg, 0.14 mmol, 1.0 eq) in DMF (0.3 mL) was added via syringe and stirred at room temperature for 30 min. 2-(5-Bromo-pentyl)-4-(3,4-dimethoxyphenyl)-4a,5,8,8a-tetrahydro-2H-phthalazin-1-one (72 mg, 0.16 mmol, 1.2 eq) in DMF (0.3 mL) was added and continued to stir for 24 hr at room temperature. The reaction was filtered through paper with EtOAc (30 mL) and then the filtrate was washed with water in a seperatory funnel. The organic layer was dried with Na$_2$SO$_4$, filtered through paper, and concentrated to give an oil. The product was purified with prep TLC eluted with 5% MeOH in CH$_2$Cl$_2$ to afford a yellow oil (27 mg, 0.04 mmol, 31%).

Similar methods were used to prepare 4-(3,4-Dimethoxyphenyl)-2-[5-(2-{5-[2-(5-fluoro-2-methoxyphenyl)-propyl]-tetrahydrofuran-2-yl}-ethylamino)-pentyl]-4a,5,8,8a-tetrahydro-2H-phthalazin-1-one, 4-(3-Cyclopentyloxy-4-methoxy-phenyl)-1-[5-(2-{5-[2-(5-fluoro-2-methoxy-phenyl)-ethyl]-tetrahydro-furan-2-yl}-ethylamino)-pentyl]-pyrrolidin-2-one, 4-(3-Cyclopentyloxy-4-methoxy-phenyl)-1-[5-(2-{5-[3-(5-fluoro-2-methoxy-phenyl)-propyl]-tetrahydro-furan-2-yl}-ethylamino)-pentyl]-pyrrolidin-2-one, 4-(3,4-Dimethoxy-phenyl)-2-{5-[3-phenyl-3-(4-trifluoromethyl-phenoxy)-propylamino]-pentyl}-4a,5,8,8a-tetrahydro-2H-phthalazin-1-one, 4-(3-Cyclopentyloxy-4-methoxy-phenyl)-1-{5-[3-phenyl-3-(4-trifluoromethyl-phenoxy)-propylamino]-pentyl}-pyrrolidin-2-one, 2-(3-{5-[4-(3,4-Dimethoxy-phenyl)-1-oxo-4a,5,8,8a-tetrahydro-1H-phthalazin-2-yl]-pentylamino}-propyl)-2-(4-fluoro-phenyl)-2,3-dihydro-benzofuran-6-carbonitrile, 2-(3-{5-[4-(3-Cyclopentyloxy-4-methoxy-phenyl)-2-oxo-pyrrolidin-1-yl]-pentylamino}-propyl)-2-(4-fluoro-phenyl)-2,3-dihydro-benzofuran-6-carbonitrile, 4-(3,4-Dimethoxy-phenyl)-2-(5-{[5-(4-methoxy-phenyl)-tetrahydro-furan-2-ylmethyl]-amino}-pentyl)-4a,5,8,8a-tetrahydro-2H-phthalazin-1-one, 4-(3-Cyclopentyloxy-4-methoxy-phenyl)-1-(5-{[5-(4-methoxy-phenyl)-tetrahydro-furan-2-ylmethyl]-amino}-pentyl)-pyrrolidin-2-one, 2-{5-[(5-Cyclohexyl-tetrahydro-furan-2-ylmethyl)-amino]-pentyl}-4-(3,4-dimethoxy-phenyl)-4a,5, 8,8a-tetrahydro-2H-phthalazin-1-one, 1-{5-[(5-Cyclohexyl-tetrahydro-furan-2-ylmethyl)-amino]-pentyl}-4-(3-cyclopentyloxy-4-methoxy-phenyl)-pyrrolidin-2-one, 4-(3,4-Dimethoxy-phenyl)-2-(5-{[5-(3-fluoro-4-methyl-phenyl)-tetrahydro-furan-2-ylmethyl]-amino}-pentyl)-4a,5,8,8a-tetrahydro-2H-phthalazin-1-one, 4-(3-Cyclopentyloxy-4-methoxy-phenyl)-1-(5-{[5-(3-fluoro-4-methyl-phenyl)-tetrahydro-furan-2-ylmethyl]-amino}-pentyl)-pyrrolidin-2-one.

Example 18

(S)-2-Pyrrolidine Methanol

A suspension of lithium aluminium hydride (3.8 g, 0.1 mol) in 160 mL THF was refluxed for 15 min. (S)-Proline (7.4 g, 0.06 mol) was added in small portions to the refluxing mixture at a rate to keep the reaction under reflux without external heating. The mixture was refluxed for an additional 1 hr. The reaction was stopped by careful addition of potassium hydroxide solution (1.8 g in 7.2 mL H2O) with reduced heat. The mixture was then refluxed for 15 min and the hot solution was filtered. The precipitate was refluxed with THF for an hour and filtered once more. The combined filtrates were concentrated under reduced pressure and used for the next step without further purification in quantitative yield.

Example 19

1-tBoc-2-Hydroxymethyl Pyrrolidine

Pyrrolidine methanol (2 g, 20 mmol) in 20 mL dichloromethane was placed in a round bottom flask. To the dichloromethane solution, di-t-butyldicarbonate (4.8 g, 2.2 mmol) in 10 mL dichloromethane was slowly added at 0° C. The mixture was stirred for 30 min at 0° C. and the reaction was stopped by addition of 30 mL saturated sodium carbonate at 0° C. The aqueous layer was separated and extracted three times with 30 mL dichloromethane. The organic layers were combined, dried over sodium sulfate, filtered, and concentrated in vacuo. The residue was purified by silica column chromatography MeOH/$CH_2Cl_2$ (5:95, v:v) to give 1-tBoc-2-hydroxymethylpyrrolidine in 92% yield.

Example 20

1-tBoc-2-Formyl Pyrrolidine

Dimethyl sulfoxide (2.66 mL, 37.5 mmol) in 6 mL dichloromethane was added dropwise to oxalyl chloride (2.1 g, 16.5 mmol) in 30 mL dichloromethane at −78° C. After 5 min, 1-tBoc-2-hydroxymethylpyrrolidine (3 g, 15 mmol) was added dropwise to the solution. After another 15 min, 10 mL of triethylamine was added dropwise to the solution and the mixture was stirred for 5 min. The mixture was brought to 25° C. and the reaction was stopped by the addition of 50 mL water. The aqueous layer was separated and extracted three times with 50 mL dichloromethane. The organic layers were combined and washed with 100 mL each of water, 5% sodium carbonate, water, and saturated sodium chloride. The organic solution was then dried over sodium sulfate, filtered, and concentrated in vacuo to give 1-tBoc-2-formyl pyrrolidine. The product was used for the next step without further purification: 52% yield.

Example 21

1-tBoc-2-Styrenyl Pyrrolidine

Benzyltriphenylphosphonium chloride (3.89 g, 10 mmol) in 10 mL diethyl ether was placed in a round bottom flask. The solution was cooled to −78° C. and nBuLi (4 mL of 2.5M nBuLi in hexane, 10 mmol) was added dropwise to the solution. After 30 min, the suspension was added dropwise to 1-tBoc-2-formyl pyrrolidine (2 g, 10 mmol) in 10 mL diethyl ether at −78° C. and the mixture was stirred for 3 hours. The reaction was stopped with 50 mL $H_2O$, the organic layer was separated from the aqueous layer, and the aqueous layer was extracted 3 times with 50 mL diethyl ether. The combined organic layer was washed with $H_2O$ until the pH of the aqueous layer was 7, dried over $Na_2SO_4$, filtered and concentrated in vacuum. The residue was purified by silica column chromatography EtOAc/hexane (10:90, v:v), 1.1 g, 40% yield.

Example 22

2-Styrenyl Pyrrolidine

A solution of 1-tBoc-2-phenethyl pyrrolidine (230 mg, 0.84 mmol) in 5 mL trifluoroacetic acid was stirred for 30 min at 0° C. The trifluoroacetic acid was removed under reduced pressure. The residue was dissolved in 5 mL diethyl ether and the ethereal solution was washed with 5 mL saturated $Na_2CO_3$ and extracted twice with 2 mL of 1N HCl. The combined HCl solution was then basicified with saturated $Na_2CO_3$ to pH=10 and extracted three times with 5 mL dichloromethane. The combined dichloromethane layers were washed with 10 mL saturated NaCl, dried over $Na_2SO_4$, filtered, and concentrated in vacuum. The residue was purified on thin layer chromatography to give 2-phenethyl pyrrolidine: 120 mg, 82% yield.

Example 23

1-Methyl-2-Styrenyl Pyrrolidine

Sodium cyanoborohydride (17.4 mg, 0.27 mmol) was added portion-wise to a stirred solution of 2-phenethyl pyrrolidine (30 mg, 0.17 mmol) and 37% aqueous formaldehyde (0.07 mL, 0.87 mmol) in 1.5 mL acetonitrile at 25° C. The mixture was stirred for 15 min, acetic acid was added dropwise until the reaction was neutral, and the mixture was stirred for an additional 2 hours. The solvent was removed under reduced pressure. The residue was dissolved in 10 mL diethyl ether and the ethereal solution was washed with 10 mL of saturated $Na_2CO_3$ and extracted twice with 5 mL of 1N HCl. The combined HCl solutions were then basicified with saturated $Na_2CO_3$ to obtain a pH=10 and extracted three times with 10 mL dichloromethane. The combined dichloromethane layers were washed with 10 mL of saturated NaCl, dried over $Na_2SO_4$, filtered, and concentrated in vacuo. The residue was purified on thin layer chromatography to give 1-methyl-2-phenethyl pyrrolidine free base; 18 mg, 55% yield.

Example 24

(2-{5-[2-(5-Fluoro-2-methoxy-phenyl)-ethyl]-tetrahydro-furan-2-yl}-ethyl)-carbamic ethyl ester In a flame dried 20 mL scintillation vial was placed $K_2CO_3$ (239 mg, 1.73 mmol, 6.0 eq) and of anhydrous THF (5.0 mL).

The vial was purged with $Ar_{(g)}$ and then chilled in an ice bath. Ethyl chloroformate (156 mg, 1.44 mmol, 5.0 eq) was then added via syringe followed by a slow addition of the primary amine (77 mg, 0.29 mmol, 1.0 eq) dissolved in THF (1.5 mL). The reaction stirred at 0° C. for 0.5 hrs and then let warm to rt and let stir an additional 3 hrs. The reaction was then quenched with sat. $NaHCO_{3(aq)}$ and extracted with EtOAc (3×20 mL). The organic layer was washed with brine and dried over $Na_2SO_4$, filtered through paper, and concentrated under reduced pressure to yield crude product that was a mixture of cis and trans and used in the next step of the synthesis.

Similar methods were used to prepare (2-{5-[3-(5-Fluoro-2-methoxy-phenyl)-propyl]-tetrahydro-furan-2-yl}-ethyl)-carbamic acid ethyl ester.

Example 25

N-Methyl-2-aminoethyl-5-(2'-methoxy-5'-fluoro phenethyltetrahydro furan

In a flame dried round bottom flask, purged with $Ar_{(g)}$, was put the carbamate (112 mg, 0.33 mmol, 1.0 eq) and anhydrous THF (1.6 mL). The flask was then cooled with an ice bath while stirring for 15 min. LAH (1.0 M, 1.32 mL, 1.32 mmol, 4.0 eq) was then slowly added via a syringe over a period of 5 min. The reaction was allowed to warm to rt and stirred an additional 4 hrs. The reaction was then quenched with ice cold MeOH and then stirred at rt for an additional 15 min. The resulting solution was transferred to a beaker with the aid of 1N $HCl_{(aq)}$ and then made basic with 10M $NaOH_{(aq)}$. The basic solution was then extracted with $Et_2O$ (3×20 mL) and then the organic layer was washed with brine. The $Et_2O$ layer was dried over $Mg_2SO_4$ for 15 min and then filtered through paper and concentrated to oil under reduced pressure to afford the crude product. The oil was purified with PTLC and $MeOH:CH_2Cl_2$ (5:95) in 45% yield.

Similar methods were used to prepare N-Methyl-2-aminoethyl-5-((2"-methoxy-5"-fluorophenyl)-3'-propyl)tetrahydrofuran.

Example 26

High Throughput Kinase Assay for Identifying Stimulators of GRK2

A homogenous KinaseGlo assay was developed and conducted in a 96-well format. Briefly, the assay design allowed large numbers of tests to be done in a high throughput fashion using a 96-well plate reader system. The KinaseGlo assay involved transfer of γ-phosphate from [γ$^{33}$P]ATP by GRK2 to tubulin. The assay was robust and efficient. GRK2 was chosen as our target protein for several important reasons including: a) GRK2 was available in highly purified form from our collaborator (Professor Benovic, Thomas Jefferson University), b) GRK2 and GRK3 are highly homologous and are anticipated to be stimulated similarly by ligands, c) the crystal structure of GRK2 was recently solved and allows the modeling of difficult-to-predict distal sites that could stimulate the enzyme and d) GRK3 was scheduled to be produced commercially.

Figure 6:
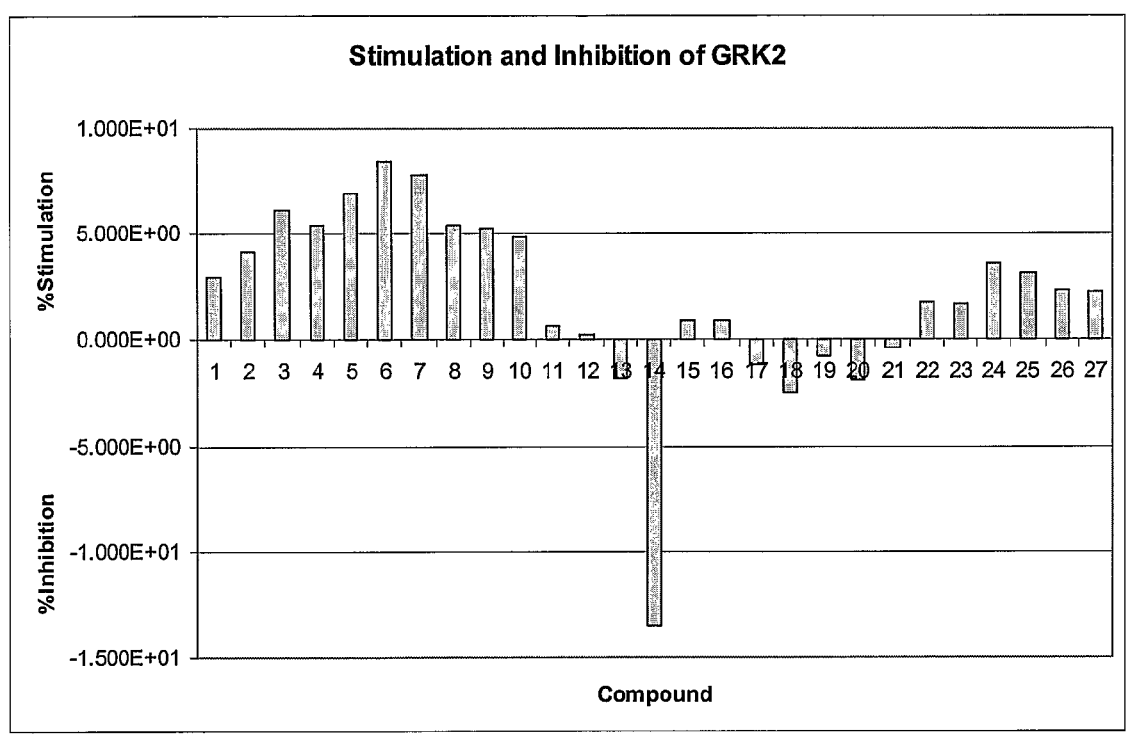
FIG. 6 depicts testing of exemplary compounds for GRK2 stimulation or inhibition.

Stimulators of GRK2, as well as of GRK3, have been identified. FIG. 6 summarizes results of testing of compounds for GRK2 stimulation and inhibition. Compound 28 (Table 1) and 2-(pyridine-3-yl)cyclopropanamine were potent stimulators of GRK2. Epinephrine hydroxylamine was a very potent inhibitor of GRK2 and is also expected to be useful in ameliorating CNS diseases.

Example 27

Results of Biological Studies

In Vitro

Methods

Antagonism of Neurotransmitter Transporters and Release

Chemical compounds were tested for their ability to inhibit uptake, displace radioligand and modulate release from human embryonic kidney (HEK) cells that contain the human dopamine (DAT), human serotonin (SERT), and human norepinephrine (NET) transporters. Nine concentrations were used with the highest concentrations being in the high micromolar range (where possible). Three independent experiments for each compound were done.

Stable transfections: Stable transfections of HEK293 cells were carried out by seeding exponentially growing cells in 10 mL DMEM/10 cm plates and incubating overnight. Plasmid DNA, including pcDNA1-hDAT, pcDNA-hSERT, or pcDNA1-hNET and pBabePuro, which confers resistance to puromycin, was mixed with 0.5 mL of 0.25M CaCl2. An equal volume of 2× BES-buffered saline is added, and the mixture was incubated at room temperature for 20 minutes before the dropwise addition to the medium in the plates. Cells were incubated overnight in a 3% $CO_2$ environment. The next day, medium was removed and replaced with DMEM supplemented with 5% FCS and 5% BCS; cells were incubated in a 10% $CO_2$ environment. Puromycin-resistant cells have been isolated by selection at a concentration of 2 μg/mL, a concentration that kills control HEK293 cells within one week.

Radioligand Binding: Cells were grown on 150 mm diameter tissue culture dishes. Medium was poured off the plate, the plate was washed with 10 mL of phosphate buffered saline and 10 mL of lysis buffer (2 mM HEPES, 1 mM EDTA) was added. After 10 min, cells were scraped from plates and poured into centrifuge tubes and centrifuged for 20 min at 30,000×g. Supernatant was removed, and the pellet was resuspended in 20 mL 0.32 M sucrose with a Polytron at setting 7 for 10 sec.

Assay: Each assay contained 50 μL membrane preparation (approximately 50 μg protein), 25 μL of the individual compound, and 25 μL of [$^{125}$I]RTI-55 (40-80 pMol) in a final volume of 250 μl. Krebs HEPES was used for assays. Membranes were preincubated with individual compounds for 10 min prior to addition of [$^{125}$I]RTI-55. The reaction was incubated for 90 min at room temperature in the dark and was terminated by filtration onto GF/C filters using a Tomtech harvester. Radioactivity remaining on the filter was determined using a Wallac β-plate reader. Competition experiments were conducted with duplicate determinations. Data was analyzed using GraphPad Prism, with $IC_{50}$ values converted to $K_i$ values using the Cheng-Prusoff equation. For binding to HEKbNET cells [$^3$H]nisoxetine was used instead of [$^{125}$I]RTI-55, and the rest of the assay was identical.

[$^3$H]Neurotransmitter Uptake: For experiments involving uptake of [$^3$H]dopamine by HEKhDAT cells, [$^3$H]5HT uptake by HEKhSERT cells, or [$^3$H]NE uptake by HEKhNET cells, the medium was removed from the cells and 2.5 mL of calcium-magnesium-free phosphate buffered saline was added to 10 cm plates, and cells were removed by gentle scraping. Aliquots (50 µL) of the cell suspension was added in triplicate to tubes containing Krebs HEPES (25 mM HEPES, 122 mM NaCl, 5 mM KCl, 1.2 mM MgSO$_4$, 2.5 mM CaCl$_2$, 1 µM pargyline, 0.2 g/100 mL glucose, 0.02 g/100 mL ascorbic acid, pH 7.4) and individual compounds in a final volume of 0.5 mL. Uptake was initiated by the addition of [$^3$H] dopamine, for example, (20 nM, specific activity 20-53 Ci/mmol) in a final volume of 500 µL. Mazindol (5 µM) was used to define nonspecific uptake. Cells were pre-incubated for 10 min with the desired compound before addition of radioligand. Uptake was terminated after a 10 min incubation (depending on the cell line) by filtration of the contents of each tube over Whatman GF/C filters that have been soaked in 0.05% polyethylenimine, using a Tomtech 96-well cell harvester. Radioactivity remaining on the filters was determined with a Wallac β-plate reader. $K_i$ and $IC_{50}$ values were organized and inactive and active compounds were identified. All $K_i$ and $IC_{50}$ experiments were conducted with triplicate determinations. Multiple concentrations of many of the individual compounds were used to determine the $t_{1/2}$, the time point at which 50% of a drugs maximal effect is observed. Dose-response curves were conducted at time points approximating the $t_{1/2}$ for each drug. Data was analyzed using the nonlinear curve fitting computer program GraphPAD. ANOVA was used to determine significant differences among previously described drug groups. Triplicate determinations allowed us to present the results±the standard error of the mean.

Transporter-Mediated Release. C-6 hDAT cells were used for these experiments because there is a clear quantitative difference in the effects of drugs on Ca$^{2+}$-independent release of neurotransmitter from these cells. When cells are confluent in 24 well plates, [$^3$H]-MPP$^+$ (20 nM) in Krebs-HEPE buffer, 1 µM pargyline, 2 mg/mL glucose and 0.2 mg/mL ascorbic acid) was added to each well. Loading of the cells was conducted for 20 min at room temperature at which time the intracellular [$^3$H-MPP$^+$] concentration reaches steady state. Nonspecific binding was defined as the difference in uptake observed in the absence of sodium or in the presence of 5 µM mazindol. The loading buffer was removed and cells were quickly washed with ice-cold release buffer which is the same as loading buffer except it lacks Ca$^{2+}$. Release buffer, ice cold, was added to the plates and initiated by placing the incubations in a 37° C. water bath. At each time point, the buffer was aspirated from each well. TCA, 3%, was added and radioactivity remaining in the cells was determined by liquid scintillation counting. All experiments were conducted in triplicate. Multiple concentrations were used to determine the $t_{1/2}$. Subsequent dose-response curves were conducted at time points approximating the $t_{1/2}$ for each compound. Data was analyzed using the nonlinear curve fitting computer program GraphPAD. ANOVA was used to determine significant differences among previously described drug groups. Triplicate determinations allowed us to present the results±the standard error of the mean.

Binding and Reuptake Inhibition of Dual PDE4 inhibitor/SSRIs in HEK Cells. The dual inhibitors were evaluated for inhibition of [$^{125}$I]-RTI-55 binding in human embryonic kidney (HEK) cells containing either DAT, SERT or NET (n=3) and separately as reuptake inhibitors. Results shown in Table 3 shows that the dual PDE4 inhibitor/SSRIs retained potency and selectivity for the hSERT. The data cannot be directly compared with Table 1 because the compounds of Table 3 were mixtures of diastereomers and isomers at all centers of chirality. Compared with the dual PDE4 inhibitor/SSRIs, the PDE4 inhibitor, 4-(3,4-Dimethoxy-phenyl)-4a,5,8,8a-tetrahydro-2H-phthalazin-1-one, and the alkyl bromide derivative showed no transporter inhibition potency.

Inhibition of PDE4 with dual SSRIs/PDE4 inhibitors. The measurement of inhibitor interaction with high- and low-affinity rolipram binding sites on PDE4 was done as follows: Two radioligands were used to label high- and low-affinity rolipram binding sites on PDE4 and to determine $K_i$ values for the interaction of inhibitors with these sites (Jacobitz et al., 1996). $^3$H-rolipram is used to label the high-affinity site. $IC_{50}$ values for inhibitor interaction with this site were calculated by nonlinear regression analysis of competition curves for unlabeled PDE4 inhibitors; $K_i$ values were determined according to the method of Cheng and Prusoff (1973). Although, $^3$H-rolipram can be used to label the low-affinity site, this involves the use of equilibrium filtration assays that are too cumbersome and variable for routine use. $^3$H-piclamilast was used to label the low affinity site (and high-affinity site; see below); this radioligand has equal affinity for both the high- and low-affinity rolipram binding site on PDE4. This radioligand binds specifically to PDE4, but, in contrast to rolipram, it is not selective for the two binding sites for PDE4 inhibitors (i.e., the rolipram binding sites). Competition curves for the PDE4 inhibitors were subjected to nonlinear regression analysis and $IC_{50}$ values with which the inhibitors bind to each of the binding sites was determined; $K_i$ values were determined according to the method of Cheng and Prusoff (1973). Density of the high-affinity rolipram binding site was determined using saturation isotherms with $^3$H-rolipram. The density of the combined low-affinity and high-affinity rolipram binding site was determined directly using saturation isotherms with $^3$H-piclamilast. Density of the low-affinity rolipram binding site was determined by subtracting $^3$H-rolipram binding from $^3$H-piclamilast binding. Inhibitor interaction with the high-affinity rolipram binding site was determined using competition experiments with unlabeled inhibitor and $^3$H-rolipram. Inhibitor interaction with the low-affinity rolipram binding site was determined in two ways. Nonlinear regression analysis of competition curves generated using unlabeled inhibitor and $^3$H-piclamilast showed affinity for the low- and high-affinity rolipram binding sites. Second, potency for inhibiting $^3$H-piclamilast binding with 1 µM rolipram (to block $^3$H-piclamilast binding to the high-affinity state) showed its affinity for the low-affinity site. The inhibition results are listed in Table 4.

Preparation of human PDE 4D3 with dual SSRIs/PDE4 inhibitors. The PDE construct was transfected into Cos 7 cells in round culture dish (100×20 mm). The cells were then harvested and homogenized with lysis buffer. The crude homogenate was spun at maximum speed in a microfuge. The supernatant fluid was saved as an extract. Cold ethylene glycol was added to make a final concentration of 33% and then stored at −20° C. Inhibition of human PDE 4D3 with dual SSRIs/PDE4 inhibitors is shown in Table 5. The PDE construct and Cos 7 cells were a kind gift from Dr. Conti at the Stanford University School of Medicine.

Results

Table 1 and Table 2 present the data for the binding assays described in the methods section above. $K_i$ is the parameter that describes the inhibition of binding of radioligand to the transporter by the test compound. $K_r$ is the parameter that describes the inhibition of re-uptake of radioligand to the transporter by the test compound. Table 3 shows the data for binding and reuptake of the dual SSRIs/PDE4 inhibitors in HEK cells. Table 4 is the data for inhibition of PDE4 with dual SSRIs/PDE4 inhibitors. Table 5 is the data for inhibition of highly purified human PDE4D3 with dual SSRIs/PDE4 inhibitors.

TABLE 1

Binding and Re-uptake of Primary Amines and Related Compounds

| Names | Structures | Binding ($K_i$, nM) | | | Reuptake ($K_r$, nM) | | |
| --- | --- | --- | --- | --- | --- | --- | --- |
| | | hDAT | hSERT | hNET | hDAT | hSERT | hNET |
| trans-2-aminomethyl-5-((2"-methoxy-5"-fluorophenyl)-3'-propyl)tetrahydrofuran | 26 | 7328 | 0.8 | 8541 | | | |
| 2-aminoethyl-5-((2"-methoxy-5"-fluorophenyl)-3'-propyl)tetrahdrofuran | 128 | 7307.0 | 1.1 | 10600.0 | 16987 | 2.3 | 1930.0 |
| 2-aminomethyl-5-(2'-methoxy-5'-fluorophenethyl tetrahydrofuran | 27 | >10 k | 609 | 1658 | 887 | 1.64 | 188 |
| 2-aminoethyl-5-(2'-methoxy-5'-fluoro phenethyltetrahydrofuran | 28 | >10 k | 4.5 | 6452 | >10 k | 3.1 | 638 |
| 2-(aminomethyl)-5-(1'-naphethyl)tetra hydrofuran | 29 | >10 k | 18.5 | >10 k | — | — | — |
| trans-2-aminoethyl-5-(2'-methoxy-5'-fluorobenzyl) tetrahydrofuran | 30 | 51018 | 20 | 1782 | — | — | — |

TABLE 1-continued

Binding and Re-uptake of Primary Amines and Related Compounds

| Names | Structures | Binding ($K_i$, nM) | | | Reuptake ($K_r$, nM) | | |
|---|---|---|---|---|---|---|---|
| | | hDAT | hSERT | hNET | hDAT | hSERT | hNET |
| cis-2-aminoethyl-5-(2'-methoxy-5'-fluorobenzyl)tetrahydrofuran | 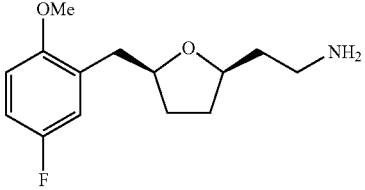 31 | 34791 | 21 | 455 | — | — | — |
| 2-(aminoethyl)-5-(1'-naphethyl)tetrahydrofuran | 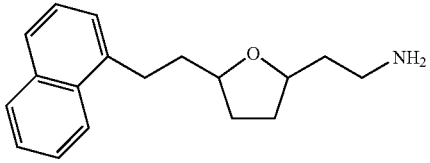 32 | 9298<br>4737 | 30<br>39 | 8059<br>5262 | >10 k<br>— | 73<br>— | >10 k<br>— |
| 2-(aminomethyl)-5-phenyltetrahydrofuran | 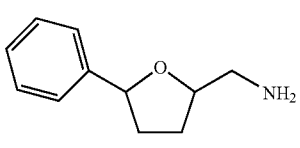 33 | 916 | 43 | 2767 | 147 | — | — |
| 2-(aminomethyl)-5-(2'-naphthyl)tetrahydrofuran | 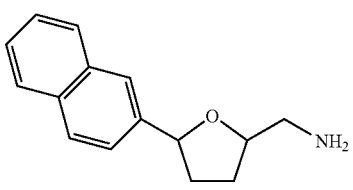 34 | 512 | 45 | >10 k | 28 | 4 | 58 |
| 2-(aminoethyl)-5-phenyltetrahydrofuran | 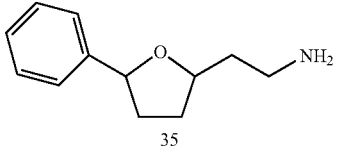 35 | 4066 | 54 | >10 K | 1463 | — | — |
| 2-(aminomethyl)-5-(phenethyl)tetrahydrofuran | 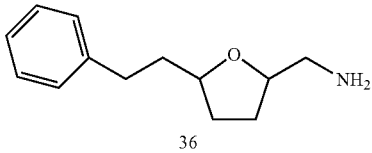 36 | 1505 | 68 | 2736 | 867 | — | — |
| 2-(aminoethyl)-5-(2'-methoxy-1'-naphethyl)tetrahydrofuran, | 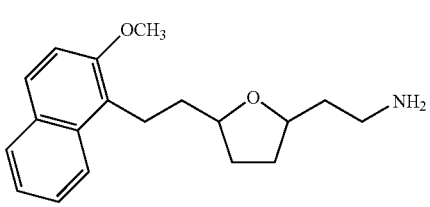 37 | >10 k | 86 | >10 k | — | — | — |

TABLE 1-continued

Binding and Re-uptake of Primary Amines and Related Compounds

| Names | Structures | Binding ($K_i$, nM) | | | Reuptake ($K_r$, nM) | | |
|---|---|---|---|---|---|---|---|
| | | hDAT | hSERT | hNET | hDAT | hSERT | hNET |
| 2-(aminomethyl)-5-(2'-chloro-5'-trifluoromethylphenethyl) tetrahydrouran | 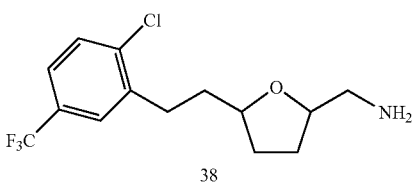 38 | >10 k | 92 | 9460 | — | — | — |
| 2-(aminoethyl)-5-(4'-methoxy-1'-naphthylethyl) tetrahydrofuran | 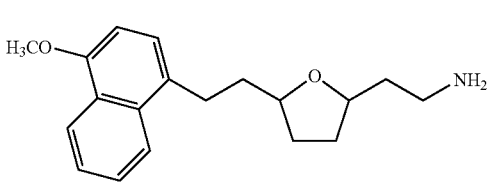 39 | >10 k | 93 | >10 k | — | — | — |
| cis-2-(aminomethyl)-5-(5'-fluoro-2'-methoxybenzyl) tetrahydrofuran | 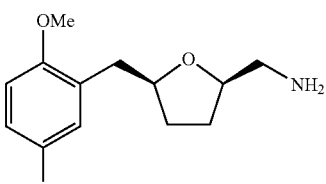 40 | 97181 | 151 | 9085 | — | — | — |
| 2-(aminomethyl)-5-(1'-naphethyl)tetra hydro furan | 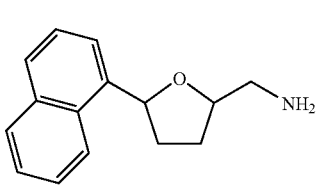 41 | 8519 | 174 | 1494 | 463 | 24 | 210 |
| trans-2-(aminomethyl)-5-(5'-fluoro-2'-methoxybenzyl) tetrahydrofuran | 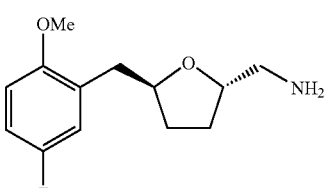 42 | 27238 | 192 | 24116 | — | — | — |
| 2-(aminomethyl)-5-(2'-methoxy-1'-naphethyl) tetrahydrofuran | 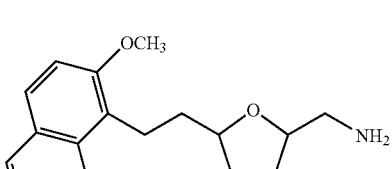 43 | >10 k | 228 | >10 k | — | — | — |
| 2-(aminomethyl)-5-(4'-fluoro-3'-methylphenethyl) tetrahydrouran | 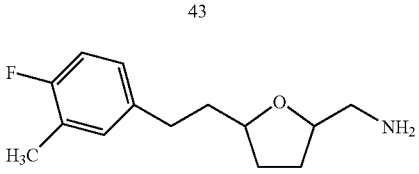 44 | 7294 | 256 | 880 | 2364 | 125 | 526 |

TABLE 1-continued

Binding and Re-uptake of Primary Amines and Related Compounds

| Names | Structures | Binding ($K_i$, nM) | | | Reuptake ($K_r$, nM) | | |
|---|---|---|---|---|---|---|---|
| | | hDAT | hSERT | hNET | hDAT | hSERT | hNET |
| 2-(aminomethyl)-5-(3'-phenylpropyl) tetrahydrofuran | 45 | 1297 | 381 | 576 | 1883 | — | — |
| 2-(aminoethyl)-5-(2'-naphthylethyl) tetrahydrofuran | 46 | 1491 | 489 | 1611 | 655 | 712 | 665 |
| 2-(aminoethyl)-5-(4'-fluorophenethyl) tetrahydrofuran | 47 | >10 k | 538 | >10 k | 3280 | 278 | >10 k |
| 2-(aminoethyl)-5-(4'-fluoro-3'-methylphenethyl tetrahydrofuran | 48 | 6376 | 688 | 882 | 509 | 30 | 374 |
| 2-(aminomethyl)-5-(2'-methoxy-1'-naphethyl) tetrahydrofuran | 49 | >10 k | 843 | 439 | 603 | 78 | 339 |
| 2-(aminoethyl)-5-(4'-bromophenyl) tetrahydrofuran | 50 | >10 k | 944 | >10 k | — | — | — |
| 2-(aminoethyl)-5-(phenethyl) tetrahydrofuran | fumaric salt 51 | 27 | 1094 | 409 | 2314 | 2801 | 325 |
| 2-(aminomethyl)-5-(4'-chlorophenyl) tetrahydrafuran | 52 | 6830 | 1105 | 1106 | 313 | 32 | 61 |

TABLE 1-continued

Binding and Re-uptake of Primary Amines and Related Compounds

| Names | Structures | Binding ($K_i$, nM) | | | Reuptake ($K_r$, nM) | | |
|---|---|---|---|---|---|---|---|
| | | hDAT | hSERT | hNET | hDAT | hSERT | hNET |
| 2-(aminomethyl)-5-(4'-bromophenyl)tetrahydrofuran | 53 | 6117 | 1114 | >10 k | 167 | 50 | 60 |
| MM-II-41 MM-II-152C 2-(aminoethyl)-5-(phenethyl)tetrahydrofuran | 54 | 6494 5106 | 1299 2727 | 7537 6375 | 2784 2697 | 161 1590 | 2934 3213 |
| 2-(aminoethyl)-5-(phenethyl)tetrahydrofuran | 55 | 1334 | 1362 | 2443 | 1007 | — | — |
| 2-(aminoethyl)-5-(3'-fluoro-4'-methylphenethyl)tetrahydrafuran | 56 | 8844 | 1487 | 5631 | — | — | — |
| 2-(aminoethyl)-5-(4'-trifluoromethoxyphenethyl)tetrahydrafuran | 57 | >10 k | 1796 | >10 k | >10 k | 519 | >10 k |
| trans-2-(aminoethyl)-5-(2'-methoxy-5'-fluorophenyl)tetrahydrofuran | 58 | 32934 | 1808 | 27495 | >10 k | 1046 | >10 k |
| 2-(aminomethyl)-5-(pentafluorophenethyl)tetrahydrofuran | 59 | >10 k | 2126 | 180 | 4589 | 225 | 1541 |
| 2-(aminoethyl)-5-(4'-methoxyphenethyl)tetrahydrofuran | 60 | >10 k | 2517 | 6013 | >10 k | 628 | >10 k |

TABLE 1-continued

Binding and Re-uptake of Primary Amines and Related Compounds

| Names | Structures | Binding ($K_i$, nM) | | | Reuptake ($K_r$, nM) | | |
|---|---|---|---|---|---|---|---|
| | | hDAT | hSERT | hNET | hDAT | hSERT | hNET |
| 2-(aminomethyl)-5-(3'-fluoro-4'-methyphenyl)tetrahydrofuran | 61 | 6852 | 2665 | 305 | 337 | 178 | 94 |
| 2-(aminoethyl)-5-(4'-phenylphenethyl)tetrahydrofuran | 62 fumaric salt | 7897 | 3587 | 1273 | 1901 | 2987 | 6094 |
| 2-(aminoethyl)-5-(4'-methylphenethyl)tetrahydrofuran | 63 | 7610 | 3740 | >10 k | >10 k | 3763 | 919 |
| 2-(aminoethyl-5-benzyltetrahydrofuran | 64 | >10 k | 3822 | >10 k | — | — | — |
| 2-(aminomethyl)-5-(3',4'dimethoxyphenethyl)tetrahydrofuran | 65 | 7920 | 4521 | 8641 | — | — | — |
| 2-(aminomethyl)-5-(3'-pyridylethyl)tetrahydrofuran | 662 | >10 k | 4546 | 8517 | >10 k | 2548 | >10 k |
| cis-2-(aminoethyl)-5-(2'-methoxy-5'-fluorophenyl)tetrahydrofuran | 67 | >10 K | 4772 | 48874 | >10 K | 2411 | >10 K |

TABLE 1-continued

Binding and Re-uptake of Primary Amines and Related Compounds

| Names | Structures | Binding ($K_i$, nM) | | | Reuptake ($K_i$, nM) | | |
|---|---|---|---|---|---|---|---|
| | | hDAT | hSERT | hNET | hDAT | hSERT | hNET |
| 2-(aminoethyl)-5-(3'-pyridylethyl)tetrahydrofuran | 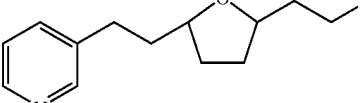 68 | >10 k | 5691 | 5345 | >10 k | 6685 | >10 k |
| trans-2-(aminomethyl)-5-(3'-quinoline)tetrahydrofuran | 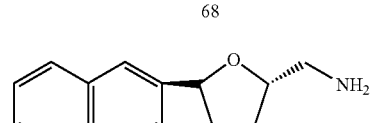 69 | 62205 | 5857 | 19856 | — | — | — |
| trans-2-(aminomethyl)-5-(2'-methoxy-5'-fluorophenyl)tetrahydrofuran | 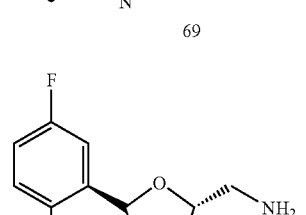 70 | >10 k | 6307 | 71991 | >10 k | 1939 | >10 k |
| 2-(aminomethyl)-5-(4'-methoxyphenyl)tetrahydrofuran | 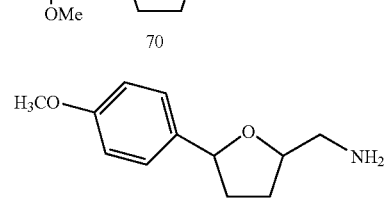 71 | >10 k | 6877 | 2013 | 668 | 617 | 92 |
| 2-(aminomethyl)-5-(2'-methoxy-5'-fluorophenyl)tetrahydrofuran | 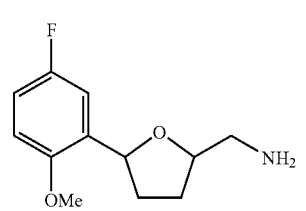 trans:cis = 0.58:0.42 72 | 42764 | 6886 | 57016 | >10 k | 8452 | >10 k |
| 2-(aminoethyl)-5-(4'-hydroxyphenethyl)tetrahydrofuran | 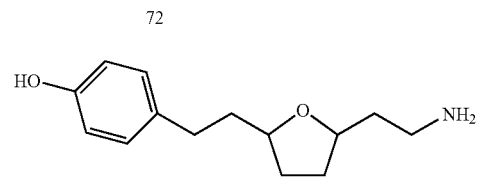 73 | 5498 | 7483 | 5947 | 2532 | 4041 | 2126 |
| 2-(aminomethyl)-5-(4'-fluorophenethyl)tetrahydrofuran | 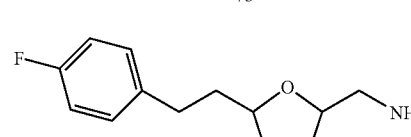 74 | >10 k | 9190 | >10 k | — | — | — |
| 2-(aminomethyl)-5-(-2''-tetrahydrofuryl-2'-ethyl)tetrahydrofuran. | 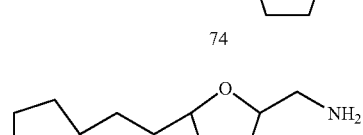 75 | 142265 | 10296 | 72075 | >10 k | >10 k | >10 k |

TABLE 1-continued

Binding and Re-uptake of Primary Amines and Related Compounds

| Names | Structures | Binding ($K_i$, nM) | | | Reuptake ($K_r$, nM) | | |
|---|---|---|---|---|---|---|---|
| | | hDAT | hSERT | hNET | hDAT | hSERT | hNET |
| 2-(aminomethyl)-5-(3-'quinoline)tetrahydrofuran | 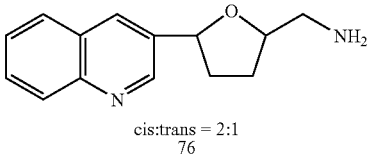<br>cis:trans = 2:1<br>76 | 63720 | 11370 | 22740 | — | — | — |
| 2-(aminoethyl)-5-(2'-furyl)tetrahydrofuran | 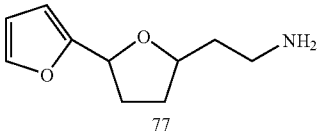<br>77 | 89441 | 12145 | 50646 | >10 k | >10 k | >10 k |
| Cis-2-(Phenethylaminoethyl)-5-(2'-methoxy-5'-fluorophenyl)tetrohydrofuran | 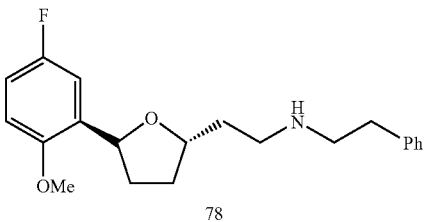<br>78 | 3350 | 13790 | 589 | — | — | — |
| 2-(aminoethyl)-5-(4'-pyridylethyl)tetrahydrofuran, | 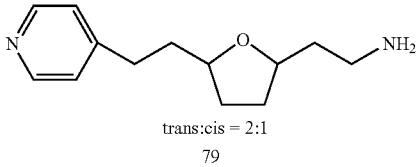<br>trans:cis = 2:1<br>79 | 55163 | 15433 | 13261 | — | — | — |
| Cis-2-(Phenethylaminoethyl)-5-(2'-methoxy-5'-fluorophenyl)tetrahydrofuran | 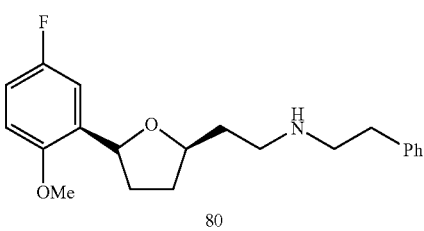<br>80 | 3139 | 17466 | 363 | — | — | — |
| 2-(aminomethyl)-5-(4'-pyridylethyl)tetrahydrofuran | 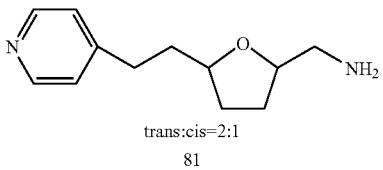<br>trans:cis=2:1<br>81 | 145733 | 18578 | 57448 | — | — | — |
| trans-2-(aminomethyl)-5-(2'-pyridyl)tetrahydrofuran | 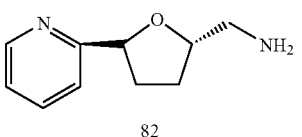<br>82 | 483667 | 78170 | 93411 | — | — | — |
| 2-(aminomethyl)-5-cyclohexyl tetrahydrofuran | 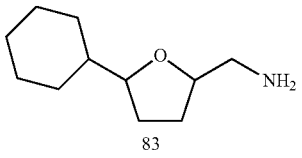<br>83 | >10 k | >10 k | 405 | 2573 | 939 | 317 |

TABLE 1-continued

Binding and Re-uptake of Primary Amines and Related Compounds

| Names | Structures | Binding ($K_i$, nM) | | | Reuptake ($K_r$, nM) | | |
| --- | --- | --- | --- | --- | --- | --- | --- |
| | | hDAT | hSERT | hNET | hDAT | hSERT | hNET |
| 2-(aminomethyl)-5-benzyltetrahydrofuran | 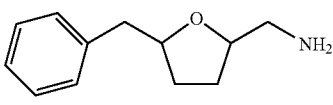 84 | 1760 | >10 k | 1905 | 876 | — | — |
| 2-(aminomethyl)-5-(4'-t-butylphenyl)tetrahydrofuran | 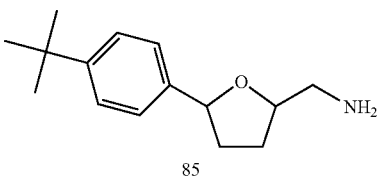 85 | >10 k | >10 k | 4543 | 4301 | 637 | 2322 |
| 2-(aminoethyl)-5-phenyltetrahydrofuran | 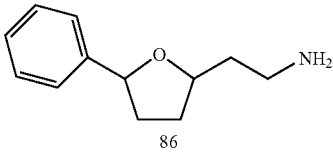 86 | >10 k | >10 k | >10 k | — | — | — |
| 2-(aminoethyl)-5-(4'-fluorophenyl)tetrahydrofuran | 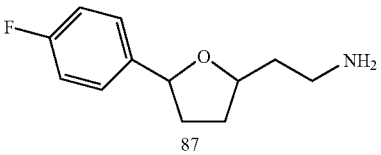 87 | >10 k | >10 k | >10 k | — | — | — |
| 2-(aminoethyl)-5-cyclohexyltetrahydrofuran, | 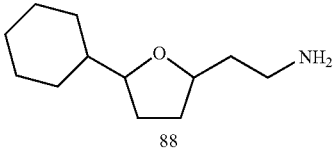 88 | >10 k | >10 k | >10 k | — | — | — |
| 2-(aminoethyl)-5-(4'-t-butylphenethyl)tetrahydrofuran | 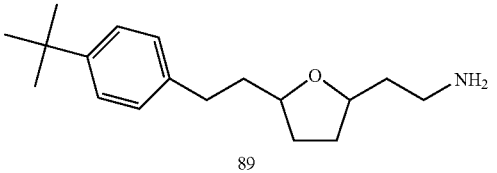 89 | >10 k | >10 k | >10 k | >10 k | >10 k | 556 |
| 2-(aminoethyl)-5-(cyclohexylethyl)tetrahydrofuran | 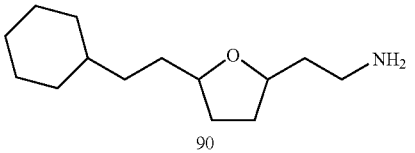 90 | >10 k | >10 k | >10 k | >10 k | 217 | >10 k |

TABLE 1-continued
Binding and Re-uptake of Primary Amines and Related Compounds
| Names | Structures | Binding ($K_i$, nM) | | | Reuptake ($K_i$, nM) | | |
|---|---|---|---|---|---|---|---|
| | | hDAT | hSERT | hNET | hDAT | hSERT | hNET |
| 2-(aminoethyl)-5-(4'-t-butylphenyl)tetrahydrofuran | 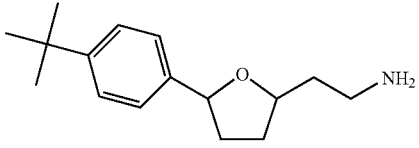 91 | >10 k | >10 k | >10 k | — | — | — |
| 2-(aminomethyl)-5-(4'-methoxy-1'-naphthylethyl)tetrahydrofuran | 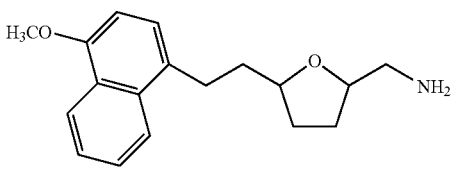 92 | — | — | — | 2112 | 53 | 2125 |

TABLE 2

Binding and Re-uptake of Secondary Amines and Related compounds

| Names | Structures | Binding (ki, nM) | | | Reuptake (kup, nM) | | |
|---|---|---|---|---|---|---|---|
| | | hDAT | hSERT | hNET | hDAT | hSERT | hNET |
| N,N-bis (cis-5'-2''-methoxy-5''-fluorobenzyl-2'-tetrahydrofuryl)-2-ethyl) amine | 93 | 1441 | 22 | 682 | — | — | — |
| N,N-bis (5'-(p-fluorophenyl)-2'-tetrahydrofuryl)ethyl) Amine | 94 | 709 | 53 | 431 | — | — | — |
| N,N-Bis (trans-5'-(2''-methoxy-5''-fluorobenzyl-2'-tetrahydrofuryl)-2-ethyl) amine | 95 | 2390 | 61 | 727 | — | — | — |
| N,N-bis (5'-(5''-(5'''-fluoro-2''-methoxyphenethyl)-2'-tetrahydrofurylethyl) Amine | 96 | 236 | 75 | 507 | — | — | — |

TABLE 2-continued

Binding and Re-uptake of Secondary Amines and Related compounds

| Names | Structures | Binding (ki, nM) | | | Reuptake (kup, nM) | | |
|---|---|---|---|---|---|---|---|
| | | hDAT | hSERT | hNET | hDAT | hSERT | hNET |
| N,N-bis (5'-phenethyl-2'-tetrahydrofurylethyl) Amine | 97 | 30<br>18 | 87<br>660 | 1562 | —<br>3472 | —<br>169 | — |
| N,N-bis (5'-(p-bromophenyl)-2'-tetrahydrofurylethyl) Amine | 98 | 443 | 128 | 2690 | — | — | — |
| N,N-bis (trans-5''-(2''-methoxy-5''-fluorophenyl)-2'-tetrahydrofuryl)ethyl) Amine | 99 | 1386 | 148 | 2638 | 1389 | 375 | 2963 |
| N,N-bis (cis-5''-(2''-methoxy-5''-fluorophenyl)-2'-tetrahydrofuryl)ethyl) Amine | 100 | 2654 | 150 | 3032 | 2980 | 306 | 4180 |

TABLE 2-continued

Binding and Re-uptake of Secondary Amines and Related compounds

| Names | Structures | Binding (ki, nM) | | | Reuptake (kup, nM) | | |
|---|---|---|---|---|---|---|---|
| | | hDAT | hSERT | hNET | hDAT | hSERT | hNET |
| N,N-bis (5'-(2"-naphthyl)-2'-tetrahydrofuryl)ethyl) Amine | 101 | 75 | 252 | 1299 | 51 | 3358 | 2291 |
| N,N-bis (5'-(1"-naphthethyl)-2'-tetrahydrofuryl)ethyl) amine | 102 | 1075 | 283 | 4337 | >10 K | 718 | >10 K |
| N,N-bis (5'-(p-hydroxyphenethyl)-2'-tetrahydrofuryl)ethyl) amine | 103 | 36 | 386 | 92 | — | — | — |
| N,N-bis (5'-phenethyl-2'-tetrahydrofurylethyl) methylamine | 104 | 84 | 730 | 168 | 582 | 3692 | 1278 |

TABLE 2-continued

Binding and Re-uptake of Seconary Amines and Related compounds

| Names | Structures | Binding (ki, nM) | | | Reuptake (kup, nM) | | |
|---|---|---|---|---|---|---|---|
| | | hDAT | hSERT | hNET | hDAT | hSERT | hNET |
| N,N-bis (5'-(p-fluoro-m-methylphenethyl)-2'-tetrahydrofurylethyl)amine | 105 | 798 | 743 | 1570 | 5744 | 2375 | 7680 |
| N,N-bis (5'-(3"-pyridylethyl)-2'-tetrahydrofurylethyl)amine | 106 | 12339 | 886 | 7752 | >10 k | 1788 | >10 k |
| N,N-bis (5'-benzyl-2'-tetrahydrofuryl)-2'-ethyl)amine | 107 | 1310 | 937 | 605 | 564 | 2260 | 347 |
| N,N-bis (5'-phenyl-2'-tetrahydrofurylethyl)amine | 108 | 970 | 1089 | 777 | 609 | 2016 | 802 |

TABLE 2-continued

Binding and Re-uptake of Seconary Amines and Related compounds

| Names | Structures | Binding (ki, nM) | | | Reuptake (kup, nM) | | |
|---|---|---|---|---|---|---|---|
| | | hDAT | hSERT | hNET | hDAT | hSERT | hNET |
| N,N-bis (5'-(2''-methoxy-1''-naphthethyl)-2'-tetrahydrofurylethyl)amine | 109 | 5512 | 2032 | >10 K | — | — | — |
| N,N-bis (5'-(m-fluoro-p-methylphenethyl)-2'-tetrahydrofurylethyl)amine | 110 | 474 | 2578 | 4099 | — | — | — |
| N,N-bis (5'-(4''-methoxy-1''-naphthethyl)-2'-tetrahydrofurylethyl)amine | 111 | 5672 | 3671 | >10 K | — | — | — |
| N,N-bis (5'-(4''-pyridylethyl)-2'-tetrahydrofurylethyl)amine | 112 | 9329 | 6614 | 1617 | — | — | — |

TABLE 2-continued

Binding and Re-uptake of Secondary Amines and Related compounds

| Names | Structures | Binding (ki, nM) | | | Reuptake (kup, nM) | | |
|---|---|---|---|---|---|---|---|
| | | hDAT | hSERT | hNET | hDAT | hSERT | hNET |
| N,N-bis (5'-cyclohexyl-2'-tetrahydrofurylethyl)amine | 113 | 5960 | 6762 | 8430 | — | — | — |
| N,N-bis (5'-(p-t-butylphenyl)-2'-tetrahydrofurylethyl)amine | 114 | 8893 | >10 K | >10 K | — | — | — |

TABLE 3

Binding and reuptake of the dual SSFIs/PDE4 inhibitors in HEK cells

| Names | Structures | Binding (Ki, nM) | | | Reuptake (IC$_{50}$, nM) | | |
|---|---|---|---|---|---|---|---|
| | | hDAT | hSERT | hNET | hDDAT | hSERT | hNET |
| 4-(3,4-Dimethoxy-phenyl)-4a,5,8,8a-tetrahydro-2H-phthalazin-1-one | 19 | >100 uM | >100 uM | >100 uM | >100 uM | >100 uM | >100 uM |
| 4-(3,4-Dimethoxyphenyl)-2-[5-(2-{5-[2-(5-fluoro-2-methoxyphenyl)-ethyl]-tetrahydrofuran-2-yl}-ethylamino)-pentyl]-4a,5,8,8a-tetrahydro-2H-phthalazin-1-one | 115 | 872 ± 65 | 80 ± 7 | 1450 ± 247 | 5388 ± 1056 | 286 ± 134 | 1808 ± 744 |
| 4-(3,4-Dimethoxyphenyl)-2-[5-(2-{5-[2-(5-fluoro-2-methoxyphenyl)-propyl]-tetrahydrofuran-2-yl}-ethylamino)-pentyl]-4a,5,8,8a-tetrahydro-2H-phthalazin-1-one | 21 | 5340 ± 1083 | 194 ± 87 | 7441 ± 1269 | 5340 ± 1083 | 194 ± 87 | 7441 ± 1269 |

TABLE 4

Inhibition of rodent PDE4 with dual SSRIs/PDE4 inhibitors

| Number | Structures | pIC$_{50}$ |
|---|---|---|
| 4-(3,4-Dimethoxy-phenyl)-4a,5,8,8a-tetrahydro-2H-phthalazin-1-one | 19 | 6.7 |

TABLE 4-continued

Inhibition of rodent PDE4 with dual SSRIs/PDE4 inhibitors

| Number | Structures | pIC$_{50}$ |
|---|---|---|
| 4-(3,4-Dimethoxyphenyl)-2-[5-(2-{5-[2-(5-fluoro-2-methoxyphenyl)-ethyl]-tetrahydrofuran-2-yl}-ethylamino)-pentyl]-4a,5,8,8a-tetrahydro-2H-phthalazin-1-one | 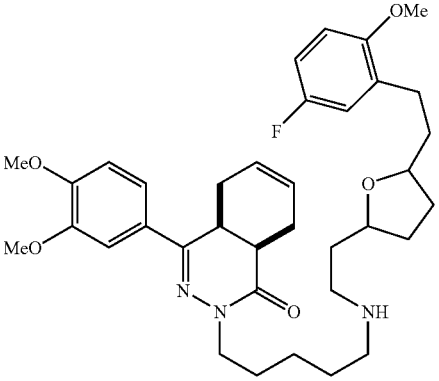 115 | 6.6 |
| 4-(3,4-Dimethoxyphenyl)-2-[5-(2-{5-[2-(5-fluoro-2-methoxyphenyl)-propyl]-tetrahydrofuran-2-yl}-ethylamino)-pentyl]-4a,5,8,8a-tetrahydro-2H-phthalazin-1-one | 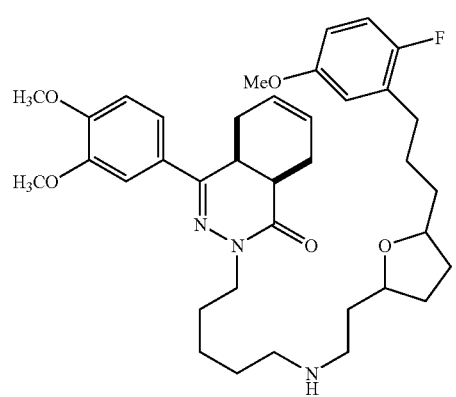 21 | 6.3 |

TABLE 5

Inhibition of recombinant human PDE 4D3 with dual SSRIs/PDE4 inhibitors

| Names | Structures | pIC$_{50}$ | K$_i$ nM |
|---|---|---|---|
| 4-(3,4-Dimethoxy-phenyl)-4a,5,8,8a-tetrahydro-2H-phthalazin-1-one | 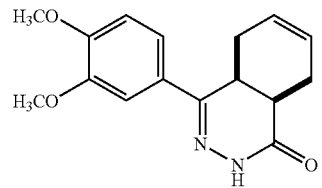 19 | -2.2 | 6.3 |

TABLE 5-continued

Inhibition of recombinant human PDE 4D3 with dual SSRIs/PDE4 inhibitors

| Names | Structures | pIC$_{50}$ | K$_i$ nM |
|---|---|---|---|
| 4-(3,4-Dimethoxyphenyl)-2-[5-(2-{5-[2-(5-fluoro-2-methoxyphenyl)-ethyl]-tetrahydrofuran-2-yl}-ethylamino)-pentyl]4a,5,8,8a-tetrahydro-2H-phthalazin-1-one | 115 | −2.7 | 2 |
| 4-(3,4-Dimethoxyphenyl)-2-[5-(2-{5-[2-(5-fluoro-2-methoxyphenyl)-propyl]-tetrahydrofuran-2-yl}-ethylamino)-pentyl]-4a,5,8,8a-tetrahydro-2H-phthalazin-1-one | 21 | −2.9 | 1.2 |

TABLE 6

Inhibition of radioligand binding and uptake inhibition in HEK-hDAT, HEK-hSERT and HEK-hNET by monomethyl disubstituted tetrahydrofuran and pyrrolidine derivatives

| | | Binding (k$_i$, nM) | | | Reuptake (IC$_{50}$, nM) | | |
|---|---|---|---|---|---|---|---|
| Names | Structures | hDAT | hSERT | hNET | hDAT | hSERT | hNET |
| 2-Styrenyl Pyrrolidine | 116 | 4130 | 4580 | >10 k | 1270 | ND | 104 |
| 1-Methyl-2-Styrenyl Pyrrolidine | 117 | 3240 | >10 k | 2780 | 1030 | ND | 250 |

TABLE 6-continued

Inhibition of radioligand binding and uptake inhibition in HEK-hDAT, HEK-hSERT and HEK-hNET by monomethyl disubstituted tetrahydrofuran and pyrrolidine derivatives

| Names | Structures | Binding ($k_i$, nM) | | | Reuptake (IC$_{50}$, nM) | | |
|---|---|---|---|---|---|---|---|
| | | hDAT | hSERT | hNET | hDAT | hSERT | hNET |
| N-Methyl-2-aminoethyl-5-(2'-methoxy-5'-fluoro phenethyltetrahydrofuran | 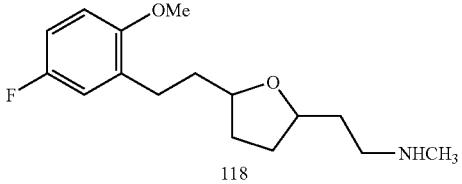 118 | >10 k | 21.2 | >10 k | >10 k | 18.4 | >10 k |
| N-Methyl-2-aminoethyl-5-((2''-methoxy-5''-fluorophenyl)-3'-propyl)tetrahydrofuran | 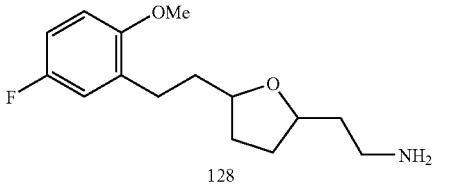 128 | >10 k | 4.5 | >10 k | >10 k | 3.1 | >10 k |

TABLE 7

Dual SSRI/PDE4 inhibtors to treat depression and memory and cognition-enhancement functional activity

| Name | Structure |
|---|---|
| 4-(3-Cyclopentyloxy-4-methoxy-phenyl)-1-[5-(2-{5-[2-(5-fluoro-2-methoxy-phenyl)-ethyl]-tetrahydro-furan-2-yl}-ethylamino)-pentyl]-pyrrolidin-2-one | 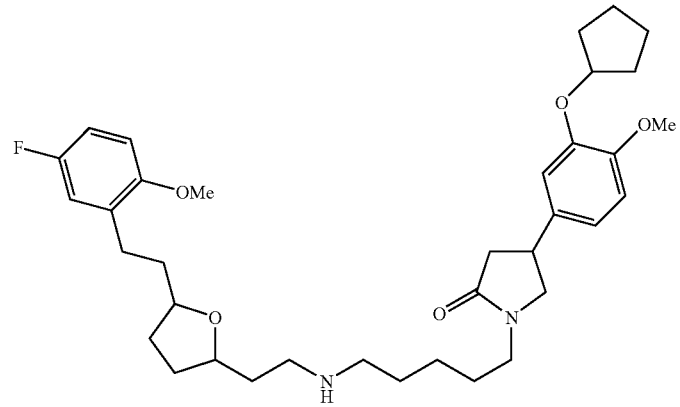 116 |
| 4-(3-Cyclopentyloxy-4-methoxy-phenyl)-1-[5-(2-{5-[3-(5-fluoro-2-methoxy-phenyl)-propyl]-tetrahydro-furan-2-yl}-ethylamino)-pentyl]-pyrrolidin-2-one | 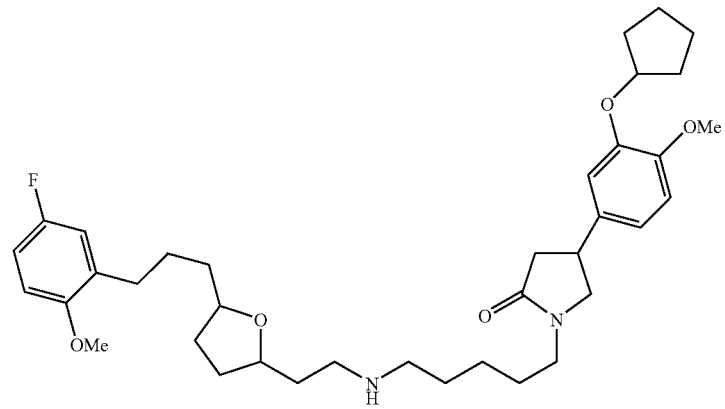 117 |

TABLE 7-continued

Dual SSRI/PDE4 inhibtors to treat depression and memory and cognition-enhancement functional activity

| Name | Structure |
|---|---|
| 4-(3-Cyclopentyloxy-4-methoxy-phenyl)-1-{5-[3-phenyl-3-(4-trifluoromethyl-phenoxy)-propylamino]-pentyl}-pyrrolidin-2-one | 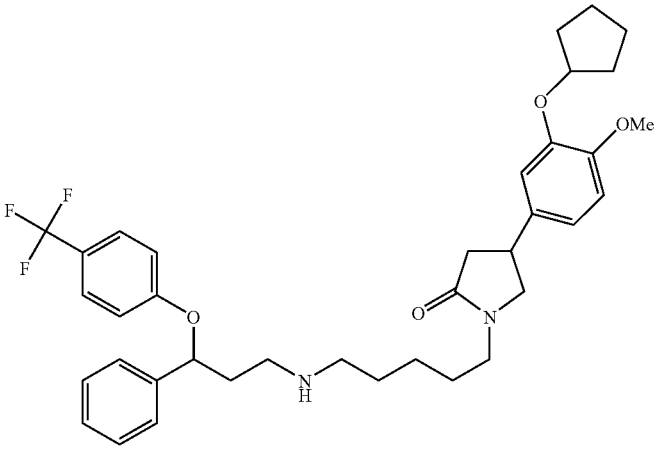<br>118 |
| 4-(3,4-Dimethoxy-phenyl)-2-{5-[3-phenyl-3-(4-trifluoromethyl-phenoxy)-propylamino]-pentyl}-4a,5,8,8a-tetrahydro-2H-phthalazin-1-one | 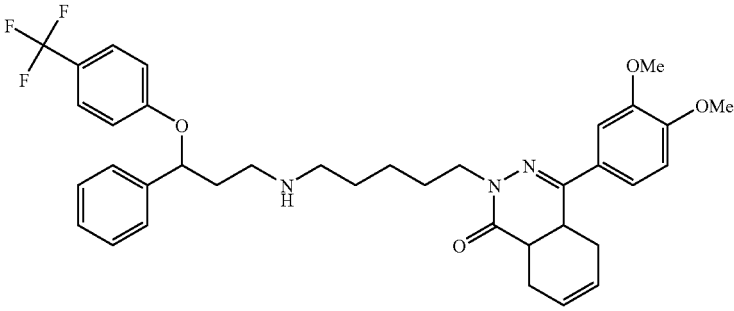<br>119 |
| 2-(3-{5-[4-(3,4-Dimethoxy-phenyl)-1-oxo-4a,5,8,8a-tetrahydro-1H-phthalazin-2-yl]-pentylamino}-propyl)-2-(4-fluoro-phenyl)-2,3-dihydro-benzofuran-6-carbonitrile | 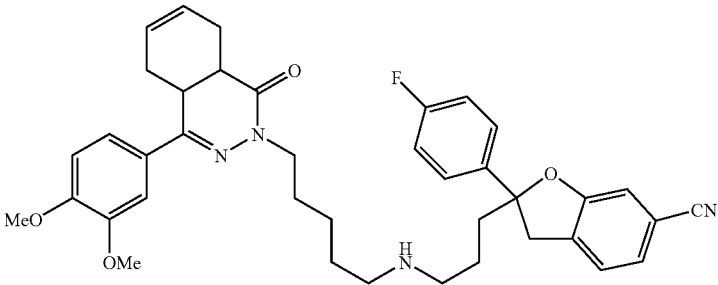<br>120 |
| 2-(3-{5-[4-(3-Cyclopentyloxy-4-methoxy-phenyl)-2-oxo-pyrrolidin-1-yl]-pentylamino}-propyl)-2-(4-fluoro-phenyl)-2,3-dihydro-benzofuran-6-carbonitrile | 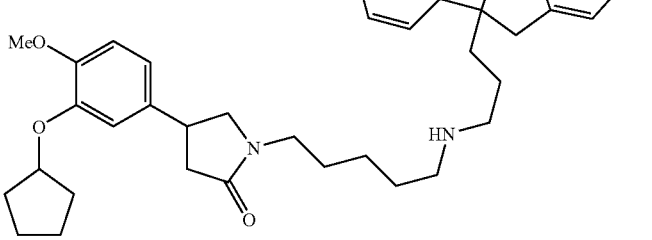<br>121 |

TABLE 8

Dual norepinephrine3 reuptake inhibitors/PDE4 inhibtors

| Name | Structure |
| --- | --- |
| 4-(3,4-Dimethoxy-phenyl)-2-(5-{[5-(4-methoxy-phenyl)-tetrahydro-furan-2-ylmethyl]-amino}-pentyl)-4a,5,8,8a-tetrahydro-2H-phthalazin-1-one | 122 |
| 4-(3-Cyclopentyloxy-4-methoxy-phenyl)-1-(5-{[5-(4-methoxy-phenyl)-tetrahydro-furan-2-ylmethyl]-amino}-pentyl)-pyrrolidin-2-one | 123 |
| 2-{5-[(5-Cyclohexyl-tetrahydro-furan-2-ylmethyl)-amino]-pentyl}-4-(3,4-dimethoxy-phenyl)-4a,5,8,8a-tetrahydro-2H-phthalazin-1-one | 124 |
| 1-{5-[(5-Cyclohexyl-tetrahydro-furan-2-ylmethyl)-amino]-pentyl}-4-(3-cyclopentyloxy-4-methoxy-phenyl)-pyrrolidin-2-one | 125 |

TABLE 8-continued

Dual norepinephrine3 reuptake inhibitors/PDE4 inhibtors

| Name | Structure |
|---|---|
| 4-(3,4-Dimethoxy-phenyl)-2-(5-{[5-(3-fluoro-4-methyl-phenyl)-tetrahydro-furan-2-ylmethyl]-amino}-pentyl-4a,5,8,8a-tetrahydro-2H-phthalazin-1-one | 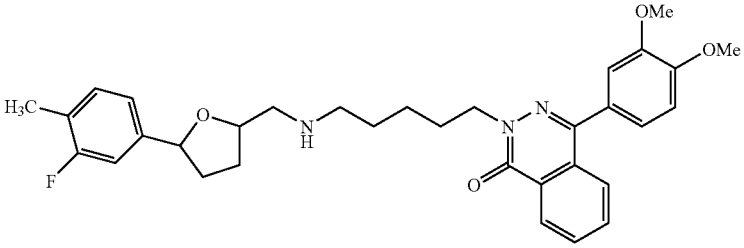<br>126 |
| 4-(3-Cyclopentyloxy-4-methoxy-phenyl)-1-(5-{[5-(3-fluoro-4-methyl-phenyl)-tetrahydro-furan-2-ylmethyl]-amino}-pentyl)-pyrrolidin-2-one | 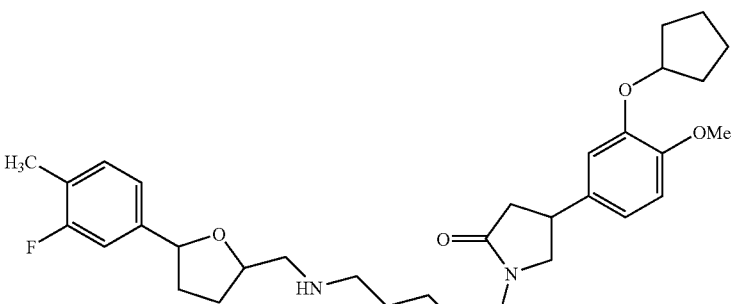<br>127 |

In vivo 2-(Aminoethyl)-5-(phenethyl)tetrahydrofuran was studied in vivo as described below. In this study this compound is also referred to as compound 54 (see Table 1) or compound 31,646 (see, e.g., FIG. 8).

Summary

Treatment with compound 54 resulted in time- and dose-dependent depression of locomotor activity following 30 and 100 mg/kg. Depressant effects of 30 and 100 mg/kg occurred within 10 minutes following injection and lasted 50 to 100 minutes. An $ID_{50}$ of 39.8 mg/kg was estimated based on a 30-minute time period in which maximal depressant effects occurred (0 to 30 minutes following injection). Note: The vehicle used in this study was 2% methylcellulose. Cocaine was used as a control stimulant.

Cocaine Alone Study

Method

A time course/dose response study of cocaine-induced locomotor stimulation was conducted beginning Feb. 21, 2000, according to a locomotor activity studies time course protocol. The study was conducted using 40 Digiscan locomotor activity testing chambers (40.5×40.5×30.5 cm) housed in sets of two, within sound-attenuating chambers. A panel of infrared beams (16 beams) and corresponding photodetectors were located in the horizontal direction along the sides of each activity chamber. A 7.5-W incandescent light above each chamber provided dim illumination. Fans provided an 80-dB ambient noise level within the chamber. Separate groups of 8 non-habituated male Swiss-Webster mice (Hsd: ND4, aged 2-3 mo.) were injected via the intra peritoneal (IP) route with either vehicle (0.9% saline) or cocaine (5, 10, 20, or 40 mg/kg), immediately prior to locomotor activity testing. In all studies, horizontal activity (interruption of photocell beams) was measured for 8 hours within 10-min periods, beginning at 0800 hrs (2 hours after lights on). Testing was conducted with one mouse per activity chamber.

Results

Figure 7:
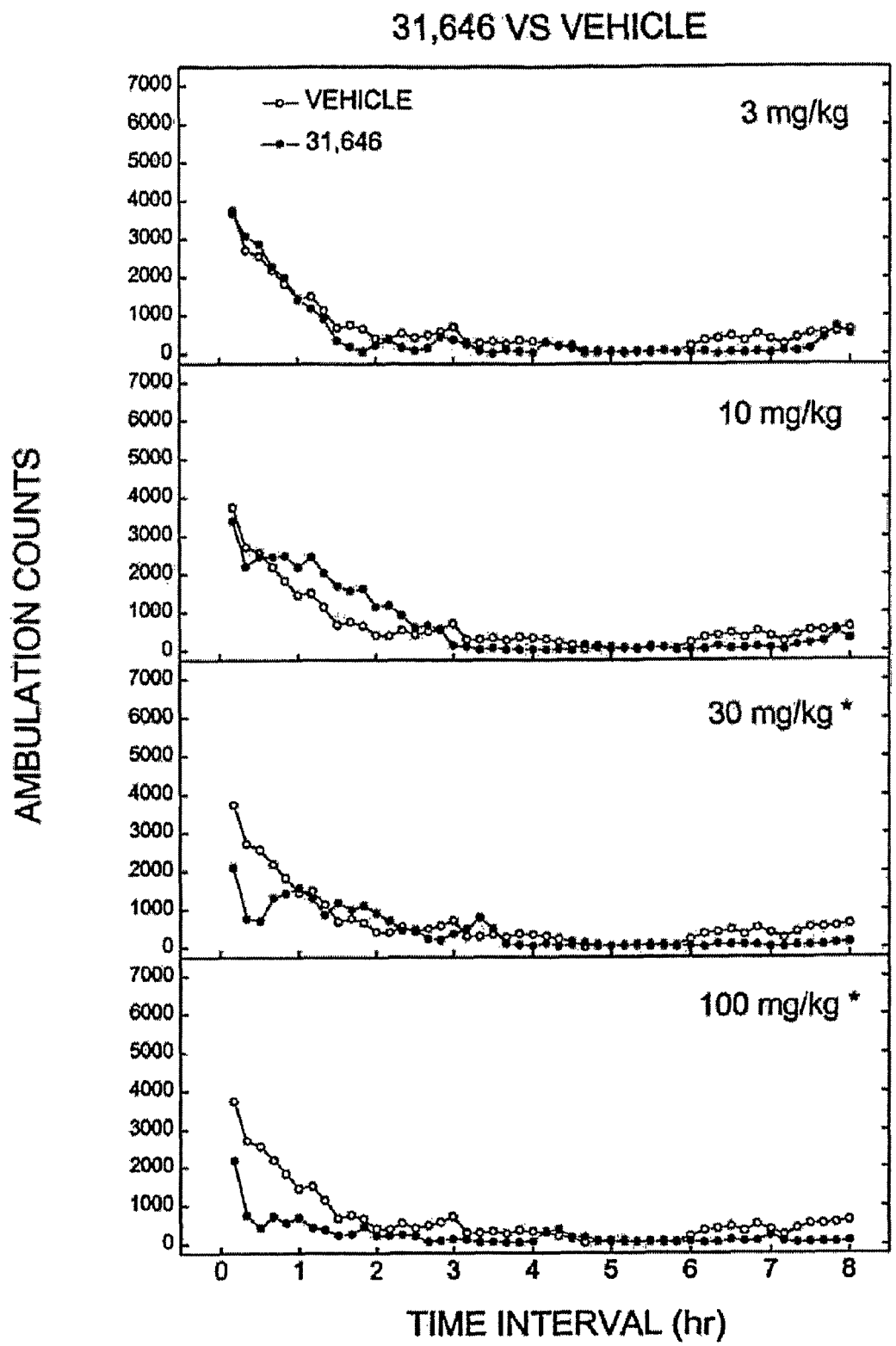
FIG. 7 depicts the effect of cocaine on horizontal activity counts/10 min as a function of dose (top to bottom panels) and time interval during an 8-hr session. Each panel shows one dose group compared with vehicle control. *$p<0.05$ Compared with saline for stimulant effect (0-30 min)

FIG. 7 shows average horizontal activity counts/10 mm as a function of time (0-8 hr) and dose of cocaine (top to bottom panels). Treatment with cocaine resulted in time- and dose-dependent stimulation of locomotor activity in doses from 10 to 40 mg/kg. Stimulant effects of 10 and 20 mg/kg occurred within 10 minutes following injection and lasted 80 to 210 minutes. The period 0-30 mm was selected for analysis of dose-response data because this was the time period in which cocaine produced maximal effects. Using TableCurve 2D v2.03 software (Jandel Scientific), the mean average horizontal activity counts for this 30-mm period were fit to a 3-parameter logistic peak function of log 10 dose (with the constant set to 3224, the mean of the saline-treated group), and the maximum was estimated from the resulting curve (maximum=5520 counts/10 min at 23.4 mg/kg). The $ED_{50}$ (dose producing ½ maximal stimulant activity, where maximal stimulant activity=maximum−mean control counts/10 min) was estimated at 5.8 mg/kg from a linear regression against log 10 dose of the ascending portion of the dose-effect curve (5-20 mg/kg cocaine).

A two-way analysis of variance conducted on horizontal activity counts/10 min indicated significant effects of Treatment $F(4,35)=3.36$, $p=0.02$, 10-Minute Periods $F(47,1645)=95.22$, $p<0.001$, and the interaction of those factors $F(188,1645)=2.02$, $p<0.001$. A one-way analysis of variance conducted on log 10 horizontal activity counts for the 0-30 mm time period (maximal stimulant effect) indicated a significant effect of Treatment $F(4,35)=4.90$, $p=0.003$, and planned comparisons (a priori contrast) against the vehicle group showed a significant stimulant effect for 10, 20 and 40 mg/kg (ps<0.05 denoted on FIG. 7 with an asterisk).

Compound 31,646 Alone Study
Method

A time course/dose response study of compound 31,646-induced locomotor depression was conducted under the same conditions as outlined for the cocaine alone study described above. Separate groups of 8 mice were injected with either vehicle (2% methylcellulose) or compound 31,646 (3, 10, 30 or 100 mg/kg), immediately prior to locomotor activity testing. Behavioral observations were recorded on each mouse at 30, 120 and 480 minutes following 100 mg/kg compound 31,646.

Results

Figure 8:
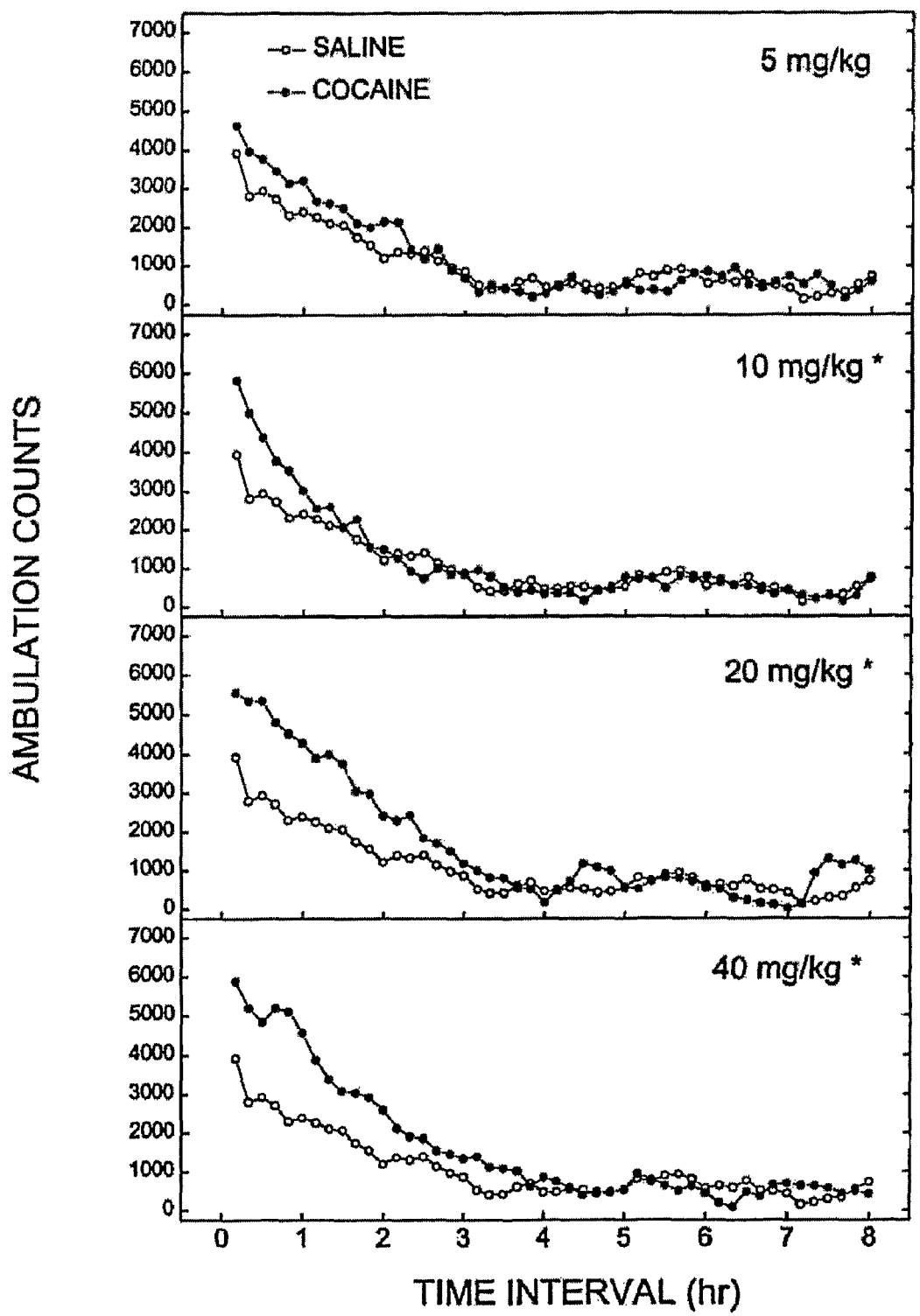
FIG. 8 depicts the effect of compound 31,646 on horizontal activity counts/10 min as a function of dose (top to bottom panels) and time interval during an 8-hr session. Each panel shows one dose group compared with vehicle control. *$p<0.05$ Compared with vehicle for depressant effect (0-30 min).

FIG. 8 shows average horizontal activity counts/10 min as a function of time (0-8 hr) and dose of compound 31,646 (top to bottom panels). Treatment with compound 31,646 resulted in time- and dose-dependent depression of locomotor activity following 30 and 100 mg/kg. Depressant effects of 30 and 100 mg/kg occurred within 10 minutes following injection and lasted 50 to 100 minutes. The period 0-30 min was selected for analysis of dose-response data because this was the time period in which maximal suppression first appeared as a function of dose. The mean average horizontal activity counts/10 min for this 30-min period were fit to a linear function of log 10 dose of the descending portion of the dose-effect curve (3 to 100 mg/kg dose range). The $ID_{50}$ (dose producing ½ maximal depressant activity, where maximal depression=0 counts/30 min) was calculated as 39.8 mg/kg. A small stimulant effect was apparent during the third hour following 10 mg/kg 31,646, although these differences were not statistically significant.

A two-way analysis of variance conducted on horizontal activity counts/10 min indicated significant effects of Treatment $F(4,35)=3.84$, $p=0.011$, 10-Minute Periods $F(47,1645)=59.93$, $p<0.001$. and the interaction of Periods and Treatment $F(188,1645)=3.81$, $p<0.001$. A one-way analysis of variance conducted on log 10 horizontal activity counts for the 0-30 mm time period (maximal depressant effect) indicated a significant effect of Treatment $F(4,35)=21.39$, $p<0.001$, and planned comparisons (a priori contrast) against the vehicle group showed a significant depressant effect for 30 and 100 mg/kg ($ps<0.05$ denoted on FIG. 8 with an asterisk).

Other Observations. No unusual effects were observed following 100 mg/kg of compound 31,646.

Conclusion

Compound 31,646 as a representative member of the CNS agents synthesized and described herein was tested in an animal model of locomotor activity. Compound 31,646 did not cause CNS stimulation but in fact, depressed CNS stimulant activity. The data suggests that compound 31,646 and congeners readily penetrates into the brain and are CNS active but do not cause CNS stimulation.

In Vivo Activity of Dual PDE4 Inhibitor/SSRI

Compounds 19 and 115 were tested in a Morris water maze test. The escape latency (time to climb onto a hidden platform) for each mouse was recorded as a memory test. Previously, it has been shown that rolipram (a PDE4 inhibitor) increases memory and restores cognitive function in a stroke model in rats. Compared to a group of control mice, compound 19 and 115 caused a 30% improvement in memory at 3 mg/kg. The effect was dose-dependent as a 0.3 mg/kg dose produced a significantly lower response. Compound 28 showed only about a 10% improvement in memory at 3 mg/kg. This is not completely unexpected as SSRIs often require repeated dosing to see a large and significant effect. The data shows that despite the large molecular weight, the compounds get into the brain and are pharmacologically active in vivo. Multiple dosing likely will increase the efficacy of the compounds tested. In contrast to simple SSRIs, the in vivo pharmacological effects had a very fast onset of action.

Example 28

2,5-Disubstituted Tetrahydrofurans as Selective Serotonin Reuptake Inhibitors

On the basis of molecular dissection of cocaine, a series of 2,5-disubstituted tetrahydrofurans were synthesized. The compounds were evaluated for their ability of compete with radiolabelled RTI-55 binding and to inhibit reuptake of neurotransmitters at the human dopamine, serotonin and norepinephrine transporters. Highly potent (i.e., $K_i=800$ pM) and selective ($IC_{50}$ ratios for human dopamine:serotonin or norepinephrine:serotonin, $\geq 1397$) functional activity suggested efficacious selective serotonin reuptake inhibitors were identified. Factors playing a dominant role in binding avidity and reuptake inhibition included substitution on the aromatic moiety, relative stereochemistry of the 2,5-disubstituted tetrahydrofuran portion, and the carbon chain length between the amine and the aromatic group. Two selective serotonin transporter inhibitors were evaluated in vivo, and acute administration for one agent suggested a tendency for activity in the forced swim test, but the result did not reach significance.

Introduction

Serotonin systems and related transporters are important in modulating motor, endocrine and emotional functions (Broekkamp et al., *J. Med. Chem.*, 38:4615-4633 (1995)). Serotonin (5-HT) is altered in neurological and psychiatric disorders associated with depression and other conditions including depression and drug abuse (Broekkamp et al., *J. Med. Chem.*, 38:4615-4633 (1995)). Brain 5-HT may play a role in normal and neurological and psychiatric disorders. New agents provide insight into new structure-activity relationships, and may lead to more selective ligands for improved understanding of differences in potency and selectivity at different transporters and for understanding 5-HT in brain physiology and disease (Blough et al., *J. Med. Chem.*, 40:3861-3864 (1997)). Synthesis of novel, highly potent and selective reuptake inhibitors of hSERT could provide a significant amount of structure activity information required for producing more effective antidepressants with fewer side effects. This may also lead to highly potent ligands needed for brain tomography studies that could help to elucidate the pathophysiological mechanism of 5-HT neurotransmission and the relationship between hSERT occupancy and central nervous system drug action (Oya, S. et al., *J. Med. Chem.*, 42:333-335 (1999)).

Figure 9:
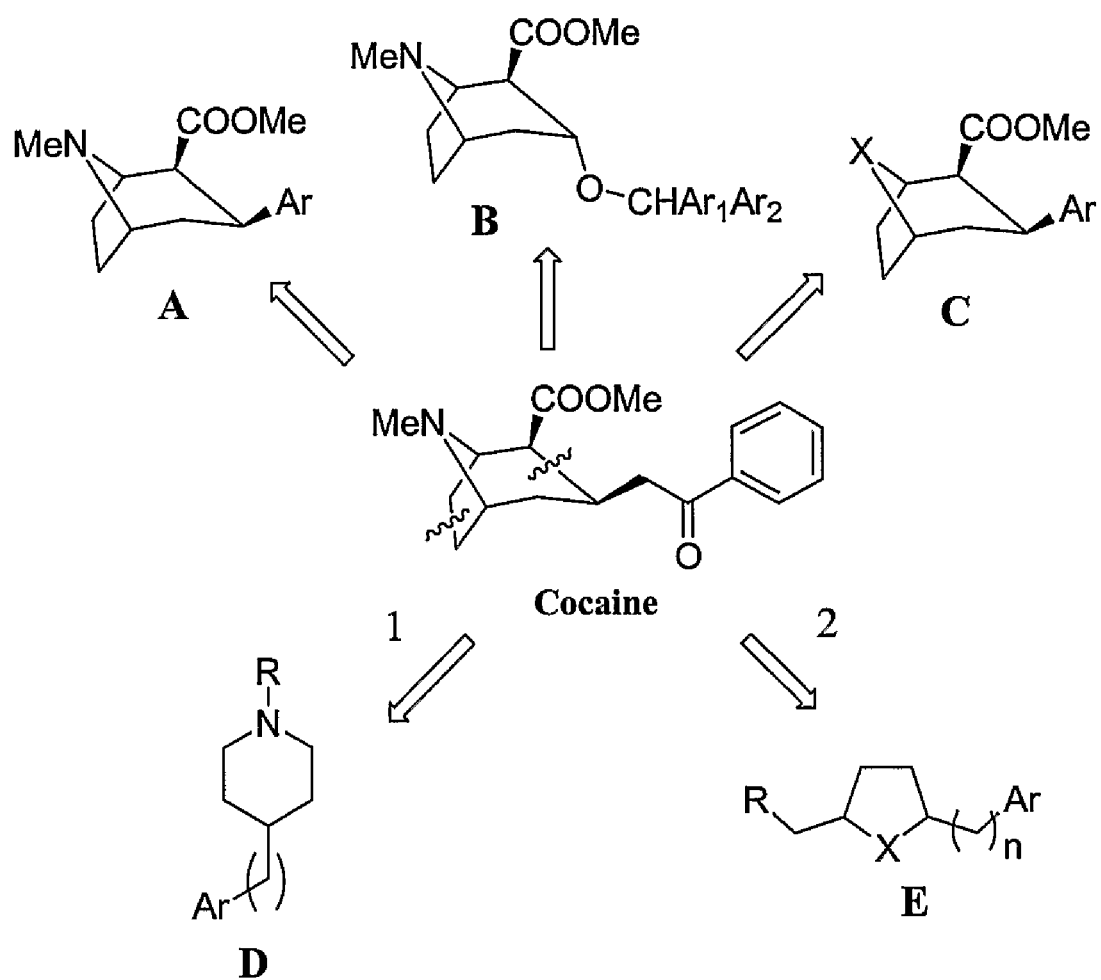
FIG. 9 depicts a molecular dissection of cocaine to afford 2,5-disubstituted tetrahydrofuran compounds.
Figure 10:
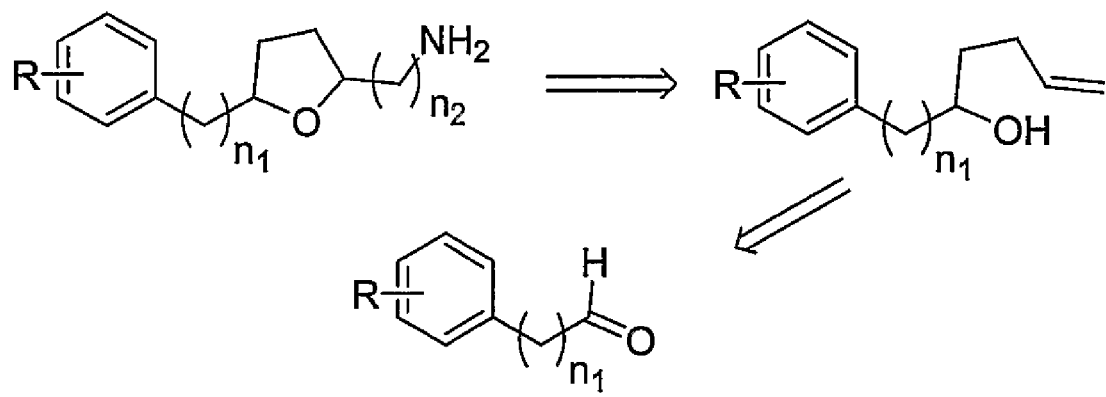
FIG. 10 depicts a retrosynthesis of 2,5-disubstituted tetrahydrofuran compounds.

Cocaine blocks the reuptake of dopamine (DA), serotonin (5-HT) and nor epinephrine (NE) (Eshleman et al., *J. Pharmacol. Exp. Ther.*, 289:877-885 (1999)). Cocaine is more potent than DA at inhibiting 5-HT uptake and influences 5-HT neurotransmission (Carroll et al., *J. Med. Chem.*, 35:969-981 (1992); Wolf et al., *Neurochem. Int.*, 18:33-38 (1991)). Cocaine was utilized as a starting point to develop selective serotonin reuptake inhibitors (SSRIs). Theoretically, molecular dissection of cocaine (FIG. 9) via cleavage of the 2,3-carbon bond or cleavage of the 6,7-carbon bond leads to 5- and 6-membered ring systems (i.e., E and D, respectively, see FIG. 9) (Feng, X. et al., *Bioorg. Med. Chem.*, 11:775-780 (2003); Tamiz et al., *J. Med. Chem.*, 43:1215-1222 (2000)). Taking advantage of the observation that aryltropanes (Holmquist et al., *J. Med. Chem.*, 39:4139-4141

(1996)) or "WIN Compounds" (Clarke et al., *J. Med. Chem.*, 16:1260-1267 (1973)) were more metabolically stable than cocaine analogs that possess aryl ester functionality, metabolically stable compounds derived from molecular dissection of aryltropanes were designed and synthesized. The observation that oxa (Meltzer et al., *J. Med. Chem.*, 40:2661-2673 (1997)) or carbon (Meltzer et al., *J. Med. Chem.*, 42:2982-2991 (2000); Javanmard et al., *J. Med. Chem.*, 42:4836-4843 (1999)) analogs of aryltropanes (structure C, see FIG. 9) were potent ligands for neurotransmitter transporters (Boja et al., *J. Med. Chem.*, 37, 1220-1223 (1994)) and that nortropanes (Blough et al., *J. Med. Chem.*, 40:3861-3864 (1997)) possessed greater binding selectivity for the serotonin transporter (SERT) prompted the synthesis of 2,5-disubstituted tetrahydrofuran analogues (structure E, see FIG. 9). During the process of identifying highly potent and selective human SERT reuptake inhibitors, the process of dynamic medicinal chemistry was employed where metabolic stability considerations were built into the design and synthesis of increasingly more potent and selective compounds. As observed previously, it was also noted that certain alkyl- and halogen-substitutions of the aromatic moiety of aryltropanes led to significant increases in affinity for the human SERT (Blough et al., *J. Med. Chem.*, 40:3861-3864 (1997)). While our investigations of substituents of aromatic ring analogues of 2,5-disubstituted tetrahydrofurans was not exhaustive, it supported the hypothesis that appropriate substitution markedly enhanced the potency and selectivity of reuptake inhibitors for the human SERT. Herein is described the synthesis and characterization of a new class of 2,5-disubstituted tetrahydrofurans that show potent, selective reuptake inhibition of hSERT and low affinity for hDAT and hNET. Studies in small animal models suggest that the compounds possess in vivo efficacy.

Results:

The approach to the identification of highly potent and selective SSRIs utilized molecular dissection and dynamic medicinal chemistry. Molecular dissection of (−)-cocaine derivatives (i.e., "WIN Compounds" or aryltropanes) afforded 2,5-disubstituted tetrahydrofurans. When appropriately substituted, 2,5-disubstituted tetrahydrofurans afforded potent and selective reuptake inhibitors of the human serotonin transporter (hSERT). High throughput chemical synthesis was combined with a strategy to decrease metabolism of the lead compounds (i.e., dynamic medicinal chemistry) to produce metabolically stable, potent SSRIs.

Lead Discovery

Chemical synthesis of a mixture of cis and trans 2,5-disubstituted tetrahydrofurans was done by liquid phase parallel synthesis. To accelerate the lead compound discovery process, a mixture of cis and trans diastereomers was carried through to the final products and pharmacologically tested in vitro. The ratio of diastereomers was determined by high resolution $^1$H NMR and in most cases, the diastereomer ratio was cis:trans=1:2. Binding affinity (i.e., $K_i$ value) was measured for each compound by assessing the potency of inhibition of binding radiolabeled RTI-55 to the human dopamine transporter (hDAT), human SERT (hSERT) and human norepinephrine transporter (hNET). In vitro functional potency was measured by determining the reuptake inhibition (i.e., $IC_{50}$ value) of [$^3$H]-DA, [$^3$H]-5-HT or [$^3$H]-NE at the recombinant hDAT, hSERT or hNET in the presence of HEK-293 cells transfected with the respective cDNA. In the series of 2,5-disubstituted tetrahydrofuran analogs examined, both the unsubstituted- and methoxy-substituted naphthyl compounds (e.g., 15a, $K_i$=18.5 nM, $IC_{50}$=23.3 nM, 15c, $K_i$=45 nM, $IC_{50}$=4.1 nM, 17a, $K_i$=85.6 nM, 17b, $K_i$=92.3 nM, and 15e, $K_i$=174 nM) showed good to modest potency at blocking hSERT binding and reuptake (see Table 9). Unsubstituted phenyl compounds (e.g., 15b, $K_i$=43.0 nM, $IC_{50}$=1714 nM, 15d, $K_i$=68 nM, $IC_{50}$=129 nM, and 17d, $K_i$=3822 nM) showed modest to poor potency at blocking radioligand binding to the hSERT, and poor potency at blocking reuptake of [$^3$H] 5-HT via the hSERT. Aryl compounds with electron withdrawing groups (e.g., 15f, $K_i$=1105 nM, $IC_{50}$=31.9 nM, 15 g, $K_i$=1114 nM, $IC_{50}$=50.3 nM, and 15h, $K_i$=2126 nM, $IC_{50}$=225 nM) all had poor potency at blocking binding to the hSERT, but were fairly potent at blocking reuptake by the transporter. Aryl compounds with electron donating groups (15j, $K_i$=6877 mM, $IC_{50}$=617 nM, 17e, $K_i$=7483 nM, $IC_{50}$=4041 nM and 15k, $K_i$=>10 k nM, 636 nM) were also generally more potent at blocking reuptake by the hSERT as compared to their potencies at blocking binding. Aromatic groups with heteroatoms (e.g., 15i, $K_i$=4546 nM, $IC_{50}$=2721 nM and 17f, $K_i$=>10 k nM, $IC_{50}$=>10 k nM) also possessed poor potency for blocking hSERT binding and were also not very potent at blocking uptake by the hSERT. Substituents on the aryl group that contained both electron donating and electron withdrawing groups (e.g., 17c, $K_i$=688 nM, $IC_{50}$=30 nM) were potent at blocking reuptake via the hSERT, but had low potency at blocking binding to the hSERT.

Generally, the 2,5-disubstituted tetrahydrofurans examined possessed very poor potency for inhibition of binding of radiolabeled RTI 55 to hDAT (i.e., range 512 to >10,000 nM) or to hNET (i.e., 634 to >10,000 nM). However, in some cases, (i.e., 15b, 15c, 15f and 15g for the hNET and 15b and 15c for the hDAT) the compounds possessed considerable potency at blocking transporter reuptake. Lead discovery activity was focused on compounds that potently interacted with the hSERT.

Structure Activity Studies

During the lead discovery phase, it was observed that methoxy substituents increased the affinity of the compounds for the hSERT (e.g., 17a). The fluoro methoxy disubstituted aryl analogs 18a-r were synthesized to further investigate the structure activity relationship for this series. Human SERT binding and reuptake inhibition was dependent on both the chain length between the aryl moiety and amine group and the cis/trans orientation of the 2,5-disubstituted tetrahydrofuran ring (see Table 10). Overall, the trans orientation (e.g., 18k, $K_i$=0.8 nM, $IC_{50}$=2.5) provided compounds that were more potent than the compound with the cis orientation (e.g., 18l, $K_i$=19.3 nM, $IC_{50}$=17.5 nM). Generally, the trans orientation increased the potency in the binding and reuptake assays approximately 7-fold compared to the corresponding cis compound. By increasing the chain length between the aryl group and tetrahydrofuran ring, the potency was increased (e.g., 18a, $K_i$=6307 nM, $IC_{50}$=2071 nM to 18m, $K_i$=0.8 nM, $IC_{50}$=2.1 nM). Based on the compounds tested thus far, a three carbon atom span between the aryl group and the tetrahydrofuran was optimal. Functional activity was also dependent on the number of carbon atoms between the tetrahydrofuran moiety and the terminal amine with two carbon atoms generally being superior to one carbon atom. The overall chain length between the substituted aryl group, tetrahydrofuran, and the terminal amine was optimal with a total of five carbon atoms (i.e., 18o, $K_i$=1.1 mM, $IC_{50}$=2.3 nM, cis/trans 1:2.5). Analogs 18a-r were also tested for binding and reuptake inhibition against hDAT and hNET, and these results are listed in Table 10. Generally, 18a-r possessed very low affinity for the hDAT (i.e., $K_i$ values in the range 6,288-41,257 nM) and very low affinity for the hNET (i.e., $K_i$ values in the range 481-10,000 nM). Thus, the selectivity for interacting with the hSERT was great. The selectivity ratios for inhibition of binding and reuptake of biogenic amines by these compounds are listed in Table 11. Potency for binding inhibition and reuptake inhibition at the hSERT correlated very well for the most active compounds such as 18a-18p (i.e., average reuptake ($IC_{50}$)/binding ($K_i$) correlation=1.04). However, reuptake ($IC_{50}$)/binding ($K_i$) correlations calculated for 18q ($IC_{50}/K_i$=21.0) and 18r ($IC_{50}/K_i$=15.5) suggested that the properties controlling binding and reuptake for these latter compounds were not exactly the same.

The selectivity of 18k, 18m and 18p for hSERT versus other biogenic amine transporters expressed as ratios of binding ($K_i$s) or reuptake ($IC_{50}$s) values listed in Table 11 showed that the most potent compounds possessed excellent transporter selectivity ($K_i$ ratios ranging from 1162 to 10,676 or $IC_{50}$ ratios ranging from 192 to 11,140) for hDAT/hSERT and hNET/hSERT, respectively.

In Vivo Efficacy Studies

Balb/c mice have been reported to exhibit a relatively high immobility baseline and have shown sensitivity to fluoxetine challenge in the forced-swim test (FST) (Lucki et al., *Psychopharmacol.*, 155:315-322 (2001)). Fluoxetine and a 1:2 cis:trans ratio of compounds 18k/l and 18o/p were examined in the FST. Acute administration of fluoxetine (20 mg/kg), 18k/l (10 mg/kg), or 18o/p (10 mg/kg) the latter two compounds as a mixture of 1:2 cis:trans diastereomers, did not significantly alter the duration of immobility in the FST in Balb/c mice although there was a tendency for 18o/p to show an effect (FIG. 3). In contrast, subchronic administration of a lower dose of fluoxetine (10 mg/kg) significantly decreased immobility ($P<0.05$) (data not shown) but subchronic treatment with 18k/l (10 mg/kg) did not change immobility compared to the vehicle control (data not shown).

In Vitro Metabolic Stability Studies

Metabolic stability tests were done with 18k/l in the presence of both mouse and rat liver microsomes supplemented with NADPH using a general protocol described before (Denton et al., *J. Med Chem.* 48:224-239 (2004)). Compound 18k/l was more stable in the presence of rat liver microsomes (i.e., half life of 106 min) than in the presence of mouse liver microsomes (i.e., a half life of 56 min). The N-methyl amine, compound 20, was synthesized to potentially increase metabolic stability and act as a pro-drug. In vitro microsomal metabolism studies of compound 20 showed an increase in the metabolic stability in the presence of rat liver microsomes (i.e., a half life of 129 min). However, compound 20 was not more stable than 18k/l and had a half life of 58.5 min in the presence of mouse liver microsomes.

Discussion

Based on molecular dissection of cocaine and the closely related aryltropane structures, 5- and 6-membered compounds were prepared. 2,5-Disubstituted tetrahydrofuran compounds with 0, 1, 2, or 3 carbons between the tetrahydrofuran ring and various substituted or unsubstituted aryl or naphthyl groups as well as compounds with carbon chains of 1 or 2 carbon atoms between the tetrahydrofuran ring and the amine were tested for binding and reuptake inhibition at hDAT, hSERT, and hNET. In general, low binding potency and reuptake inhibition potency for the 2,5-disubstituted tetrahydrofurans were observed for the hDAT and hNET. For certain 2,5-disubstituted tetrahydrofurans, significant reuptake inhibition of the hSERT was observed and this was explored in detail. Unsubstituted phenyl compounds possessed modest potency. Compounds with electron withdrawing or electron donating groups on the aryl group showed decreased affinity towards the hSERT. Binding affinity was decreased with bulky substituents on the aryl ring but affinity was maintained when large aromatic groups such as 1- or 2-naphthyl groups were present. Affinity for the hSERT was decreased when a heteroaryl group (i.e., furan or pyridine) was introduced as a replacement for the aryl group. When 2-methoxy 5-fluorophenyl substituents were present in the aryl portion of the molecule, highly potent and selective hSERT reuptake inhibitors were observed. It is possible that the methoxy and furan oxygen atoms work together to coordinate cations and facilitate hSERT mechanism of action. However, this was not examined in detail in this study. Nevertheless, synthesis of additional compounds with various carbon atom side chains with a 2-methoxy 5-fluorophenyl moiety present afforded highly potent compounds. The most potent hSERT reuptake inhibitors contained side chains of a total of 5 carbon atoms in length. In the 2-methoxy 5-fluorophenyl 2,5-disubstituted tetrahydrofuran series, compounds with the trans configuration at the 2,5-tetrahydrofuran junction afforded on average, about 7-fold more potency than the corresponding cis diastereomers. However, the absolute stereochemistry at the 2,5-position of the tetrahydrofuran was not investigated.

Figure 11:
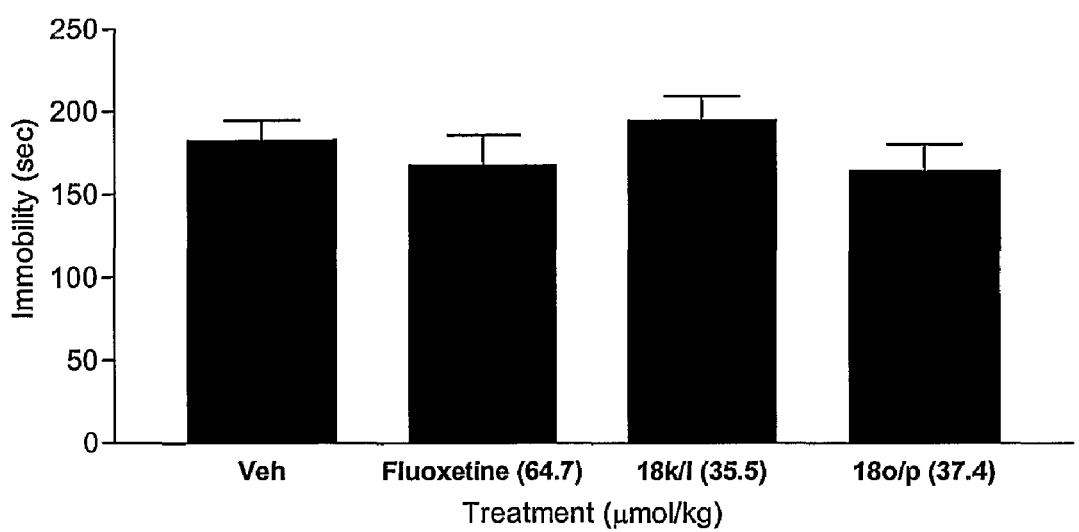
FIG. 11 depicts an effect of acute treatment with fluoxetine (64.7 µmol/kg, 20 mg/kg), compound 18k/l, (35.5 µmol/kg, 10 mg/kg) and compound 18o/p, (37.4 µmol/kg, 10 mg/kg), on immobility in the forced-swim test in Balb/c mice. Vehicle or compounds were injected i.p. 30 min prior to the test. n=10-11.
Figure 12:
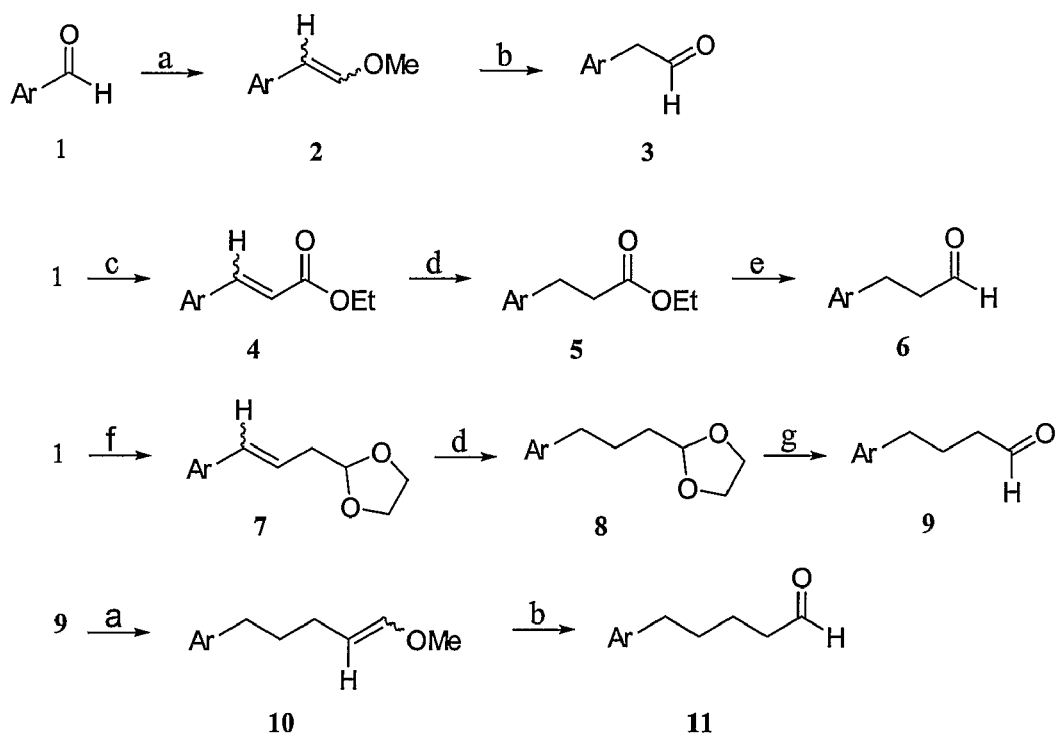
FIG. 12 depicts scheme 6 (of schemes 6 to 8) of a method for synthesis of certain embodiments of the present invention. (See Example 28.)
Figure 13:
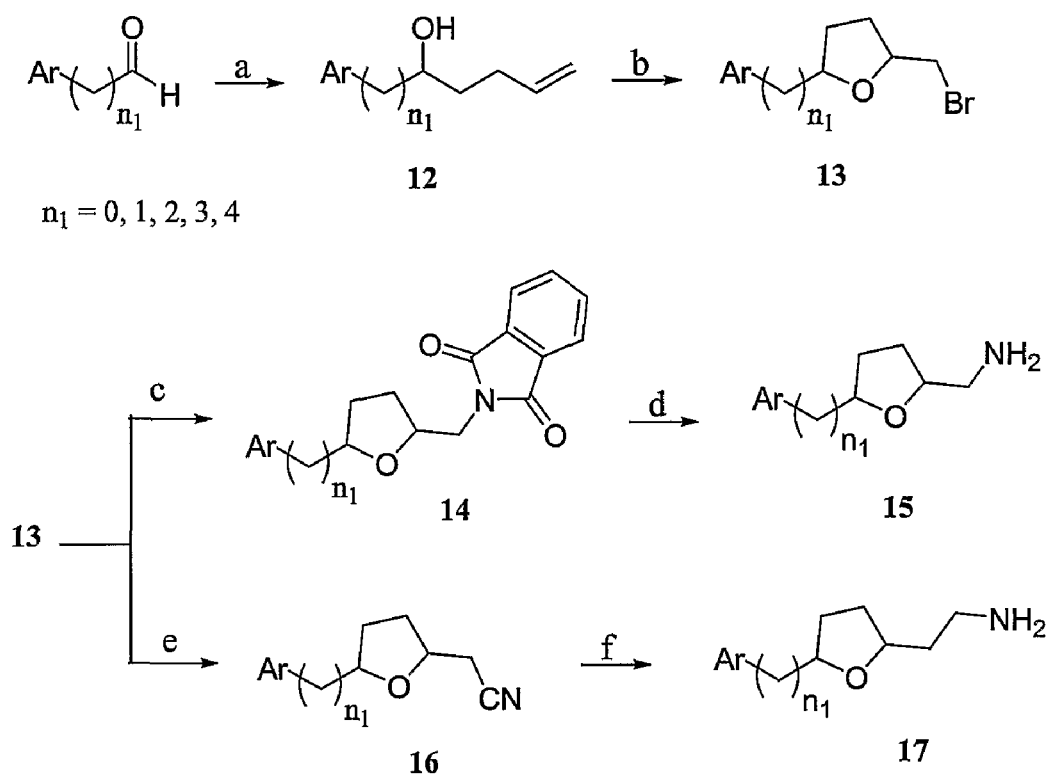
FIG. 13 depicts scheme 7 (of schemes 6 to 8) of a method for synthesis of certain embodiments of the present invention. (See Example 28.)
Figure 14:
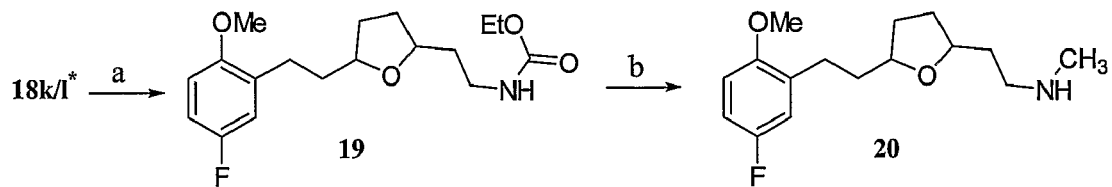
FIG. 14 depicts scheme 8 (of schemes 6 to 8) of a method for synthesis of certain embodiments of the present invention. (See Example 28.)

Acute treatment of mice with 18k/l at doses of 10 and 30 mg/kg or 18o/p tended to decrease immobility, but it was not statistically significant. (See FIG. 11.) Subchronic treatment of mice with 18k/l at doses of 10 mg/kg did not change immobility compared to the vehicle control. Under the same conditions, fluoxetine (10 mg/kg) did cause significantly decreased immobility in the FST. These in vivo results could be due to relatively rapid metabolism of the primary amine to inactive metabolites or the amount and duration of the dose.

Experimental Section:

General. Commercially available reagents were purchased from Aldrich chemical company or VWR and were used as received. All moisture sensitive reactions were carried out in flame-dried glassware under an argon atmosphere. Tetrahydrofuran (THF) and toluene were freshly distilled from calcium hydride under an argon atmosphere. Methanol ($CH_3OH$) was passed through a column of neutral alumina and stored over 3 Å molecular sieves prior to use.

Analytical thin-layer chromatography (TLC) was done on K6F silica gel 60 Å (Whatman) glass-backed plates. Compounds were detected using UV absorption at 254 nm and/or stained with $I_2$ (iodine). Flash chromatography was done on Merck (60 Å) pore silica. NMR spectra were recorded at 500 MHz by NuMega Resonance Labs, Inc., (San Diego, Calif.) or at 300 MHz by the Human BioMolecular Research Institute using the solvent specified. Chemical shifts were reported in parts per million (ppm, δ) using residual solvent signals as internal standards. Low resolution mass spectroscopy (LRMS) was done with an HP 1100 mass spectrometer at HT Laboratories (San Diego, Calif.) using electrospray ionization (ESI) or at the Human BioMolecular Research Institute on a Hitachi M-8000 3DQMS (ion trap) mass spectrometer using ESI. High resolution mass spectroscopy (HRMS) was done with a Micromass LCT time of flight mass spectrometer at the University of Montana Mass Spectrometry Facility (Missoula, Mont.) using ESI.

The 2,5-disubstituted tetrahydrofuran analogues were characterized by $^1$H NMR, LRMS, HRMS and their purities (>95%) were determined by HPLC in two distinct solvent systems. Analytical HPLC measurements were run on a Hitachi L-6200 system equipped with a Hitachi L-7400 UV detector. Separations were done (straight-phase) with an Axxichrom silica column (4.6 mm×250 mm, 5 µm) or (reverse-phase) with a Supelco HS F5 pentafluorophenyl column (4.6 mm×250 mm, 5 µm). Standard conditions utilized an isocratic, ternary-solvent system consisting of solvents A (methanol), B (isopropanol), C (acetonitrile), and D ($HClO_4$)

set at a flow rate of 1.5 mL/min (straight-phase), or A, E (water) and F (HCO$_2$H) set at a flow rate of 1.0 mL/min (reverse-phase), λ=254 nm with retention times (t$_R$) evaluated in minutes. Typical analyses involved two distinct isocratic elutions per compound of interest. Solvent conditions for the isocratic elutions were varied depending on the compound and its specific chromatographic properties. $^1$H NMR and mass spectra are consistent with the assigned structures.

Transporter Binding and Reuptake Inhibition Assays. For [$^{125}$I]RTI-55 binding studies, the HEK-hDAT, -hSERT, or hNET cells were grown as described previously (Eshleman et al., *J. Pharmacol. Exp. Ther.*, 289:877-885 (1999)). Binding studies were done as described before (Eshleman et al., *J. Pharmacol. Exper. Ther.*, 274:276-283 (1995)). Two or three independent competition experiments were done with duplicate determinations. GraphPad Prism was used to analyze the data with IC$_{50}$ values converted to K$_i$±SEM values using the Cheng-Prusoff equation. For uptake inhibition assays, Krebs-HEPES and test compound were added to cells described above. The assay was initiated by addition of tritiated neurotransmitter (20 mM final concentration). Specific uptake was defined as the difference in uptake observed in the presence and absence of 5 µM mazindol or 5 µM imipramine (i.e., for the hSERT). Filtration of the cells through a filter and calculation of IC$_{50}$ values were as described before (Fandrick et al., *Biorganic Med. Chem. Lett.*, 13:2151-2154 (2003)). Triplicate determinations from curves made up of six drug concentrations each afforded each IC$_{50}$ value±SEM.

Animal Testing

Forty Balb/c male mice weighing 22.4±0.1 g were used in the experiment and were housed in a temperature-controlled room (22-23° C.) and maintained on a 12-hour on/12-hour off light cycle (lights on at 6:00 AM). The study was conducted according to a standard operation procedure and in accordance with all Federal regulations. Water and food were freely available in the home cages. The mice were randomly divided into four groups: Vehicle (saline containing 5% DMSO), (B) fluoxetine 20 mg/kg, (C) 18k/l 10 mg/kg and 18o/p 10 mg/kg. The forced-swim test (FST) was carried out as described previously (Zhang et al., *Neuropsychopharmacol.*, 27:587-595 (2002)). Mice were given a swimming pretest session, once a day for two successive days. Twenty-four hours after the last session, mice were injected i.p. with vehicle or the lower dose of each drug 30 min prior to the FST. During the pretest and test sessions, each mouse was placed for 6 min in a plastic cylinder (45 cm high×20 cm diameter), which was filled to a depth of 28 cm with water (23±1° C.). The duration of immobility, which was defined as floating in an upright position without additional activity other than that necessary for the animal to keep its head above water, was recorded. For the subchronic administration tests, the animals were separated as above and vehicle or chemicals were given by i.p. administration 23, 5 and 1 hr before the FST. The subchronic experiments were done similar to the study described above except for the pretest training that was not carried out.

Mouse and Rat Liver Microsome Stability Assay.

A typical assay mixture contained either mouse or rat liver microsomes (0.5 mg of protein), 100 µM potassium phosphate buffer (pH 7.4), 40 µM test compounds, 0.5 mM NADP+, 0.5 mM glucose-6-phosphate, 5 IU/mL glucose-6-phosphate dehydrogenase, 1 mg/mL diethylenetriaminepentaacetic acid (DETAPAC) and 5 mM MgCl$_2$ in a final incubation volume of 0.1 mL. After 0, 10, 25, 40 and 60 min, the incubations were stopped by the addition of 1 ml CH$_2$Cl$_2$/2-propanol (3:1 v:v). The mixture was centrifuged at 12,000×g for 1 min, and the organic layer was separated from the aqueous fraction. The organic fraction was evaporated with a stream of argon and the residue was taken up in methanol (200 µL) and injected into the HPLC system described above.

Chemical Synthesis

5-Fluoro-2-methoxyphenylacetaldehyde (2a): To a suspension of methoxymethyltriphenylphosphonium chloride (10.0 g, 30.0 mmol) in THF (30 mL) under Ar was added NaH (60% in mineral oil, 1.2 g, 30 mmol) and then heated to reflux for 1 h. The orange colored suspension was cooled to 0° C. and 5-fluoro-2-methoxybenzaldehyde (4.2 g, 26.0 mmol) was added and the mixture was stirred for 12 h at room temperature. The reaction mixture was then poured into a separatory funnel containing ammonium chloride aqueous solution (sat. NH$_4$Cl/H$_2$O, 1:1, v:v, 100 mL). The organic material was extracted with ethyl acetate (3×80 mL) and the combined organic layers were washed with brine (60 mL) and dried over Na$_2$SO$_4$. The solvent was then removed in vacuo and the crude product (2a) obtained was dissolved in acetone (50 mL). H$_2$SO$_4$ (1 M, 1.5 mL) was then added and the mixture obtained was heated to reflux for 6 h while stirring. The reaction was then cooled to room temperature and the solvent was removed in vacuo to obtain the crude product that was then purified by flash column chromatography (R$_f$=0.15, EtOAc/Hexane, 10:90, v:v) to afford the product (2.63 g, 66%) as an oil: $^1$H NMR (CDCl$_3$, 500 MHz): δ 9.68 (s, 1 H), 6.97 (dt, J=3.1, 8.7 Hz, 1 H), 6.89 (dd, J=3.1, 8.7 Hz, 1 H), 6.83 (dd, J=4.3, 8.7 Hz, 1 H), 3.80 (s, 3 H), 3.63 (d, J=1.7 Hz, 2 H).

Ethyl-3-(5'-fluoro-2'-methoxyphenyl)-2-propenoate (4a): To a solution of 5-fluoro-2-methoxybenzaldehyde (4.3 g, 28.0 mmol) in CH$_2$Cl$_2$ (30 mL) at 0° C. was added portionwise carbethoxymethylenetriphenylphosphorane (10.7 g, 30.1 mmol). The mixture was then warmed to room temperature and stirred for 12 h. The solvent was removed in vacuo and the residue was purified by flash column chromatography (R$_f$=0.2, EtOAc/Hexane, 10:90, v:v) to provide the product (6.0 g, 95%) as oil in a 4:1 mixture of tran:cis isomers; $^1$H NMR (CDCl$_3$, 500 MHz): δ 7.93 (d, J=16.2 Hz, 0.8 H), 7.33 (dd, J=3.1, 9.2 Hz, 0.2 H), 7.21 (dd, J=3.1, 9.2, Hz, 0.8 H), 7.08 (d, J=12.5 Hz, 0.2 H), 7.03 (dt, J=3.0, 8.8 Hz, 0.8 H), 6.99 (dt, J=3.0, 8.8 Hz, 0.2 H), 6.84 (dd, J=3.1, 8.6 Hz, 0.8 H), 6.79 (dd, J=3.3, 9.1 Hz, 0.2 H), 6.47 (d, J=16.2 Hz, 0.8 H), 5.99 (d, J=12.5 hz, 0.2 H), 4.25 (q, J=7.1 Hz, 1.6 H), 4.15 (q, J=7.0 Hz, 0.4 H), 3.86 (s, 2.4 H), 3.81 (s, 0.6 H), 1.34 (t, J=7.1 Hz, 2.4 H), 1.22 (t, J=7.0 Hz, 0.6 H).

(R$_f$=0.4, EtOAc/Hexane, 6:94, v:v)

The following compounds were prepared in a similar fashion as that for compound 4a.

Ethyl 3-pentafluorophenyl-2-propenoate (4b): The product (6.64 g, 94%) was obtained by chromatography on silica as oil; (R$_f$=0.39, EtOAc/Hexane, 6:94, v:v); $^1$H NMR (CDCl$_3$, 500 MHz): δ 7.64 (d, J=16.6 Hz, 1 H), 6.73 (d, J=16.5 Hz, 1 H), 4.29 (q, J=7.2 Hz, 2 H), 1.35 (t, J=7.2 Hz, 3 H).

Ethyl-3-(3-pyridine) 2-propenoate (4c): The product as an oil (5.3 g, quantitative yield) was obtained by chromatography on silica; (R$_f$=0.24, EtOAc/Hexane, 50:50, v:v); $^1$H NMR (500 MHz, CDCl$_3$) δ 8.70 (d, J=1.9 Hz, 1 H), 8.55 (t, J=5.2 Hz, 1 H), 7.79 (d, J=9.8 Hz, 1 H), 7.63 (d, J=18.9 Hz, 1 H), 7.28 (dd, J=5.3, 4.7 Hz, 1 H), 6.45 (d, J=15.6 Hz, 1 H), 4.23 (q, J=7.2 Hz, 2 H), 1.30 (t, J=7.2 Hz, 3 H).

Ethyl 3-(1-naphthyl)-2-propenoate (4d): The product as an oil (14.3 g, 98.4%) was obtained by chromatography on silica; (R$_f$=0.61, EtOAc/Hexane, 25:75, v:v); $^1$H NMR (500 MHz, CDCl$_3$) δ 8.53 (d, J=15.9 Hz, 1 H), 8.20 (d, J=8.4 Hz, 1 H), 7.88 (t, J=7.5 Hz, 2 H), 7.74 (d, J=7.2 Hz, 1 H), 7.58 (t, J=5.6 Hz, 1 H), 7.53 (t, J=7.0 Hz, 1 H), 7.47 (t, J=7.8 Hz, 1 H), 6.53 (d, J=15.6 Hz, 1 H), 4.34 (q, J=7.2 Hz, 2 H), 1.40 (t, J=7.1 Hz, 3 H).

Ethyl 3-(2'-methoxy-1'-naphthyl)-2-propenoate (4e): The product as an oil (6.32 g, 93%) was obtained by chromatography on silica; ($R_f$=0.54, EtOAc/Hexane, 25:75, v:v); $^1$H NMR (500 MHz, CDCl$_3$) δ 8.35 (d, J=15.8 Hz, 1 H), 8.19 (d, J=8.6 Hz, 1 H), 7.85 (d, J=9.1 Hz, 1 H), 7.79 (d, J=7.9 Hz, 1 H), 7.52 (m, 1 H), 7.38 (t, J=7.7 Hz, 1 H), 7.29 (d, J=8.8 Hz, 1 H), 6.76 (d, J=15.6 Hz, 1 H), 3.95 (s, 3 H), 3.42 (t, J=7.7 Hz, 3 H), 2.74 (td, J=7.7, 1.9 Hz, 3 H).

Ethyl 3-(4'-methoxy-1'-naphthyl)-2-propenoate (4f): The product as an oil (4.3 g, 92%) was obtained by chromatography on silica; ($R_f$=0.55, EtOAc/Hexane, 25:75, v:v); $^1$H NMR (300 MHz, CDCl$_3$) δ 8.48 (d, J=15.6 Hz, 1 H), 8.32 (d, J=8.7 Hz, 1 H), 8.18 (d, J=8.7 Hz, 1 H), 7.73 (d, J=7.8 Hz, 1 H), 7.63-7.50 (m, 2 H), 6.82 (d, J=8.4 Hz, 1 H), 6.46 (d, J=15.6 Hz, 1 H), 4.32 (q, J=7.2 Hz, 2 H), 4.02 (s, 3 H), 1.38 (t, J=7.2 Hz, 3 H).

Ethyl 3-(4'-fluoro-3'-methylphenyl)-2-propenoate (4g): The product as an oil (4.53 g, 99%) was obtained by chromatography on silica; ($R_f$=0.54, EtOAc/Hexane, 25:75, v:v); $^1$H NMR (300 MHz, CDCl$_3$) δ 7.58 (d, J=16.2 Hz, 1 H), 7.34-7.28 (m, 2 H), 6.98 (t, J=9.3 Hz, 1 H), 6.31 (d, J=16.2 Hz, 1 H), 4.23 (q, J=7.2 Hz, 2 H), 2.26 (s, 3 H), 1.31 (t, J=7.2 Hz, 3 H).

Ethyl-4-(5'-fluoro-2'-methoxyphenyl)propanoate (5a): To a solution of 4a (6.0 g, 27.0 mmol) in ethanol (200 proof, 40 mL) under Ar was added 10% Pd/C (250 mg). The flask containing the mixture was then evacuated and purged with H$_2$ three times. A balloon containing H$_2$ gas was attached to the flask and the reaction was allowed to stir for 15 h at room temperature. Then the reaction mixture was filtered through celite with ethanol. The crude product obtained by removal of the solvent in vacuo was purified by flash column chromatography ($R_f$=0.27, EtOAc/Hexane, 10:90, v:v) to give the product as an oil (5.8 g, 95%); $^1$H NMR (CDCl$_3$, 500 MHz): δ 6.89-6.84 (m, 2 H), 6.74 (dd, J=4.7, 9.8 Hz, 1 H), 4.12 (q, J=7.1 Hz, 2 H), 3.79 (s, 3 H), 2.91 (t, J=7.7 Hz, 2 H), 2.59 (t, J=7.7 Hz, 2 H), 1.24 (t, J=7.2 Hz, 3 H).

The following compounds were prepared in a similar fashion as that for compound 5a.

Ethyl 3-pentafluorophenyl-2-propanoate (5b): The product as an oil (6.5 g, 96%) was obtained by chromatography on silica; ($R_f$=0.65, EtOAc/Hexane, 25:75, v:v); $^1$H NMR (500 MHz, CDCl$_3$) δ 4.14 (q, J=7.2 Hz, 2 H), 3.02 (t, J=7.7 Hz, 2 H), 2.60 (q, J=8.0 Hz, 2 H), 1.25 (t, J=7.2 Hz, 3 H).

Ethyl 3-(3'-pyridine)propanoate (5c): The product as an oil (5.4 g, quantitative yield) was obtained by chromatography on silica; ($R_f$=0.33, EtOAc/Hexane, 40:60, v:v); $^1$H NMR (500 MHz, CDCl$_3$) δ 8.48 (s, 1 H), 8.46, (d, J=4.7 Hz, 1 H), 7.53 (d, J=7.8 Hz, 1 H), 7.21 (m, 1 H), 4.12 (q, J=7.2 Hz, 2 H), 2.95 (t, J=7.6 Hz, 2 H), 2.63 (t, J=7.6 Hz, 2 H), 1.23 (t, J=7.2 Hz, 3 H).

Ethyl 3-(1-napthyl)-propanoate (5d): The product as an oil (12.4 g, 86.2%) was obtained by chromatography on silica; ($R_f$=0.50, EtOAc/Hexane, 20:80, v:v); $^1$H NMR (500 MHz, CDCl$_3$) δ 8.05 (d, J=8.3 Hz, 1 H), 7.87 (d, J=1 H), 7.74 (d, J=8.0 Hz, 1 H), 7.55 (t, J=7.2 Hz, 1 H), 7.50 (t, J=6.9 Hz, 1 H), 7.42 (t, J=7.3 Hz, 1 H), 7.37 (d, J=6.8 Hz, 1 H), 4.18 (t, J=7.1 Hz, 2 H), 3.45 (t, J=8.0 Hz, 2 H), 2.78 (q, J=8.2 Hz, 2 H), 1.25 (t, J=7.2 Hz, 3 H).

Ethyl 3-(2'-methoxy-1'-naphthyl)-2-propanoate: The product as an oil (4.42 g, 91%) was obtained by chromatography on silica; ($R_f$=0.54, EtOAc/Hexane, 25:75, v:v); $^1$H NMR (300 MHz, CDCl$_3$) δ 7.98 (d, J=8.7 Hz, 1 H), 7.89 (d, J=8.2 Hz, 1 H), 7.75 (d, J=8.9 Hz, 1 H), 7.50 (t, J=7.7 Hz, 1 H), 7.34 (t, J=7.5 Hz, 1 H), 7.26 (m, 1 H), 4.16 (q, J=7.1 Hz, 2 H), 3.96 (s, 3 H), 3.42 (t, J=7.7 Hz, 2 H), 2.61 (m, 2 H), 1.26 (m, 3 H).

Ethyl 3-(4'-methoxy-1'-naphthyl)-2-propanoate: The product as an oil (2.59 g, 94%) was obtained by chromatography on silica; ($R_f$=0.22, EtOAc/Hexane, 10:90, v:v); $^1$H NMR (300 MHz, CDCl$_3$) δ 8.31 (d, J=8.2 Hz, 1 H), 7.96 (d, J=8.4 Hz, 1 H), 7.54 (m, 1 H), 7.49 (t, J=7.8 Hz, 1 H), 7.25 (d, J=7.8 Hz, 1 H), 6.73 (d, J=8.1 Hz, 1 H), 4.15 (q, J=7.2 Hz, 2 H), 3.99 (s, 3 H), 3.34 (t, J=8.0 Hz, 2 H), 2.72 (t, J=7.9 Hz, 2 H), 1.25 (t, J=7.2 Hz, 3 H).

Ethyl 3-(4'-fluoro-3'-methylphenyl)-2-propanoate: The product as an oil (4.32 g, 95%) was obtained by chromatography on silica; ($R_f$=0.54, EtOAc/Hexane, 25:75, v:v); $^1$H NMR (300 MHz, CDCl$_3$) δ 7.00-6.86 (m, 3 H), 4.11 (q, J=7.2 Hz, 2 H), 2.87 (t, J=7.5 Hz, 2 H), 2.57 (t, J=7.5 Hz, 2 H), 2.23 (s, 3 H), 1.22 (t, J=7.2 Hz, 3 H).

3-(5'-Fluoro-2'-methoxyphenyl)propanal (6a): To a solution of ethyl-3-(5'-fluoro-2'-methoxyphenyl)propionate (5.8 g, 25.7 mmol) in dry toluene (40 mL) under Ar was added DIBAL solution (1 M in toluene, 30 mL, 30 mmol) at −78° C. The reaction was then stirred at this temperature for 2 h. Methanol (2 mL) was added to the reaction mixture and the reaction was allowed to warm to 0° C. The reaction mixture was then poured into a separatory funnel containing an HCl solution (1 N, 100 mL). The organic material was extracted with ethyl acetate (3×60 mL) and the combined organic layers were washed with brine (80 mL) and dried over sodium sulfate. The crude product obtained by removal of the solvent in vacuo was purified by a flash column chromatography ($R_f$=0.10, EtOAc/Hexane, 10:90, v:v) to give the product (3.1 g, 66%); $^1$H NMR (CDCl$_3$, 500 MHz): δ 9.80 (s, 1 H), 6.88-6.86 (m, 2 H), 6.75 (dd, J=4.6, 8.6 Hz, 1 H), 3.79 (s, 3 H), 2.91 (t, J=7.4 Hz, 2 H), 2.72 (t, J=7.4 Hz, 2 H).

The following compounds were prepared in a similar manner from 6a.

3-Pentafluorophenylpropanal (6b): The product as an oil (1.60 g, 30%) was obtained by chromatography on silica; ($R_f$=0.30, EtOAc/Hexane, 5:95, v:v); $^1$H NMR (500 MHz, CDCl$_3$) δ 9.81 (s, 1 H), 3.02 (t, J=7.3 Hz, 2 H), 2.79 (t, J=7.3 Hz, 2 H).

3-(3-Pyridine) propanal (6c): The product as an oil (0.50 g, 67%) was obtained by chromatography on silica; ($R_f$=0.29, EtOAc/Hexane, 20:80, v:v); $^1$H NMR (500 MHz, CDCl$_3$) δ 9.83 (s, 1 H), 8.48 (s, 1 H), 8.46 (d, J=4.7 Hz, 1 H), 7.52 (d, J=7.8 Hz, 1 H), 7.22 (m, 1 H), 2.96 (t, J=7.5 Hz, 2 H), 2.82 (t, J=7.5 Hz, 2 H).

3-(1'-Naphthyl)propanal (6d): The product as an oil (4.10 g, 74%) was obtained by chromatography on silica; ($R_f$=0.32, EtOAc/Hexane, 15:85, v:v); $^1$H NMR (500 MHz, CDCl$_3$) δ 9.88 (s, 1 H), 7.99 (d, J=8.3 Hz, 1 H), 7.88 (d, J=8.0 Hz, 1 H), 7.75 (d, J=8.2 Hz, 1 H), 7.55 (t, J=7.2 Hz, 1 H), 7.51 (t, J=6.9 Hz, 1 H), 7.41 (t, J=7.3 Hz, 1 H), 7.35 (d, J=7.0 Hz, 1 H), 3.43 (t, J=7.8 Hz, 2 H), 2.91 (t, J=8.1 Hz, 2 H).

3-(2'-Methoxy-1'-naphthyl)propanal (6e): The product as an oil (3.18 g, 94%) was obtained by chromatography on silica; ($R_f$=0.43, EtOAc/Hexane, 25:75, v:v); $^1$H NMR (500 MHz, CDCl$_3$) δ 9.87 (s, 1 H), 7.90 (d, J=8.7 Hz, 1 H), 7.81 (d, J=8.2 Hz, 1 H), 7.77 (d, J=8.9 Hz, 1 H), 7.49 (m 1 H), 7.35 (m, 1 H), 7.27 (d, J=9.2 Hz, 1 H), 3.95 (s, 3 H), 3.41 (m, 2 H), 2.74 (td, J=7.7, 1.9 Hz, 2 H).

3-(4'-Methoxy-1'-naphthyl)propanal (6f): The product as an oil (1.70 g, 84%) was obtained by chromatography on silica; ($R_f$=0.33, EtOAc/Hexane, 25:75, v:v); $^1$H NMR (500 MHz, CDCl$_3$) δ 9.87 (s, 1 H), 8.32 (d, J=8.1 Hz, 1 H), 7.91 (d, J=8.4 Hz, 1 H), 7.55 (m, 1 H), 7.49 (t, J=7.9 Hz, 1 H), 7.24 (d, J=7.7 Hz, 1 H), 6.74 (d, J=7.9 Hz, 1 H), 3.99 (s, 3 H), 3.34 (t, J=7.6 Hz, 2 H), 2.74 (m, 2 H).

3-(4'-Fluoro-3'-methylphenethyl)propanal (6g): The product as an oil (2.64 g, 77%) was obtained by chromatography on silica; ($R_f$=0.37, EtOAc/Hexane, 25:75, v:v); $^1$H NMR (500 MHz, CDCl$_3$) δ 9.81 (s, 1 H), 7.00-6.88 (m, 3 H), 2.89 (t, J=7.4 Hz, 2 H), 2.75 (t, J=7.2 Hz, 2 H), 2.24 (s, 3 H).

1-(5'-Fluoro-2'-methoxyphenyl)-4-ethylenedioxy-1-butene (7): To a suspension of 2-(1,3-dioxolan-2-yl)ethyltriphenylphosphonium bromide (5.0 g, 11.3 mmol) in THF (30 mL) under Ar was added NaH (60% in mineral oil, 0.48 g, 11.3 mmol). The reaction was heated to reflux for 1 h. The resulting orange colored suspension was cooled to 0° C. and 5-fluoro-2-methoxybenzaldehyde (1.54 g, 10.0 mmol) was added and the reaction was stirred for 12 h at room temperature. The mixture was poured to a separatory funnel containing ammonium chloride aqueous solution (sat. NH$_4$Cl/H$_2$O=1:1, v:v, 30 mL). The organics were extracted with EtOAc (3×80 mL) and the combined organic layers were washed with brine (60 mL) and dried over Na$_2$SO$_4$. The solvent was removed in vacuo and product was purified by flash column chromatography ($R_f$=0.15, EtOAc/Hexane, 7:93, v:v) to result in the product (2.63 g, 66%) as a mixture of cis and trans (cis:trans=4:1): $^1$H NMR (the major isomer): (CDCl$_3$, 500 MHz): δ 7.08 (dd, J=3.1, 8.7 Hz, 1 H), 6.93 (dt, J=3.1, 8.7 Hz, 1 H), 6.78 (dd, J=4.3, 8.7 Hz, 1 H), 6.63 (d, J=11.9 Hz, 1 H), 5.83 (td, J=7.3 Hz, 11.9 Hz, 1 H), 4.99 (t, J=4.6 Hz, 1 H), 4.02-3.99 (m, 2 H), 3.90-3.87 (m, 2 H), 3.80 (s, 3 H), 2.64-2.62 (m, 2 H).

4-(5'-Fluoro-2'-methoxyphenyl)-1-ethylenedioxybutane (8): To a solution 7 (1.75 g, 7.3 mmol) in ethanol (200 proof, 80 mL) under Ar was added Pd/C (10%, 300 mg). The flask containing the mixture was evacuated to the point of boiling and purged with H$_2$ three times. Then a H$_2$ balloon was attached to the flask and the reaction was stirred for 72 h at room temperature. The reaction mixture was then filtered through a pad of Celite eluted with EtOH. The crude product was obtained by removal of the solvent in vacuo. $^1$H NMR (CDCl$_3$, 500 MHz): δ 6.87-6.72 (m, 3 H), 4.87 (t, J=3.8 Hz, 1 H), 3.97-3.95 (m, 2 H), 3.86-3.83 (m, 2 H), 3.79 (s, 3 H), 2.64-2.62 (m, 2 H), 2.44 (td, J=1.7, 7.2 Hz, 2 H), 1.92 (quintet, J=7.5 Hz, 2 H).

4-(5'-Fluoro-2'-methoxyphenyl)butyraldehyde (9): To a solution of 8 (1.7 g, 7.0 mmol) in THF (60 mL) was added HCl (1 N, 3 mL) and the reaction was stirred at room temperature for 48 h. The reaction mixture was then poured into a separatory funnel containing water (60 mL). The organics were extracted with EtOAc (3×60 mL) and the combined organic layers were washed with brine (80 mL) and dried over Na$_2$SO$_4$. The crude product obtained by removal of the solvent in vacuo was purified by flash column chromatography ($R_f$=0.10, EtOAc/Hexane, 10:90, v:v) to give the product (1.03 g, 53% from 3a) as oil; $^1$H NMR (CDCl$_3$, 500 MHz): δ 9.76 (s, 1 H), 6.88-6.83 (m, 2 H), 6.75 (dd, J=4.6, 8.6 Hz, 1 H), 3.79 (s, 3 H), 2.63 (t, J=7.4 Hz, 2 H), 2.44 (t, J=7.4 Hz, 2 H), 1.92 (quintet, J=7.4 Hz, 2 H).

5-(5'-Fluoro-2'-methoxyphenyl)-1-pentene methyl ether (10): To a suspension of methoxymethyltriphenylphosphonium chloride (2.0 g, 5.8 mmol) in THF (20 mL) under Ar was added NaH (60% in mineral oil, 0.27 g, 6.7 mmol). The reaction was heated to reflux for 1 h. The resulting orange colored suspension was cooled to 0° C. and 4-(5'-fluoro-2'-methoxyphenyl)butyraldehyde (9) (0.92 g, 4.7 mmol) was added and the mixture was stirred for 12 h at room temperature. The reaction mixture was poured to a separatory funnel containing ammonium chloride aqueous solution (sat. NH$_4$Cl:H$_2$O=1:1, 50 mL). The organics were extracted with EtOAc (3×50 mL) and the combined organic layers were washed with brine (50 mL) and dried over Na$_2$SO$_4$. The solvent was then removed in vacuo and crude product was purified by flash column chromatography on silica ($R_f$=0.30, EtOAc/Hexane, 5:95, v:v) to result in the product (0.46, 43%) as an oil and a mixture of cis and trans (cis:trans=1:2): $^1$H NMR (CDCl$_3$, 500 MHz): δ 6.87-6.72 (m, 3 H), 6.30 (d, J=12.5 Hz, 0.66 H), 5.90 (d, J=6.2 Hz, 0.33 H), 4.75 (td, J=7.2, 12.5 Hz, 0.66 H), 4.36 (m, 0.33 H), 3.79 (s, 3 H), 3.59 (s, 1 H), 3.51 (s, 2 H), 2.61-2.57 (m, 2 H), 2.11 (q, J=7.2 Hz, 0.66 H), 1.97 (q, J=7.2 Hz, 1.34 H), 1.65-1.58 (m, 2 H).

5-(5'-Fluoro-2'-methoxyphenyl)pentanal (11): To a solution of 9 (0.46 g, 2.0 mmol) in acetone (20 mL) was added H$_2$SO$_4$ (5%, 2 mL) and the reaction was heated to reflux for 1.6 h. After the reaction was cooled to room temperature, most of the solvent was then removed in vacuo. A solution of NaHCO$_3$ (sat. 40 mL) was added and the organics were extracted with EtOAc (3×40 mL) and the combined organic layers were washed with brine (30 mL) and dried over Na$_2$SO$_4$. The crude product obtained by removal of the solvent in vacuo was purified by flash column chromatography on silica ($R_f$=0.10, EtOAc/Hexane, 10:90, v:v) to give the product (0.20 g, 50%) as oil; $^1$H NMR (CDCl$_3$, 500 MHz): δ 9.76 (s, 1 H), 6.88-6.82 (m, 2 H), 6.74 (dd, J=4.6, 8.6 Hz, 1 H), 3.79 (s, 3 H), 2.61 (t, J=7.3 Hz, 2 H), 2.45 (m, 2 H), 1.69-1.60 (m, 4 H).

1-(2'-Methoxy-5'-fluorophenyl)pent-4-en-1-ol (12a): To a solution of 2-methoxy-5-fluorobenzaldehyde (3.0 g, 19.5 mmol) in THF (20 mL) at 0° C. was added a solution 1-butenylmagnesium bromide (0.5 M in THF, 45 mL, 22.5 mmol) dropwise for 15 min. Then the reaction mixture was poured into a separatory funnel containing solution of saturated ammonium chloride (80 mL). The organics were extracted with EtOAc (3×60 mL) and the combined organic layers were washed with brine (50 mL) and dried over Na$_2$SO$_4$. The solvent then was removed in vacuo and crude product was purified by flash column chromatography ($R_f$=0.11, EtOAc/Hexane, 10:90, v:v) on silica to afford the product as oil (3.27 g, 93%); $^1$H NMR (CDCl$_3$, 500 MHz): δ 7.07 (dd, J=3.1, 9.2 Hz, 1 H), 6.91 (dt, J=3.1, 9.0 Hz, 1 H), 6.79 (dd, J=4.2, 8.5 Hz, 1 H), 5.85 (m, 1 H), 5.04 (d, J=18.0 Hz, 1 H), 4.97 (d, J=13.5 Hz, 1 H), 4.90 (t, J=6.3 Hz, 1 H), 3.83 (s, 3 H), 2.42 (bs, 1 H), 2.23-2.13 (m, 2 H), 1.84 (q, J=7.7 Hz, 2 H).

The following compounds were prepared in a similar manner as 12a.

5-Phenyl-1-penten-5-ol (12b): The product (1.14 g, 82%) was obtained as a yellow oil by chromatography on silica; ($R_f$=0.36, EtOAc/Hexane, 20:80, v:v); $^1$H NMR (500 MHz, CDCl$_3$) δ 7.36-7.27 (m, 5H), 5.83 (m, 1 H), 5.04 (dt, J=15.7, 1.8 Hz, 1 H), 4.98 (d, J=10.4 Hz, 1 H), 4.70 (t, J=6.5 Hz, 1 H), 2.21-1.80 (m, 5H).

7-Pentafluorophenyl-1-hepten-5-ol (12c): The product (0.95 g, 48%) was obtained as an oil by chromatography on silica; ($R_f$=0.10, EtOAc/Hexane, 10:90, v:v); $^1$H NMR (500 MHz, CDCl$_3$) δ 5.83 (m, 1 H), 5.05 (dd, J=1.8, 15.8 Hz, 1 H), 4.98 (dd, J=1.3, 10.3 Hz, 1 H), 3.64 (m, 1 H), 2.91-2.75 (m, 2 H), 2.24-2.11 (m, 2 H), 1.78-1.65 (m, 2 H), 1.63-1.55 (m, 3 H).

5-(4'-Chlorophenyl)-1-penten-5-ol (12d): The product (1.97 g, 43%) was obtained as an oil by chromatography on silica; ($R_f$=0.43, EtOAc/Hexane, 25:75, v:v); $^1$H NMR (300 MHz, CDCl$_3$) δ 7.34-7.27 (m, 4 H), 5.90-5.66 (m, 1 H), 5.04 (d, J=17.4 Hz, 1 H), 4.99 (d, J=9.9 Hz, 1 H), 4.69 (m, 1 H), 2.17-2.08 (m, 2 H), 1.91-1.75 (m, 2 H).

5-(4'-Bromophenyl)-1-penten-5-ol (12e) The product (2.45 g, 94%) was obtained as an oil by chromatography on silica; ($R_f$=0.40, EtOAc/Hexane, 25:75, v:v); $^1$H NMR (300

MHz, CDCl$_3$) δ 7.46 (d, J=8.4 Hz, 2 H), 7.21 (d, J=8.4 Hz, 2 H), 5.82 (m, 1 H), 5.01 (m, 2 H), 4.66 (t, J=6.6 Hz, 1 H), 2.16-2.05 (m, 2 H), 1.92-1.74 (m, 2 H).

5-(4'-Methoxyphenyl)-1-penten-5-ol (12l): The product (2.98 g, 93%) was obtained as an oil by chromatography on silica; (R$_f$=0.15, DCM/Hexane, 80:20, v:v); $^1$H NMR (300 MHz, CDCl$_3$) δ 7.27 (d, J=8.7 Hz, 2 H), 6.88 (d, J=8.7 Hz, 2 H), 5.83 (m, 1 H), 4.98 (m, 2 H), 4.65 (t, J=6.6 Hz, 1 H), 3.81 (s 3 H), 2.17-2.04 (m, 2 H), 2.03-1.67 (m, 2 H).

5-(4'-t-Butylphenyl)-1-penten-5-ol (12g): The product (2.04 g, 76%) was obtained as an oil by chromatography on silica; (R$_f$=0.35, DCM/Hexane, 80:20, v:v); $^1$H NMR (300 MHz, CDCl$_3$) δ 7.36 (d, J=8.4 Hz, 2 H), 7.27 (d, J=8.4 Hz, 2 H), 5.84 (m, 1 H), 5.04 (d, J=17.2 Hz, 1 H), 4.98 (d, J=10.0 Hz, 1 H), 2.20-2.06 (m, 2 H), 1.96-1.75 (m, 2 H), 1.31 (s, 9 H).

5-(2'-Naphthyl)-1-penten-5-ol (12h): The product (1.47 g, 71%) was obtained as an oil by chromatography on silica; (R$_f$=0.32, DCM/Hexane, 80:20, v:v); $^1$H NMR (CDCl$_3$, 500 MHz): δ 7.86-7.78 (m, 4 H), 7.50-7.46 (m, 3 H), 5.85 (m, 1 H), 5.04 (d, J=17.2 Hz, 1 H), 4.99 (d, J=10.0 Hz, 1 H), 4.88 (t, J=6.9 Hz, 1 H), 2.22-2.09 (m, 2 H), 2.05-1.85 (m, 2 H).

5-(2'-Furanyl)pent-1-en-5-ol (12i): The product (3.34 g, 85%) was obtained as an oil by chromatography on silica; (R$_f$=0.19, EtOAc/Hexane, 15:85, v:v); $^1$H NMR (CDCl$_3$, 500 MHz): δ 7.38 (s, 1 H), 6.33 (t, J=2.2 Hz. 1 H), 6.24 (d, J=3.2 Hz, 1 H), 5.83 (m, 1 H), 5.04 (d, J=12.3 Hz, 1 H), 4.99 (d, J=9.6 Hz, 1 H), 4.71 (t, J=6.8 Hz, 1 H), 2.17 (m, 2 H), 1.96 (q, J=7.2 Hz, 2 H), 1.89 (bs, 1 H).

6-Phenylhex-1-en-5-ol (12j): The product (1.22 g, 95%) was obtained as an oil by chromatography on silica; (R$_f$=0.12, EtOAc/Hexane, 10:90, v:v); $^1$H NMR: (500 MHz, CDCl$_3$) δ 7.33-7.20 (m, 5 H), 5.04 (m, 1 H), 5.00 (m, 2 H), 3.85 (m, 1 H), 2.84 (m, 1 H), 2.69-2.65 (m, 1 H), 2.29-2.16 (m, 2 H), 1.67-1.58 (m, 2 H).

7-Phenyl-1-hepten-5-ol (12k): The product (2.45 g, 58%) was obtained as an oil by chromatography on silica; (R$_f$=0.43, EtOAc/Hexane, 25:75, v:v); $^1$H NMR (CDCl$_3$, 500 MHz) δ 7.29-7.19 (m, 5 H), 5.85 (m, 1 H), 5.04 (td, J=2.2, 14.0 Hz, 1 H), 4.97 (dd, J=1.7, 10.4 Hz, 1 H), 3.67 (m, 1 H), 2.80 (m, 1 H), 2.68 (m, 1 H), 2.22-2.13 (m, 2 H), 1.83-1.73 (m, 2 H), 1.62-1.54 (m, 3 H).

7-(3'-Pyridinyl)-1-hepten-5-ol (12l): The product (1.8 g, 52%) was obtained as an oil by chromatography on silica; (R$_f$=0.15, EtOAc/Hexane, 60:40, v:v); $^1$H NMR (500 MHz, CDCl$_3$) δ 8.46 (s, 1 H), 8.42 (d, J=4.2 Hz, 1 H), 7.51 (d, J=8.0 Hz, 1 H), 7.20 (dd, J=4.9, 7.8 Hz, 1 H), 5.82 (m, 1 H), 5.03 (d, J=16.0 Hz, 1 H), 4.96 (d, J=10.3 Hz, 1 H), 3.65 (m, 1 H), 2.81 (m, 1 H), 2.68 (m, 1 H), 2.23-2.11 (m, 2 H), 1.94 (bs, 1 H), 1.81-1.72 (m, 2 H), 1.63-1.56 (m, 2 H).

7-(1'-Naphthyl)-1-hepten-5-ol (12m): The product (1.52 g, 56%) was obtained as an oil by chromatography on silica; (R$_f$=0.12, EtOAc/Hexane, 10:90, v:v); $^1$H NMR (300 MHz, CDCl$_3$) δ 8.06 (d, J=7.8 Hz, 1 H), 7.85 (d, J=7.8 Hz, 1 H), 7.71 (d, J=7.8 Hz, 1 H), 7.54-7.33 (m, 4 H), 5.84 (m, 1 H), 5.04 (dd, J=1.8, 17.4 Hz, 1 H), 4.99 (dd, J=2.1, 10.2 Hz, 1 H), 3.75 (m, 1 H), 3.47-3.25 (m, 1 H), 3.16-3.06 (m, 1 H), 2.24-2.13 (m, 2 H), 1.94-1.85 (m, 2 H), 1.65-1.55 (m, 2 H).

7-(p-(t-Butyldimethylsilyloxy)phenyl)-1-hepten-5-ol (12n): The product (0.85 g, 52%) was obtained as an oil by chromatography on silica; (R$_f$=0.41, EtOAc/Hexane, 25:75, v:v); $^1$H NMR (500 MHz, CDCl$_3$) δ 7.04 (d, J=8.4 Hz, 2 H), 6.76 (d, J=8.4 Hz, 2 H), 5.85-5.08 (m, 1 H), 5.50 (dd, J=1.8, 15.8 Hz, 1 H), 4.96 (d, J=10.4 Hz, 1 H), 3.66-3.62 (m, 1 H), 2.75-2.68 (m, 1 H), 2.64-2.57 (m, 1 H), 2.21-2.12 (m, 2 H), 1.77-1.71 (m, 2 H), 1.60-1.52 (m, 2 H), 0.98 (s, 9 H), 0.18 (s, 6 H).

7-(2'-Methoxy-1'-naphthyl)-1-hepten-5-ol (12o): The product (0.78 g, 43%) was obtained as an oil by chromatography on silica; (R$_f$=0.11, EtOAc/Hexane, 10:90, v:v); $^1$H NMR (500 MHz, CDCl$_3$) δ 7.90 (d, J=8.4 Hz, 1 H), 7.77 (d, J=8.4 Hz, 1 H), 7.72 (d, J=8.4 Hz, 1 H), 7.48 (t, J=7.8 Hz, 1 H), 7.36-7.24 (m, 2 H), 5.81 (m, 1 H), 5.00 (m, 2 H), 3.93 (s 3 H), 3.45 (m, 1 H), 3.09 (t, J=8.2 Hz, 2 H) 2.14-2.07 (m, 2 H), 1.89-1.82 (m, 2 H), 1.78-1.73 (m, 2 H).

7-(4'-Methoxy-1'-naphthyl)-1-hepten-5-ol (12p): The product (0.67 g, 41%) was obtained as an oil by chromatography on silica; (R$_f$=0.10, EtOAc/Hexane, 10:90, v:v); $^1$H NMR (300 MHz, CDCl$_3$) δ 88.33 (d, J=7.5 Hz, 1 H), 8.02 (d, J=7.2 Hz, 1 H), 7.53 (m, 2 H), 7.26 (d, J=7.8 Hz, 1 H), 6.76 (d, J=6.0 Hz, 1 H), 5.87 (m, 1 H), 5.04 (dd, J=1.8, 15.3 Hz, 4.99 (dd, J=1.2, 10.2 Hz, 1 H), 4.01 (s, 3 H), 3.77 (m, 1 H), 3.28-3.18 (m, 1 H), 3.11-3.01 (m, 1 H), 2.26-2.16 (m, 2 H), 1.84-1.84 (m, 2 H), 1.67-1.57 (m, 2 H).

5-(1'-Naphthyl)-1-penten-5-ol (12q): The product (0.46 g, 23%) was obtained as an oil by chromatography on silica; (R$_f$=0.11, EtOAc/Hexane, 10:90, v:v); $^1$H NMR (300 MHz, CDCl$_3$) δ 8.08 (m, 1 H), 7.87 (m, 1 H), 7.78 (d, J=8.1 Hz, 1 H), 7.65 (d, J=6.9 Hz, 1 H), 7.50 (m, 3 H), 5.89 (m, 1 H), 5.49 (m, 1 H), 5.04 (dd, J=1.8, 15.6 Hz, 1 H), 4.99 (dd, J=1.8, 10.2 Hz, 1 H), 2.30-2.24 (m, 2 H), 2.06-1.97 (m, 2 H).

7-(4'-Fluoro-3'-methylphenyl)-1-hepten-5-ol (12r): The product (1.33 g, 38%) was obtained as an oil by chromatography on silica; (R$_f$=0.41, EtOAc/Hexane, 25:75, v:v); $^1$H NMR (500 MHz, CDCl$_3$) δ 7.00-6.88 (m, 3 H), 5.88-5.80 (m, 1 H), 4.05 (dt, J=1.9, 15.7 Hz, 1 H), 4.99-4.95 (m, 1 H), 3.67-3.62 (m, 1 H), 2.74-2.70 (m, 1 H), 2.64-2.57 (m, 1 H), 2.25 (s, 3 H), 2.24-2.05 (m, 2 H), 1.77-1.70 (m, 2 H), 1.63-1.53 (m, 3 H).

7-(5'-Fluoro-2'-methoxyphenyl)hept-1-en-5-ol (12s): The product (3.7 g, 94%) was obtained as an oil by chromatography on silica; (R$_f$=0.20, EtOAc/Hexane, 15:85, v:v); $^1$H NMR (CDCl$_3$, 500 MHz): δ 6.86-6.82 (m, 2 H), 6.76 (dd, J=4.6, 8.6 Hz, 1 H), 5.82 (m, 1 H), 5.04 (d, J=17.3 Hz, 1 H), 4.95 (d, J=10.2 Hz, 1 H), 3.81 (s, 3 H), 3.55 (m, 1 H), 2.75-2.69 (m, 2 H), 2.20 (m, 1 H), 2.10 (m, 1 H), 1.96 (bs, 1 H), 1.73-1.68 (m, 2 H), 1.60-1.53 (m, 3 H).

1-(2'-Methoxy-5'-fluorophenyl)hex-5-en-2-ol (12t): The product (0.64 g, 74%) was obtained as an oil by chromatography on silica; (R$_f$=0.18, EtOAc/Hexane, 12:88, v:v); $^1$H NMR (CDCl$_3$, 500 MHz): δ 6.90-6.88 (m, 2 H), 6.79 (dd, J=4.7, 9.8 Hz, 1 H), 5.83 (m, 1 H), 5.04 (d, J=17.1 Hz, 1 H), 4.97 (d, J=10.1 Hz, 1 H), 3.85 (m, 1 H), 3.81 (s, 3 H), 2.85 (dd, J=4.0, 13.7 Hz, 1 H), 2.69 (dd, J=8.1, 13.7 Hz, 1 H), 2.26 (m, 1 H), 2.17 (m, 1 H), 1.82 (bs, 1 H), 1.60 (m, 2 H).

8-(5'-Fluoro-2'-methoxyphenyl)oct-1-en-5-ol (12u): The product (1.06 g, 61%) was obtained as an oil by chromatography on silica; (R$_f$=0.15, EtOAc/Hexane, 12:88, v:v); $^1$H NMR (CDCl$_3$, 500 MHz): δ 6.86-6.82 (m, 2 H), 6.74 (dd, J=4.6, 8.6 Hz, 1 H), 5.85 (m, 1 H), 5.04 (d, J=17.3 Hz, 1 H), 4.97 (d, J=10.2 Hz, 1 H), 3.79 (s, 3 H), 3.66 (m, 1 H), 2.60 (m, 2 H), 2.22-2.10 (m, 2 H), 1.74-1.47 (m, 7 H).

9-(5'-Fluoro-2'-methoxyphenyl)non-1-en-5-ol (12v): The product (0.19 g, 71%) was obtained as an oil by chromatography on silica; (R$_f$=0.25, EtOAc/Hexane, 20:80, v:v); $^1$H NMR (CDCl$_3$, 500 MHz): δ 6.85-6.81 (m, 2 H), 6.74 (dd, J=4.6, 8.6 Hz, 1 H), 5.84 (m, 1 H), 5.04 (dd, J=15.8, 1.9 Hz, 1 H), 4.98 (d, J=10.2, 1.3 Hz, 1 H), 3.79 (s, 3 H), 3.63 (m, 1 H), 2.59 (t, J=7.6 Hz, 2 H), 2.23-2.11 (m, 2 H), 1.62-1.36 (m, 9 H).

2-(Bromomethyl)-5-(2'-methoxy-5'-fluorophenyl)tetrahydrofuran (13a): To a solution of 1-(2'-methoxy-5'-fluorophenyl)pent-4-en-1-ol (3.24 g, 18.0 mmol) in dry CH$_2$Cl$_2$ (50 mL) at 0° C. was added N-bromosuccinimide (NBS, 3.56 g, 20.0 mmol) portionwise and the reaction was warmed to room temperature for 12 h. The solvent was then removed in vacuo and the remaining residue was purified by flash column chromatography ($R_f$=0.28, EtOAc/Hexane, 10:90, v:v) to afford the product (2.28 g, 44%) as oil; $^1$H NMR (CDCl$_3$, 500 MHz): δ 7.15 (dd, J=3.1, 9.2 Hz, 1 H), 6.88 (dt, J=3.1, 9.0 Hz, 1 H), 6.76 (dd, J=4.2, 8.5 Hz, 1 H), 5.30 (t, J=7.0 Hz, 0.65 H). 5.18 (t, J=7.0 Hz, 0.35 H), 4.48 (p, J=6.6 Hz, 0.65 H), 4.31 (p, J=6.6 Hz, 0.35 H), 3.79 (s, 3 H), 3.56 (m, 1 H), 3.44 (m, 1 H), 2.51-2.42 (m, 1 H), 2.18 (m, 1 H), 1.90 (m, 1 H), 1.78-1.70 (m, 1 H).

The following compounds were prepared in a similar manner as 13a.

2-Bromomethyl-5-phenyltetrahydrofuran (13b): The product (1.58 g, 94%) was obtained as an oil by chromatography on silica; ($R_f$=0.45, EtOAc/Hexane, 25:75, v:v); $^1$H NMR (CDCl$_3$, 500 MHz): δ 7.38-7.24 (m, 5 H), 5.09 (t, J=6.9 Hz, 0.66 H), 4.95 (m, 0.33 H), 4.47 (m, 0.66 H), 4.34 (m, 0.33 H), 3.58-3.44 (m, 2 H), 2.46-1.87 (m, 4 H).

2-Bromomethyl-2-(pentafluorophenyl)tetrahydrofuran (13c): The product (0.79 g, 65%) was obtained as an oil by chromatography on silica; ($R_f$=0.17, EtOAc/Hexane, 3:97, v:v); $^1$H NMR (CDCl$_3$, 500 MHz) δ 4.24 (m, 1 H), 4.04 (m, 1 H), 3.43 (dd, J=5.2, 15.3 Hz, 1 H), 3.35 (dd, J=6.5, 10.3 Hz, 1 H), 2.83 (m, 1 H), 2.73 (1 H), 2.19-2.11 (m, 2 H), 1.83-1.57 (m, 4 H).

5-Bromomethyl-2-(4'-chlorophenyl)tetrahydrofuran (13d): The product (0.29 g, 23%) was obtained as an oil by chromatography on silica and mixture of cis and trans isomers (cis:trans, 2:1); ($R_f$=0.40, EtOAc/Hexane, 10:90, v:v); $^1$H NMR (CDCl$_3$, 300 MHz): δ 7.29 (m, 4 H), 5.06 (dd, J=1.8, 7.8 Hz, 0.67 H), 4.91 (dd, J=2.1, 8.4 Hz, 0.33 H), 4.47 (m, 0.67 H), 4.33 (m, 0.33 H), 3.50 (m, 2 H), 2.44-2.14 (m, 2 H), 1.99-1.78 (m, 2 H).

2-Bromomethyl-5-(4'-bromophenyl)-tetrahydrofuran (13e): The product (1.74 g, 55%) was obtained as an oil by chromatography on silica; ($R_f$=0.49, DCM/Hexane, 50:50, v:v); $^1$H NMR (CDCl$_3$, 300 MHz): δ 7.46 (d, J=8.1 Hz, 2 H), 7.20 (d, J=8.1 Hz, 2 H), 5.04 (dd, J=1.8, 7.8 Hz, 0.67 H), 4.90 (dd, J=1.8, 8.1 Hz, 0.33 H), 4.47 (m, 0.67 H), 4.34 (m, 0.33 H), 3.50 (m, 2 H), 2.44-2.13 (m, 2 H), 2.00-1.71 (m, 2 H).

2-Bromomethyl-5-(4'-methoxyphenyl)tetrahydrofuran (13f): The product (3.33 g, 81%) was obtained as an oil by chromatography on silica; ($R_f$=0.36, DCM/Hexane, 50:50, v:v); $^1$H NMR (CDCl$_3$, 500 MHz): δ 7.30 (d, J=8.7 Hz, 1 H), 7.24 (d, J=8.7 Hz, 1 H), 6.87 (d, J=8.7 Hz, 1 H), 6.86 (d, J=8.7 Hz, 1 H), 5.02 (dd, J=1.8, 7.8 Hz, 0.67 H), 4.88 (dd, J=2.7, 8.4 Hz, 0.33 H), 4.45 (m, 0.67 H), 4.30 (m, 0.33 H), 3.78 (s, 3 H), 3.49 (m, 2 H), 2.37-2.14 (m, 2 H), 2.00-1.83 (m, 2 H).

2-(Bromomethyl)-5-(4'-(t-Butylphenyl)tetrahydrofuran (13g): The product (2.38 g, 87%) was obtained as an oil by chromatography on silica; ($R_f$=0.54, DCM/Hexane, 50:50, v:v); $^1$H NMR (CDCl$_3$, 500 MHz): δ 7.30 (m, 4 H), 5.05 (dd, J=1.5, 7.8 Hz, 0.67 H), 4.91 (dd, J=1.8, 8.1 Hz, 0.33 H), 4.45 (m, 0.67 H), 4.32 (m, 0.33 H), 3.48 (m, 2 H), 2.43-2.21 (m, 2H), 1.98-1.87 (m, 2 H), 1.30 (s, 12 H).

2-Bromomethyl-5-(2'-naphthyl)tetrahydrofuran (13h): The product (1.37 g, 65%) was obtained as an oil by chromatography on silica; ($R_f$=0.37, DCM/Hexane, 50:50, v:v); $^1$H NMR (CDCl$_3$, 500 MHz): δ 7.81 (m, 4 H), 7.44 (m, 3 H), 5.27 (m, 0.70 H), 5.12 (m, 0.30 H), 4.57 (m, 0.7 H), 4.40 (m, 0.30 H), 3.55 (m, 2 H), 2.53-2.22 (m, 2 H), 2.07-1.94 (m, 2 H).

2-Bromomethyl-5-(1'-furanyl)tetrahydrofuran (13i): The product (1.65 g, 50%) was obtained as an oil by chromatography on silica; ($R_f$=0.20, EtOAc/Hexane, 20:80, v:v); $^1$H NMR (CDCl$_3$, 500 MHz) δ 7.38 (s, 1 H), 6.32 (s, 1 H), 6.27 (dd, J=3.2, 8.3 Hz, 1 H), 5.10 (t, J=6.8 Hz, 0.5 H), 5.00 (t, J=6.7 Hz, 0.5 H), 4.39 (m, 0.5 H), 4.29 (m, 0.5 H), 3.51-3.35 (m, 2 H), 2.32-1.89 (m, 4 H).

2-Benzyl-5-bromomethyltetrahydrofuran (13j): The product (0.45 g, 65%) was obtained as an oil by chromatography on silica; ($R_f$=0.55, DCM/Hexane, 50:50, v:v); $^1$H NMR (CDCl$_3$, 500 MHz) δ 7.20-7.29 (m, 5 H), 4.15-4.33 (m, 1 H), 3.27-3.45 (m, 2 H), 2.96 (dd, J=5.6, 13.5 Hz, 1 H), 2.70-2.79 (m, 1 H), 1.91-2.11 (m, 2 H), 1.63-1.78 (m, 3 H).

2-Bromomethyl-5-phenethyltetrahydrofuran (13k): The product (2.58 g, 74%) was obtained as an oil by chromatography on silica as a mixture of trans:cis=2:1; ($R_f$=0.26, EtOAc/Hexane, 20:80, v:v); $^1$H NMR (500 MHz, CDCl$_3$) δ 7.28-7.19 (m, 5H), 4.26 (m, 0.66 H), 4.15 (m, 0.33 H), 4.06 (m, 0.66 H), 3.94 (m, 0.33 H), 3.47-3.44 (m, 1 H), 3.37-3.34 (m, 1 H), 2.77-2.63 (m, 2 H), 2.19-1.76 (m, 5H), 1.62-1.58 (m, 1 H).

2-Bromomethyl-5-(3'-pyridinylethyl)tetrahydrofuran (13l): The product (2.06 g, 81%) was obtained as a yellow oil by chromatography on silica; ($R_f$=0.28, EtOAc/Hexane, 60:40, v:v); $^1$H NMR (500 MHz, CDCl$_3$) δ 8.53 (s, 1 H), 8.49 (d, J=4.6 Hz, 1 H), 7.75 (m, 1 H), 7.38 (m, 1 H), 4.25 (m, 0.6 H), 4.14 (m, 0.4 H), 4.02 (m, 0.6 H), 3.92 (m, 0.4 H), 3.45-3.33 (m, 2 H), 2.85-2.72 (m, 2 H), 2.17-2.04 (m, 2 H), 1.91-1.77 (m, 3 H), 1.59 (m, 1 H).

2-Bromomethyl-5-(1'-naphthyl)tetrahydrofuran (13m): The product (0.59 g, 93%) was obtained as an oil by chromatography on silica; ($R_f$=0.50, DCM/Hexane, 50:50, v:v); $^1$H NMR (500 MHz, CDCl$_3$) δ 7.95-7.85 (m, 3 H), 7.76 (d, J=8.1 Hz, 1 H), 7.64-7.44 (m, 3 H), 5.85 (t, J=6.7 Hz, 0.30H), 5.71 (t, J=6.9 Hz, 0.70H), 4.62 (m, 0.30H), 4.43 (m, 0.7H), 3.62 (m, 2 H), 2.67-2.55 (m, 1 H), 2.33-2.23 (m, 1 H), 2.08-1.92 (m, 2 H).

2-(Bromomethyl)-5-(p-(t-Butyldimethylsilyloxyphenethyl)-tetrahydrofuran (13n): The product (0.75 g, 70%) was obtained as an oil by chromatography on silica; ($R_f$=0.47, EtOAc/Hexane, 15:85, v:v); $^1$H NMR (500 MHz, CDCl$_3$) δ 7.03 (d, J=8.4 Hz, 2 H), 6.76 (d, J=8.4 Hz, 2 H), 4.28-4.13 (m, 1 H), 4.05-3.90 (m, 1 H), 3.46-3.42 (m, 1 H), 3.36-3.32 (m, 1 H), 2.67-2.56 (m, 2 H), 2.16-1.55 (m, 6 H), 0.98 (s, 9 H), 0.18 (s, 6 H).

2-Bromomethyl-5-(2'-methoxy-1'-naphthethyl)tetrahydrofuran (13o): The product (1.512 g, 97%) was obtained as an oil by chromatography on silica; ($R_f$=0.50, EtOAc/Hexane, 25:75, v:v); $^1$H NMR: (500 MHz, CDCl$_3$) δ 8.32-6.74 (m, 6 H), 4.30 (m, 0.67 H), 4.19 (m, 0.33 H), 4.12 (m, 0.67 H), 4.03 (m, 0.33 H), 3.99 (s, 3 H), 3.50-3.47 (m, 1 H), 3.41-3.37 (m, 1 H), 3.19-3.13 (m, 1 H), 3.05-2.99 (m, 1 H), 2.18-1.76 (m, 5 H), 1.66-1.59 (m, 1 H).

2-Bromomethyl-5-(4'-methoxy-1'-naphthethyl)tetrahydrofuran (13p): The product (1.31 g, 88%) was obtained as an oil by chromatography on silica; ($R_f$=0.30, DCM/Hexane, 50:50, v:v); $^1$H NMR: (300 MHz, CDCl$_3$) δ 8.27 (d, J=8.4 Hz, 1 H), 8.16 (d, J=8.4 Hz, 1 H), 8.07 (d, J=8.4 Hz, 1 H), 7.79 (d, J=8.4 Hz, 1 H), 7.67-7.38 (m, 2 H), 4.41-4.26 (m, 1 H), 4.21-4.02 (m, 1 H), 3.99 (s, 3 H), 3.83 (m, 2 H), 2.22-1.71 (M, 8 H).

2-(Bromomethyl)-5-(4'-fluoro-3'-methylphenethyl)-tetrahydrofuran (13q): The product (0.53 g, 30%) was obtained as an oil by chromatography on silica; ($R_f$=0.30, EtOAc/Hexane, 20:80, v:v); $^1$H NMR (500 MHz, CDCl$_3$) δ 7.00-6.87 (m, 3 H), 4.27-3.90 (m, 2 H), 3.46-3.42 (m, 1 H), 3.37-3.32 (m, 1 H), 2.69-2.57 (m, 2 H), 2.24 (s, 3 H), 2.23-1.56 (m, 6 H).

2-(Bromomethyl)-5-(2'-methoxy-5'-fluorophenethyl)tetrahydrofuran (13r): The product (0.45 g, 72%) was obtained as an oil by chromatography on silica with a mixture of trans:cis=2:1; ($R_f$=0.10, EtOAc/Hexane, 5:95, v:v); $^1$H NMR (CDCl$_3$, 500 MHz): δ 6.86-6.81 (m, 2 H), 6.72 (dd, J=4.6, 8.6 Hz, 1 H), 4.22 (m, 1 H), 4.03 (m, 1 H), 3.78 (s, 3 H), 3.44 (dd, J=4.3, 9.7 Hz, 1 H), 3.34 (dd, J=6.4, 9.7 Hz, 1 H), 2.60 (t, J=7.3 Hz, 2 H), 2.13 (m, 1 H), 2.05 (m, 1 H), 1.75 (m, 1 H), 1.67-1.46 (m, 5 H).

2-(bromomethyl)-5-(2'-methoxy-5'-fluorophenethyl)tetrahydrofuran (trans, 13s; cis, 13t): The cis (13s, 0.74 g, 20%) and trans product (trans, 13t, 1.38 g, 42%) were separated as oils by chromatography on silica; (R$_f$=0.10, EtOAc/Hexane, 5:95, v:v); $^1$H NMR (CDCl$_3$, 500 MHz) 13s: δ 6.86-6.81 (m, 2 H), 6.72 (dd, J=4.6, 8.6 Hz, 1 H), 4.22 (m, 1 H), 4.03 (m, 1 H), 3.78 (s, 3 H), 3.44 (dd, J=4.3, 9.7 Hz, 1 H), 3.34 (dd, J=6.4, 9.7 Hz, 1 H), 2.60 (t, J=7.3 Hz, 2 H), 2.13 (m, 1 H), 2.05 (m, 1 H), 1.75 (m, 1 H), 1.67-1.46 (m, 5 H); $^1$H NMR (CDCl$_3$, 500 MHz) 13t: δ 6.88-6.82 (m, 2 H), 6.73 (dd, J=4.6, 8.6 Hz, 1 H), 4.25 (m, 1 H), 4.04 (quintet, J=6.7 Hz, 1 H), 3.78 (s, 3 H), 3.45 (dd, J=4.2, 9.5 Hz, 1 H), 3.34 (dd, J=6.4, 9.5 Hz, 1 H), 2.70 (m, 1 H), 2.60 (m, 1 H), 2.13 (m, 1 H), 2.05 (m, 1 H), 1.87-1.56 (m, 4 H).

2-(Bromomethyl)-5-(2'-methoxy-5'-fluorobenzyl)tetrahydrofuran (trans, 13u; cis, 13v): The cis (13v, 238 mg, 13%) and trans product (trans, 13u, 663 mg, 36%) were separated as oils by chromatography on silica; (R$_f$=0.12, EtOAc/Hexane, 5:95, v:v); $^1$H NMR (CDCl$_3$, 500 MHz) 13u: 6.93 (dd, J=3.1, 9.1 Hz, 1 H), 6.86 (dt, J=3.1, 9.1 Hz, 1 H), 6.74 (dd, J=4.7, 9.0 Hz, 1 H), 4.33 (p, J=6.7 Hz, 1 H), 4.26 (m, 1 H), 3.78 (s, 3 H), 3.45 (dd, J=4.4, 9.9 Hz, 1 H), 3.33 (dd, J=7.0, 10.2 Hz, 1 H), 2.92 (dd, J=6.3, 13.5 Hz, 1 H), 2.71 (dd, J=6.9, 13.5 Hz, 1 H), 2.14 (m, 1 H), 1.97 (m, 1 H), 1.76 (m, 1 H), 1.66 (m, 1 H); $^1$H NMR (CDCl$_3$, 500 MHz) 13v: 6.94 (dd, J=3.1, 9.1 Hz, 1 H), 6.87 (dt, J=3.1, 9.1 Hz, 1 H), 6.75 (dd, J=4.7, 9.0 Hz, 1 H), 4.21 (p, J=6.7 Hz, 1 H), 4.16 (p, J=5.8 Hz, 1 H), 3.79 (s, 3 H), 3.43 (dd, J=5.1, 10.2 Hz, 1 H), 3.31 (dd, J=6.5, 10.2 Hz, 1 H), 2.91 (dd, J=6.2, 13.5 Hz, 1 H), 2.78 (dd, J=6.3, 13.5 Hz, 1 H), 2.03 (m, 1 H), 1.93 (m, 1 H), 1.82 (m, 1 H), 1.66 (m, 1 H).

Trans-2-(bromomethyl)-5-(3'-(2"-methoxy-5"-fluorophenyl)-1'-propyl)tetrahydro furan (13w): The product (530 mg, 40%) was obtained as an oil by chromatography on silica; (R$_f$=0.10, EtOAc/Hexane, 5:95, v:v); $^1$H NMR (CDCl$_3$, 500 MHz): δ 6.86-6.81 (m, 2 H), 6.72 (dd, J=4.6, 8.6 Hz, 1 H), 4.22 (m, 1 H), 4.03 (m, 1 H), 3.78 (s, 3 H), 3.44 (dd, J=4.3, 9.7 Hz, 1 H), 3.34 (dd, J=6.4, 9.7 Hz, 1 H), 2.60 (t, J=7.3 Hz, 2 H), 2.13 (m, 1 H), 2.05 (m, 1 H), 1.75 (m, 1 H), 1.67-1.46 (m, 5 H).

Cis-2-(bromomethyl)-5-(3'-(2"-methoxy-5"-fluorophenyl)-1'-propyl)tetrahydrofuran (13x): The product (110 mg, 10%) was obtained as an oil by chromatography on silica; (R$_f$=0.10, EtOAc/Hexane, 5:95, v:v); $^1$H NMR (CDCl$_3$, 500 MHz): δ 6.86-6.81 (m, 2 H), 6.72 (dd, J=4.6, 8.6 Hz, 1 H), 4.13 (m, 1 H), 3.93 (m, 1 H), 3.78 (s, 3 H), 3.42 (m, 1 H), 3.32 (m, 1 H), 2.60 (t, J=7.3 Hz, 2 H), 2.06-1.96 (m, 2 H), 1.80-1.51 (m, 6 H).

Trans-2-(bromomethyl)-5-(4'-(2"-methoxy-5"-fluorophenyl)-1'-butyl)tetrahydro furan (13y): The product (80 mg, 32%) was obtained as an oil by chromatography on silica; (R$_f$=0.10, EtOAc/Hexane, 4:96, v:v); $^1$H NMR (CDCl$_3$, 500 MHz): δ 6.84-6.80 (m, 2 H), 6.73 (dd, J=4.6, 8.6 Hz, 1 H), 4.22 (m, 1 H), 4.01 (m, 1 H), 3.78 (s, 3 H), 3.44 (dd, J=5.1, 10.3 Hz, 1 H), 3.34 (dd, J=7.1, 10.3 Hz, 1 H), 2.58 (t, J=7.7 Hz, 2 H), 2.15 (m, 1 H), 2.06 (m, 1 H), 1.75 (m, 1 H), 1.65-1.37 (m, 7H).

2-(N-Phthilimidomethyl)-5-(2'-methoxy-5'-fluorophenyl)tetrahydrofuran (14a): To a vial under Ar was added 2-(bromomethyl)-5-(2'-methoxy-5'-fluorophenyl)tetrahydrofuran (1.28 g, 4.44 mmol), NaI (100 mg), potassium phthilimide (2.05 g, 11.1 mmol), and dry DMSO (10 mL). The reaction was heated to 70° C. and stirred under Ar for 12 h. After it was cooled to room temperature, the reaction mixture was poured into a separatory funnel containing sodium bicarbonate aqueous solution (sat. NaHCO$_3$/H$_2$O=1:1, 70 mL). The organics were extracted with EtOAc (3×60 mL) and the combined organic layers were washed with brine (50 mL) and dried over Na$_2$SO$_4$. The solvent was removed in vacuo and to afford crude product which was purified by flash column chromatography (R$_f$=0.12, EtOAc/Hexane, 20:80, v:v) to yield pure product (about 2:1 of trans:cis isomers, 1.14 g, 72%) as oil; $^1$H NMR (CDCl$_3$, 500 MHz): δ 7.88-7.84 (m, 2 H), 7.73-7.69 (m, 2 H), 7.36 (dd, J=3.1, 9.4 Hz, 0.35 H), 7.07 (dd, J=3.1, 9.4 Hz, 0.65 H), 6.85 (dt, J=3.1, 8.5 Hz. 0.35 H), 6.83 (dt, J=3.1, 8.5 Hz. 0.65 H), 6.72 (dd, J=4.2, 9.1 Hz, 1 H), 5.31 (t, J=6.8 Hz, 0.65 H), 5.09 (t, J=7.2 Hz, 0.35 H), 4.63 (m, 0.65 H), 4.39 (m, 0.35 H), 4.02 (dd, J=7.4, 13.7 Hz, 0.35 H), 3.92 (dd, J=8.1 13.7 Hz, 0.65 H), 3.87 (dd, J=7.4, 13.7 Hz, 0.35 H), 3.85 (s, 1.95 H), 3.78 (s, 1.05 H), 3.70 (dd, J=8.1 13.7 Hz, 0.65 H), 2.50 (m, 0.65 H), 2.41 (m, 0.35 H), 2.11-2.04 (m, 1 H), 1.84-1.68 (m, 2 H).

The following compounds were prepared in a similar manner as 14a.

2-Phenyl-5-(N-phthlimidomethyl)tetrahydrofuran (14b): The product (1.42 g, 74%) was obtained as an oil by chromatography on silica and a mixture of the trans:cis=2:1 isomers; (R$_f$=0.16, EtOAc/Hexane, 20:80, v:v); $^1$H NMR (CDCl$_3$, 500 MHz): δ 7.85 (m, 2 H), 7.71 (m, 2 H), 7.39-7.21 (m, 5 H), 5.10 (t, J=6.9 Hz, 0.66 H), 4.90 (t, J=7.2 Hz, 0.33 H), 4.64 (m, 0.66 H), 4.46 (m, 0.33 H), 4.01 (dd, J=7.3, 13.5 Hz, 0.33 H), 3.95 (dd, J=8.2, 14.3 Hz, 0.66 H), 3.82 (dd, J=5.2, 13.5 Hz, 0.66 H), 2.46-2.12 (m, 2 H), 1.92-1.81 (m, 2 H).

2-(Pentafluorophenethyl)-5-(N-phthlimidomethyl)tetrahydrofuran (14c): The product (0.25 g, 58%) was obtained as an oil by chromatography on silica; (R$_f$=0.10, EtOAc/Hexane, 10:90, v:v); $^1$H NMR (CDCl$_3$, 500 MHz) δ 7.85 (dd, J=Hz, 2 H), 7.72 (dd, J=Hz, 2 H), 4.38 (m, 1 H), 4.04 (quintet, J=Hz, 1 H), 3.80 (dd, J=Hz, 1 H), 3.59 (dd, J=Hz, 1 H), 2.73 (m, 2 H), 2.17-2.05 (m, 2 H), 1.76-1.53 (m, 4 H).

2-(4'-Chlorophenyl)-5-(N-phthalimidomethyl)tetrahydrofuran (14d): The product (0.11 g, 99%) was obtained as an oil by chromatography on silica; (R$_f$=0.38, EtOAc/Hexane, 40:60, v:v); $^1$H NMR (CDCl$_3$, 300 MHz); δ 7.86-7.84 (m, 2 H), 7.72-7.69 (m, 2 H), 7.30-7.22 (m, 4 H), 5.06 (t, J=6.9 Hz, 0.67 H), 4.85 (t, J=7.2 Hz, 0.33 H), 4.61 (m, 0.67 H), 4.44 (m, 0.33 H), 3.90 (m, 0.66 H), 3.80 (m, 1.34H), 2.44-2.25 (m, 1 H), 2.22-2.08 (m, 1 H), 1.88-1.74 (m, 2 H).

2-(4'-Bromophenyl)-5-(N-phthalimidomethyl)tetrahydrofuran (14e): The product (4.6 g, 74%) was obtained as an oil by chromatography on silica; (R$_f$=0.69, EtOAc/Hexane, 40:60, v:v); $^1$H NMR (CDCl$_3$, 300 MHz); δ 7.85-7.68 (m, 4 H), 7.45-7.39 (m, 2 H), 7.26-7.14 (m, 2 H), 5.04 (t, J=6.9 Hz, 0.67 H), 4.84 (t, J=7.2 Hz, 0.33 H), 4.61 (m, 0.67 H), 4.44 (m, 0.33 H), 3.89 (m, 0.66 H), 3.80 (m, 1.34 H), 2.45-2.37 (m, 1 H), 2.21-2.11 (m, 1 H), 1.88-1.77 (m, 2 H).

2-(4'-Methoxyphenyl)-5-(N-phthalimidomethyl)tetrahydrofuran (14f): The product (0.74 g, 99%) was obtained as an oil by chromatography on silica; (R$_f$=0.40, EtOAc/Hexane, 30:70, v:v); $^1$H NMR (CDCl$_3$, 300 MHz); δ 7.87-7.67 (m, 4 H), 7.31-7.20 (m, 2 H), 6.87-6.80 (m, 2 H), 5.03 (t, J=6.9 Hz, 0.67 H), 4.83 (t, J=7.1 Hz, 0.33 H), 4.60 (m, 0.67 H), 4.43 (m, 0.33 H), 3.88 (m, 0.66 H), 3.79 (m, 1.34 H), 3.76 (s, 3 H), 2.41-2.31 (m, 1 H), 2.26-2.11 (m, 1 H), 1.92-1.75 (m, 2 H).

2-(4'-t-Butylphenyl)-5-(phthalimidomethyl)tetrahydrofuran (14g): The product (0.52 g, 68%) was obtained as an oil by chromatography on silica; (R$_f$=0.52, EtOAc/Hexane, 30:70, v:v); $^1$H NMR (CDCl$_3$, 300 MHz); δ 7.86-7.81 (m, 2 H), 7.71-7.67 (m, 2 H), 7.36-7.21 (m, 4 H), 5.06 (t, J=6.9 Hz, 0.67 H), 4.87 (t, J=7.1 Hz, 0.33 H), 4.61 (m, 0.67 H), 4.44 (m, 0.33

H), 3.99 (m, 0.33 H), 3.93 (m, 0.67 H), 3.80 (m, 0.33 H), 3.67 (m, 0.67 H), 2.44-2.24 (m, 1 H), 2.42-2.06 (m, 1 H), 1.96-1.78 (m, 2 H) 1.28 (s, 9 H).

2-(2'-Naphthyl)-5-(phthalimidomethyl)tetrahydrofuran (14 H): The product (0.58 g, 77%) was obtained as an oil by chromatography on silica; ($R_f$=0.49, EtOAc/Hexane, 30:70, v:v); $^1$H NMR (CDCl$_3$, 500 MHz); δ 7.87-7.68 (m, 7 H), 7.48-7.37 (m, 4 H), 5.27 (t, J=6.9 Hz, 0.53 H), 5.08 (t, J=6.9 Hz, 0.47 H), 4.71 (m, 0.53 H), 4.52 (m, 0.47 H), 3.97 (m, 0.94 H), 3.85 (m, 1.06 H), 2.55-2.33 (m, 1 H), 2.25-2.12 (m, 1 H), 2.02-1.83 (m, 2 H).

2-Phenethyl-5-(N-phthlimidomethyl)tetrahydrofuran (14i): The product (0.43 g, 95%) was obtained as an oil by chromatography on silica; ($R_f$=0.49, EtOAc/Hexane, 30:70, v:v); $^1$H NMR (CDCl$_3$, 500 MHz): δ 7.85 (m, 2 H), 7.71 (m, 2 H), 7.25-7.17 (m, 5 H), 4.39 (m, 0.66 H), 4.27 (m, 0.33 H), 4.05 (m, 0.66 H), 3.88 (m, 0.33 H), 3.86-3.80 (m, 1 H), 3.71 (dd, J=5.3, 13.6 Hz, 0.33 H), 3.61 (dd, J=5.2, 13.5 Hz, 0.66 H), 2.72-2.57 (m, 2 H), 2.17-1.53 (m, 4 H).

5-(N-Phthalimidomethyl)-2-(3'-pyridinylethyl)tetrahydrofuran (14j): The product (233 mg, 26.5%) was obtained as an oil by chromatography on silica as a mixture of diastereomers, trans:cis=1.5:1 isomers; ($R_f$=0.24, EtOAc/Hexane, 60:40, v:v); $^1$H NMR (CDCl$_3$, 500 MHz): δ 8.44 (s, 1 H), 8.41 (m, 1 H), 7.85 (m, 2 H), 7.72 (m, 2 H), 7.50 (m, 1 H), 7.17 (m, 1 H), 4.39 (m, 0.6 H), 4.28 (m, 0.4 H), 4.03 (m, 0.6 H), 3.86 (m, 0.4 H), 3.86-3.80 (m, 1 H), 3.72 (dd, J=5.2, 13.5 Hz, 0.4 H), 3.62 (dd, J=4.5, 13.5 Hz, 0.6 H), 2.73-2.58 (m, 2 H), 2.12-2.06 (m, 2 H), 1.80-1.54 (m, 4 H).

2-(1'-Naphthethyl)-5-(N-phthlimidomethyl)tetrahydrofuran (14k) The product (230 mg, 65%) was obtained as an oil by chromatography on silica; ($R_f$=0.54, EtOAc/Hexane, 30:70, v:v); $^1$H NMR (CDCl$_3$, 500 MHz): δ 8.09-8.01 (m, 1 H), 7.88-7.81 (m, 3 H), 7.74-7.68 (m, 3 H), 7.53-7.31 (m, 4 H), 4.43 (m, 0.65 H), 4.33 (m, 0.35 H), 4.16 (m, 0.65 H), 3.97 (m, 0.35 H), 3.81 (m, 0.7 H), 3.76 (m, 1.3 H), 3.19 (m, 1 H), 3.04 (m, 1 H), 2.17-1.53 (m, 6 H).

2-(1'-Naphthyl)-5-(N-phthlimidomethyl)tetrahydrofuran (14l) The product (570 mg, 79%) was obtained as an oil by chromatography on silica; ($R_f$=0.53, EtOAc/Hexane, 30:70, v:v); $^1$H NMR (300 MHz, CDCl$_3$): δ 87.86 (m, 4 H), 7.72 (m, 4 H), 7.48 (m, 3 H), 5.86 (t, J=6.5 Hz, 0.3 H), 5.64 (t, J=7.1 Hz, 0.7H), 4.78 (m, 0.3 H), 4.53 (m, 0.7 H), 4.04 (m, 1.4 H), 3.91 (m, 0.6 H), 2.73-2.56 (m, 1 H), 2.25-2.14 (m, 1 H), 2.07-1.78 (m, 2 H).

Trans-2-(N-phtilimidomethyl)-5-(2'-methoxy-5'-fluorobenzyl)tetrahydrofuran (14m): The product (385 mg, 70%) was obtained as a white solid by chromatography on silica; ($R_f$=0.50, EtOAc/Hexane, 30:70, v:v); $^1$H NMR (CDCl$_3$, 500 MHz): δ 7.85-7.84 (m, 2 H), 7.72-7.70 (m, 2 H), 6.91 (dd, J=3.1, 9.1 Hz, 1 H), 6.82 (dt, J=3.1, 9.1 Hz. 1 H), 6.72 (dd, J=4.7, 9.1 Hz, 1 H), 4.41 (m, 1 H), 4.34 (p, J=6.7 Hz, 1 H), 3.83 (dd, J=8.1, 13.5 Hz, 1 H), 3.77 (s, 3 H), 3.62 (dd, J=5.3 13.5 Hz, 1 H), 2.85 (dd, J=6.4, 13.7 Hz, 1 H), 2.70 (dd, J=6.4, 13.7 Hz, 1 H), 2.03 (m, 2 H), 1.64 (m, 2 H).

Cis-2-(N-phtilimidomethyl)-5-(2'-methoxy-5'-fluorobenzyl)tetrahydrofuran (14n): The product (138 mg, 47%) was obtained as a white solid by chromatography on silica; ($R_f$=0.52, EtOAc/Hexane, 30:70, v:v); $^1$H NMR (CDCl$_3$, 500 MHz): δ 7.87-7.85 (m, 2 H), 7.71-7.70 (m, 2 H), 6.94 (dd, J=3.1, 9.1 Hz, 1 H), 6.80 (dt, J=3.1, 9.1 Hz. 1 H), 6.71 (dd, J=4.7, 9.1 Hz, 1 H), 4.25 (m, 1 H), 4.11 (p, J=6.7 Hz, 1 H), 3.84 (dd, J=8.1, 13.8 Hz, 1 H), 3.75 (s, 3 H), 3.68 (dd, J=5.2 13.8 Hz, 1 H), 2.84 (d, J=6.3 Hz, 2 H), 1.98-1.92 (m, 2H), 1.73-1.67 (m, 2 H).

Trans-2-(5'-fluoro-2'-methoxyphenethyl)-5-(phthalimidomethyl)tetrahydrofuran (14o): The product (0.70 g, 57%) was obtained as a white solid by chromatography on silica; ($R_f$=0.20, EtOAc/Hexane, 20:80, v:v); $^1$H NMR (CDCl$_3$, 500 MHz): δ 7.85-7.84 (m, 2 H), 7.72-7.71 (m, 2 H), 6.86 (dd, J=3.1, 9.1 Hz, 1 H), 6.80 (dt, J=3.1, 9.1 Hz. 1 H), 6.71 (dd, J=4.7, 9.1 Hz, 1 H), 4.38 (m, 1 H), 4.05 (quintet, J=6.6 Hz, 1 H), 3.83 (dd, J=8.0, 13.8 Hz, 1 H), 3.76 (s, 3 H), 3.62 (dd, J=5.1 13.8 Hz, 1 H), 2.67-2.52 (m, 2 H), 2.11-2.04 (m, 2 H), 1.79-1.54 (m, 4 H).

Cis-2-(5'-fluoro-2'-methoxyphenethyl)-5-(phthalimidomethyl)tetrahydrofuran (14p): The product (0.26 g, 63%) was obtained as a white solid by chromatography on silica; ($R_f$=0.20, EtOAc/Hexane, 20:80, v:v); $^1$H NMR (CDCl$_3$, 500 MHz): δ 7.86-7.85 (m, 2 H), 7.72-7.70 (m, 2 H), 6.86 (dd, J=3.1, 9.1 Hz, 1 H), 6.81 (dt, J=3.1, 9.1 Hz. 1 H), 6.71 (dd, J=4.7, 9.1 Hz, 1 H), 4.27 (quintet J=6.1 Hz, 1 H), 3.88 (quintet, J=6.6 Hz, 1 H), 3.82 (dd, J=8.0, 13.8 Hz, 1 H), 3.77 (s, 3 H), 3.72 (dd, J=5.1 13.8 Hz, 1 H), 2.65-2.58 (m, 2 H), 2.04-1.97 (m, 2 H), 1.83-1.58 (m, 4 H).

Trans-2-(3'-(2"-methoxy-5"-fluorophenyl)-1'-propyl)-5-(N-phthilimidomethyl)tetrahydrofuran (14q): The product (0.15 g, 62%) was obtained as an oil by chromatography on silica; ($R_f$=0.10, EtOAc/Hexane, 15:85, v:v); $^1$H NMR (CDCl$_3$, 500 MHz): δ 7.84 (m, 2 H), 7.70 (m, 2 H), 6.84-6.79 (m, 2 H), 6.72 (dd, J=4.6, 8.6 Hz, 1 H), 4.37 (m, 1 H), 4.05 (m, 1 H), 3.82 (dd, J=8.3, 13.5 Hz, 1 H), 3.76 (s, 3 H), 3.59 (dd, J=5.0, 13.5 Hz, 1 H), 2.57 (t, J=7.1 Hz, 2 H), 2.06 (m, 2 H), 1.68-1.45 (m, 6 H).

Cis-2-(3'-(2"-methoxy-5"-fluorophenyl)-1'-propyl)-5-(N-phthilimidomethyl)tetrahydrofuran (14r): The product (95 mg, 73%) was obtained as an oil by chromatography on silica; ($R_f$=0.10, EtOAc/Hexane, 15:85, v:v); $^1$H NMR (CDCl$_3$, 500 MHz): δ 7.84 (m, 2 H), 7.70 (m, 2 H), 6.84-6.80 (m, 2 H), 6.72 (dd, J=4.6, 8.6 Hz, 1 H), 4.25 (m, 1 H), 3.86 (m, 1 H), 3.81 (dd, J=8.3, 13.5 Hz, 1 H), 3.77 (s, 3 H), 3.68 (dd, J=5.0, 13.5 Hz, 1 H), 2.58 (t, J=7.1 Hz, 2 H), 2.00-1.95 (m, 2 H), 1.74-1.49 (m, 6 H).

Trans-2-(3'-(2'-methoxy-5"-fluorophenyl)-1'-propyl)-5-(N-phthilimidomethyl)tetrahydrofuran (14s): The product (67 mg, 69%) was obtained as an oil by chromatography on silica; ($R_f$=0.15, EtOAc/Hexane, 20:80, v:v); $^1$H NMR (CDCl$_3$, 500 MHz): δ 7.84 (m, 2 H), 7.70 (m, 2 H), 6.83-6.79 (m, 2 H), 6.72 (dd, J=4.3, 8.3 Hz, 1 H), 4.36 (m, 1 H), 4.01 (m, 1 H), 3.81 (dd, J=8.3, 13.5 Hz, 1 H), 3.77 (s, 3 H), 2.55 (, J=7.8 Hz, 2 H), 2.07 (m, 2 H), 1.68-1.39 (m, 8 H).

Trans-2-(Cyanomethyl)-5-(2'-methoxy-5'-fluorophenyl) tetrahydrofuran (16a) and cis-2-(cyanomethyl)-5-(2'-methoxy-5'-fluorophenyl)tetrahydrofuran (16b): To a vial under Ar was added 2-(bromomethyl)-5-(2'-methoxy-5'-fluorophenyl)tetrahydrofuran (1.23 g, 4.3 mmol), NaI (100 mg), potassium cyanide (0.7 g, 10.6 mmol), and dry DMSO (15 mL). The mixture was heated to 70° C. and stirred under Ar for 12 h. After it was cooled to room temperature, the reaction mixture was poured into a separatory funnel containing sodium bicarbonate aqueous solution (sat. NaHCO$_3$:H$_2$O=1:1, 80 mL). The organics were extracted with EtOAc (3×60 mL) and the combined organic layers were washed with brine (50 mL) and dried over Na$_2$SO$_4$. The solvent was removed in vacuo and the crude product was purified by flash column chromatography ($R_f$=0.2, EtOAc/Hexane, 20:80, v:v) A very careful analysis and collection of early fractions resulted in the trans isomer (16a, 0.55 g, 55%): $^1$H NMR (CDCl$_3$, 500 MHz): δ 7.11 (dd, J=3.1 9.2 Hz, 1 H), 6.89 (dt, J=3.1, 9.0 Hz, 1 H), 6.76 (dd, J=4.2, 8.5 Hz, 1 H), 5.33 (t, J=7.1 Hz, 1 H), 4.49 (p, J=6.1 Hz, 1 H), 3.79 (s, 3 H), 2.69 (dd, J=6.1, 16.7 Hz, 1 H), 2.66 (dd, J=6.1 16.7 Hz, 1 H), 2.57 (m, 1H), 2.25 (m, 1 H), 1.92 (m, 1 H), 1.77 (m, 1 H); The rest of the fractions were collected and upon removal of the solvent a white colored solid formed.

Further purification of this solid by triturating with hexane resulted in the cis isomer (16b, 250 mg, 25%); δ 7.24 (dd, J=3.1 9.2 Hz, 1 H), 6.90 (dt, J=3.1, 9.0 Hz, 1 H), 6.76 (dd, J=4.2, 8.5 Hz, 1 H), 5.14 (t, J=7.4 Hz, 1H), 4.28 (p, J=6.1 Hz, 1 H), 3.80 (s, 3 H), 2.73 (d, J=5.8 Hz, 1 H), 2.46 (m, 1 H), 2.24 (m, 1 H), 1.83 (m, 1 H), 1.77 (m, 1 H);

The following compounds were prepared in a similar manner as 16a.

2-Cyanomethyl-5-(2'-furanyl)tetrahydrofuran (16c): The product (0.2 g, 43%) was obtained as an oil by chromatography on silica as a mixture of trans:cis=1:1 isomers; ($R_f$=0.20, EtOAc/Hexane, 20:80, v:v); $^1$H NMR (CDCl$_3$, 500 MHz): δ 7.39 (s, 1 H), 6.33-6.25 (m, 2 H), 5.15 (t, J=6.8 Hz, 0.5 H), 4.98 (t, J=6.7 Hz, 0.5 H), 4.38 (m, 0.5 H), 4.30 (m, 0.5 H), 2.66 (m, 2 H), 2.38-1.90 (m, 4 H).

2-Benzyl-5-cyanomethyltetrahydrofuran (16d): The product (0.33 g, 74%) was obtained as an oil by chromatography on silica as a mixture of the trans:cis=2:1 isomers; ($R_f$=0.50, EtOAc/Hexane, 25:75, v:v); $^1$H NMR: (300 MHz, CDCl$_3$) δ 7.30-7.18 (m, 5 H), 4.28-4.24 (m, 0.67 H), 4.15-4.08 (m, 1 H), 3.91-3.89 (m, 0.33 H), 2.78-2.53 (m, 4 H), 2.68-2.25 (m, 4 H).

2-(Cyanomethyl)-5-(4'-hydroxyphenethyl) tetrahydrofuran (16e): The product (0.34 g, 78%) was obtained as an oil by chromatography on silica; ($R_f$=0.31, EtOAc/Hexane, 50:50, v:v); $^1$H NMR (500 MHz, CDCl$_3$) δ 7.76-7.73 (m, 2 H), 7.05-7.03 (m, 2 H), 5.27 (m, 2 H), 4.27-4.09 (m, 1 H), 4.08-3.88 (m, 1 H), 2.69-2.53 (m, 4 H), 2.13-2.09 (m, 2 H), 1.86-1.57 (m, 4 H).

2-Cyanomethyl-5-(2'-methoxy-1'-naphthethyl)tetrahydrofuran (16f): The product (0.43 g, 56%) was obtained as an oil by chromatography on silica; ($R_f$=0.31, EtOAc/Hexane, 25:75, v:v); $^1$H NMR: (500 MHz, CDCl$_3$) δ 8.0-7.27 (m, 6 H), 4.31 (m, 0.5 H), 4.18 (m, 0.5 H), 4.01 (m, 0.5 H), 3.95 (s, 3 H), 3.72 (m, 0.5 H), 3.22-3.08 (m, 2 H), 2.64-2.55 (m, 1 H), 2.24-2.16 (m, 2 H), 1.91-1.65 (m, 3 H), 1.58 (bs, 1 H), 1.24 (t, J=7.1 Hz, 1 H).

2-Cyanomethyl-5-(4'-methoxy-1'-naphthethyl)tetrahydrofuran (16g): The product (0.31 g, 45%) was obtained as an oil by chromatography on silica; TLC (SiO$_2$) $R_f$=0.30, 25% EtOAc/Hexanes; $^1$H NMR: (300 MHz, CDCl$_3$) δ 8.1-7.27 (m, 6 H), 4.40-4.24 (m, 1 H), 4.21-4.03 (m, 1 H), 3.99 (s, 3 H), 3.15 (m, 2 H), 2.64-1.24 (m, 8 H).

2-Cyanomethyl-5-(4'-fluoro-3'-methylphenethyl)tetrahydrofuran (16h): The product (0.22 g, 85%) was obtained as an oil by chromatography on silica; ($R_f$=0.25, EtOAc/Hexane, 20:80, v:v); $^1$H NMR (500 MHz, CDCl$_3$) δ 7.00-6.88 (m, 3 H), 4.28-3.87 (m, 2 H), 2.70-2.56 (m, 4 H), 2.24 (s, 3 H), 2.23-1.58 (m, 6 H).

Trans-2-(Cyanomethyl)-5-(2'-methoxy-5'-fluorobenzyl)tetrahydrofuran (16i) and cis-2-(cyanomethyl)-5-(2'-methoxy-5'-fluorobenzyl)tetrahydrofuran (16j): The product was obtained as an oil by chromatography on silica; ($R_f$=0.11, EtOAc/Hexane, 10:90, v:v); trans isomer (161, 170 mg, 27%): $^1$H NMR (CDCl$_3$, 500 MHz): δ 6.89 (dt, J=3.1, 9.0 Hz, 1 H), 6.86 (dd, J=3.1 9.2 Hz, 1 H), 6.76 (dd, J=4.2, 8.5 Hz, 1 H), 4.38 (p, J=6.8 Hz, 1 H), 4.27 (p, J=6.1 Hz, 1 H), 3.79 (s, 3 H), 2.90 (dd, J=6.3, 13.5 Hz, 1 H), 2.72 (dd, J=6.5 13.5 Hz, 1 H), 2.58 (m, 2 H), 2.19 (m, 1 H), 2.06 (m, 1 H), 1.77 (m, 1 H), 1.68 (m, 1 H); cis isomer (16j, 77 mg, 12%): δ 6.90 (dd, J=3.1 9.2 Hz, 1 H), 6.83 (dt, J=3.1, 9.0 Hz, 1 H), 6.71 (dd, J=4.2, 8.5 Hz, 1 H), 4.14 (p, J=6.8 Hz, 1 H), 4.10 (p, J=6.1 Hz, 1 H), 3.75 (s, 3 H), 2.87 (dd, J=6.5, 13.5 Hz, 1 H), 2.78 (dd, J=6.2 13.5 Hz, 1 H), 2.52 (m, 2 H), 2.06 (m, 1 H), 1.92 (m, 1 H), 1.76-1.69 (m, 2 H).

Trans-2-Cyanomethyl-5-(5'-fluoro-2-methoxyphenethyl)tetrahydrofuran (16k): The product (0.45 g, 86%) was obtained as an oil by chromatography on silica; ($R_f$=0.11, EtOAc/Hexane, 10:90, v:v); $^1$H NMR (500 MHz, CDCl$_3$) δ 6.87-6.82 (m, 2 H), 6.74 (dd, J=4.3, 8.5 Hz, 1 H), 4.26 (quintet, J=6.2 Hz, 1 H), 4.09 (m, 1 H), 3.79 (s, 3 H), 2.72-2.53 (m, 4H), 2.22-2.04 (m, 2 H), 1.84-1.60 (m, 4 H).

Cis-2-Cyanomethyl-5-(5'-fluoro-2-methoxyphenethyl)tetrahydrofuran (16l): The product (0.20 g, 80%) was obtained as an oil by chromatography on silica; ($R_f$=0.11, EtOAc/Hexane, 10:90, v:v); $^1$H NMR (500 MHz, CDCl$_3$) δ 6.88-6.82 (m, 2 H), 6.74 (dd, J=4.3, 8.5 Hz, 1 H), 4.26 (quintet, J=6.1 Hz, 1 H), 3.90 (quintet, J=6.7 Hz, 1 H), 3.79 (s, 3 H), 2.73 (m, 1 H), 2.59 (t, J=5.2 Hz, 2 H), 2.53 (m, 1 H), 2.14-2.02 (m, 2 H), 1.89-1.57 (m, 4 H).

Trans-2-Cyanomethyl-5-(3'-(2"-methoxy-5"-fluorophenyl)-1'-propyl)tetrahydrofuran: The product (71 mg, 85%) was obtained as an oil by chromatography on silica; ($R_f$=0.10, EtOAc/Hexane, 10:90, v:v); $^1$H NMR (CDCl$_3$, 500 MHz): δ 6.84-6.81 (m, 2 H), 6.73 (dd, J=4.2, 8.5 Hz, 1 H), 4.22 (p, J=6.8 Hz, 1 H), 4.09 (m, 1 H), 3.79 (s, 3 H), 2.62-2.52 (m, 4 H), 2.18 (m, 1 H), 2.12 (m, 1 H), 1.78 (m, 1 H), 1.69-1.46 (m, 3 H).

Cis-2-Cyanomethyl-5-(3'-(2"-methoxy-5"-fluorophenyl)-1'-propyl)tetrahydrofuran (16n, 22 mg, 18%): The product (22 mg, 18%) was obtained as an oil by chromatography on silica; ($R_f$=0.11, EtOAc/Hexane, 10:90, v:v); $^1$H NMR (CDCl$_3$, 500 MHz): δ 6.86-6.81 (m, 2 H), 6.73 (dd, J=4.2, 8.5 Hz, 1 H), 4.11 (m, 1 H), 3.90 (m, 1 H), 3.79 (s, 3 H), 2.62-2.55 (m, 4 H), 2.10 (m, 1 H), 2.01 (m, 1 H), 1.78 (m, 1 H), 1.69-1.46 (m, 3H).

2-Cyanomethyl-5-(4'-(2"-methoxy-5"-fluorophenyl)-1'-butyl)tetrahydrofuran (16o): The product (40 mg, 33%) was obtained as an oil by chromatography on silica; ($R_f$=0.12, EtOAc/Hexane, 15:85, v:v); $^1$H NMR (CDCl$_3$, 500 MHz): δ 6.84-6.80 (m, 2 H), 6.74 (dd, J=4.2, 8.5 Hz, 1 H), 4.22 (quintet, J=6.4 Hz, 0.5 H), 4.11 (quintet, J=6.2 Hz, 0.5 H), 4.07 (m, 0.5 H), 3.87 (quintet, J=6.6 Hz, 0.5 H), 3.78 (s, 3 H), 2.61-2.55 (m, 4 H), 2.21-1.95 (m, 2 H), 2.01 (m, 1 H), 1.77 (m, 1 H), 1.66-1.34 (m, 6 H).

2-Aminomethyl-5-(2'-methoxy-5'-fluorophenyl)tetrahydrofuran (18a): To a vial under Ar was added 2-(N-phthalimidomethyl)-5-(2'-methoxy-5'-fluorophenyl)tetrahydrofuran (225 mg, 0.63 mmol), hydrazine hydrate (150 mg, 4.9 mmol), and methanol (10 mL). The mixture was stirred at room temperature for 12 h. The solvent was then removed in vacuo and the crude product was purified by column flash chromatography to yield the pure product ($R_f$=0.10, Methanol/DCM, 10:90, v:v) (90 mg, 60%, trans:cis=3:2) as a viscous oil; $^1$H NMR (CDCl$_3$, 500 MHz): δ 7.19 (m 1 H), 6.87 (m 1 H), 6.75 (m 1 H), 5.20 (t, J=7.1 Hz, 0.58 H),), 5.11 (t, J=7.1 Hz, 0.42 H), 4.24 (m, 0.58H), 4.04 (m, 0.42 H), 2.93-2.78 (m, 2 H), 2.41 (m, 1 H), 2.03 (m, 1 H), 1.79 (s, 2 H), 1.75-1.63 (m, 2 H); HRMS (ESI) [M+H]$^+$ m/z cacld for C$_{12}$H$_{17}$FNO$_2$ 226.1243, found 226.1255; HPLC>96% ($t_R$=4.30 min, 40 (A):55(B):5 (C):0.01(D); $t_R$=5.04 min, 20(A):75(B):5(C):0.01(D)).

The following compounds were prepared in a similar manner as 18a.

2-Aminomethyl-5-phenyltetrahydrofuran (15b): The product (33 mg, 65%) was obtained as an oil by chromatography on silica; ($R_f$=0.11, Methanol/DCM, 10:90, v:v); $^1$H NMR: (CDCl$_3$, 500 MHz): δ 7.33 (m, 5 H), 4.97 (m, 0.66 H), 4.90 (t, J=7.7 Hz, 0.34 H), 4.25 (m, 0.66 H), 4.06 (m, 0.34 H), 2.93-2.78 (m, 2 H), 2.35 (m, 1 H), 2.09 (m, 1 H), 1.96-1.70 (m, 2 H), 1.62 (bs, 2 H); LRMS (ESI) [M+H]$^+$ m/z cacld for C$_{11}$H$_{15}$NO 178 found 178.

2-(Aminomethyl)-5-(2'-naphthyl)tetrahydrofuran (15c): The product (27 mg, 66%) was obtained as an oil by chromatography on silica; ($R_f$=0.14, Methanol/DCM, 15:85, v:v); $^1$H NMR (500 MHz, CDCl$_3$) δ 7.84-7.78 (m, 4 H), 7.47-7.41 (m, 3 H), 5.14 (t, J=7.2 Hz, 0.33 H), 5.04 (t, J=7.4 Hz, 0.67 H), 4.38-4.33 (m, 0.33 H), 4.16-4.14 (m, 0.66 H), 3.01-2.83 (m, 2 H), 2.60 (bs, 2 H), 2.42-2.34 (m, 1 H), 2.16-2.07 (m, 1 H), 1.97-1.86 (m, 1 H), 1.79-1.72 (1 H); LRMS (ESI) [M+H]$^+$ m/z cacld for $C_{15}H_{17}NO$ 228 found 228.

2-(Aminomethyl)-5-phenethyltetrahydrofuran (15d): The product (23 mg, 55%) was obtained as an oil by chromatography on silica; ($R_f$=0.12, Methanol/DCM, 15:85, v:v); $^1$H NMR (500 MHz, CDCl$_3$) δ 7.27-7.19 (m, 5 H), 4.01-3.85 (m, 2 H), 2.83-2.62 (m, 4 H), 2.03-1.50 (m, 8 H); LRMS (ESI) [M+H]$^+$ m/z cacld for $C_{13}H_{19}NO$ 206 found 206.

2-(Aminomethyl)-5-(1'-naphthethyl)tetrahydrofuran (15a): The product (43 mg, 52%) was obtained as an oil by chromatography on silica; ($R_f$=0.13, Methanol/DCM, 15:85, v:v); $^1$H NMR (500 MHz, CDCl$_3$) δ 8.08-8.06 (m, 1 H), 7.85 (d, J=7.6 Hz, 1 H), 7.71 (d, J=7.6 Hz, 1 H), 7.52-7.45 (m, 2 H), 7.39 (t, J=7.6 Hz, 1 H), 7.35 (d, J=6.8 Hz, 1 H), 4.05-3.90 (m, 2 H), 3.25 (m, 1 H), 3.11 (m, 1 H), 2.86-2.70 (m, 2 H), 2.07-1.89 (m, 4 H), 1.63-1.55 (m, 2 H), 1.48 (bs, 2 H); LRMS (ESI) [M+H]$^+$ m/z cacld for $C_{17}H_{21}NO$ 256 found 256.

2-(Aminomethyl)-5-(1'-naphthyl)tetrahydrofuran (15e): The product (39 g, 85%) was obtained as an oil by chromatography on silica; ($R_f$=0.13, Methanol/DCM, 15:85, v:v); $^1$H NMR (500 MHz, CDCl$_3$) δ 7.96-7.93 (m, 1 H), 7.89-7.85 (1 H), 7.76-7.74 (m, 1 H), 7.71-7.69 (m, 1 H), 7.63 (d, J=7.1 Hz, 1 H), 7.50-7.43 (m, 3 H), 5.74 (t, J=7.0 Hz, 0.33 H), 5.61 (t, J=7.3 Hz, 0.67 H), 4.38-4.28 (m, 0.33 H), 4.19-4.16 (m, 0.67 H), 3.02-2.88 (m, 1 H), 2.62-2.52 (m, 1 H), 2.15 (bs, 2 H), 2.14-1.71 (m, 3 H); LRMS (ESI) [M+H]$^+$ m/z cacld for $C_{15}H_{17}NO$ 228 found 228.

2-Aminomethyl-5-(p-chlorophenyltetrahydrofuran (15f): The product (16 mg, 71%) was obtained as an oil by chromatography on silica; ($R_f$=0.14, Methanol/DCM, 15:85, v:v); $^1$H NMR: (CDCl$_3$, 500 MHz): δ 7.34-7.27 (m, 4 H), 4.95 (t, J=6.9 Hz, 0.66 H), 4.83 (t, J=6.7 Hz, 0.34 H), 4.35 (m, 0.66 H), 4.15 (m, 0.34 H), 3.40 (bs, 2 H), 2.99-2.81 (m, 2 H), 2.32 (m, 1 H), 2.08 (m, 1 H), 1.84-1.68 (m, 2 H); LRMS (ESI) [M+H]$^+$ m/z cacld for $C_{11}H_{14}ClNO$ 212 found 212.

2-Aminomethyl-5-(p-bromophenyltetrahydrofuran (15g): The product (16 mg, 48%) was obtained as an oil by chromatography on silica; ($R_f$=0.13, Methanol/DCM, 15:85, v:v); $^1$H NMR: (CDCl$_3$, 500 MHz): δ 7.42-7.20 (m, 4 H), 4.95 (t, J=6.9 Hz, 0.66 H), 4.86 (t, J=6.7 Hz, 0.34 H), 4.26 (m, 0.66 H), 4.08 (m, 0.34 H), 2.83-2.79 (m, 2 H), 2.38-1.71 (m, 6 H); LRMS (ESI) [M+H]$^+$ m/z cacld for $C_{11}H_{14}BrNO$ 256 found 256.

2-Aminomethyl-5-pentafluorophenethyltetrahydrofuran (15h): The product (30 mg, 53%) was obtained as an oil by chromatography on silica; ($R_f$=0.14, Methanol/DCM, 15:85, v:v); $^1$H NMR: (CDCl$_3$, 500 MHz): δ 4.05 (m, 0.60 H), 3.92 (m, 1 H), 3.86 (m, 0.40 H), 2.89-2.70 (m, 2 H), 2.74 (m, 2 H), 2.63 (bs, 2 H), 2.08-1.99 (m, 2 H), 1.82-1.54 (m, 4 H); LRMS (ESI) [M+H]$^+$ m/z cacld for $C_{13}H_{14}F_5NO$ 296 found 296.

2-(Aminomethyl)-5-(3'-pyridinylethyl)tetrahydrofuran (15i): The product (12 mg, 35%) was obtained as an oil by chromatography on silica; ($R_f$=0.09, Methanol/DCM, 15:85, v:v); $^1$H NMR (500 MHz, CDCl$_3$) δ 8.46 (s, 1 H), 8.42 (d, J=4.1 Hz, 1 H), 7.51 (m, 1 H), 7.19 (dd, J=4.8, 7.7 Hz, 1 H), 4.02-3.83 (m, 2 H), 2.82-2.63 (m, 4 H), 2.07-1.53 (m, 8H); LRMS (ESI) [M+H]$^+$ m/z cacld for $C_{12}H_{18}N_2O$ 207 found 207.

2-Aminomethyl-5-(p-methoxyphenyl)tetrahydrofuran (15j): The product (18 mg, 55%) was obtained as an oil by chromatography on silica; ($R_f$=0.10, Methanol/DCM, 15:85, v:v); $^1$H NMR: (CDCl$_3$, 500 MHz): δ 7.27 (m, 2 H), 6.87 (m, 2 H), 4.92 (m, 0.66 H), 4.83 (t, J=6.7 Hz, 0.34 H), 4.26 (m, 0.66 H), 4.07 (m, 0.34 H), 3.79 (s, 1 H), 3.78 (s, 2 H), 2.92-2.78 (m, 2 H), 2.57 (bs, 2 H), 2.29 (m, 1 H), 2.10, m, 1 H), 1.88-1.69 (m, 2 H); LRMS (ESI) [M+H]$^+$ m/z cacld for $C_{12}H_{17}NO_2$ 208 found 208.

2-Aminomethyl-5-(p-t-butylphenyl)tetrahydrofuran (15k): The product (21 mg, 54%) was obtained as an oil by chromatography on silica; ($R_f$=0.10, Methanol/DCM, 10:90, v:v); $^1$H NMR: (CDCl$_3$, 500 MHz): δ 7.36-7.24 (m, 4 H), 4.96 (m, 0.66 H), 4.86 (m, 0.34 H), 4.46 (bs, 2 H), 4.34 (m, 0.66 H), 4.13 (m, 0.34 H), 3.00-2.80 (m, 2 H), 2.29 (m, 1 H), 2.10 (m, 1 H), 1.97-1.68 (m, 2 H), 1.30 (s, 9 H); LRMS (ESI) [M+H]$^+$ m/z cacld for $C_{15}H_{23}NO$ 234 found 234.

Trans-2-aminomethyl-5-(2'-methoxy-5'-fluorophenyl)tetrahydrofuran (18a): The product (41 mg, 30%, trans:cis=0.95:0.05) was obtained as an oil by chromatography on silica; ($R_f$=0.08, Methanol/DCM, 10:90, v:v); $^1$H NMR: (CDCl$_3$, 500 MHz): δ 7.18 (dd, J=3.1, 9.4 Hz, 1 H), 6.87 (dt, J=3.1, 8.5 Hz. 1 H), 6.75 (dd, J=4.2, 9.1 Hz, 1 H), 5.20 (t, J=7.1 Hz, 1 H),), 4.24 (m, 1 H), 2.82 (m, 2 H), 2.44 (m, 1 H), 2.04 (m, 1 H), 1.71-1.69 (m, 2 H), 1.67 (s, 2 H); HRMS (ESI) [M+H]$^+$ m/z cacld for $C_{12}H_{17}FNO_2$ 226.1243, found 226.1257; HPLC>96% ($t_R$=4.30 min, 40(A):55(B):5(C):0.01 (D); $t_R$=5.04 min, 20(A):75(B):5(C):0.01(D)).

Trans-2-aminomethyl-5-(2'-methoxy-5'-fluorophenylmethyl)tetrahydrofuran (18e): The product (54 mg, 60%) was obtained as an oil by chromatography on silica; ($R_f$=0.10, Methanol/DCM, 10:90, v:v); $^1$H NMR (CDCl$_3$, 500 MHz): δ 6.93 (dd, J=3.1, 8.8 Hz, 1 H), 6.86 (dt, J=3.1, 8.8 Hz, 1 H), 6.75 (dd, J=3.1, 8.8 Hz, 1 H), 4.23 (m, 1 H),), 4.08 (m 1 H), 3.79 (s, 3 H), 2.91 (dd, J=13.5, 6.5 Hz, 2 H), 2.78 (m, 1 H), 2.72 (m, 1 H), 2.18 (bs, 2H), 2.02-1.92 (m, 2 H), 1.64-1.55 (m, 2 H); HRMS (ESI) [M+H]$^+$ m/z cacld for $C_{13}H_{19}FNO_2$ 240.1400, found 240.1423; HPLC>98% ($t_R$=4.68 min, 40(A):55(B):5(C):0.01(D); $t_R$=5.04 min, 20(A):75(B):5(C):0.01(D)).

Cis-2-aminomethyl-5-(2'-methoxy-5'-fluorophenylmethyl)tetrahydrofuran (18f): The product (26 mg, 73%) was obtained as an oil by chromatography on silica; ($R_f$=0.09, Methanol/DCM, 10:90, v:v); $^1$H NMR (CDCl$_3$, 500 MHz): δ 6.93 (dd, J=3.1, 8.8 Hz, 1 H), 6.86 (dt, J=3.1, 8.8 Hz, 1 H), 6.77 (dd, J=3.1, 8.8 Hz, 1 H), 4.15 (m, 1 H),), 3.97 (m 1 H), 3.79 (s, 3 H), 2.91 (dd, J=13.5, 6.6 Hz, 2 H), 2.76 (dd, J=13.5, 6.6 Hz, 2 H), 2.43 (bs, 2H), 1.93 (m, 2 H), 1.63 (m, 2 H); HRMS (ESI) [M+H]$^+$ m/z cacld for $C_{13}H_{19}FNO_2$ 240.1400, found 240.1423; HPLC>98% ($t_R$=4.69 min, 40(A):55(B):5 (C):0.01(D); $t_R$=5.06 min, 20(A):75(B):5(C):0.01(D)).

Trans-2-(aminomethyl)-5-(2'-methoxy-5'-fluorophenethyl)tetrahydrofuran (18i) The product (197 mg, 85%) was obtained as an oil by chromatography on silica; ($R_f$=0.09, Methanol/DCM, 10:90, v:v); $^1$H NMR (CDCl$_3$, 500 MHz): δ 6.87 (dt, J=3.0, 8.9 Hz, 1 H), 6.82 (dd, J=3.0, 8.5 Hz, 1 H), 6.74 (dd, J=4.3, 8.5 Hz, 1 H), 4.01 (m, 1 H), 3.93 (quintet, J=6.8 Hz, 1 H), 3.78 (s, 3 H), 2.76-2.67 (m, 3 H), 2.60 (m, 1 H), 2.06-1.99 (m, 2H), 1.84 (m, 1 H), 1.78 (bs, 2 H), 1.70 (m, 1 H), 1.59-1.54 (m, 2 H); HRMS (ESI) [M+H]$^+$ m/z cacld for $C_{14}H_{21}FNO_2$ 254.1556, found 254.1573; HPLC>98% ($t_R$=4.48 min, 40(A):55(B):5(C):0.01(D); $t_R$=5.76 min, 20(A):75(B):5(C):0.01(D)).

Cis-2-(aminomethyl)-5-(2'-methoxy-5'-fluorophenethyl) tetrahydrofuran 18j): The product (125 mg, 73%) was obtained as an oil by chromatography on silica; ($R_f$=0.10, Methanol/DCM, 10:90, v:v); $^1$H NMR (CDCl$_3$, 500 MHz): δ 6.87 (dt, J=3.0, 8.9 Hz, 1 H), 6.82 (dd, J=3.0, 8.5 Hz, 1 H), 6.72 (dd, J=4.3, 8.5 Hz, 1 H), 3.91-3.87 (m, 2 H), 3.79 (s, 3 H), 2.83-2.57 (m, 4 H), 2.00-1.52 (m, 6 H) 1.84 (bs, 2 H); HRMS (ESI) [M+H]$^+$ m/z cacld for $C_{14}H_{21}FNO_2$ 254.1556, found 254.1551; HPLC>98% ($t_R$=4.50 min, 40(A):55(B):5(C):0.01 (D); $t_R$=5.81 min, 20(A):75(B):5(C):0.01(D)).

Trans-2-aminomethyl-5-((2"-methoxy-5"-fluorophenyl)-3'-propyl)tetrahydrofuran (18m): The product (42 mg, 87%) was obtained as an oil by chromatography on silica; ($R_f$=0.10, Methanol/DCM, 10:90, v:v); $^1$H NMR (CDCl$_3$, 500 MHz): δ 6.86-6.80 (m, 2 H), 6.74 (dd, J=4.7, 8.8 Hz, 1 H), 4.01 (p, J=6.2 Hz, 1 H), 3.93 (p, J=7.2 Hz, 1 H), 3.78 (s, 3 H), 2.85-2.67 (m, 2 H), 2.60 (t, J=7.2 Hz, 2 H), 2.34 (bs, 2 H), 2.03-1.98 (m, 2 H), 1.68-1.46 (m, 6 H); HRMS (ESI) [M+H]$^+$ m/z cacld for C$_{15}$H$_{23}$FNO$_2$ 268.1713, found 268.1709; HPLC>95% ($t_R$=4.70 min, 40(A):55(B):5(C):0.01(D); $t_R$=5.10 min, 10(A):85(B):5(C):0.01(D)).

Cis-2-aminomethyl-5-(3'-(2"-methoxy-5"-fluorophenyl)-3'-propyl)tetrahydrofuran (18n): The product (42 mg, 87%) was obtained as an oil by chromatography on silica; ($R_f$=0.10, Methanol/DCM, 10:90, v:v); $^1$H NMR (CDCl$_3$, 500 MHz): δ 6.85 (dd, J=3.0, 9.6 Hz, 1 H), 6.82 (dd, J=3.0, 8.3 Hz, 1 H), 6.73 (dd, J=4.7, 8.9 Hz, 1 H), 3.94 (m, 1 H), 3.85 (m, 1 H), 3.78 (s, 3 H), 3.00-2.60 (m, 4 H), 2.60 (t, J=7.2 Hz, 2 H), 1.98-1.92 (m, 2 H), 1.68-1.46 (m, 6 H); HRMS (ESI) [M+H]$^+$ m/z cacld for C$_{15}$H$_{23}$FNO$_2$ 268.1713, found 268.1702; HPLC>98% ($t_R$=4.71 min, 40(A):55(B):5(C):0.01(D); $t_R$=5.10 min, 10(A):85(B):5(C):0.01(D)).

Trans-2-Aminomethyl-5-(5"-fluoro-2"-methoxyphenyl)-4'-butyl)tetrahydrofuran (18q): The product (33 mg, 95%) was obtained as an oil by chromatography on silica; ($R_f$=0.10, Methanol/DCM, 10:90, v:v); $^1$H NMR (CDCl$_3$, 500 MHz): δ 6.85-6.80 (m, 2 H), 6.72 (dd, J=4.7, 8.9 Hz, 1 H), 4.02 (m, 1 H), 3.92 (m, 1 H), 3.78 (s, 3 H), 2.90-2.70 (bm, 2 H), 2.58 (t, J=7.6 Hz, 2 H), 2.32 (bs, 2 H), 2.02 (m, 1 H), 1.64-1.35 (m, 9 H); MS: 282 (MH$^+$), 264, 139; HRMS (ESI) [M+H]$^+$ m/z cacld for C$_{16}$H$_{25}$FNO$_2$ 282.2869, found 282.1889; HPLC>98% ($t_R$=4.83 min, 40(A):55(B):5(C):0.01(D); $t_R$=5.17 min, 10(A):85(B):5(C):0.01(D)).

Trans-2-aminoethyl-5-(2'-methoxy-5'-fluorophenyl)tetrahydrofuran (18c): To a vial under Ar was added Raney Ni that was washed with ethanol (200 proof, 3 times) and trans-2-(cyanomethyl)-5-(2'-methoxy-5'-fluorophenyl)tetrahydrofuran (80 mg, 0.35 mmol) that was treated with a small amount of Raney Ni in ethanol. The vial was then evacuated to boiling and purged with H$_2$ three times. A balloon filled with H$_2$ was attached to the flask and the reaction was stirred for 48 h at room temperature. The reaction mixture was then filtered through a plug of Celite and the crude product obtained after the removal of the solvent was purified by flash column chromatography ($R_f$=0.10, Methanol/DCM, 10:90, v:v) to result in the pure product (43.7 mg, 52%); $^1$H NMR: (CDCl$_3$, 500 MHz): δ 7.15 (dd, J=3.1, 9.4 Hz, 1 H), 6.86 (dt, J=3.1, 8.5 Hz. 1 H), 6.74 (dd, J=4.2, 9.1 Hz, 1 H), 5.21 (t, J=7.1 Hz, 1 H),), 4.25 (m 1 H), 3.78 (s, 3 H), 2.91 (m, 2 H), 2.46 (m, 1 H), 2.08 (m, 1 H), 1.73-1.66 (m, 6 H); HRMS (ESI) [M+H]$^+$ m/z cacld for C$_{13}$H$_{19}$FNO$_2$ 240.1400, found 240.1401; HPLC>95% ($t_R$=4.71 min, 40(A):55(B):5(C):0.01 (D); $t_R$=5.25 min, 10(A):85(B):5(C):0.01(D)).

The following compounds were prepared in a similar manner as 18c.

2-Aminoethyl-5-(2'-methoxyl-1'-naphthethyl)tetrahydrofuran (17a): The product (43 mg, 56%) was obtained as an oil by chromatography on silica; ($R_f$=0.10, Methanol/DCM, 10:90, v:v); $^1$H NMR (500 MHz, CDCl$_3$) δ 8.00 (bs, 2 H), 7.92 (d, J=8.6 Hz, 1 H), 7.75 (m, 1 H), 7.69 (m, 1 H), 7.50 (m, 1 H), 7.31 (m, 1 H), 7.23 (m, 1 H), 4.05 (m, 1.3 H), 3.94 (s, 1 H), 3.93 (s, 2 H), 3.85 (m, 0.7 H), 3.28 (m, 1 H), 3.14-3.07 (m, 3 H), 2.04-1.80 (m, 7H), 1.52 (m, 1 H); LRMS (ESI) [M+H]$^+$ m/z cacld for C$_{19}$H$_{25}$NO$_2$ 300 found 300.

2-Aminoethyl-5-(4'-methoxyl-1'-naphthethyl)tetrahydrofuran (17b): The product (33 mg, 35%) was obtained as an oil by chromatography on silica; ($R_f$=0.10, Methanol/DCM, 10:90, v:v); $^1$H NMR (500 MHz, CDCl$_3$) δ 8.35 (bs, 2 H), 7.30 (d, J=8.6 Hz, 1 H), 7.94 (d, J=8.6 Hz, 1 H), 7.69 (m, 1 H), 7.50 (m, 1 H), 7.20 (m, 1 H), 6.73 (m, 1 H), 4.05 (m, 1.3 H), 3.96 (s, 1 H), 3.95 (s, 2 H), 3.90 (m, 0.7 H), 3.29 (m, 1 H), 3.16-2.92 (m, 3 H), 2.06-1.77 (m, 7 H), 1.52 (m, 1 H); LRMS (ESI) [M+H]$^+$ m/z cacld for C$_{19}$H$_{25}$NO$_2$ 300 found 300.

2-Aminoethyl-5-(4'-fluoro-3'-methylphenethyl)tetrahydrofuran (17c): The product (117 mg, 45%) was obtained as an oil by chromatography on silica; ($R_f$=0.10, Methanol/DCM, 10:90, v:v); $^1$H NMR (500 MHz, CDCl$_3$) δ 7.00-6.87 (m, 3 H), 4.08-3.79 (m, 1 H), 3.28-3.25 (m, 1 H), 3.14-3.09 (m, 1 H), 2.63-2.52 (m, 2 H), 2.23 (m, 1 H), 2.06-1.48 (m, 8 H); LRMS (ESI) [M+H]$^+$ m/z cacld for C$_{15}$H$_{22}$FNO 252 found 252.

2-(2'-aminoethyl)-5-benzyltetrahydrofuran (17d): The product (133 mg, 34%) was obtained as an oil by chromatography on silica; ($R_f$=0.10, Methanol/DCM, 10:90, v:v); $^1$H NMR: (CDCl$_3$, 500 MHz): δ 7.29-7.20 (m, 5 H), 4.19 (quintet, J=6.6 Hz, 0.66 H), 4.04 (m, 1 H), 3.91 (m, 0.34 H), 2.94 (dd, J=5.8, 13.4 Hz, 1 H), 2.81 (bs, 2 H), 2.70 (dd, J=7.1, 13.4 Hz, 1 H), 2.17-1.48 (m, 6 H); LRMS (ESI) [M+H]$^+$ m/z cacld for C$_{12}$H$_{17}$NO 192 found 192.

2-Aminoethyl-5-(4'-hydroxyphenethyl)tetrahydrofuran (17e): The product (112 mg, 32%) was obtained as an oil by chromatography on silica; ($R_f$=0.11, Methanol/DCM, 10:90, v:v); $^1$H NMR (500 MHz, CDCl$_3$) δ 7.01 (d, J=8.3 Hz, 2 H), 6.78 (d, J=8.2 Hz, 2H), 3.98-3.94 (M, 1 H), 3.90-3.82 (m, 1 H), 2.99-2.94 (m, 1 H), 2.88-2.84 (m, 1 H), 2.64-2.58 (m, 2 H), 2.03-1.93 (m, 2 H), 1.84-1.67 (m, 4 H), 1.51-1.48 (m, 2 H); LRMS (ESI) [M+H]$^+$ m/z cacld for C$_{14}$H$_{21}$NO$_2$ 236 found 236.

2-(2'-aminoethyl)-5-(2"-furyl)tetrahydrofuran (17f): The product (16 mg, 40%) was obtained as an oil by chromatography on silica; ($R_f$=0.09, Methanol/DCM, 10:90, v:v); $^1$H NMR: (CDCl$_3$, 500 MHz): δ 7.34 (d, J=1.2 Hz, 1 H), 6.31 (t, J=2.1 Hz, 1 H), 6.24 (dd, J=3.2, 6.6 Hz, 1 H), 5.01 (t, J=7.0 Hz, 0.5 H), 4.89 (t, J=7.0 Hz, 0.5 H), 4.17 (m, 0.5 H), 4.06 (m, 0.5 H), 2.85 (m, 2 H), 2.30-1.70 (m, 6 H), 2.09 (s, 2 H); LRMS (ESI) [M+H]$^+$ m/z cacld for C$_{10}$H$_{15}$NO$_2$ 182 found 182.

Cis-2-aminoethyl-5-(2'-methoxy-5'-fluorophenyl)tetrahydrofuran (18d) The product (43 mg, 42%) was obtained as an oil by chromatography on silica; ($R_f$=0.11, Methanol/DCM, 10:90, v:v); $^1$H NMR: (CDCl$_3$, 500 MHz): δ 7.21 (dd, J=3.1, 9.4 Hz, 1 H), 6.87 (dt, J=3.1, 8.5 Hz. 1 H), 6.74 (dd, J=4.2, 9.1 Hz, 1 H), 5.10 (t, J=7.1 Hz, 1 H),), 4.06 (p, J=5.8 Hz, 1 H), 3.79 (s, 3 H), 2.92 (m, 2 H), 2.36 (m, 1 H), 2.04 (m, 1 H), 1.88 (m, 1 H), 1.79 (m, 1 H), 1.65 (m, 1 H), 1.56 (m, 1 H), 1.46 (bs, 2 H); HRMS (ESI) [M+H]$^+$ m/z cacld for C$_{13}$H$_{19}$FNO$_2$ 240.1400, found 240.1403; HPLC>96% ($t_R$=4.72 min, 40(A):55(B):5(C):0.01(D); $t_R$=5.27 min, 10(A):85(B):5(C): 0.01(D)).

Trans-2-aminoethyl-5-(2'-methoxy-5'-fluorobenzyl)tetrahydrofuran (18g) The product (41 mg, 45%) was obtained as an oil by chromatography on silica; ($R_f$=0.09, Methanol/DCM, 10:90, v:v); $^1$H NMR: (CDCl$_3$, 500 MHz): δ 6.92 (dd, J=8.8. 3.1 Hz, 1 H), 6.85 (dt, J=3.1, 8.8 Hz, 1 H), 6.75 (dd, J=4.5, 8.7 Hz, 1 H), 4.23 (p, J=6.6 Hz, 1 H), 4.06 (m 1 H), 3.78 (s, 3 H), 2.88 (dd, J=6.4, 13.5 Hz, 1 H), 2.82 (broad, 2 H),), 2.70 (dd, J=6.4, 13.5 Hz, 1 H), 2.03 (m, 1 H), 1.92 (m, 1 H), 1.91 (bs, 2 H), 1.69-1,48 (m, 4 H); HRMS (ESI) [M+H]$^+$ m/z cacld for C$_{14}$H$_{21}$FNO$_2$ 254.1556, found 254.1548; HPLC>96% ($t_R$=4.35 min, 40(A):55(B):5(C):0.01(D); $t_R$=5.53 min, 20(A):75(B):5(C):0.01(D)).

Cis-2-aminoethyl-5-(2'-methoxy-5'-fluorobenzyl)tetrahydrofuran (18h) The product (31 mg, 41%) was obtained as an oil by chromatography on silica; ($R_f$=0.10, Methanol/DCM, 10:90, v:v); $^1$H NMR: (CDCl$_3$, 500 MHz): δ 6.95 (dd, J=9.2, 3.1 Hz, 1 H), 6.88 (dt, J=3.1, 8.5 Hz, 1 H), 6.78 (dd, J=4.7, 9.1 Hz, 1 H), 4.11 (p, J=6.8 Hz, 1 H), 3.94 (p, J=6.4 Hz, 1 H), 3.81 (s, 3 H), 2.91 (dd, J=6.6, 13.5 Hz, 1 H), 2.87 (broad, 2 H), 2.78 (dd, J=6.6, 13.5 Hz, 1 H), 1.96 (m, 2 H), 1.88 (bs, 2 H), 1.72 (m, 2 H), 1.64-1.55 (m, 2 H); HRMS (ESI) [M+H]$^+$ m/z cacld for C$_{14}$H$_{21}$FNO$_2$ 254.1556, found 254.1546; HPLC>96% (t$_R$=4.35 min, 40(A):55(B):5(C):0.01(D); t$_R$=5.53 min, 20(A):75(B):5(C):0.01(D)).

Trans-2-(aminoethyl)-5-(2'-methoxy-5'-fluorophenethyl)tetrahydrofuran (18k) The product (192 mg, 40%) was obtained as an oil by chromatography on silica; ($R_f$=0.12, Methanol/DCM, 10:90, v:v); $^1$H NMR: (CDCl$_3$, 500 MHz): δ 6.87 (dt, J=3.0, 8.9 Hz, 1 H), 6.82 (dd, J=3.0, 8.5 Hz, 1 H), 6.72 (dd, J=4.3, 8.5 Hz, 1 H), 4.03 (m, 1 H), 3.96 (m, 1 H), 3.78 (s, 3 H), 2.84 (bm, 2 H), 2.68 (m, 1 H), 2.58 (m, 1 H), 2.03 (m, 2 H), 1.83 (bs, 2 H), 1.72-1.60 (m, 4 H), 1.54 (m, 2 H); HRMS (ESI) [M+H]$^+$ m/z cacld for C$_{15}$H$_{23}$FNO$_2$ 268.1713, found 268.1733; HPLC>97% (t$_R$=4.67 min, 40(A):55(B):5(C):0.01(D); t$_R$=5.05 min, 10(A):85(B):5(C):0.01(D)).

Cis-2-Aminoethyl-5-(2'-methoxy-5'-fluorophenethyl)tetrahydrofuran (18l): The product (29 mg, 34%) was obtained as an oil by chromatography on silica; ($R_f$=0.10, Methanol/DCM, 10:90, v:v); $^1$H NMR: (CDCl$_3$, 500 MHz): δ 6.87-6.72 (m, 3 H), 4.05-3.81 (m, 2 H), 3.79 (s, 3 H), 2.71-2.56 (m, 2 H), 2.30 (bs, 2 H), 2.07-1.50 (m, 10 H); HRMS (ESI) [M+H]$^+$ m/z cacld for C$_{15}$H$_{23}$FNO$_2$ 268.1713, found 268.1701; HPLC>96% (t$_R$=4.65 min, 40(A):55(B):5(C):0.01(D); t$_R$=5.05 min, 10(A):85(B):5(C):0.01 (D)).

Cis-2-(aminoethyl)-5-(2'-methoxy-5'-fluorophenethyl)tetrahydrofuran (18l) The product (118 mg, 54%) was obtained as an oil by chromatography on silica; TLC (SiO$_2$) $R_f$=0.10, 90% DCM/MeOH; $^1$H NMR: (CDCl$_3$, 500 MHz): δ 6.86 (dt, J=3.0, 8.9 Hz, 1 H), 6.82 (dd, J=3.0, 8.5 Hz, 1 H), 6.73 (dd, J=4.3, 8.5 Hz, 1 H), 3.89 (m, 1 H), 3.82 (m, 1 H), 3.78 (s, 3 H), 2.85 (t, J=6.9 Hz, 2 H), 2.68 (m, 1 H), 2.60 (m, 1 H), 1.96 (m, 2 H), 1.86-1.67 (m, 4 H), 1.76 (bs, 2 H), 1.53 (m, 2 H); HRMS (ESI) [M+H]$^+$ m/z cacld for C$_{15}$H$_{23}$FNO$_2$ 268.1713, found 268.1701; HPLC>96% (t$_R$=4.65 min, 40(A):55(B):5(C):0.01(D); t$_R$=5.05 min, 10(A):85(B):5(C):0.01(D)).

Trans-2-aminoethyl-5-(3'-(2"-methoxy-5"-fluorophenyl)-1'-propyl)tetra hydrofuran (18o): The product (24 mg, 47%) was obtained as an oil by chromatography on silica; ($R_f$=0.10, Methanol/DCM, 10:90, v:v); $^1$H NMR: (CDCl$_3$, 500 MHz): δ 6.86-6.80 (m, 2 H), 6.73 (dd, J=4.4, 8.5 Hz, 1 H), 4.02 (m, 1 H), 3.96 (m, 1 H), 3.78 (s, 3 H), 2.88 (b, 2 H), 2.61 (bs, 2 H), 2.58 (t, J=7.0 Hz, 2 H), 2.02 (m, 2 H), 1.72-1.44 (m, 8 H); HRMS (ESI) [M+H]$^+$ m/z cacld for C$_{16}$H$_{25}$FNO$_2$ 282.1869, found 282.1875; HPLC>95% (t$_R$=4.70 min, 40(A):55(B):5(C):0.01(D); t$_R$=5.09 min, 10(A):85(B):5(C):0.01(D)).

Cis-2-aminoethyl-5-(3'-(2"-methoxy-5"-fluorophenyl)-1'-propyl)tetrahydrofuran (18p): The product (11 mg, 46%) was obtained as an oil by chromatography on silica; ($R_f$=0.09, Methanol/DCM, 10:90, v:v); $^1$H NMR: (CDCl$_3$, 500 MHz): δ 6.84 (dd, J=3.1, 9.2 Hz, 1 H), 6.82 (dd, J=3.1, 8.4 Hz, 1 H), 6.73 (dd, J=4.7, 9.1 Hz, 1 H), 3.92 (m, 1 H), 3.82 (m, 1 H), 3.79 (s, 3 H), 3.09 (m, 1 H), 2.99 (m, 1 H), 2.60 (t, J=7.0 Hz, 2 H), 1.96 (m, 2 H), 1.83-1.77 (m, 2 H), 1.65-1.47 (m, 8 H); HRMS (ESI) [M+H]$^+$ m/z cacld for C$_{16}$H$_{25}$FNO$_2$ 282.1869, found 282.1875; HPLC>95% (t$_R$=4.70 min, 40(A):55(B):5(C):0.01(D); t$_R$=5.09 min, 10(A):85(B):5(C):0.01(D)).

2-Aminoethyl-5-(3'-(2"-methoxy-5"-fluorophenyl)-1'-butyl)tetrahydrofuran (18r): The product (20 mg, 46%) was obtained as an oil by chromatography on silica; ($R_f$=0.10, Methanol/DCM, 10:90, v:v); $^1$H NMR: (CDCl$_3$, 500 MHz): δ 6.84-6.72 (m, 2 H), 6.72 (dd, J=4.7, 9.1 Hz, 1 H), 4.03 (m, 0.5 H), 3.93 (m, 0.5 H), 3.89 (m, 0.5 H), 3.81 (m, 0.5 H), 3.78 (s, 3 H), 2.88 (bm, 2 H), 2.57 (t, J=7.5 Hz, 2 H), 2.27 (bs, 2 H), 2.17-1.93 (m, 2 H), 1.73-1.33 (m, 10 H); HRMS (ESI) [M+H]$^+$ m/z cacld for C$_{17}$H$_{27}$FNO$_2$ 296.2026, found 296.2015; HPLC>96% (t$_R$=4.74 min, 40(A):55(B):5(C):0.01(D); t$_R$=5.17 min, 10(A):85(B):5(C):0.01(D)).

(2-{5-[2-(5-Fluoro-2-methoxy-phenyl)-ethyl]-tetrahydrofuran-2-yl}-ethyl)-carbamic ethyl ester (19): In a flame dried 20 mL scintillation vial was placed K$_2$CO$_3$ (239 mg, 1.73 mmol, 6.0 eq) and anhydrous THF (5.0 mL). The vial was purged with Ar$_{(g)}$ and then chilled in an ice bath. Ethyl chloroformate (156 mg, 1.44 mmol, 5.0 eq) was added via syringe followed by a slow addition of 18k/l (77 mg, 0.29 mmol, 1.0 eq) dissolved in THF (1.5 mL). The reaction was stirred at 0° C. for 0.5 hrs and then warmed to rt and stirred for an additional 3 hrs. The reaction was then stopped by addition of sat. NaHCO$_{3(aq)}$ and extracted with EtOAc (3×20 mL). The organic layer was washed with brine and dried over Na$_2$SO$_4$, filtered through paper, and concentrated under reduced pressure to yield crude product that was used in the next step of the synthesis. ($R_f$=0.40, Methanol/DCM, 2:98, v:v); $^1$H NMR (CDCl$_3$, 500 MHz) 6.87-6.82 (m, 2 H), 6.74-6.71 (m, 1 H), 4.12 (q, J=7.1 Hz, 2 H), 4.05-3.77 (m, 2 H), 3.78 (s, 3 H), 2.71-2.56 (m, 2 H), 2.08-1.51 (m, 10 H) 1.3 (t, J=7.2 Hz, 3 H). LRMS (ESI) [M+H]$^+$ calcd for C$_{18}$H$_{27}$FNO$_4$ 340 found 340.

(2-{5-[2-(5-Fluoro-2-methoxy-phenyl)-ethyl]-tetrahydrofuran-2-yl}-ethyl)-methyl-amine (20): In a flame dried round bottom flask, purged with Ar$_{(g)}$, was placed 19 (112 mg, 0.33 mmol, 1.0 eq) and anhydrous THF (1.6 mL). The flask was then cooled with an ice bath while stirring for 15 min. LAH (1.0 M, 1.32 mL, 1.32 mmol, 4.0 eq) was then slowly added via a syringe over a period of 5 min. The reaction was allowed to warm to rt and stirred an additional 4 hrs. The reaction was then stopped by addition of ice cold MeOH and then stirred at rt for an additional 15 min. The resulting solution was transferred to a beaker with the aid of 1N HCl$_{(aq)}$ and then made basic with 10 M NaOH$_{(aq)}$. The basic solution was then extracted with Et$_2$O (3×20 mL) and the organic layer was washed with brine. The Et$_2$O layer was dried over Mg$_2$SO$_4$ for 15 min and filtered through paper and concentrated to an oil under reduced pressure to afford the crude product. The oil was purified with PTLC and eluted with MeOH:CH$_2$Cl$_2$ (5:95). ($R_f$=0.05, Methanol/DCM, 5:95, v:v); $^1$H NMR (CDCl$_3$, 500 MHz) 6.87-6.82 (m, 2 H), 6.74-6.71 (m, 1 H), 4.05-3.77 (m, 2 H), 3.78 (s, 3 H), 2.71-2.56 (m, 5 H), 2.08-1.51 (m, 10 H); HRMS (ESI) [M+H]$^+$ calcd for C$_{16}$H$_{25}$FNO$_2$ 282.3784, found 282.3762; HPLC>97% (t$_R$=30.23 min, 100 (A):0.5(D); t$_R$=26.05 min, 90(A):10(C):0.5(D)).

TABLE 9

Inhibition of radioligand binding in HEK-hDAT, HEK-hSERT, and HEK-hNET cells by 2,5-disubstituted tetrahydrofuran analogs[a]

Structure 15: Ar-(CH₂)$_{n1}$-[tetrahydrofuran]-CH₂NH₂

Structure 17: Ar-(CH₂)$_{n1}$-[tetrahydrofuran]-CH₂CH₂NH₂

| Cmpd | Structures | Trans:Cis | Binding ($K_i$, nM) hDAT | hSERT | hNET | Reuptake ($IC_{50}$, nM) hDAT | hSERT | hNET |
|---|---|---|---|---|---|---|---|---|
| 15a | Cocaine | 2:1 | 371.2 ± 81 | 276.7 ± 87 | 1115.7 ± 198 | 590 ± 170 | 642 ± 183 | 1281 ± 307 |
|  | (1-naphthyl-ethyl-THF-CH₂NH₂) |  | >10,000 | 18.5 ± 0.8 | >10,000 | >10,000 | 23.3 ± 2.6 | 3420.0 ± 655.0 |
| 15b | (phenyl-THF-CH₂NH₂) | 2:1 | 916.0 ± 12.0 | 43.0 ± 11.0 | 2767.0 ± 111.0 | 147.3 ± 22.2 | 1714.0 ± 437.0 | 23.0 ± 5.0 |
| 15c | (2-naphthyl-THF-CH₂NH₂) | 2:1 | 512.0 ± 33.0 | 45.0 ± 4.0 | >10 k | 28.0 ± 10 | 4.1 ± 0.8 | 58.5 ± 13.8 |
| 15d | (phenyl-ethyl-THF-CH₂NH₂) | 2:1 | 1505 ± 278 | 68 ± 10 | 2736 ± 480 | 513.0 ± 68.0 | 129.0 ± 38.0 | 360.0 ± 14.8 |
| 17a | (2-OCH₃-1-naphthyl-ethyl-THF-CH₂CH₂NH₂) | 2:1 | >10,000 | 85.6 ± 9.2 | >10,000 | ND[b] | ND | ND |
| 17b | (4-OCH₃-1-naphthyl-ethyl-THF-CH₂CH₂NH₂) | 2:1 | >10,000 | 92.3 ± 19.1 | >10,000 | ND | ND | ND |

TABLE 9-continued

Inhibition of radioligand binding in HEK-hDAT, HEK-hSERT, and HEK-hNET cells by 2,5-disubstitued tetrahydrofuran analogs[a]

15: Ar-(CH₂)$_{n_1}$-[tetrahydrofuran]-CH₂NH₂

17: Ar-(CH₂)$_{n_1}$-[tetrahydrofuran]-CH₂CH₂NH₂

| Cmpd | Structures | Trans:Cis | Binding ($K_i$, nM) hDAT | hSERT | hNET | Reuptake ($IC_{50}$, nM) hDAT | hSERT | hNET |
|---|---|---|---|---|---|---|---|---|
| 15e | 1-naphthyl | 1.5:1 | 8519.0 ± 229.0 | 174.0 ± 32.0 | 1494.0 ± 88.0 | 463.0 ± 119 | 24.0 ± 1.2 | 210.0 ± 19.5 |
| 17c | 4-F,3-CH₃-phenyl (ethyl linker, ethylamine) | 1.5:1 | 6376.0 ± 893.0 | 688.0 ± 119.0 | 882.0 ± 22.0 | 509.0 ± 136.0 | 30.0 ± 4.0 | 374.0 ± 110.0 |
| 15f | 4-Cl-phenyl | 2:1 | 6830.0 ± 419.0 | 1105.0 ± 110.0 | 1106.0 ± 203.0 | 313.1 ± 76.1 | 31.9 ± 4.0 | 61.2 ± 18.9 |
| 15g | 4-Br-phenyl | 2:1 | 6117.0 ± 895.0 | 1114.0 ± 36.0 | >10,000 | 167.1 ± 68.6 | 50.3 ± 2.7 | 59.5 ± 20.5 |
| 15h | pentafluorophenyl (ethyl linker) | 1.5:1 | >10,000 | 2126.0 ± 1180.0 | 634.0 ± 179.0 | 4589 ± 692.0 | 225.0 ± 88.0 | 1541.0 ± 99.0 |
| 17d | benzyl (ethylamine) | 2:1 | >10,000 | 3822.3 ± 881.8 | >10,000 | 564.8 ± 154 | 2260 ± 203 | 347 ± 70.1 |
| 15i | 3-pyridyl (ethyl linker, ethylamine) | 2:1 | >10,000 | 4546.0 ± 2125.9 | 8517.3 ± 977.0 | >10,000 | 2721.3 ± 718.2 | >10,000 |
| 15j | 4-CH₃-phenyl | 2:1 | >10,000 | 6877.0 ± 414.0 | 2013.0 ± 67.0 | 667.5 ± 214.8 | 617.1 ± 150.2 | 92.0 ± 29.5 |

TABLE 9-continued

Inhibition of radioligand binding in HEK-hDAT, HEK-hSERT, and HEK-hNET cells by 2,5-disubstitued tetrahydrofuran analogs[a]

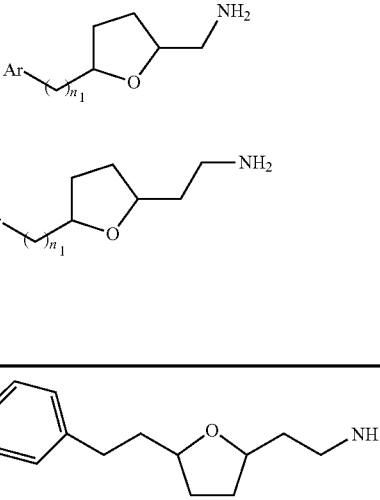

| Cmpd | Structures | Trans:Cis | Binding ($K_i$, nM) hDAT | hSERT | hNET | Reuptake ($IC_{50}$, nM) hDAT | hSERT | hNET |
|---|---|---|---|---|---|---|---|---|
| 17e | HO-C6H4-(CH2)2-THF-(CH2)2-NH | 1.5:1 | 5498.0 ± 381.0 | 7483.0 ± 977.0 | 5947.0 ± 550.0 | 2532 ± 298 | 4041 ± 845 | 2126 ± 345 |
| 15k | tBu-C6H4-THF-CH2-NH2 | 2:1 | >10,000 | >10,000 | 4543.0 ± 266.0 | 4300.7 ± 918.9 | 636.5 ± 190.7 | 2333.3 ± 800.7 |
| 17f | furan-THF-(CH2)2-NH2 | 1:1 | >10,000 | >10,000 | >10,000 | >10,000 | >10,000 | >10,000 |

[a]Drug inhibition of [$^{125}$I]-RTI-55 binding in HEK-hDAT, HEK-hSERT, or HEK-hNET cell membranes. Values represent the mean ± SEM for three to four experiments unless the mean of three experiment exceeded 10 μm;
[b]ND, not done.

TABLE 10

Inhibition of radioligand binding in HEk-hDAT, HEK-hSERT, and HEK-hNET cells by 2,5-disubstituted tetrahydrofuran analogs with a methoxy flouro substituted aromatic group[a]

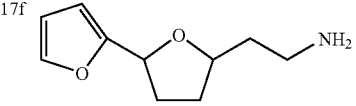

18

| Cmpd | Isomers | Chain Length $n_1$ | $n_2$ | total | Binding ($K_i$, nM) hDAT | hSERT | hNET | Reuptake ($IC_{50}$ nM) hDAT | hSERT | hNET |
|---|---|---|---|---|---|---|---|---|---|---|
| 18a | trans | 0 | 1 | 1 | >10,000 | 6307.3 ± 790.4 | 71991.5 ± 4395.5 | >10,000 | 2071.0 ± 903.1 | >10,000 |
| 18b | trans:cis 1.5:1 | 0 | 1 | 1 | 42764.3 ± 56016.1 | 6885.8 ± 1645.5 | 57015.9 ± 13820.0 | >10,000 | 9029.0 ± 12154.2 | >10,000 |
| 18c | trans | 0 | 2 | 2 | 32934.5 ± 21884.8 | 1808.1 ± 616.2 | 27495.3 ± 5017.8 | >10,000 | 1117.4 ± 812.8 | >10,000 |
| 18d | cis | 0 | 2 | 2 | >10,000 | 4772.3 ± 297.0 | 48874.3 ± 10868.4 | >10,000 | 2575.7 ± 424.4 | >10,000 |
| 18e | trans | 1 | 1 | 2 | 27238.0 ± 10600.0 | 192.0 ± 25.0 | 24116.0 ± 3005.0 | 28935.0 ± 1866.0 | 122.0 ± 40.0 | 7983.0 ± 1966.0 |
| 18f | cis | 1 | 1 | 2 | 97181.0 ± 11971.0 | 151.0 ± 20.0 | 9085.0 ± 1600.0 | 18675.0 ± 3384.0 | 111.0 ± 37.0 | 3392.0 ± 1278.0 |

TABLE 10-continued

Inhibition of radioligand binding in HEk-hDAT, HEK-hSERT, and HEK-hNET cells by 2,5-disubstituted tetrahydrofuran analogs with a methoxy flouro substituted aromatic group[a]

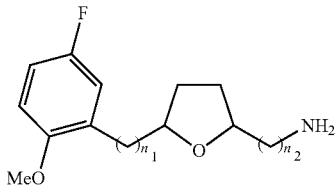

18

| Cmpd | Isomers | Chain Length $n_1$ | $n_2$ | total | Binding ($K_i$, nM) hDAT | hSERT | hNET | Reuptake ($IC_{50}$ nM) hDAT | hSERT | hNET |
|---|---|---|---|---|---|---|---|---|---|---|
| 18g | trans | 1 | 2 | 3 | 51018.0 ± 847.0 | 20.0 ± 1.0 | 1782.0 ± 313.0 | 38435.0 ± 14472 | 27.0 ± 8.0 | 1774.0 ± 566.0 |
| 18h | cis | 1 | 2 | 3 | 34971.0 ± 125.0 | 21.0 ± 2.0 | 455.0 ± 44.0 | 36335.0 ± 9680.0 | 23.0 ± 6.0 | 1864.0 ± 536.0 |
| 18i | trans | 2 | 1 | 3 | 14499.0 ± 3185.0 | 3.2 ± 0.2 | 5993.0 ± 283.0 | 8555.0 ± 741.0 | 2.5 ± 0.7 | 628.0 ± 66.0 |
| 18j | cis | 2 | 1 | 3 | 30316.0 ± 3020.0 | 21.9 ± 3.6 | 8520.0 ± 108.0 | 34303.0 ± 7696.0 | 11.7 ± 3.0 | 4746.0 ± 1608.0 |
| 18k | trans | 2 | 2 | 4 | 6500.0 ± 828.0 | 2.1 ± 0.2 | 2440.0 ± 215.0 | 27850.0 ± 5129.0 | 2.5 ± 0.6 | 481.0 ± 158.0 |
| 18l | cis | 2 | 2 | 4 | 16371.0 ± 2006.0 | 19.3 ± 0.9 | 12100.0 ± 810.0 | 36710.0 ± 1174.0 | 17.5 ± 2.7 | 3101.0 ± 1234.0 |
| 18m | trans | 3 | 1 | 4 | 7328.0 ± 315.0 | 0.8 ± 0.3 | 8541.0 ± 1289.0 | 7618.3 ± 722.6 | 2.1 ± 0.6 | 2934.0 ± 611.0 |
| 18n | cis | 3 | 1 | 4 | 4576.0 ± 1112.0 | 2.8 ± 0.1 | 20180.0 ± 2470.0 | 6288.0 ± 1470.0 | 2.6 ± 0.7 | 2857.0 ± 539.0 |
| 18o | trans:cis 2.5:1 | 3 | 2 | 5 | 7307.0 ± 1331.0 | 1.1 ± 0.1 | 10600.0 ± 1880.0 | 16987 ± 1352 | 2.3 ± 0.6 | 1930.0 ± 463.0 |
| 18p | trans:cis 1:3 | 3 | 2 | 5 | 21186.0 ± 2687.0 | 7.0 ± 0.8 | 30430.0 ± 1630.0 | 41257.0 ± 11506.0 | 7.4 ± 0.3 | 5133 ± 1742.0 |
| 18q | trans | 4 | 1 | 5 | 3868.0 ± 423.0 | 4.0 ± 1.1 | 2222.0 ± 350.0 | 16540.0 ± 4025.0 | 84.0 ± 31.0 | 7124.0 ± 2043.0 |
| 18r | trans:cis 1:1 | 4 | 2 | 6 | 3387.0 ± 266.0 | 2.0 ± 0.7 | 4064.0 ± 1204.0 | 37460.0 ± 1854 | 31.0± 9.0 | 8530.0 ± 1511.0 |

[a]Drug inhibition of [$^{125}$I]-RTI-55 binding in HEK-hDAT,HEK-hSERT, or HEK-hNET cell membranes. Values represent the mean ± SEM for three to four experiments unless the mean of three experiments exceeded 10 μM.

TABLE 11

Calculated correlation ratios for binding and reuptake selectivity for hSERT

| | Binding Selectivity | | Reuptake Selectivity | |
|---|---|---|---|---|
| Compound | hDAT/hSERT $K_i/K_i$ | hNET/hSERT $K_i/K_i$ | hDAT/hSERT $IC_{50}/IC_{50}$ | hNET/hSERT $IC_{50}/IC_{50}$ |
| 18a | 1.6 | 11.4 | 4.8 | 4.8 |
| 18b | 6.2 | 8.3 | 1.1 | 1.1 |
| 18c | 18.2 | 15.2 | 8.9 | 8.9 |
| 18d | 2.1 | 10.2 | 3.9 | 3.9 |
| 18e | 141.9 | 125.6 | 237.2 | 65.4 |
| 18f | 643.6 | 60.2 | 168.2 | 30.6 |
| 18g | 2550.9 | 89.1 | 1423.5 | 65.7 |
| 18h | 1656.7 | 21.7 | 1579.8 | 81.0 |
| 18i | 4530.9 | 1872.8 | 3422.0 | 251.2 |
| 18j | 1384.3 | 389.0 | 2931.9 | 405.6 |
| 18k | 3095.2 | 1161.9 | 11140.0 | 192.4 |
| 18l | 848.2 | 626.9 | 2097.7 | 177.2 |
| 18m | 9160.0 | 10676.3 | 3627.8 | 1397.1 |
| 18n | 1634.3 | 7207.1 | 2418.5 | 1098.8 |
| 18o | 6642.7 | 9636.4 | 7385.7 | 839.1 |
| 18p | 3026.6 | 4347.1 | 5575.3 | 693.6 |
| 18q | 967.0 | 555.5 | 196.9 | 84.8 |
| 18r | 1693.5 | 2032.0 | 1208.4 | 275.2 |

TABLE 12

Calculated correlation ratios of uptake inhibition to binding affinity for the hSERT

| Compound | hSERT $IC_{50}/K_i$[a] |
|---|---|
| 18a | 0.33 |
| 18b | 1.31 |
| 18c | 0.62 |
| 18d | 0.54 |
| 18e | 0.64 |
| 18f | 0.74 |
| 18g | 1.35 |
| 18h | 1.10 |
| 18i | 0.78 |
| 18j | 0.53 |
| 18k | 1.19 |
| 18l | 0.91 |
| 18m | 2.63 |
| 18n | 0.93 |
| 18o | 2.09 |
| 18p | 1.06 |
| 18q | 21.00 |
| 18r | 15.50 |

[a]The $IC_{50}$ value for potency of uptake inhibition was divided by the $K_i$ value for potency of binding to obtain the correlation ratio listed.

TABLE 13

Effect of Hepatic Microsomes on Metabolic Stability of SSRIs

| Compound | MLM[a] | | RLM[b] | |
| --- | --- | --- | --- | --- |
| | $t_{1/2}$ (min) | k | $t_{1/2}$ (min) | k |
| 18k/1 | 56.0 | 0.0124 | 106.3 | 0.00652 |
| 20 | 58.5 | 0.0118 | 129.0 | 0.00537 |

[a]MLM, mouse liver microsomes;
[b]RLM, rat liver microsomes.

Example 29

Dual Inhibitors of Phosphodiesterase-4 and Serotonin Reuptake

A new class of compounds showing antidepressant-like activity in the forced swim test in mice was synthesized by linking a novel selective serotonin reuptake inhibitor (SSRI) to a PDE4 inhibitor. The SSRIs 2-aminoethyl-5-(2'-methoxy-5'-fluorophenethyl)tetrahydrofuran and 2-aminoethyl-5-(3'-(2''-methoxy-5''-fluorophenyl)-1'-propyl)tetrahydrofuran were both individually linked to the PDE4 inhibitor 4-(3,4-dimethoxy-phenyl)-4a,5,8,8a-tetrahydro-2 H-phthalazin-1-one via a five carbon chain. The dual PDE4 inhibitor/SSRI showed potent and selective serotonin reuptake inhibition ($IC_{50}$ values of 127-194 nM). The dual PDE4 inhibitor/SSRI also inhibited PDE4D3 with $K_i$ values ranging from 1.2-2.0 nM. The dual PDE4 inhibitor/SSRI was significantly more effective than the individual SSRI alone or fluoxetine at standard doses and on a molar basis, the antidepressant-like effect of the dual PDE4 inhibitor/SSRI 21 showed a 129-fold increase in in vivo efficacy compared to fluoxetine.

Introduction

A central hypothesis is that anti-depressant activity is due to a deficiency of excitatory neurotransmitters at post-synaptic sites of the brain. This has been an attractive theory because tricyclics inhibit the re-uptake of certain biogenic amines including norepinephrine (NE), serotonin (5-HT) and dopamine (DA). Agents such as fluoxetine and fluvoxamine are selective serotonin reuptake inhibitors (SSRIs). Although the biogenic amine/selective uptake inhibitor theory has achieved considerable prominence, much remains to be discovered concerning existing anti-depressant therapies as well as new modalities.

Conventional tricyclic anti-depressants may require 1 to 4 weeks of therapy to observe clinical improvement and may involve longer-term adaptive changes in receptor sensitivity. Animals treated repeatedly with SSRIs, such as fluoxetine, down-regulate the serotonin transporter (SERT). The extent of SSRI uptake inhibition after repeated treatment is greater than that observed after acute drug treatment. This results in progressive increase in extracellular 5-HT concentrations and stimulation of postsynaptic receptors. Tricyclics are extensively metabolized and high concentrations are found in the liver, lung and brain. Metabolism of antidepressants may play a significant role in overall efficacy. With acute treatment, SSRIs will increase 5-HT receptor-mediated cAMP signaling. Upon repeated treatment with SSRIs, this effect will be blunted (i.e., some tolerance development), since phosphodiesterases (PDEs) are up-regulated and cAMP hydrolysis is increased.

Cyclic nucleotide PDEs comprise a diverse group of enzymes that are important regulators of signal transduction pathways (Beavo et al., Mol. Pharmacol., 46, 399-405 (1994); Conti, M. and Jin, S. L., Prog. Nucleic Acid Res., 63, 1-38 (1999); Houslay, M. D., Prog. Nucleic Acid Res. Mol. Biol., 69, 249-315 (2001); Loughney, K. and Ferguson, K., "Identification and quantification of PDE isoenzymes and subtypes by molecular biological methods," in Phosphodiesterase Inhibitors; Schudt et al., Eds.; Academic Press: San Diego; pp 1-19 (1996)). PDEs within a family that are coded by distinct genes, (e.g., PDE4A, PDE4B, PDE4C, and PDE4D), are referred to as "subtypes" and their selective inhibitors as "subtype-selective" inhibitors. Enzymes in the PDE4 family have been shown to be particularly important in neuropsychopharmacology (Houslay, M. D., Prog. Nucleic Acid Res. Mol. Biol., 69, 249-315 (2001)). PDE4 hydrolyzes cAMP formed by stimulation of beta adrenergic receptor-linked adenylyl cyclase in rat cerebral cortical slices (Ye, Y. and O'Donnell, J. M., J. Neurochem., 66, 1894-1902 (1996)). Rolipram, a selective inhibitor of PDE4, has been reported to have antidepressant activity in both preclinical and clinical tests and to produce memory-enhancing effects in a number of animal models. It has been shown that increased cAMP increases the expression of a number of PDE4 variants in neurons. Thus, in this case, the adaptation of PDE4 that occurs in response to repeated treatment with SSRIs is homeostatic and in opposition to the acute effect of the drugs.

Selective inhibitors of PDE4, such as rolipram, produce antidepressant-like effects in a number of preclinical tests sensitive to antidepressants. They antagonize the behavioral and physiological effects of reserpine (Wachtel, H., J. Pharm. Pharmacol., 35, 440-444 (1983); Wachtel et al., Neuropharmacology, 25, 1119-1126 (1986)) reduce the time of immobility in the forced-swim test in rats and mice (Overstreet, D. H., Neurosci. Biobehav. Rev., 17, 51-68 (1993); Saccomano et al., J. Med. Chem., 34, 291-298 (1991); Zhang et al., Neuropsychopharmacology, 27, 587-595 (2002)) and reduce response rate and increase reinforcement rate of rats under a differential-reinforcement-of-low-rate (DRL) schedule (O'Donnell, J. M., J. Pharmacol. Exp. Ther., 254, 147-157 (1990); O'Donnell, J. M. and Frith, S., Pharmacol. Biochem. Behav., 63, 185-192 (1999)). Results of a number of clinical reports support the conclusion that PDE4 inhibitors have antidepressant activity (Eckmann et al., Curr. Ther. Res. 43, 291-295 (1988); Fleischhacker et al., Neuropsychobiology, 26, 59-64 (1992); Horowski et al., Curr. Ther. Res., 38, 23-29 (1985); Scott et al., Eur. J. Clin. Pharmacol., 40, 127-129 (1991); Zeller et al., Pharmacopsychiatry, 17, 188-190 (1984)).

If tricyclics and fluoxetine produce their effects in part via activation of cAMP signaling, then loss of the PDE4 subtype involved in this pathway actually would enhance their ability to increase cAMP and alter subsequent pharmacology. Dual PDE4 inhibitor/SSRIs offer advantages beyond simple additive effects. Dual PDE4 inhibitors/SSRIs block the effect of the up-regulation of PDE4. The overall increase in 5-HT-mediated cAMP signaling will be preserved with repeated treatment. To verify this hypothesis, an SSRI was chemically linked to a PDE4 inhibitor and the dual PDE4 inhibitor/SSRI was examined in vitro and in vivo for pharmacological activity.

Results

PDE4 Inhibitors

Compound 19 is a known PDE4 inhibitor (Van der Mey et al., J Med. Chem., 44, 2523-2535 (2001)) and derivatives were synthesized to examine whether additional pharmacological properties could be introduced into 19 while still preserving PDE4 inhibitory activity. Thus, a template with potent PDE4 inhibitory activity was chemically combined with a molecule possessing potent SSRI function to make a compound with a dual inhibitory profile. Compounds 19, 21, and 22 were tested for inhibition of cAMP hydrolysis by recombinant isoforms of human PDE4D3, human PDE4B3, and human PDE4A1, in vitro. The $K_i$ value for inhibition of human PDE4D3 for 19, 21 and 22 was 6.3,nM, 2.0 nM and 1.2 nM, respectively (see Table 14). The increase in potency for 21 and 22 compared with 19 suggested that N-substitution increased inhibition of human PDE4D (Van der Mey et al., *J. Med. Chem.*, 45, 2526-2533 (2002)). For human PDE4B3, the $K_i$ values for inhibition of cAMP hydrolysis for 19, 21 and 22 were 250 nM, 199 nM and 500 nM, respectively. In the case of human PDE4A1, compounds 19, 21 and 22 all showed $K_i$ values for inhibition of cAMP hydrolysis with values greater than 1 μM. Thus, 19, 21 and 22 possessed PDE4B3/PDE4D3 and PDE4A1/PDE4D3 inhibitory selectivity ratios of 40-, 100-, 417- and <159-, <500- and <833-fold, respectively.

Selective Serotonin Reuptake Inhibitors

Compounds 14 and 15 were derived from molecular dissection of aryltropanes (Feng et al., *Bioorg. Med. Chem.*, 11, 775-780 (2003)) and are potent inhibitors of serotonin reuptake (see Table 15). Compounds 19, 20, 21, and 22 were also tested for binding and reuptake inhibition of the human DA transporter (hDAT), the human serotonin transporter (hSERT), and the human norepinephrine transporter (hNET), in vitro. Compounds 14 and 15 were potent inhibitors of radiolabeled RTI-55 binding to the hSERT (i.e., $K_i$ values of 2.1 and 1.1 nM, respectively) (see Table 15). Compounds 14 and 15 were equal to or more potent and selective than fluoxetine in reuptake inhibition of the hSERT. Compounds related to the PDE4 inhibitor (i.e., 19 and 20) were ineffective at inhibiting RTI-55 binding to the hSERT (i.e., $K_i$ values >100 μM). For inhibition of neurotransmitter uptake, 14 and 15 were most efficacious (i.e., $K_i$ values of 2.5 and 2.3 nM, respectively) (see Table 15). For 14 and 15, the selectivity of either binding potency or reuptake efficacy for hSERT was very large. Thus, the binding selectivity ratios $K_i$(hDAT)/$K_i$(hSERT) and $K_i$(hNET)/$K_i$(hSERT) for 14 and 15 were 3095, 1162 and 6642, 9636, respectively. The reuptake inhibition selectivity ratios $IC_{50}$(hDAT)/$IC_{50}$(hSERT) and $IC_{50}$(hNET)/$IC_{50}$(hSERT) for 14 and 15 were 11,140, 192 and 7386, 839, respectively. The PDE4 inhibitors 19 and 20 had essentially no measurable effect on inhibition of radiolabeled RTI-55 binding or reuptake of any of the neurotransmitter transporters examined (see Table 15).

Dual PDE4 Inhibitor/SSRIs

The dual PDE4 inhibitor/SSRIs (i.e., compounds 21 and 22) were potent inhibitors of binding of radiolabeled RTI-55 to the hSERT having $K_i$ values for of 156 and 194 nM, respectively. For compounds 21 and 22, inhibition of neurotransmitter uptake was highly selective for the hSERT (i.e., $IC_{50}$ values of 127 and 104 nM, respectively) (see Table 15). For 21 and 22, the selectivity of either binding potency or reuptake efficacy was greatest for hSERT. Thus, the binding selectivity ratios $K_i$(hDAT)/$K_i$(hSERT) and $K_i$(hNET)/$K_i$(hSERT) for 21 and 22 were 16, 11 and 28, 38, respectively. The reuptake inhibition selectivity ratios $IC_{50}$(hDAT)/$IC_{50}$(hSERT) and $IC_{50}$(hNET)/$IC_{50}$(hSERT) for 21 and 22 were 28, 8 and 28, and 38, respectively. In so far as the pharmacological values of Table 15 are concerned, SSRIs 14 and 15 cannot be directly compared with dual PDE4 inhibitor/SSRIs 21 and 22 because the former are pure trans diastereomers and the latter are a mixture of diastereomers. Finally, the data shows that SSRIs 14 and 15 and the PDE4 inhibitor/SSRIs 21 and 22 were relatively selective for the hSERT and did not potently interact with hDAT or hNET (Table 15).

In Vivo Studies

Figure 15:
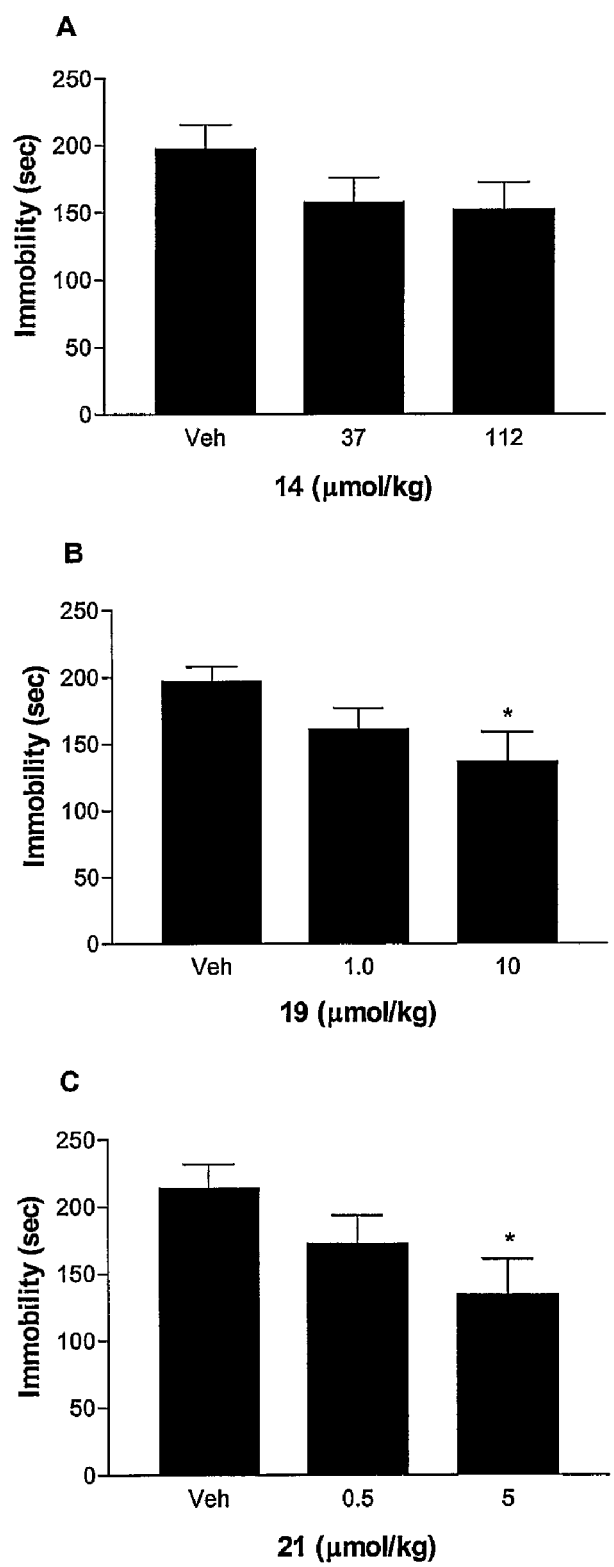
FIG. 15 depicts an effect of acute treatment of test compounds on immobility in the forced-swim test in ICR mice: (A) compound 14 (10 mg/kg, 37 µmol/kg and 30 mg/kg, 112 µmol/kg); (B) compound 19 (0.3 mg/kg, 1.0 µmol/kg and 3 mg/kg, 10 µmol/kg) and (C) compound 21 (0.3 mg/kg, 0.5

The PDE4 inhibitor (i.e., 19), the SSRI (i.e., 14) and the dual PDE4 inhibitor/SSRI (i.e., 21) were examined for acute and subchronic antidepressant-like effects in vivo. (See FIG. 15.) Acute treatment of ICR mice with either 19 or 21, at doses of 0.3 and 3 mg/kg, decreased duration of immobility in a dose-dependent manner in the forced-swim test (FST). Compared to vehicle control, the higher dose of 19 or 21 (3 mg/kg) significantly reduced immobility in the FST (P<0.05). In contrast, acute administration of fluoxetine (40 mg/kg) or repeated treatment with rolipram (0.5 mg/kg, i.p., once a day for 8 days) was required to produce similar antidepressant-like effects in the FST (Zhang et al., *Neuro-psychopharmacology*, 27, 587-595 (2002)). On a molar basis, compound 21 (0.5 μmol/kg) was 129-fold more efficacious than fluoxetine (65 μmol/kg) in the FST. Acute treatment with rolipram (0.5 mg/kg, did not alter FST behavior in agreement with the literature (Zhang et al., *Neuro-psychopharmacology*, 27, 587-595 (2002)). The SSRI, compound 14, at the doses used (i.e., 10 and 30 mg/kg) tended to decrease immobility, but it was not statistically significant.

Because Balb/c mice have been reported to exhibit a relatively high immobility baseline and are sensitive to fluoxetine challenge in the FST (Lucki et al., *Psychopharmacology*, 155, 315-322 (2001)) the in vivo studies described above were repeated. Acute administration of fluoxetine (20 mg/kg), 14 (10 mg/kg), or 15 (10 mg/kg) did not markedly alter the duration of immobility in the FST in Balb/c mice. (See FIG. 16.) In contrast, subchronic administration of a lower dose of fluoxetine (10 mg/kg) significantly decreased immobility (P<0.05). (See FIG. 17.) However, subchronic treatment with 14 (10 mg/kg) or 21 (1 mg/kg) did not change immobility compared to vehicle control. (See id.) It is possible that these in vivo results for 14 or 15 were a consequence of metabolic instability. To test this possibility, the in vitro metabolic stability of 14, 15, 19, 21, 22 and 24 was examined.

In Vitro Metabolic Studies

The in vitro metabolism of compounds 14, 15, and 24 were examined in the presence of mouse and human liver microsomes supplemented with NADPH to examine the metabolic stability of the compounds. Compounds 19, 21 and 22 were examined in the presence of mouse and human liver microsomes supplemented with NADPH. An efficient HPLC method was established to afford separation of the starting material from any putative metabolites (e.g., aldehyde, hydroxylamine, nitrone). Aerobic incubations of 14 and 24 in the presence of mouse and rat liver microsomes supplemented with NADPH showed a time-dependent loss of substrate. For 14 and 24, the calculated half life was 56 or 106 and 58 or 129 mins, respectively, in the presence of mouse and rat liver microsomes (see Table 16). In the presence of mouse liver microsomes, compounds 19 and 21 showed considerable metabolic stability having calculated half lives of 211 and 154 mins, respectively. Compound 21 was not detectably metabolized in the presence of human liver microsomes. No detectable metabolic instability of compound 22 was observed in the presence of either mouse or human liver microsomes up to 60 min (see Table 16).

Discussion

A dual PDE4 inhibitor/SSRI was synthesized by linking an SSRI with a PDE4 inhibitor via a five carbon linker. Previously, it was shown that the potency of PDE4 inhibition of 19 was not diminished by addition of lipophilic bulk to the phthalazin-1-one nitrogen atom. Thus, elaboration of 21 and 22 afforded a PDE4 inhibitor linked to an SSRI that retained considerable pharmacological activity. Thus, compared to 19, compounds 21 and 22 had more potency at inhibiting PDE4.

The dual PDE4 inhibitor/SSRIs 21 and 22 possessed considerable potency for inhibition of binding of RTI-55 and inhibition of 5-HT reuptake in the presence of the hSERT. Compared to 14 and 15, however, some loss of functional activity was lost. A significant amount of loss of functional activity was due to the fact that 21 and 22 was tested as a 2:1 and 3:1 mixture of trans:cis diastereomers. Studies have shown that the trans diastereomer of 14 or 15 possess about 7-fold more hSERT reuptake inhibition activity than the cis diastereomer (unpublished data). While some loss in in vitro binding potency and reuptake inhibition of the hSERT was observed in chemically linking SSRIs 14 and 15 to compound 20, nevertheless, significant in vivo activity was retained.

PDE4D inhibition results in a pattern of behavior that is indicative of an anti-depressant-like effect (Lucki, I., *Behav. Pharmacol.*, 8, 523-532 (1997); Porsolt, R. D., *Rev Neurosci.*, 11, 53-58 (2000)). This suggests that PDE4D is critical in mediating the antidepressant-like effects of PDE4 inhibitors. The PDE4 inhibitor 19 and the dual PDE4 inhibitor/SSRI 21 at doses of 0.3 and 3 mg/kg, decreased duration of immobility in the FST in a dose-dependent manner in ICR mice. Compared to the vehicle control, 3 mg/kg significantly reduced immobility in the FST ($P<0.05$). Acute administration of 14 decreased immobility in the FST but this was not reach statistical significance. In contrast, 40 mg/kg of fluoxetine or repeated treatment with rolipram (0.5 mg/kg, i.p., once a day for 8 days) was required to produce similar antidepressant-like effects in the FST; acute treatment with 0.5 mg/kg rolipram did not alter FST behavior.

Acute administration of fluoxetine (20 mg/kg), or 14 (10 mg/kg) did not alter the duration of immobility in the FST in Balb/c mice but SSRIs are known to not significantly affect changes in FST after acute administration. In contrast, subchronic administration of a lower dose of fluoxetine (10 mg/kg) significantly decreased immobility ($P<0.05$). However, subchronic treatment with 14 or 15 (10 or 1 mg/kg, respectively) did not change immobility compared to the vehicle control. The lack of an affect may be partially explained on the basis of metabolic instability because 14 and 15 are metabolized at an appreciable rate while dual PDE4 inhibitor/SSRIs 21 and 22 are quite metabolically stable.

Reduction in the catabolism of cAMP might be expected to increase the sensitivity to and effectiveness of antidepressants. Evidence points to the PDE4D subtype as an important component of the signaling pathway involved in mediation of antidepressant effects on behavior. A potent and selective inhibitor of PDE4D might show antidepressant activity with a more limited side-effect profile. By combining a selective PDE4 inhibitor with an SSRI, synergistic antidepressant effects might be observed. On a molar basis, the dual PDE4 inhibitor/SSRI 21 showed a 129-fold increase in in vivo efficacy compared to fluoxetine.

Dual PDE4 inhibitor/SSRIs offer an advantage over simple additive effects. Dual PDE4 inhibitor/SSRIs offer the advantage of blocking the effect of the up-regulation of the PDE4. While PDE4 expression will still increase, its hydrolytic functional activity will be blocked. Thus, the overall increase in serotonin receptor-mediated cAMP signaling will be preserved with repeated treatment.

Experimental Section:

General. Chemicals used in this study were of the highest purity available. Commercially available reagents were purchased from Aldrich Chemical Company (Milwaukee, Wis.) or VWR (San Diego, Calif.) and were used as received. All moisture sensitive reactions were carried out in flame-dried glassware under an argon atmosphere. Tetrahydrofuran (THF) and toluene were freshly distilled from calcium hydride under an argon atmosphere. Methanol ($CH_3OH$) was passed through a column of neutral alumina and stored over 3 Å molecular sieves prior to use. Rolipram, fluoxetine, diethyleneaminetetracetic acid (DETAPAC) and all the compounds of the NADPH-generating system were obtained from Sigma Chemical Company (St. Louis, Mo.). Human liver, pooled female liver and pooled male rat liver microsomes were purchased from BD Gentest Corp. (Woburn, Mass.). The human liver microsomes had the following functional activities (nmol/min/mg of protein): phenacetin O-deethylase (0.18), coumarin 7-hydroxylase (2.0), (S)-mephenyloin N-demethylase (0.05), diclofenac 4'-hydroxylase (1.9), (S)-mephenyloin 4'-hydroxylase (0.03), bufuralol 1'-hydroxylase (0.12), chlorzoxazone 6-hydroxylase (1.5), testosterone 6β-hydroxylase (4.6), and methyl p-tolyl sulfide oxidase (4.3). The pooled male rat liver microsomes had the following functional activities (nmol/min/mg of protein): testosterone 6β-hydroxylase (5.8) and nicotine oxidase (2.2). The pooled female mouse liver microsomes had the following functional activities (nmol/min/mg of protein): 7-ethoxyresorufin O-deethylase (0.39), p-nitrophenol hydroxylase (1.9), lauric acid-hydroxylase (0.86), and testosterone 6β-hydroxylase (5.0). Cocaine was provided by the National Institute on Drug Abuse, NIH (Bethesda, Md.). RTI-55 was a kind gift of Dr. Ivy Carroll (RTI, Research Triangle Park, N.C.). [$^3$H]-DA, [$^3$H]-5-HT, [$^3$H]-NE and [$^{125}$I]-RTI-55 were purchased from Dupont-New England Nuclear (Boston, Mass.). The preparation of the hDAT used was described previously (Eshleman et al., *J. Pharmacol. Exper. Ther.*, 274, 276-283 (1995)). The hSERT cDNA and HEK cells transfected with hNET cDNA was supplied by Dr. Randy Blakely (Vanderbilt University, Nashville, Tenn.). Analytical thin-layer chromatography (TLC) was done on K6F silica gel 60 Å glass-backed plates from Whatman (Clifton, N.J.). Compounds were detected using UV absorption at 254 nm and/or stained with $I_2$ (iodine). Flash chromatography was done on (60 Å) pore silica gel from E. Merck (Darmstadt, Germany).

Instrument Analysis. NMR spectra were recorded with a Bruker spectrometer operating at 500 MHz (NuMega Resonance Labs, Inc., San Diego, Calif.) or at 300 MHz by an inhouse Varian spectrometer (Palo Alto, Calif.) using the solvent specified. Chemical shifts were reported in parts per million (ppm, δ) using residual solvent signals as internal standards. Low resolution mass spectroscopy (LRMS) was done with an HP 1100 mass spectrometer (HT Laboratories, San Diego, Calif.) using electrospray ionization (ESI) or with an inhouse Hitachi M-8000 3DQMS (ion trap) mass spectrometer using ESI. High resolution mass spectroscopy (HRMS) was done with a Micromass LCT time of flight mass spectrometer at the University of Montana Mass Spectral Facility (Missoula, Mont.) using ESI.

The 2,5-disubstituted tetrahydrofurans and the dual PDE4 inhibitor/SSRIs were characterized by $^1$H NMR, LRMS, HRMS and their purities (>95%) were quantified by HPLC in two distinct solvent systems. Analytical HPLC measurements were run on a Hitachi L-6200 system equipped with a Hitachi L-7400 UV detector. Separations were done with a 5 μm, 4.6 mm×250 mm, Axxi-chrom silica column (Richard Scientific, Novato, Calif.) or with a 5 μm, 4.6 mm×250 mm Supelco HS F5 pentafluorophenyl column (Supelco Inc., Bellefonte, Pa.). For analysis of the SSRIs and dual PDE4 inhibitor/SSRIs, standard HPLC conditions utilized an isocratic, ternary-solvent system consisting of solvents A (methanol), B (isopropanol) and C($HClO_4$) set at a flow rate of 1.5 mL/min (straight-phase), or A, D (water) and E ($HCO_2H$) set at a flow rate of 1.0 mL/min (reverse-phase)

with UV-vis detection (λ=254 nm) with retention times ($t_R$) evaluated in minutes. Typical HPLC analyses involved two distinct isocratic elution systems per compound of interest. Solvent conditions for the isocratic elution systems were varied depending on the compound and its specific chromatographic properties. $^1$H NMR and mass spectra were consistent with the assigned structures.

Transporter Binding Assays. HEK-hDAT, -hSERT, or -hNET cells were grown until confluent as described previously (Eshleman et al., *J. Pharmacol. Exper. Ther.,* 289, 877-885 (1999)). Cells were scraped from plates and centrifuged for 20 min at 30,000×g and the pellet was re-suspended in 0.32 M sucrose with a Polytron at a setting of 1 for 5 sec. Assays contained 50 μL of membrane preparation, 25 μL of the test compound and 25 μL of [$^{125}$I]RTI-55 (40-80 pM final concentration) in a final volume of 250 μL Krebs HEPES buffer (25 mM HEPES, 122 mM NaCl, 5 mM KCl, 1.2 mM MgSO$_4$, 2.5 mM CaCl$_2$, 1 μM pargyline, 100 μM tropolone, 2 mg glucose/mL and 0.2 mg ascorbic acid/mL at pH 7.4). Membranes were pre-incubated with test compounds for 10 min before addition of [$^{125}$I]RTI-55. Specific binding was determined as the difference in binding observed in the presence and absence of 5 μM mazindol (HEK-hDAT and hNET) or 5 μM imipramine (HEK-hSERT). The incubations were done in the dark and terminated by filtration onto a Whatman GF/C filters using a 96-well Tomtech cell harvester (Tomtech, Orange, Conn.). Scintillation fluid was added to each filter spot and radioactivity remaining on the filter was determined using a Wallace β-plate reader (Wallace Labs, Cranbury, N.J.).

Inhibition of Substrate Uptake. HEK-hDAT, -hSERT or -hNET cells were grown as described above. Cells were scraped from the plates and suspended cells were added to a 96-well plate containing test compounds and Krebs-HEPES buffer in a final assay volume of 0.5 mL. After a 10 min preincubation in a 25° C. water bath, [$^3$H]-labeled neurotransmitter (50 mL, 20 nM final concentration) was added and the assay was initiated. After 10 min the incubation was terminated by filtration onto GF/C filters presoaked with 0.05% polyethylenimine using a Tomtech call harvester and scintillation counting as described above. Specific uptake was defined as the difference in uptake in the presence and absence of 5 mM mazindol (hDAT and hNET) or 5 mM imipramine (hSERT).

PDE4 Assay. PDE4 enzyme assays were carried out as described previously. Studies with recombinant PDE4 enzymes were carried out in the laboratory of Professor Marco Conti (Stanford University, Palo Alto, Calif.).

Data Analysis. GraphPad Prism (GraphPad Software, San Diego, Calif.) was used to determine the saturation and binding kinetic data. IC$_{50}$ values were converted to K$_i$ values using the Cheng-Prusoff equation.

Mouse and Rat Liver Microsome Stability Assay. Microsomal incubations (final volume 0.25 mL) with the SSRIs, dual PDE4 inhibitor/SSRIs or PDE4 inhibitor was done with an HPLC assay as described above. Diluted stocks of either mouse, human or rat liver microsomes (0.5 mg of protein), 100 μM potassium phosphate buffer (pH 7.4), 0.5 mM NADP$^+$, 0.5 mM glucose-6-phosphate, 5 IU/mL glucose-6-phosphate dehydrogenase, 0.6 mM DETAPAC, and 3 mM MgCl2 were combined and placed on ice. For a metabolic stability assay, either vehicle or 40 μM test compound was added and the incubation was initiated at 37° C. with constant shaking. After 0, 10, 25, 40 and 60 min, the incubations were stopped by the addition of 1 mL CH$_2$Cl$_2$/2-propanol (3:1, v:v). After thorough mixing, the organic layer was separated from the aqueous portion by centrifugation at 12,000×g. The organic material was evaporated with a stream of argon. The residue was dissolved in methanol (200 μL) and the sample was analyzed by HPLC.

In Vivo Evaluation of Selected Compounds. Separate non-habituated male mice were used in the conduct of this work. Fully approved animal protocols were used and the studies were done in keeping with the NIH standards for use of experimental animals.

Experiment 1. Forty male ICR mice, weighed 26.2±0.3 g, were housed in a temperature-controlled room (22-23° C.) and maintained on a 12-hour on 12-hour off light cycle (lights on at 6:00 AM). Water and food were freely available in the home cages. The mice were randomly divided into four groups: (A) vehicle; (B) compound 14; (C) compound 19; and (D) compound 21 and administered compounds dissolved in 0.9% saline containing 5% dimethyl sulfoxide (DMSO). Saline containing the same percentage of DMSO was used as vehicle. The lower doses were tested followed by the larger doses 1 week later, when the mice were again randomly divided into four groups as described above. The forced-swim test (FST) was carried out as described previously. Mice were given a swimming pretest session, once a day for two successive days. Twenty-four hours after the last session, mice were injected vehicle or the lower dose of each test compound by the i.p. route 30 min prior to the FST. One week later, administration of the larger dose of each of the test compounds was repeated. During the pretest and test sessions, each mouse was placed for 6 min in a plastic cylinder (45 cm high×20 cm diameter), which was filled to a depth of 28 cm with water (23±1° C.). The duration of immobility, which was defined as floating in an upright position without additional activity other than that necessary for the animal to keep its head above water, was recorded.

Experiment 2 Forty Balb/c male mice weighing 22.4±0.1 g were used in this experiment, which was carried out in two sessions. In each session, the mice were divided in four groups: (A) Vehicle (saline containing 5% DMSO), (B) fluoxetine 20 mg/kg, (C) TV-II-101 10 mg/kg, and (D) TV-093 10 mg/kg for the first session; (A) Vehicle, (B) Fluoxetine 10 mg/kg, (C) TV-II-093 10 mg/kg, and (D) TV-II-099 mg/kg for the second session, which was carried out 4 weeks later. Mice in the first session were treated with vehicle or the drugs acutely, whereas mice in the second sessions were treated subchronically, i.e., vehicle or drugs were given i.p. 23, 5, and 1 hr before the FST. The experiment was performed similar to Experiment 1 except for the pretest training, which was not carried out in the second session.

Statistics All in vivo data were analyzed by one-way analyses of variance (ANOVA) followed by Dunnett's tests for post hoc comparisons of individual means.

Synthesis

Ethyl-3-(5'-fluoro-2'-methoxyphenyl)-2-propenoate (2): To a solution of 5-fluoro-2-methoxybenzaldehyde (4.3 g, 28.0 mmol) in dry CH$_2$Cl$_2$ (30 mL) at 0° C. was added carbethoxymethylenetriphenylphosphorane (10.7 g, 30.1 mmol) portion-wise and the reaction was warmed to room temperature and stirred for 12 h. The solvent was then removed in vacuo and the residue was purified by flash column chromatography (EtOAc/hexane, 10:90, v:v, R$_f$=0.2) to yield the product (6.0 g, 95%) as a 4:1 mixture of trans:cis diastereomers; $^1$H NMR (CDCl$_3$, 500 MHz): δ 7.93 (d, J=16.2 Hz, 0.8 H), 7.33 (dd, J=3.1, 9.2 Hz, 0.2 H), 7.21 (dd, J=3.1, 9.2, Hz, 0.8 H), 7.08 (d, J=12.5 Hz, 0.2 H), 7.03 (dt, J=3.0, 8.8 Hz, 0.8 H), 6.99 (dt, J=3.0, 8.8 Hz, 0.2 H), 6.84 (dd, J=3.1, 8.6 Hz, 0.8 H), 6.79 (dd, J=3.3, 9.1 Hz, 0.2 H), 6.47 (d, J=16.2 Hz, 0.8 H), 5.99 (d, J=12.5 hz, 0.2 H), 4.25 (q, J=7.1

Hz, 1.6 H), 4.15 (q, J=7.0 Hz, 0.4 H), 3.86 (s, 2.4H), 3.81 (s, 0.6 H), 1.34 (t, J=7.1 Hz, 2.4 H), 1.22 (t, J=7.0 Hz, 0.6 H).

Ethyl-4-(5'-fluoro-2'-methoxyphenyl)propanoate (3): To a solution of 2 (6.0 g, 27.0 mmol) in ethanol (200 proof, 40 mL) under Ar was added Pd/C (10%, 250 mg) and the flask containing the mixture was evacuated and purged with $H_2$ three times. A balloon containing $H_2$ was attached to the flask and the reaction was allowed to stir for 15 h at room temperature. The reaction mixture was filtered through a pad of silica and eluted with EtOAc/hexane, 50:50, v:v. The crude product obtained by removal of the solvent in vacuo was purified by a flash column chromatography (EtOAc/hexane, 10:90, v:v, $R_f$=0.27) to give the product (5.8 g, 95%); $^1$H NMR (CDCl$_3$, 500 MHz): δ 6.89-6.84 (m, 2 H), 6.74 (dd, J=4.7, 9.8 Hz, 1 H), 4.12 (q, J=7.1 Hz, 2 H), 3.79 (s, 3 H), 2.91 (t, J=7.7 Hz, 2 H), 2.59 (t, J=7.7 Hz, 2 H), 1.24 (t, J=7.2 Hz, 3 H).

3-(5'-Fluoro-2'-methoxyphenyl)propanal (4): To a solution of 3 (5.8 g, 25.7 mmol) in dry toluene (40 mL) under an atmosphere of Ar was added a DIBAL solution (1 M in toluene, 30 mL, 30 mmol) at −78° C. The reaction was stirred at −78° C. for 2 h. Methanol (2 mL) was then added to the mixture and the reaction was allowed to warm to 0° C. The reaction mixture was then poured into a separatory funnel containing HCl solution (1 N, 100 mL). The organic fraction was extracted with EtOAc (3×60 mL) and the combined organic layers were washed with brine (80 mL) and dried over sodium sulfate. The crude product obtained by removal of the solvent in vacuo was purified by flash column chromatography (EtOAc/hexane, 10:90, v:v, $R_f$=0.1) to give the product (3.1 g, 66%); $^1$H NMR (CDCl$_3$, 500 MHz): δ 9.80 (s, 1 H), 6.88-6.86 (m, 2 H), 6.75 (dd, J=4.6, 8.6 Hz, 1 H), 3.79 (s, 3 H), 2.91 (t, J=7.4 Hz, 2 H), 2.72 (t, J=7.4 Hz, 2 H).

1-(5'-Fluoro-2'-methoxyphenyl)-4-ethylenedioxy-1-butene (5): To a suspension of 2-(1,3-dioxolan-2-yl)ethyltriphenylphosphonium bromide (5.0 g, 11.3 mmol) in THF (30 mL) under an atmosphere of Ar was added NaH (60% in mineral oil, 0.48 g, 11.3 mmol) and the mixture obtained was heated to reflux for 1 h. The orange suspension obtained was cooled to 0° C. and 5-fluoro-2-methoxybenzaldehyde (1.54 g, 10.0 mmol) was added and the reaction was warmed to room temperature and continued with stirring for 12 h. The reaction mixture was poured to a separatory funnel containing ammonium chloride aqueous solution (sat. NH$_4$Cl/H$_2$O 50:50, v:v, 50 mL). The organics were extracted with EtOAc (3×80 mL) and the combined organic layers were washed with brine (60 mL) and dried over sodium sulfate. The solvent was then removed in vacuo and the crude product obtained was purified by flash column chromatography (EtOAc/hexane, 7:93, v:v, $R_f$=0.15) to give the product (2.63 g, 66%) as a 4:1 mixture of cis and trans diastereomers: $^1$H NMR (major isomer): (CDCl$_3$, 500 MHz): δ 7.08 (dd, J=3.1, 8.7 Hz, 1 H), 6.93 (dt, J=3.1, 8.7 Hz, 1 H), 6.78 (dd, J=4.3, 8.7 Hz, 1 H), 6.63 (d, J=11.9 Hz, 1 H), 5.83 (td, J=7.3 Hz, 11.9 Hz, 1 H), 4.99 (t, J=4.6 Hz, 1 H), 4.02-3.99 (m, 2 H), 3.9-3.87 (m, 2 H), 3.8 (s, 3 H), 2.64-2.62 (m, 2 H).

4-(5'-Fluoro-2'-methoxyphenyl)-1-ethylenedioxybutane (6): To a solution of 5 (1.75 g, 7.3 mmol) in ethanol (200 proof, 80 mL) under an atmosphere of Ar was added Pd/C (10%, 300 mg) and the flask containing the mixture was evacuated and purged with $H_2$ three times. A balloon of $H_2$ gas was attached to the flask and the reaction was allowed to proceed for 72 h at room temperature. The reaction mixture was then filtered through a pad of Celite eluted with EtOH. The crude product was obtained by removal of the solvent in vacuo. $^1$H NMR (CDCl$_3$, 500 MHz): δ 6.87-6.72 (m, 3 H), 4.87 (t, J=3.8 Hz, 1 H), 3.97-3.95 (m, 2 H), 3.86-3.83 (m, 2 H), 3.79 (s, 3 H), 2.64-2.62 (m, 2 H), 2.44 (td, J=1.7, 7.2 Hz, 2 H), 1.92 (quintet, J=7.5 Hz, 2 H).

4-(5'-Fluoro-2'-methoxyphenyl)butyraldehyde (7): To a solution of 6 (1.7 g, 7.0 mmol) in THF (60 mL) was added HCl (1 N, 3 mL) and the reaction was stirred at room temperature for 48 h. The reaction mixture was then poured into a separatory funnel containing water (60 mL). The organic fraction was extracted with EtOAc (3×60 mL) and the combined organic layers were washed with brine (80 mL) and dried over sodium sulfate. The crude product obtained by removal of the solvent in vacuo was purified by flash column chromatography (EtOAc/hexane, 10:90, v:v, $R_f$=0.1) to give the product (1.03 g, 53% from 3a); $^1$H NMR (CDCl$_3$, 500 MHz): δ 9.76 (s, 1 H), 6.88-6.83 (m, 2 H), 6.75 (dd, J=4.6, 8.6 Hz, 1 H), 3.79 (s, 3 H), 2.63 (t, J=7.4 Hz, 2 H), 2.44 (t, J=7.4 Hz, 2 H), 1.92 (quintet, J=7.4 Hz, 2 H).

7-(5'-Fluoro-2'-methoxyphenyl)hept-1-en-5-ol (8): To a solution of 4 (3.0 g, 19.5 mmol) in THF (20 mL) at 0° C. was added a solution 1-butenylmagnesium bromide (0.5 M in THF, 45 mL, 22.5 mmol) dropwise for 15 min. The reaction mixture was poured into a solution of saturated ammonium chloride (80 mL) in a separatory funnel. The organic fraction was extracted with EtOAc (3×60 mL) and the combined organic layers were washed with brine (50 mL) and dried over sodium sulfate. The product was purified by flash column chromatography (EtOAc/hexane, 15:85, v:v, $R_f$=0.2) to give the product as a colorless oil (3.7 g, 94%); $^1$H NMR (CDCl$_3$, 500 MHz): δ 6.86-6.82 (m, 2 H), 6.76 (dd, J=4.6, 8.6 Hz, 1 H), 5.82 (m, 1 H), 5.04 (d, J=17.3 Hz, 1 H), 4.95 (d, J=10.2 Hz, 1 H), 3.81 (s, 3 H), 3.55 (m, 1 H), 2.75-2.69 (m, 2 H), 2.2 (m, 1 H), 2.1 (m, 1 H), 1.96 (bs, 1 H), 1.73-1.68 (m, 2 H), 1.6-1.53 (m, 3 H).

The following compound was prepared in a similar manner.

8-(5'-Fluoro-2'-methoxyphenyl)oct-1-en-5-ol (9): The product was purified by flash column chromatography (EtOAc/hexane, 12.5:87.5, v:v, $R_f$=0.15) as a colorless oil (1.06 g, 61%); $^1$H NMR (CDCl$_3$, 500 MHz): δ 6.86-6.82 (m, 2 H), 6.74 (dd, J=4.6, 8.6 Hz, 1 H), 5.85 (m, 1 H), 5.04 (d, J=17.3 Hz, 1 H), 4.97 (d, J=10.2 Hz, 1 H), 3.79 (s, 3 H), 3.66 (m, 1 H), 2.6 (m, 2 H), 2.22-2.1 (m, 2 H), 1.74-1.47 (m, 7H).

2-(Bromomethyl)-5-(2'-methoxy-5'-fluorophenethyl)tetrahydrofuran (10): To a solution of 8 (3.24 g, 18.0 mmol) in dry CH$_2$Cl$_2$ (50 mL) at 0° C. was added N-bromosuccinimide (3.56 g, 20.0 mmol) portion-wise and the reaction was warmed to room temperature and stirred for 12 h. Solvent was then removed in vacuo and the product was purified by flash column chromatography (EtOAc/hexane, 5:95, v:v, $R_f$=0.1) and resulted in a colorless oil as a 2:1 mixture of trans:cis diastereomers; $^1$H NMR (CDCl$_3$, 500 MHz): δ 6.86-6.81 (m, 2 H), 6.72 (dd, J=4.6, 8.6 Hz, 1 H), 4.22 (m, 1 H), 4.03 (m, 1 H), 3.78 (s, 3H), 3.44 (dd, J=4.3, 9.7 Hz, 1 H), 3.34 (dd, J=6.4, 9.7 Hz, 1 H), 2.6 (t, J=7.3 Hz, 2 H), 2.13 (m, 1 H), 2.05 (m, 1 H), 1.75 (m, 1 H), 1.67-1.46 (m, 5 H).

The following compound was prepared in a similar manner.

2-(Bromomethyl)-5-(3'-(2"-methoxy-5"-fluorophenyl)-1'-propyl)tetrahydrofuran (11): the product was purified by flash column chromatography (EtOAc/hexane, 5:95, v:v, $R_f$=0.1) to provide a product (530 mg, 40%) as a colorless oil; $^1$H NMR (CDCl$_3$, 500 MHz): δ 6.86-6.81 (m, 2 H), 6.72 (dd, J=4.6, 8.6 Hz, 1 H), 4.22 (m, 1 H), 4.03 (m, 1 H), 3.78 (s, 3 H), 3.44 (dd, J=4.3, 9.7 Hz, 1 H), 3.34 (dd, J=6.4, 9.7 Hz, 1 H), 2.6 (t, J=7.3 Hz, 2 H), 2.13 (m, 1 H), 2.05 (m, 1 H), 1.75 (m, 1 H), 1.67-1.46 (m, 5 H).

2-Cyanomethyl-5-(5'-fluoro-2-methoxyphenethyl)tetrahydrofuran (12): To a vial under an atmosphere of Ar$_{(g)}$ was added 10 (1.23 g, 4.3 mmol), NaI (100 mg), potassium cyanide (0.7 g, 10.6 mmol) and dry DMSO (15 mL). The mixture obtained was heated to 70° C. under an atmosphere of Ar for 12 h. After cooling to room temperature, the reaction mixture was poured into a separatory funnel containing sodium bicarbonate aqueous solution (sat. NaHCO$_3$/H$_2$O, 50:50, v:v, 80 mL). The organic fraction was extracted with EtOAc (3×60 mL) and the combined organic layers were washed with brine (50 mL) and dried over sodium sulfate. The solvent was then removed in vacuo and the crude product obtained (0.45 g, 86%) was purified by flash column chromatography (EtOAc/hexane, 10:90, v:v, R$_f$=0.11); as a 2:1 mixture of trans/cis diastereomers. $^1$H NMR (500 MHz, CDCl$_3$) δ 6.88-6.82 (m, 2 H), 6.74 (dd, J=4.3, 8.5 Hz, 1 H), 4.26 (m, 1 H), 4.09 (m, 0.65 H), 3.90 (m, 0.35 H) 3.79 (s, 3 H), 2.72-2.53 (m, 4 H), 2.22-2.04 (m, 2 H), 1.84-1.6 (m, 4 H).

The following compound was prepared in a similar manner.

2-Cyanomethyl-5-(3'-(2"-methoxy-5"-fluorophenyl)-1'-propyl)tetrahydrofuran (13): the product (0.2 g, 80%) was purified by chromatography (EtOAc/hexane, 10:90, v:v, R$_f$=0.11) as a 2:1 mixture of trans/cis diastereomers; $^1$H NMR (CDCl$_2$, 500 MHz): δ 6.86-6.81 (m, 2 H), 6.73 (dd, J=4.2, 8.5 Hz, 1 H), 4.22 (p, J=6.8 Hz, 0.65 H), 4.11 (m, 0.35 H) 4.09 (m, 0.65 H), 3.9 (m, 0.35 H), 3.79 (s, 3 H), 2.62-2.52 (m, 4 H), 2.18 (m, 1 H), 2.12 (m, 1 H), 1.78 (m, 1 H), 1.69-1.46 (m, 3 H).

2-Aminoethyl-5-(2'-methoxy-5'-fluorophenethyl)tetrahydrofuran (14): To a round bottom flask under an atmosphere of Ar was added Raney Ni that was washed with methanol. Compound 12 (80 mg, 0.3 mmol), dissolved in 2 M NH$_3$ in methanol was added to the flask. The flask was evacuated and purged with H$_2$ once. A balloon containing H$_2$ gas was then attached to the flask and the reaction was allowed to stir for 4 h at room temperature. The reaction mixture was filtered through a plug of Celite and the crude product obtained after the removal of the solvent was purified by preparative TLC and eluted with (MeOH/CH$_2$Cl$_2$, 10:90, v:v, R$_f$=0.1) to give the product (55 mg, 70%) as a 2:1 mixture of trans/cis diastereomers; $^1$H NMR: (CDCl$_3$, 500 MHz): δ 6.87 (m, 1 H), 6.82 (dd, J=3.0, 8.5 Hz, 1 H), 6.72 (m, 1 H), 4.03 (m, 0.65 H), 3.96 (m, 0.65 H), 3.89 (m, 0.35 H), 3.82 (m, 0.35 H), 3.78 (s, 3 H), 2.68 (m, 1 H), 2.58 (m, 1 H), 2.03 (m, 2 H), 1.83 (bs, 2 H), 1.86-1.6 (m, 4 H), 1.54 (m, 2 H); HRMS (ESI) [M+H]$^+$ calcd for C$_{15}$H$_{23}$FNO$_2$ 268.1713, found 268.1701; HPLC>96% pure (t$_R$=4.66 min, 40(A):55(B):5(C):0.01(D); t$_R$=5.05 min, 10(A):85(B):5(C):0.01(D)).

The following compound was prepared in a similar manner.

2-Aminoethyl-5-(3'-(2"-methoxy-5"-fluorophenyl)-1'-propyl)tetrahydrofuran (15): the product (24 mg, 47%), was isolated as 3:1 mixture of trans/cis diastereomers (MeOH/CH$_2$Cl2, 10:90, v:v, R$_f$=0.1): $^1$H NMR: (CDCl$_3$, 500 MHz): δ 6.86-6.8 (m, 2 H), 6.73 (m, 1 H), 4.02 (m, 0.65 H), 3.96 (m, 0.65 H), 3.92 (m, 0.35 H), 3.82 (m, 0.35 H), 3.78 (s, 3 H), 3.09 (m, 1 H), 2.99 (m, 1 H), 2.6 (bs, 2 H), 1.96 (m, 2 H), 1.83-1.77 (m, 2 H), 1.65-1.47 (m, 8 H); HRMS (ESI) [M+H]$^+$ calcd for C$_{16}$H$_{25}$FNO$_2$ 282.1875, found 282.1869; HPLC>95% pure (t$_R$=4.70 min, 40(A):55(B):5(C):0.01(D), t$_R$=5.09 10(A):85(B):5(C):0.01(D)).

3,4-Dimethoxyphenylmagnesium bromide (17): Into a flame dried round bottom flask with a magnetic stir bar was placed anhydrous THF (150 mL) and Mg$_{(s)}$ turlings (1.43 g, 58.8 mmol, 1.0 eq). The flask was then fitted with a pressure equalizing addition funnel containing 4-bromo-1,2-dimethoxybenzene solution that was added slowly over a period of 45 min while stirring at rt. Once the addition was complete I$_{2(s)}$ (500 mg) was added and the reaction was brought to reflux and stirred for 12 hrs. The Grignard reagent was cooled and used immediately in the following reaction.

6-(3,4-Dimethoxy-benzoyl)-cyclohex-3-enecarboxylic acid (18): A solution of 17 (59 mmol, 0.29 M) in THF was added dropwise to an ice-cooled solution of cis-1,2,3,6-tetrahydrophthalic anhydride in THF (120 mL) over a 1 hr period. After the addition was complete, the resulting mixture was stirred for another 30 min at 0° C. The reaction mixture was allowed to warm to rt and stirred overnight. The reaction was then stopped with sat. NH$_4$Cl and the pH adjusted to 2 with concentrated HCl$_{(aq)}$ and then extracted with diethyl ether. The organic layer was washed with water and subsequently extracted with 1 M NaOH. The combined aqueous extract was acidified with concentrated HCl and extracted with EtOAc (3×100 mL). The organic layers were combined and dried over MgSO$_4$, filtered, and concentrated under reduced pressure to afford oil. The oil was dissolved CH$_2$Cl$_2$ and filtered through silica gel to remove the dicarboxylic acid formed during workup. The product was recrystallized from diethyl ether to afford pure product (1.62 g, 10%) as a white solid; mp=109° C.; LRMS ESI [m−H]$^−$ cacld for C$_{16}$H$_{18}$O$_5$ 289, found m/z 289; $^1$H NMR (CDCl$_3$, 500 MHz): δ 7.60-7.53 (m, 2 H), 6.92 (d, J=8.4 Hz, 1 H), 5.84-5.82 (m, 1 H), 5.71-5.68 (m, 1 H), 4.03-4.00 (m, 1 H), 3.98 (s, 3 H), 3.95 (s, 1 H), 3.10-3.07 (m, 1 H), 2.90-2.84 (m, 1 H), 2.54-2.44 (m, 3 H).

4-(3,4-Dimethoxy-phenyl)-4a,5,8,8a-tetrahydro-2 H-phthalazin-1-one (19): A mixture of 18 (610 mg, 2.1 mmol, 1.0 eq) and hydrazine hydrate (168 mg, 5.25 mmol, 2.5 eq) in EtOH (10 mL) was refluxed for 4 hrs. The reaction was then cooled to rt and concentrated under reduced pressure to afford a white precipitate. The precipitate was dissolved in EtOAc and washed with Na$_2$SO$_{4(aq)}$, 1 N HCl$_{(aq)}$, and water. The organic layer was then dried over MgSO$_4$, filtered, and concentrated to give a white precipitate. The precipitate was recrystallized in EtOH to afford the product as white crystals (376 mg, 63%); HRMS ESI [M+H]$^+$ calcd for C$_{16}$H$_{18}$N$_2$O$_3$ 287.3385, found m/z 287.3379; $^1$H NMR (CDCl$_3$, 500 MHz): δ 8.53 (bs, 1 H), 7.46 (d, J=2.0 Hz, 1 H), 7.23 (dd, J=2.0, 8.4 Hz, 1 H), 6.87 (d, J=8.4 Hz, 1 H), 5.8-5.77 (m, 1 H), 5.72-5.7 (m, 1 H), 3.94 (s, 3 H), 3.93 (s, 3 H), 3.40 (dt, J=5.5, 8.7 Hz, 1 H), 3.01-2.97 (m, 1 H), 2.85 (t, J=6.0 Hz, 1 H), 2.26-2.19 (m, 3 H); HRMS (ESI) [M+H]$^+$ calcd for C,16;H,19;N,2;O,3; 287.3385, found 287.3376; HPLC>98% pure (t$_R$=4.93, 70(A):30(E); t$_R$=5.33, 50(A):50(E)).

2-(5-Bromo-pentyl)-4-(3,4-dimethoxy-phenyl-4a,5,8,8a-tetrahydro-2 H-phthalazin-1-one (20): Sodium hydride (60% dispersion in oil, 44 mg, 1.1 mmol, 1.1 eq) was added to a solution 19 (287 mg, 1.0 mmol, 1.0 eq). The mixture was stirred at rt for 30 min whereupon it took on a slight yellow color. 1,5-Dibromopentane (600 mg, 2.6 mmol, 2.6 eq) was added via syringe and the reaction was stirred for 30 min at rt while the yellow color dissipated to an almost clear solution. The reaction was stopped with the addition of water and then transferred to a separatory funnel and extracted with Et$_2$O (3×30 mL). The organic fractions were combined and dried over MgSO$_4$, filtered, and concentrated to afford an oil. The product was purified on silica and eluted with CH$_2$Cl$_2$ to afford a clear oil; $^1$H NMR (CDCl$_3$, 500 MHz): δ 7.47 (d, J=2.0 Hz, 1 H), 7.25 (dd, J=2.0, 8.5 Hz, 1 H), 6.87 (d, J=8.5 Hz, 1 H), 5.8-5.77 (m, 1 H), 5.7-5.67 (m, 1 H), 4.01-3.97 (m, 1 H), 3.95 (s, 3 H), 3.92 (s, 3 H), 3.79-3.74 (m, 1 H), 2.22-2.18 (m, 2 H), 2.1-2.04 (m, 1 H), 1.94-1.86 (m, 4 H), 1.74-1.69 (m, 4 H), 1.63-1.56 (m, 1 H), 1.52-1.46 (m, 2 H); LRMS ESI [M+H]$^+$ calcd for $C_{21}H_{28}BrN_2O_3$ 436, found m/z 435 (Br$^{79}$), 437 (Br$^{81}$).

4-(3,4-Dimethoxy-phenyl)-2-[5-(2-{5-[2-(5-fluoro-2-methoxy-phenyl)-ethyl]-tetrahydro-furan-2-yl}-ethylamino)-pentyl]-4,5,8,8a-tetrahydro-2 H-phthalazin-1-one (21): Into a flame dried round bottom flask under an atmosphere of Ar$_{(g)}$, cesium hydroxide monohydrate (23 mg, 0.14 mmol, 1.0 eq) and DMF (0.5 mL) was stirred for 30 min at rt. Compound 14 (37 mg, 0.14 mmol, 1.0 eq) in DMF (0.3 mL) was then added via syringe and the resulting mixture stirred at rt. After stirring an additional 30 min, compound 20 (72 mg, 0.16 mmol, 1.2 eq) dissolved in DMF (0.3 mL) was added and stirred for an additional 18 hrs at rt. The reaction was washed with EtOAc (30 mL) and then filtered and the filtrate was washed with water in a separatory funnel. The organic layer was dried with Na$_2$SO$_4$, filtered, and concentrated to oil. The product was purified by preparative TLC (developed with MeOH/CH$_2$Cl$_2$, 5:95, v:v, R$_f$=0.2) to afford an oil (27 mg, 0.04 mmol, 31%); $^1$H NMR (CDCl$_3$, 500 MHz) δ 7.47 (d, J=2.0 Hz, 1 H), 7.25 (dd, J=2.0, 8.5 Hz, 1 H), 6.87 (d, J=8.5 Hz, 1 H), 6.86-6.81 (m, 2 H), 6.76-6.72 (m, 1 H), 5.81-5.79 (m, 1 H), 5.71 (m, 1 H), 4.01-3.97 (m, 1 H), 3.94 (s, 3 H), 3.91 (s, 3 H), 3.8 (s, 3 H), 3.79-3.74 (m, 1 H), 3.36-3.31 (m, 1 H), 3.03-3.00 (m, 1 H), 2.81-2.78 (m, 2 H), 2.73-2.37 (m, 5 H), 2.30-2.19 (m, 3 H), 2.09-1.97 (m, 3 H), 1.87-1.26 (m, 14 H); HRMS (ESI) [M+H]$^+$ cacld for $C_{36}H_{49}FN_3O_5$ 622.8007, found 622.8025; HPLC>99% pure (t$_R$=3.80 min, 55(A):45(B):0.02(D), t$_R$=4.53 min, 40(A):60(B):0.02(D)).

The following compound was prepared in a similar manner.

4-(3,4-Dimethoxy-phenyl)-2-[5-(2-{5-[3-(5-fluoro-2-methoxy-phenyl)-propyl]-tetrahydro-furan-2-yl}-ethylamino)-pentyl-4a,5,8,8a-tetrahydro-2 H-phthalazin-1-one (22): the product was isolated by preparative TLC and (developed with MeOH/CH$_2$Cl$_2$, 5:95, v:v, R$_f$=0.2); $^1$H NMR (CDCl$_3$, 500 MHz) δ 7.47 (d, J=2.0 Hz, 1 H), 7.25 (dd, J=2.0, 8.5 Hz, 1 H), 6.87 (d, J=8.5 Hz, 1 H), 6.86-6.81 (m, 2 H), 6.76-6.72 (m, 1 H), 5.80-5.77 (m, 1 H), 5.69-5.66 (m, 1 H), 4.01-3.97 (m, 1 H), 3.94 (s, 3 H), 3.91 (s, 3 H), 3.77 (s, 3 H), 3.79-3.74 (m, 1 H), 3.33-3.3 (m, 1 H), 3.0-2.96 (m, 1 H), 2.81-2.57 (m, 7H), 2.22-2.17 (m, 3 H), 2.04-1.34 (m, 19 H); HRMS (ESI) [M+H]$^+$ calcd for $C_{37}H_{51}FN_3O_5$ 636.8275, found 636.826; HPLC>98% pure (t$_R$=3.86 min, 55(A):45(B):0.02(D); t$_R$=4.54 min, 40(A):60(B):0.02(D)).

(2-{5-[2-(5-Fluoro-2-methoxy-phenyl)-ethyl]-tetrahydro-furan-2-yl}-ethyl)-carbamic ethyl ester (23): Into a flame dried 20 mL vial was placed K$_2$CO$_3$ (239 mg, 1.73 mmol, 6.0 eq) and anhydrous THF (5.0 mL). The vial was purged with Ar$_{(g)}$ and then cooled in an ice bath. Ethyl chloroformate (156 mg, 1.44 mmol, 5.0 eq) was then added via syringe followed by slow addition of 14 (77 mg, 0.29 mmol, 1.0 eq) dissolved in THF (1.5 mL). The reaction was stirred at 0° C. for 0.5 hrs and then warmed to rt and allowed to stir an additional 3 hrs. The reaction was then stopped with sat. NaHCO$_{3(aq)}$ and extracted with EtOAc (3×20 mL). The organic layer was washed with brine and dried over Na$_2$SO$_4$, filtered, and concentrated under reduced pressure to yield crude product that was used in the next step of the synthesis. TLC: MeOH/CH$_2$Cl$_2$ (2:98, v:v), R$_f$ 0.4; $^1$H NMR (CDCl$_3$, 500 MHz) 6.87-6.82 (m, 2 H), 6.74-6.71 (m, 1 H), 4.12 (q, J=7.1 Hz, 2 H), 4.05-3.77 (m, 2 H), 3.78 (s, 3 H), 2.71-2.56 (m, 2 H), 2.08-1.51 (m, 10 H) 1.3 (t, J=7.2 Hz, 3 H). LRMS (ESI) [M+H]$^+$ calcd for $C_{18}H_{27}FNO_4$ 340 found 340.

(2-{5-[2-(5-Fluoro-2-methoxy-phenyl)-ethyl]-tetrahydro-furan-2-yl}-ethyl)-methyl-amine (24): Into a flame dried round bottom flask, purged with Ar$_{(g)}$, was placed 23 (112 mg, 0.33 mmol, 1.0 eq) and anhydrous THF (1.6 mL). The flask was cooled with an ice bath and stirred for 15 min. LAH (1.0 M, 1.32 mL, 1.32 mmol, 4.0 eq) was then slowly added via syringe over a period of 5 min. The reaction was allowed to warm to rt and stirred an additional 4 hrs. The reaction was then stopped with ice cold MeOH and then stirred for an additional 15 min at rt. The resulting solution was acidified with 1N HCl$_{(aq)}$ and then transferred to a beaker and then made basic with 10 M NaOH$_{(aq)}$. The basic solution was then extracted with diethyl ether (3×20 mL) and then the organic layer was washed with brine. The diethyl ether extract was dried over Mg$_2$SO$_4$ for 15 min and then filtered and concentrated to oil under reduced pressure to afford the crude product. The oil was purified with preparative TLC (developed with MeOH/CH$_2$Cl$_2$, 5:95, v:v, R$_f$ 0.05); $^1$H NMR (CDCl$_3$, 500 MHz) 6.87-6.82 (m, 2 H), 6.74-6.71 (m, 1 H), 4.05-3.77 (m, 2 H), 3.78 (s, 3 H), 2.71-2.56 (m, 5 H), 2.08-1.51 (m, 10 H); HRMS (ESI) [M+H]$^+$ calcd for $C_{16}H_{25}FNO_2$ 282.3784, found 282.3762; HPLC>97% pure (t$_R$=30.23 min, 100(A):0.5(D); t$_R$=26.05 min, 90(A):10(C):0.5(D)).

TABLE 14

Inhibition of Recombinant PDE4 Isoforms with PDE4 inhibitors and Dual PDE4 Inhibitor/SSRIs

| | Enzyme | | |
|---|---|---|---|
| Compound | Human PDE4D3 K$_i$ (nM) | Human PDE4D3 K$_i$ (nM) | Human PDE4A1 K$_i$ (nM) |
| 19 | 6.3 | 250 | <1000 |
| 21 | 2.0 | 199 | <1000 |
| 22 | 1.2 | 500 | <1000 |
| Rolipram | 58.9 | — | — |

TABLE 15

Inhibition of radioligand binding and [$^3$H] neurotransmitter uptake in HEK-hDAT, HEK-hSERT and HEK-hNET cells$^a$

| | | Binding (K$_i$, nM) | | | Reuptake (IC$_{50}$, nM) | | |
|---|---|---|---|---|---|---|---|
| Compound | Description | hDAT | hSERT | hNET | hDAT | hSERT | hNET |
| Cocaine | | 371 ± 81 | 276 ± 87 | 1115 ± 198 | 303 ± 74 | 416 ± 135 | 835 ± 229 |
| Fluoxetine | | 6670 ± 850$^b$ | 1.1 ± 0.5 | 1560 ± 300 | 19,500 ± 7600 | 7.3 ± 2.9 | 1020 ± 180 |
| 14 | SSRI | 6500 ± 828 | 2.1 ± 0.2 | 2440 ± 215 | 27850 ± 5129 | 2.5 ± 0.6 | 481 ± 158 |
| 15 | SSRI | 7307 ± 1331 | 1.1 ± 0.1 | 10600 ± 1880 | 16987 ± 1352 | 2.3 ± 0.6 | 1930.0 ± 463.0 |
| 19 | PDE4 inhibitor | >100,000 | >100,000 | >100,000 | >100,000 | >100,000 | >100,000 |

TABLE 15-continued

Inhibition of radioligand binding and [$^3$H] neurotransmitter uptake in HEK-hDAT, HEK-hSERT and HEK-hNET cells[a]

| Compound | Description | Binding ($K_i$, nM) | | | Reuptake ($IC_{50}$, nM) | | |
|---|---|---|---|---|---|---|---|
| | | hDAT | hSERT | hNET | hDAT | hSERT | hNET |
| 20 | N-modified PDE4 inhibitor | >100,000 | >100,000 | 39119 ± 4915 | >100,000 | >100,000 | >100,000 |
| 21 | Dual inhibitor | 2478 ± 451 | 156 ± 30 | 1748 ± 257 | 3556 ± 377 | 127 ± 15 | 957 ± 146 |
| 22 | Dual inhibitor | 5340 ± 1083 | 194 ± 87 | 7441 ± 1269 | 5340 ± 1083 | 194 ± 87 | 7441 ± 1269 |
| 24 | SSRI | 66988 ± 14450 | 21.2 ± 4.3 | 19332 ± 3577 | >100,000 | 18.4 ± 6.1 | 20370 ± 3751 |

[a]Values are the mean ± S.E.M. of three to four experiments unless the mean of three experiments exceeded 100 uM. Drug inhibition of [$^{125}$I]-RTI-55 binding in HEK-hDAT, HEK-hSERT, or HEK-hNET cell membranes. Inhibition of [$^3$H]-DA, [$^3$H]-5-HT, [$^3$H]-NE in the presence of HEK-hDAT, HEK-hSERT, or HEK-hNET cells, respectively;
[b]Data taken from the literature.

TABLE 16

Effect of Hepatic Microsomes on the Metabolic Stability of SSRIs and Dual PDE4 inhibitor/SSRIs

| Compd | RLM[a] $t_{1/2}$ (min) | MLM[b] $t_{1/2}$ (min) | HLM[c] $t_{1/2}$ (min) |
|---|---|---|---|
| 14 | 106.3 | 56.0 | NA[d] |
| 19 | NA | 211.3 | ND[e] |
| 21 | NA | 153.9 | ND |
| 22 | NA | ND | ND |
| 24 | 129.0 | 58.5 | NA |

[a]RLM, rat liver microsomes;
[b]MLM, mouse liver microsomes;
[c]HLM, human liver microsomes;
[d]NA, Not available.;
[e]ND, No detectable degradation observed in the presence of animal liver microsomes supplemented with NADPH for 60 mins.

Example 30

Other Dual SSRI/PDE4 Inhibitors

Initially, a PDE4 inhibitor was combined with highly potent and selective SSRIs to form dual SSRI/PDE4 inhibitors (see, e.g., FIG. 25). Summarized below is an extension of this study showing that well-recognized SSRIs can also be combined with PDE4 inhibitors to afford novel compounds with novel pharmacological activity. For example, nor fluoxetine (both enantiomers) was combined with a PDE4 inhibitor to give new dual inhibitors (see FIG. 24). This approach can be extended, for example, to a SERT/NET reuptake inhibitor (duloxetine) by synthesizing the nor duloxetine compound and combining it with the PDE4 inhibitor (see FIG. 27). During these studies it was necessary to determine the absolute configuration and enantiomeric purity of the norfluoxetine compounds by synthesizing the diastereomeric ureas (see FIG. 26). Diagnostic NMR signals in the urea products provided a means of quantifying each enantiomer. The synthesis and characterization of the nor-compounds (see FIG. 23) and dual inhibitor compounds are summarized below. The synthesis of the PDE4 inhibitor and the coupling chemistry are also described, as well as pharmacological results of the new dual SSRI/PDE4 inhibitors (using norfluoxetine) and constituent SSRIs (as the nor compounds) in in vitro studies.

Synthesis of PDE4/SSRI Dual Inhibitors 3,4-Dimethoxyphenylmagnesium bromide: Into a flame dried round bottom flask with a magnetic stir bar was placed anhydrous THF (150 mL) and $Mg_{(s)}$ turnings (1.43 g, 58.8 mmol, 1.0 eq). The flask was then fitted with a pressure equalizing addition funnel containing 4-bromo-1,2-dimethoxybenzene solution that was added slowly over a period of 45 min while stirring at rt. Once the addition was complete $I_{2(s)}$ (500 mg) was added and the reaction was brought to reflux and stirred for 12 hrs. The Grignard reagent was cooled and used immediately in the following reaction.

6-(3,4-Dimethoxy-benzoyl)-cyclohex-3-enecarboxylic acid: A solution of grignard reagent (59 mmol, 0.29 M) in THF was added dropwise to an ice-cooled solution of cis-1,2,3,6-tetrahydrophthalic anhydride in THF (120 mL) over a 1 hr period. After the addition was complete, the resulting mixture was stirred for another 30 min at 0° C. The reaction mixture was allowed to warm to rt and stirred overnight. The reaction was then stopped with sat. $NH_4Cl$ and the pH adjusted to 2 with concentrated $HCl_{(aq)}$ and then extracted with diethyl ether. The organic layer was washed with water and subsequently extracted with 1 M NaOH. The combined aqueous extract was acidified with concentrated HCl and extracted with EtOAc (3×100 mL). The organic layers were combined and dried over $MgSO_4$, filtered, and concentrated under reduced pressure to afford oil. The oil was dissolved $CH_2Cl_2$ and filtered through silica gel to remove the dicarboxylic acid formed during workup. The product was recrystallized from diethyl ether to afford pure product (1.62 g, 10%); mp=109° C.; LRMS ESI [m−H]$^-$ cacld for $C_{16}H_{18}O_5$ 289, found m/z 289; $^1$H NMR (CDCl$_3$, 500 MHz): δ 7.60-7.53 (m, 2 H), 6.92 (d, J=8.4 Hz, 1 H), 5.84-5.82 (m, 1 H), 5.71-5.68 (m, 1 H), 4.03-4.00 (m, 1 H), 3.98 (s, 3 H), 3.95 (s, 1 H), 3.10-3.07 (m, 1 H), 2.90-2.84 (m, 1 H), 2.54-2.44 (m, 3 H).

4-(3,4-Dimethoxy-phenyl)-4a,5,8,8a-tetrahydro-2 H-phthalazin-1-one (19): A mixture of 18 (610 mg, 2.1 mmol, 1.0 eq) and hydrazine hydrate (168 mg, 5.25 mmol, 2.5 eq) in EtOH (10 mL) was refluxed for 4 hrs. The reaction was then cooled to rt and concentrated under reduced pressure to afford a white precipitate. The precipitate was dissolved in EtOAc and washed with $Na_2SO_{4(aq)}$, 1 N $HCl_{(aq)}$, and water. The organic layer was then dried over $MgSO_4$, filtered, and concentrated to give a white precipitate. The precipitate was recrystallized in EtOH to afford the product as white crystals (376 mg, 63%); HRMS ESI [M+H]$^+$ calcd for $C_{16}H_{18}N_2O_3$ 287.3385, found m/z 287.3379; $^1$H NMR (CDCl$_3$, 500 MHz): δ 8.53 (bs, 1 H), 7.46 (d, J=2.0 Hz, 1 H), 7.23 (dd, J=2.0, 8.4 Hz, 1 H), 6.87 (d, J=8.4 Hz, 1 H), 5.8-5.77 (m, 1 H), 5.72-5.7 (m, 1 H), 3.94 (s, 3 H), 3.93 (s, 3 H), 3.40 (dt, J=5.5, 8.7 Hz, 1 H), 3.01-2.97 (m, 1 H), 2.85 (t, J=6.0 Hz, 1 H), 2.26-2.19 (m, 3 H); HRMS (ESI) [M+H]$^+$ calcd for $C_{16}H_{19}N_2O_3$ 287.3385, found 287.3376; HPLC>98% pure ($t_R$=4.93, 70(A):30(E); $t_R$=5.33, 50(A):50(E)).

2-(5-Bromo-pentyl)-4-(3,4-dimethoxy-phenyl-4a,5,8,8a-tetrahydro-2 H-phthalazin-1-one (20): Sodium hydride (60% dispersion in oil, 44 mg, 1.11 mmol, 1.1 eq) was added to a solution 19 (287 mg, 1.0 mmol, 1.0 eq). The mixture was stirred at rt for 30 min whereupon it took on a slight yellow color. 1,5-Dibromopentane (600 mg, 2.6 mmol, 2.6 eq) was added via syringe and the reaction was stirred for 30 min at rt while the yellow color dissipated to an almost clear solution. The reaction was stopped with the addition of water and then transferred to a separatory funnel and extracted with $Et_2O$ (3×30 mL). The organic fractions were combined and dried over $MgSO_4$, filtered, and concentrated to give an oil. The product was purified on silica and eluted with $CH_2Cl_2$ to afford a clear oil; $^1$H NMR (CDCl$_3$, 500 MHz): δ 7.47 (d, J=2.0 Hz, 1 H), 7.25 (dd, J=2.0, 8.5 Hz, 1 H), 6.87 (d, J=8.5 Hz, 1 H), 5.8-5.77 (m, 1 H), 5.7-5.67 (m, 1 H), 4.01-3.97 (m, 1 H), 3.95 (s, 3 H), 3.92 (s, 3 H), 3.79-3.74 (m, 1 H), 2.22-2.18 (m, 2 H), 2.1-2.04 (m, 1 H), 1.94-1.86 (m, 4 H), 1.74-1.69 (m, 4 H), 1.63-1.56 (m, 1 H), 1.52-1.46 (m, 2 H); LRMS ESI [M+H]$^+$ calcd for $C_{21}H_{28}BrN_2O_3$ 436, found m/z 435 (Br$^{79}$), 437 (Br$^{81}$).

(R) or (S)-1-Chloro-3-(4-trifluormethyl-phenoxy)-3-phenyl-propane: In a flame dried round bottom flask purged with Ar$_{(g)}$ was put the PPh$_3$ (368 mg, 1.41 mmol, 1.2 eq) and 1.5 mL of THF. To this solution was added the DIAD (284 mg, 1.41 mmol, 1.2 eq) and the reaction was stirred at rt for 20 min. Then the α,α,α-trifluoro-p-cresol (190 mg, 1.17 mmol, 1.0 eq) dissolved in 0.5 mL of THF was added via syringe and the reaction was stirred at rt for 4 hrs until a light precipitate had formed and the solution had turned greenish in color. The chiral alcohol (200 mg, 1.17 mmol, 1.0 eq) dissolved in 0.5 mL of THF was then added via syringe and the precipitate and color dissipated within 3 min after addition. The reaction was then stirred at rt overnight and then concentrated to oil. The crude oil was chromatographed on silica with 5% EtOAc/Hexanes as an eluent to afford the pure product as a clear oil (242 mg, 66%); $^1$H NMR (CDCl$_3$, 300 MHz): δ 7.47 (d, J=8.7 Hz, 2 H), 7.36 (m, 5 H), 6.94 (d, J=8.7 Hz, 2 H), 5.46 (dd, J=3.9, 4.7 Hz, 1 H), 3.83 (m, 1 H), 3.62 (m, 1 H), 2.51 (m, 1 H), 2.25 (m, 1 H).

(R) or (S)-1-phthalimide-3-(4-trifluormethyl-phenoxy)-3-phenyl-propane: In a 20 mL scintillation vial was put (R) or (S)-1-Chloro-3-(4-trifluormethyl-phenoxy)-3-phenyl-propane (468 mg, 1.48 mmol, 1.0 eq), NaI (10 mg), potassium phthalimide (550 mg, 2.97 mmol, 2.0 eq) and DMSO (3 mL). The vial was then put in a 70° C. oil bath and stirred for 13 hrs. When the reaction was complete the vial was cooled to rt and then quenched with $H_2O$. The resulting solution was then put in a seperatory funnel and extracted with EtOAc (3×25 mL). The organic layers were combined and washed with brine, dried over Na$_2$SO$_4$, filtered through paper, and then concentrated to a light yellow solid. The crude material was purified with silica chromatography with 25% EtOAc/Hexanes as an eluent to afford pure product as a light yellow solid (461 mg, 73%); $^1$H NMR (CDCl$_3$, 300 MHz): δ 7.81 (m, 2 H), 7.70 (m, 2 H), 7.37 (d, J=8.7 Hz, 2 H), 7.31 (m, 5 H), 6.81 (d, J=8.7 Hz, 2 H), 5.28 (dd, J=3.9, 5.5 Hz, 1 H), 3.95 (m, 2 H), 2.43 (m, 1 H), 2.22 (m, 1 H).

(R) or (S)-norfluoxetine: In a 20 mL scintillation vial was put (R) or (S)-1-phthalimide-3-(4-trifluormethyl-phenoxy)-3-phenyl-propane (142 mg, 0.33 mmol, 1.0 eq) and DCM (1 mL) and the solution was stirred until all of the phthalimide dissolved. Then MeOH (1 mL) followed by the hydrazine monohydrate was added to the vial and the reaction was stirred at rt for 8 hr's while a creamy white precipitate formed. When the reaction was complete it was concentrated in vacuo to a white solid and then transferred to a seperatory funnel with the aid of DCM and $H_2O$. The solution was extracted with DCM (1×25 mL) and then the aqueous layer was made basic (pH=12) with 10 M NaOH and then extracted again with DCM (2×25 mL). The organic layers were combined and washed with brine, dried over Na$_2$SO$_4$, filtered through paper, and concentrated to yellow oil (97 mg, 99%). The resulting crude material was pure enough to use in the following reaction; $^1$H NMR (CDCl$_3$, 300 MHz): δ 7.43 (d, J=8.7 Hz, 2 H), 7.29 (m, 5 H), 6.90 (d, J=8.7 Hz, 2 H), 5.32 (dd, J=3.6, 4.5 Hz, 1 H), 2.89 (t, J=7.2 Hz, 2 H), 2.16 (m, 1 H), 1.97 (m, 1 H), 1.31 (bs, 2 H).

In a vial was put (R) or (S)-norfluoxetine (30 mg, 0.10 mmol, 1.0 eq), NaH (5 mg, 0.12 mmol, 1.2 eq) and DMF (0.3 mL) and then the reaction was stirred at rt for 20 min. Then the alkyl halide (44 mg, 0.10 mmol, 1.0 eq) dissolved in DMF (0.3 mL) was added via syringe and the reaction was stirred at rt overnight. When the reaction was complete it was transferred to a separatory funnel with the aid of $Et_2O$ and $H_2O$. Saturated NaHCO$_3$ was added to the solution which was then extracted with $Et_2O$ (3×20 mL). The organic layers were combined and washed with $H_2O$ (2×30 mL) and brine. The organic layer was then dried over MgSO$_4$, filtered through paper and concentrated to clear oil. The product was purified with RP PTLC using 100 mg per plate and eluting twice with $CH_3N$/MeOH (1:1 vol:vol) and four more times with MeOH $R_f$=0.1.

R enantiomer $^1$H NMR (CDCl$_3$, 300 MHz): δ 7.47-7.29 (m, 9 H), 6.90-6.86 (m, 3 H), 5.80-5.66 (m, 2 H), 5.31-5.27 (m, 1 H), 3.94 (s, 3 H), 3.92 (s, 3 H), 3.79-3.7 (m, 1 H), 3.36-3.28 (m, 1 H), 3.02-2.97 (m, 1 H), 2.77 (m, 2 H), 2.6 (m, 2 H), 2.23-2.00 (m, 5 H), 1.72-1.3 (m, 7H), 0.87 (m, 2 H); LRMS ESI [M+H]$^+$ calcd for $C_{37}H_{42}F_3N_3O_4$ 650, found m/z 650, and 364; HPLC Supelco Discovery HS F5 HPLC column 39693-02 serial #567517-U, $H_2O$ (0.35% formic acid)/$CH_3N$/MeOH (1:1:18 vol:vol) $t_R$=84.75; $H_2O$ (0.35% formic acid)/$CH_3N$/MeOH (1:1:8 vol:vol) $t_R$=110.17.

S enantiomer $^1$H NMR (CDCl$_3$, 300 MHz): δ 7.47-7.24 (m, 9 H), 6.90-6.86 (m, 3 H), 5.81-5.66 (m, 2 H), 5.31-5.27 (m, 1 H), 3.94 (s, 3 H), 3.92 (s, 3 H), 3.79-3.7 (m, 1 H), 3.36-3.28 (m, 1 H), 3.02-2.97 (m, 1 H), 2.77 (m, 2 H), 2.6 (m, 2 H), 2.23-2.00 (m, 5 H), 1.72-1.3 (m, 7 H), 0.87 (m, 2 H); LRMS ESI [M+H]$^+$ calcd for $C_{37}H_{42}F_3N_3O_4$ 650, found m/z 650, and 364; HPLC Supelco Discovery HS F5 HPLC column 39693-02 serial #567517-U, $H_2O$ (0.35% formic acid)/$CH_3N$/MeOH (1:1:18 vol:vol) $t_R$=83.68; $H_2O$ (0.35% formic acid)/$CH_3N$/MeOH (1:1:8 vol:vol) $t_R$=109.47.

4-(3,4-Dimethoxy-phenyl)-2-[5-(2-{5-[2-(5-fluoro-2-methoxy-phenyl)-ethyl]-tetrahydro-furan-2-yl}-ethylamino)-pentyl]-4,5,8,8a-tetrahydro-2 H-phthalazin-1-one (21): (See FIG. 36.) Into a flame dried round bottom flask under an atmosphere of Ar$_{(g)}$, NaH (22 mg, 0.54 mmol, 1.2 eq) and DMF (2.0 mL) and then the primary amine (120 mg, 0.45 mmol, 1.0 eq) in DMF (0.3 mL) was added via syringe. The resulting mixture stirred at rt for 30 min and then the alkyl bromide (294 mg, 0.67 mmol, 1.5 eq) dissolved in DMF (0.3 mL) was added and stirred for an additional 18 hrs at rt. The reaction was washed with EtOAc (30 mL) and then filtered and the filtrate was washed with water in a separatory funnel. The organic layer was dried with Na$_2$SO$_4$, filtered, and concentrated to oil. The product was purified by preparative TLC (developed with MeOH/CH$_2$Cl$_2$, 5:95, v:v, $R_f$=0.2) to afford an oil (27 mg, 0.04 mmol, 31%); $^1$H NMR (CDCl$_3$, 500 MHz) δ 7.47 (d, J=2.0 Hz, 1 H), 7.25 (dd, J=2.0, 8.5 Hz, 1 H), 6.87 (d, J=8.5 Hz, 1 H), 6.86-6.81 (m, 2 H), 6.76-6.72 (m, 1 H), 5.81-5.79 (m, 1 H), 5.71 (m, 1 H), 4.01-3.97 (m, 1 H), 3.94 (s, 3 H), 3.91 (s, 3 H), 3.8 (s, 3 H), 3.79-3.74 (m, 1 H), 3.36-3.31 (m, 1 H), 3.03-3.00 (m, 1 H), 2.81-2.78 (m, 2 H), 2.73-2.37 (m, 5 H), 2.30-2.19 (m, 3 H), 2.09-1.97 (m, 3 H), 1.87-1.26 (m, 14 H); HRMS (ESI) [M+H]$^+$ cacld for $C_{36}H_{49}FN_3O_5$ 622.8007, found 622.8025; HPLC>99% pure ($t_R$=3.80 min, 55(A):45(B):0.02(D), $t_R$=4.53 min, 40 (A):60(B):0.02(D)).

4-(3,4-Dimethoxy-phenyl)-2-[5-(2-{5-[3-(5-fluoro-2-methoxy-phenyl)-propyl]-tetrahydro-furan-2-yl}-ethylamino)-pentyl-4a,5,8,8a-tetrahydro-2 H-phthalazin-1-one (22): (See FIG. 37.) The product was isolated by preparative TLC and (developed with MeOH/CH$_2$Cl$_2$, 5:95, v:v, $R_f$=0.2); $^1$H NMR (CDCl$_3$, 500 MHz) δ 7.47 (d, J=2.0 Hz, 1 H), 7.25 (dd, J=2.0, 8.5 Hz, 1 H), 6.87 (d, J=8.5 Hz, 1 H), 6.86-6.81 (m, 2 H), 6.76-6.72 (m, 1 H), 5.80-5.77 (m, 1 H), 5.69-5.66 (m, 1 H), 4.01-3.97 (m, 1 H), 3.94 (s, 3 H), 3.91 (s, 3 H), 3.77 (s, 3 H), 3.79-3.74 (m, 1 H), 3.33-3.3 (m, 1 H), 3.0-2.96 (m, 1 H), 2.81-2.57 (m, 7 H), 2.22-2.17 (m, 3 H), 2.04-1.34 (m, 19 H); HRMS (ESI) [M+H]$^+$ calcd for $C_{37}H_{51}FN_3O_5$ 636.8275, found 636.826; HPLC>98% pure ($t_R$=3.86 min, 55(A):45(B): 0.02(D); $t_R$=4.54 min, 40(A):60(B):0.02(D)).

N'-(R)-[1-(1-naphthyl)ethyl]-N-(S)-3-[4-(trifluoromethyl)phenoxy]-3-phenylpropylurea: (See FIG. 38.) (R)-Norfluoxetine (44 mg, 0.15 mmol, 1.1 eq) and (R)-(−)-1-(1-napthyl)ethyl isocyanate (27 mg, 0.14 mmol, 1.0 eq) was put in a vial containing toluene (0.75 mL). The reaction stirred at room temperature for 13 hrs and then concentrated in vacuo to afford a light yellow oil. The product was purified with PTLC on silica and eluted with EtOAc/Hex (1:3, v:v, $R_f$=0.3). $^1$H NMR (CDCl$_3$, 500 MHz) δ 8.22-7.21 (m, 14 H), 6.71 (d, J=8.7 Hz, 2 H), 5.53 (t, J=6.6 Hz, 1 H), 5.01-4.93 (m, 1 H), 4.60 (bt, 1 H), 3.22 (m, 2 H), 2.04-1.96 (m, 2 H) 1.54 (d, J=6.9 Hz, 3 H).

N'-(S)-[1-(1-naphthyl)ethyl]-N-(S)-3-[4-(trifluoromethyl) phenoxy]-3-phenylpropylurea: (See FIG. 39.) (S)-Norfluoxetine (44 mg, 0.15 mmol, 1.1 eq) and (R)-(−)-1-(1-napthyl) ethyl isocyanate (27 mg, 0.14 mmol, 1.0 eq) was put in a vial containing toluene (0.75 mL). The reaction stirred at room temperature for 13 hrs and then concentrated in vacuo to afford a light yellow oil. The product was purified with PTLC on silica and eluted with EtOAc/Hex (1:3, v:v, $R_f$=0.3). $^1$H NMR (CDCl$_3$, 500 MHz) δ 8.22-7.21 (m, 14 H), 6.71 (d, J=8.7 Hz, 2 H), 5.53 (t, J=6.6 Hz, 1 H), 5.01-4.93 (m, 1 H), 4.60 (bt, 1 H), 3.22 (m, 2 H), 2.04-1.96 (m, 2 H) 1.61 (d, J=6.9 Hz, 3 H).

Pharmacological Results

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound of Formula XIV:

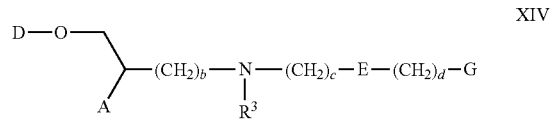

XIV wherein
D is a phenyl optionally substituted at the para position;
A is a phenyl;
E is 4a,5,8,8a-tetrahydro-2H-phthalazin-1-one or pyrrolidin-2-one;
G is a phenyl optionally substituted at the para position, the meta position, or at both the para and the meta positions;
$R^3$ is hydrogen;
subscripts b and c are each independently 1-6; and
subscript d is 0,
or a pharmaceutically acceptable salt thereof.

2. The compound of claim 1, selected from the group consisting of:
4-(3,4-Dimethoxy-phenyl)-2-{5-[3-phenyl-3-(4-trifluoromethyl-phenoxy)-propylamino]-pentyl}-4a,5,8,8a-tetrahydro-2H-phthalazin-1-one, and
4-(3-Cyclopentyloxy-4-methoxy-phenyl)-1-{5-[3-phenyl-3-(4-trifluoromethyl-phenoxy)-propylamino]-pentyl}-pyrrolidin-2-one.

3. The compound of claim 1, wherein said compound is a dual inhibitor of serotonin reuptake and phosphodiesterase 4 (PDE4) enzyme activity.

4. A pharmaceutical composition comprising:
a compound of claim 1; and
a pharmaceutically acceptable carrier.

5. A method for treating a central nervous system (CNS) disease or disorder in a subject, the method comprising:

TABLE 17

Inhibition of radioligand binding and neurotransmitter uptake in HEK-hDAT, HEK-hSERT and HEK-hNET cells[a]

| Compound | Description | Binding ($K_i$, nM) | | | Reuptake ($IC_{50}$, nM) | | |
|---|---|---|---|---|---|---|---|
| | | hDAT | hSERT | hNET | hDAT | hSERT | hNET |
| Cocaine | | 371 ± 81 | 276 ± 87 | 1115 ± 198 | 303 ± 74 | 416 ± 135 | 835 ± 229 |
| Fluoxetine | | 6670 ± 850[b] | 1.1 ± 0.5 | 1560 ± 300 | 19,500 ± 7600 | 7.3 ± 2.9 | 1020 ± 180 |
| 22(S) | SSRI | 4544 ± 1131 | 7.7 ± 1.5 | 6528 ± 1194 | ≧7658 305 | 6.8 ± 2.6 | 2806 ± 22 |
| 22(R) | SSRI | 3661 ± 456 | 22.8 ± 2.4 | 7338 ± 1390 | 7133 ± 891 | 12.6 ± 2.1 | 1995 ± 518 |
| 23(S) | Dual inhibitor | 3132 ± 194 | 1215 ± 146 | 4147 ± 693 | >10 μM | >5737 | >10 μM |
| 24(R) | Dual inhibitor | 3305 ± 408 | 82 ± 22 | 5827 ± 1754 | 6669 ± 1626 | 40 ± 15 | >8277 |

[a]Values are the mean ± S.E.M. of three to four experiments unless the mean of three experiments exceeded 100 uM. Drug inhibition of [$^{125}$I]-RTI-55 binding in HEK-hDAT, HEK-hSERT, or HEK-hNET cell membranes. Inhibition of [$^3$H]-DA, [$^3$H]-5-HT, [$^3$H]-NE in the presence of HEK-hDAT, HEK-hSERT, or HEK-hNET cells, respectively;
[b]Data taken from the literature.

administering to a subject an effective amount of a compound of claim 1, wherein said subject is suffering from a CNS disease or disorder amenable to treatment or prevention by inhibition of at least one of serotonin reuptake and phosphodiesterase 4 (PDE4) activity wherein the disease or disorder is selected from the group consisting of depression, a drug addiction, anxiety, attention-deficit disorder, schizophrenia, bipolar disorder and neurodegenerative disease or disorder.

6. The method of claim 5, wherein the compound is a dual inhibitor of serotonin reuptake and phosphodiesterase 4 (PDE4) enzyme activity.

7. The method of claim 5, wherein the neurodegenerative disease is Parkinson's Disease or Alzheimer's Disease.

8. The compound of claim 1, wherein D is 4-trifluoromethyl-phenyl.

9. The compound of claim 1, wherein b is 2.

10. The compound of claim 1, wherein c is 5.

11. The compound of claim 1, wherein E is 4a,5,8,8a-tetrahydro-2H-phthalazin-1-one, connected to $(CH_2)_c$ at position 2 and to G at position 4.

12. The compound of claim 1, wherein E is pyrrolidin-2-one, connected to $(CH_2)_c$ at position 1 and to G at position 4.

13. The compound of claim 1, wherein G is 3,4-dimethoxyphenyl or 3-cyclopentyloxy-4-methoxy-phenyl.

* * * * *